(12) United States Patent
Bassi et al.

(10) Patent No.: US 11,498,956 B2
(45) Date of Patent: Nov. 15, 2022

(54) FUSION PEPTIDES WITH ANTIGENS LINKED TO SHORT FRAGMENTS OF INVARIANT CHAIN(CD74)

(71) Applicants: GLAXOSMITHKLINE BIOLOGICALS SA, Rixensart (BE); UNIVERSITY OF COPENHAGEN, Copenhagen (DK)

(72) Inventors: Maria Rosaria Bassi, Copenhagen (DK); Riccardo Cortese, Rome (IT); Anna Morena D'Alise, Rome (IT); Antonella Folgori, Rome (IT); Peter Johannes Holst, Copenhagen (DK); Alfredo Nicosia, Rome (IT)

(73) Assignees: GLAXOSMITHKLINE BIOLOGICALS SA, Rixensart (BE); UNIVERSITY OF COPENHAGEN, Copenhagen (DK)

( * ) Notice: Subject to any disclaimer, the term of this patent is extended or adjusted under 35 U.S.C. 154(b) by 824 days.

(21) Appl. No.: 16/327,575

(22) PCT Filed: Aug. 23, 2017

(86) PCT No.: PCT/EP2017/071232
§ 371 (c)(1),
(2) Date: Feb. 22, 2019

(87) PCT Pub. No.: WO2018/037045
PCT Pub. Date: Mar. 1, 2018

(65) Prior Publication Data
US 2019/0338014 A1    Nov. 7, 2019

(30) Foreign Application Priority Data

Aug. 23, 2016  (GB) ..................................... 1614387
Mar. 28, 2017  (GB) ..................................... 1704892

(51) Int. Cl.
| | | |
|---|---|---|
| C07K 14/74 | (2006.01) |
| A61P 31/20 | (2006.01) |
| A61P 35/00 | (2006.01) |
| A61K 39/00 | (2006.01) |
| A61K 39/29 | (2006.01) |
| C07K 14/005 | (2006.01) |

(52) U.S. Cl.
CPC .... C07K 14/70539 (2013.01); A61K 39/0011 (2013.01); A61K 39/00119 (2018.08); A61K 39/29 (2013.01); A61P 31/20 (2018.01); A61P 35/00 (2018.01); C07K 14/005 (2013.01); A61K 2039/5256 (2013.01); A61K 2039/605 (2013.01); C07K 2319/00 (2013.01); C12N 2730/10122 (2013.01); C12N 2730/10134 (2013.01); C12N 2730/10171 (2013.01); C12N 2750/14143 (2013.01); C12N 2750/14171 (2013.01)

(58) Field of Classification Search
CPC ............................................... C07K 14/70539
See application file for complete search history.

(56) References Cited

U.S. PATENT DOCUMENTS

| | | |
|---|---|---|
| 2010/0278904 A1 | 11/2010 | Holst et al. |
| 2011/0293704 A1 | 12/2011 | Holst |
| 2015/0320848 A1 | 11/2015 | Rammensee et al. |
| 2016/0000904 A1 | 1/2016 | Colloca et al. |
| 2016/0304582 A1 | 10/2016 | Hill et al. |

FOREIGN PATENT DOCUMENTS

| | | |
|---|---|---|
| WO | WO 2010/057501 A1 | 5/2010 |
| WO | WO 2014/141176 A1 | 9/2014 |
| WO | WO 2015/082922 A1 | 6/2015 |

OTHER PUBLICATIONS

Colloca et al., "Generation and screening of a large collection of novel simian Adenovirus allows the identification of vaccine vectors inducing potent cellular immunity in humans," Sci. Transl. Med. (Jan. 4, 2012), vol. 4, No. 115, pp. 1-24.
Diebold et al., "MHC class II presentation of endogenously expressed antigens by transfected dendritic cells," Gene Therapy (2001), vol. 8, pp. 487-493.
Halbroth et al., "Development of a Molecular Adjuvant to Enhance Antigen-Specific CD8+ T Cell Responses," Scientific Reports (2018), vol. 8:15020, pp. 1-14.
Holmes et al., "Results of the First Phase I Clinical Trial of the Novel Ii-Key Hybrid Preventive HER-2/neu Peptide (AE37) Vaccine," J. Clin. Oncology (Jul. 10, 2008), vol. 26, No. 20, pp. 3426-3433.
Holst et al., "MHC Class II-Associated Invariant Chain Linkage of Antigen Dramatically Improves Cell-Mediated Immunity Induced by Adenovirus Vaccines," J. Immunology (2008), vol. 180, pp. 3339-3346.
Holst, Peter Johannes, "Augmentation of adenovirus induced immune responses. Evaluation of administration and antigen presentation with respect to the CD8+ T cell mediated immune response induced by replication defective adenovirus," Ph.D. Thesis, Faculty of Health Sciences, University of Copenhagen Jul. 25, 2008.
International Search Report and Written Opinion dated Nov. 3, 2017, in PCT/EP2017/071232 (Forms PCT/ISA/220, PCT/ISA/210, and PCT/ISA/237).

(Continued)

*Primary Examiner* — Scott Long
(74) *Attorney, Agent, or Firm* — Birch, Stewart, Kolasch & Birch, LLP

(57) ABSTRACT

The present application provides inter alia a fusion protein comprising a polypeptide wherein the polypeptide consists of a fragment of invariant chain which is operably linked to an antigenic sequence and wherein the fragment of invariant chain consists of a portion of residues 17-97 of SEQ ID NO: 1, wherein the portion comprises at least 5 contiguous residues from residues 77-92 of SEQ ID NO: 1.

19 Claims, 27 Drawing Sheets

Specification includes a Sequence Listing.

(56) References Cited

OTHER PUBLICATIONS

Kallinteris et al., "Ii-Key/MHC class II epitope hybrids: a strategy that enhances MHC class II epitope loading to create more potent peptide vaccines," Expert Opinion on Biological Therapy (2006), vol. 6, No. 12, pp. 1311-1321.

Mittendorf et al., "CD4+ cells in antitumor immunity: utility of an Ii-Key HER2/neu hybrid peptide vaccine (AE37)," Expert Opinion on Biological Therapy (2008), vol. 9, No. 1, pp. 71-78.

Morris et al., "Association of Intracellular Proteins with Folded Major Histocompatibility Complex Class I Molecules," Immunologic Research (2004), vol. 30, No. 2, pp. 171-179.

Pieters, J., "MHC class II restricted antigen presentation," Current Opinion in Immunology (1997), vol. 9, pp. 89-96.

Roy et al., "Complete nucleotide sequences and genome organization of four chimpanzee adenoviruses," Virology (2004), vol. 324, pp. 361-372.

Roy et al., "Creation of a panel of vectors based on ape adenovirus isolates," J. Gene Med. (2011), vol. 13, pp. 17-25.

Strubin et al., "Alternative splicing and alternative initiation of translation explain the four forms of the Ia antigen-associated invariant chain," The EMBO Journal (1986), vol. 5, No. 13, pp. 3483-3488.

Stumptner-Cuvelette, P. and P. Benaroch, "Multiple roles of the invariant chain in MHC class II function," Biochimica et Biophysica Acta (2002), vol. 1542, pp. 1-13.

Tatis, N. and H. C. J. Ertl, "Adenoviruses as Vaccine Vectors," Molecular Therapy (Oct. 2004), vol. 10, No. 4, pp. 616-629.

Walchli et al., "Invariant chain as a vehicle to load antigenic peptides on human MHC class I for cytotoxic T-cell activation," Eur. J. Immunol. (2014), vol. 44, pp. 774-784.

Schroder, Bernd, "The multifaceted roles of the invariant chain CD74- More than just a chaperone," Biochimica et Biophysica Acta (2016), vol. 1863, pp. 1269-1281.

Thayer et al., "A novel single chain I-$A^b$ molecule can stimulate and stain antigen-specific T-cells," Molecular Immunology (2003), vol. 39, pp. 861-870.

IP: Anti-Ub Lys 48
Blot: Anti-HA

```
                   *        20         *        40         *        60         *        80         *
S9XLT6_SEQ42  :    ----------..........E.........H........Q..A...................A........................ :  74
L8I7V9_SEQ43  :    ----------..........E.........H........Q.Q.....................A........................ :  74
Q7JFY1_SEQ44  :    ----------..........-.........H........Q.Q.....................A........................ :  67
Q29630_SEQ45  :    ----------..........E.........H........Q.Q.....................A........................ :  74
F6TGS3_SEQ46  :    ----------..........E.........H........Q..A...R................A........................ :  74
Q9MXD5_SEQ47  :    ----------..........E.........H........Q..A...R................A........................ :  74
G1SKK3_SEQ48  :    -F.SQ..KL.TS.ARA....................Q..Q.R.....................A.........D...P...A....... :  89
H0WQB3_SEQ49  :    ----------..........E.........H..T.SQ.A..RQ....................A........................ :  74
L9KN01_SEQ50  :    ----------..........-.........H........Q..REA...G..............A.............Q.H........ :  74
I3MCR9_SEQ51  :    ----------..........E.........H........Q..REQ.-..T.............A........................ :  73
G3X0Q6_SEQ52  :    ----------..........E.........H..Q.GSA.GQHRS.NQ..F.............A.....A.V................ :  74
```

```
                            *              200         *             220         *              240         *              260         *
P35_HUMAN_SEQ_1    : VFESWMHHWLLFEMSRHSLEQK--PTDAPPK---------------------------------------------------------------------------- : 208
P43_HUMAN_SEQ_5    : ..R.R.LG.............................................................................................. : 267
C___HUMAN_SEQ_9    : ------------------------------------------------------------------------------------------------------ : 160
P31_MOUSE_SEQ11    : ....KQ...............-K..E....VLTKCQEEVSHIPAVHPGSFRPKCDENGNYLPLQCYGSIGYCWCVFPNGTEVPHTKSRG : 191
P41_MOUSE_SEQ13    : ....KQ...............-K..E....VLTKCQEEVSHIPAVYPGAFRPKCDENGNYLPLQCHGSTGYCWCVFPNGTEVPHTKSRG : 250
H0UZ94_SEQ15       : ....N.P..............-...E....VLSKCQEEVSHIPAVHPGTFRPQCDENGNYMPLQCHGSTGYCWCVFPNGTEVPHTRSHG : 251
G5C391_SEQ16       : ....N.PG.............-...E....VLSKCQEEVSHIPAVHPGTFRPQCDENGNYMPLQCHGSTGYCWCVFPNGTEVPQTRSRG : 252
A0A091E9W3_SEQ17   : ....N.P-.............-...E....VLSKCQEEVSHIPAVHPGTFRPQCDENGNYMPLQCHGSTGYCWCVFPNGTEVPHTRSRG : 250
P10247-2_SEQ18     : ....N.................-Q..QT...------------------------------------------------------------- : 192
P10247_SEQ19       : ....KQ................-Q..QT...VLTKCQEEVSHIPDVHPGAFRPKCDENGNYMPLQCHGSTGYCWCVFPNGTEVPHTKSRG : 251
G1QEN4_SEQ20       : ....Q.................--L.EGS..VLTKCLEEASRIPAIHPGRFKPQCDENGNYMPLQCFGSIGYCWCVFPNGTEVPHTRSRG : 251
L5LQM9_SEQ21       : ....Q.................--L.EGS..VLTQCLEEASRIPAIHPGRFKPQCDENGNYMPLQCFGSIGYCWCVFPNGTEVPHTRSRG : 251
S7N2W2_SEQ22       : ....Q.................--L.EGS..VLTKCLEEASRIPAIHPGRFKPQCDENGNYMPLQCFGSIGYCWCVFPNGTEVPHTRSRG : 236
L5L1G3_SEQ23       : A...N.................PK..QV.T.VLTKCLEEVSRIPAIHPGMFKPKCDENGNYMPLQCYGSIGYCWCVFPNGTEVPHTRSRK : 253
A5A6L4_SEQ24       : ......................-...E....------------------------------------------------------------- : 208
Q5RFJ4_SEQ25       : ......................-........------------------------------------------------------------- : 208
H2QRT2_SEQ26       : ......................-........------------------------------------------------------------- : 208
G3R7S6_SEQ27       : ......................-...E....VLTKCQEEVSHIPAVHPGSFRPTCDENGNYLPLQCYGSIGYCWCVFPNGTEVPNTRSRG : 267
G1RHB8_SEQ28       : ......................-...E....VLTKCQEEVSHIPAVHPGSFRPKCDENGNYLPLQCYGSIGYCWCVFPNGTEVPNTRSRG : 267
I0FWR3_SEQ29       : ......................-........------------------------------------------------------------- : 206
G7P8P8_SEQ30       : ......................-...E....VLTKCQEEVSHIPAVHPGSFRPKCDENGNYLPLQCYGSTGYCWCVFPNGTEVPNTRSRG : 265
G7MVM5_SEQ31       : ......................-...E....VLTKCQEEVSHIPAVHPGSFRPKCDENGNYLPLQCYGSTGYCWCVFPNGTEVPNTRSRG : 265
I0FWR4_SEQ32       : ......................-...E....VLTKCQEEVSHIPAVHPGSFRPKCDENGNYLPLQCYGSTGYCWCVFPNGTEVPNTRSRG : 265
F7E9S4_SEQ33       : ......................-...E....VLTKCQEEVSHIPAVHPGSFRPKCDENGNYLPLQCYGSTGYCWCVFPNGTEVPNTRSRG : 265
A0A096MM48_SEQ34   : ......................-...E....VLTKCQEEVSHIPDVHPGSFRPKCDENGNYLPLQCYGSTGYCWCVFPNGTEVPNTRSRG : 265
A0A0D9RGK4_SEQ35   : ......................-...E....ALTKCQEEVSHIPAVHPGTFRPKCDENGNYLPLQCYGSTGYCWCVFPNGTEVPNTRSRG : 266
F7ENM4_SEQ36       : ....N.YQ..............KH-A.I.L.VLTKCQEEVSHIPAVHPGTFRPQCDENGNYKPLQCYGSTGYCWCVFPNGTEVPHSRSHG : 251
M3VXS2_SEQ37       : ......YQ.............-N--EV.L.ALTQCQEEVSRVPAVHPGTFRPQCDENGNYLPLQCYGSTGYCWCVFPNGTEVPHTRSRG : 250
M3YQS4_SEQ38       : A...N...Q............-...E..T.ALTKCQEEVSHIPAIHPGVYRPKCDENGNYLPLQCYGSTGYCWCVFPNGTEVPHTRSRG : 251
G3TJE1_SEQ39       : A...N...Q............-...E..T.ALTKCQEEVSRIPAIHPGVYRPKCDENGNYLPLQCYGSTGYCWCVFPNGTEVPHTRSRG : 251
G3U7Y6_SEQ40       : ....N.RQ.............-T---FEV.-------------------------------------------------------------- : 251
Q764N1_SEQ41       : ....N...Y.............-FEV.....------------------------------------------------------------- : 190
S9XLT6_SEQ42       : ....N...Q.Q---FEV.T.ALTKCQEEVSRIPAIHPGTFRPKCDENGNYMPLQCYGSIGYCWCVFPNGTEVPHTRSRG : 249
```

Figure 12F

```
                 *              *         200              *         220              *         240              *         260         *
L8I7V9_SEQ43  : ..........Q......................N.............FEG...VLTQCQEEVSRIPAIHPGVFKPNCDENGNYMPLQCYGSIGYCWCVFPNGTEVPHTRSRG :  249
Q7JFY1_SEQ44  : ..........Q......................N.............FEG................................................................. :  183
Q29630_SEQ45  : ..........Q......................N.............FEG................................................................. :  190
F6TGS3_SEQ46  : .......N..Q......................N.............QG.T................................................................ :  192
Q9MXD5_SEQ47  : .......N..Q......................N.............QG.T................................................................ :  192
G1SKK3_SEQ48  : ..........Q......................N...........E..T..VLSKCLEEASHVPDVHPGRFKPQCDENGNYMPLQCHGSIGYCWCVFPNGTEVPHTRSRG :  266
H0WQB3_SEQ49  : ..........Q......................N.G.........E.....VLTKCQEEFSRVPAIHPGTFRPKCDENGNYMPLQCHGSIGYCWCVFPNGTEVPHTRSRG :  251
L9KN01_SEQ50  : ..........Q......................N...........EP.T..ALTKCQEEVSRIPAVHPGTFRPKCDENGNYMPLQCHGSIGYCWCVFPNGTEVPHTRSRG :  251
I3MCR9_SEQ51  : .......N..Q......................N...........E..T..VLTKCQEEVSHIPAVHPGAFRPKCDENGNYMPLQCHGSIGYCWCVFPNGTEVPHTRSRG :  250
G3X0Q6_SEQ52  : ..N..N....Q......................KPN..N---VEKKTEPLQKG----------------------------------------------------------- :  193
```

Figure 12G

```
                        280          *         300          *         320          *         340          *         360
P35_HUMAN_SEQ_1      : ------ES--LELEDPSSGLGVTKQD--LGPVPM------------------------------------------------------- :  232
P43_HUMAN_SEQ_5      : HHNCS..................................................................................... :  296
C_HUMAN_SEQ_9        : -------------------------------............................................................ :    -
P31_MOUSE_SEQ11      : ------.P---.D...L.........E---..Q.T....................................................... :  215
P41_MOUSE_SEQ13      : RHNCS..P---.D...L.........E---..Q.T....................................................... :  279
H0UZ94_SEQ15         : HHNCS..P---.....A.L.......E---..QAS........................................................ :  280
G5C391_SEQ16         : HHNCS..P---.....A.L.......E---..AH.AARAKDSSVRKRTCTRCLGLSHRLLCRLLLGEKGDRLWSLLFLSIAA--------- :  329
A0A091E9W3_SEQ17     : HHNCSDP----.....A.L.......E-----.GLCLAKLVISSQGRGSWKNKRG----------------------------------- :  298
P10247-2_SEQ18       : -------.P---.D.............--...Q.F........................................................ :  216
P10247_SEQ19         : RHNCS..P---.D.............----..Q.F........................................................ :  280
G1QEN4_SEQ20         : RHNCS..P---.D...L..............VQAT........................................................ :  280
L5LQM9_SEQ21         : RHNCS..P---.D...L...............VQAIEDTSTQSALHGHSFLALFRPPNLATYFSPLHALLPPSPTLHLIS----------- :  323
S7N2W2_SEQ22         : RHNCS..P---.D...L...............VQEIT--SEQQIRR----ALLPKPPSISRHTR-------------------------- :  295
L5L1G3_SEQ23         : RSNCS..P---.D...L...............SQGKGACRGDAQHG----TTLVHSPT------------------------------- :  299
A5A6L4_SEQ24         : -------------------------------............................................................ :  232
Q5RFJ4_SEQ25         : -------------------------------............................................................ :  232
H2QRT2_SEQ26         : -------------------------------...A........................................................ :  232
G3R7S6_SEQ27         : HHNCS..........................................S........................................... :  296
G1RHB8_SEQ28         : HHNCS...................................................................................... :  296
I0FWR3_SEQ29         : -------------------------------............................................................ :  230
G7P8P8_SEQ30         : HQNCS...........................................HTQDIILSFMFIHFLPSPPQNHGELDVRGNSLLTFLDLLCLPQLFTMHLQGACP- :  346
G7MVM5_SEQ31         : HQNCS...........................................HTQDIILSFMFIHFLPSPPQNHGELDVRGNSLLTFLDLLCLPQLFTMHLQGACP- :  346
I0FWR4_SEQ32         : HQNCS...................................................................................... :  294
F7E9S4_SEQ33         : HQNCS...................................................................................... :  270
A0A096MM48_SEQ34     : HQNCS...................................................................................... :  294
A0A0D9RGK4_SEQ35     : HQNCS...........................A.......................................................... :  294
F7ENM4_SEQ36         : HHNCS...........................A.......................................................... :  295
M3VXS2_SEQ37         : HRNCS...D...L...........P-------.QA......................................................... :  280
M3YQS4_SEQ38         : HHNCR.P---.D...L.................Q.A........................................................ :  279
G3TJE1_SEQ39         : HHNCS..P---....L......D...G------EET........................................................ :  280
G3U7Y6_SEQ40         : HHNCS..P---....L......D...G------EGL........................................................ :  280
```

Figure 12H

```
                      280             *           300            *           320            *           340            *           360
Q764N1_SEQ41  : ------DP---..T..L......-------..Q--------------------VIL--------------------------------------------------------- : 214
S9XLT6_SEQ42  : HHNCSDP---.....L......P.---..QG.THEALSSSLGPRQMLELPSCPPRVNDQQGFQTQEAYLPPGVLQTVCSAVFFCEERGM : 335
L8I7V9_SEQ43  : HRNCSDP---.....Y......-------------------------------------------------------------------- : 268
Q7JFY1_SEQ44  : ------DP---.....Y......-------------------------------------------------------------------- : 190
Q29630_SEQ45  : ------DP---.....Y......-------------------------------------------------------------------- : 204
F6TGS3_SEQ46  : ------.P---.....L...A.-------------------------------------------------------------------- : 208
Q9MXD5_SEQ47  : ------.P---.....L...A.-------------------------------------------------------------------- : 208
G1SKK3_SEQ48  : HHNCS.P---..F.Y...D.A.PE--..K------------------------------------------------------------- : 292
H0WQB3_SEQ49  : QHNCS.P--QD.....F..EPG.KG...-------------------------------------------------------------- : 282
L9KN01_SEQ50  : HHNCSGPTC.A.W.HLDARAALL.EAY..L...ALRRSVPLSSSVGEKYERLLKLLWPPEQILGLQGCLRAGQGSASCTLQEGARGSALI : 341
I3MCR9_SEQ51  : RHDCS.P---.....V......--..Q.I.------------------------------------------------------------ : 279
G3X0Q6_SEQ52  : ------L.DE.MF.....FP..------------------------------------------------------------------- : 209
```

Figure 12I

```
                              *         380         *
P35_HUMAN_SEQ_1        : ------------------------------- : -
P43_HUMAN_SEQ_5        : ------------------------------- : -
C___HUMAN_SEQ_9        : ------------------------------- : -
P31_MOUSE_SEQ11        : ------------------------------- : -
P41_MOUSE_SEQ13        : ------------------------------- : -
H0UZ94_SEQ15           : ------------------------------- : -
G5C391_SEQ16           : ------------------------------- : -
A0A091E9W3_SEQ17       : ------------------------------- : -
P10247-2_SEQ18         : ------------------------------- : -
P10247_SEQ19           : ------------------------------- : -
G1QEN4_SEQ20           : ------------------------------- : -
L5LQM9_SEQ21           : ------------------------------- : -
S7N2W2_SEQ22           : ------------------------------- : -
L5L1G3_SEQ23           : ------------------------------- : -
A5A6L4_SEQ24           : ------------------------------- : -
Q5RFJ4_SEQ25           : ------------------------------- : -
H2QRT2_SEQ26           : ------------------------------- : -
G3R7S6_SEQ27           : ------------------------------- : -
G1RHB8_SEQ28           : ------------------------------- : -
I0FWR3_SEQ29           : ------------------------------- : -
G7P8P8_SEQ30           : ------------------------------- : -
G7MVM5_SEQ31           : ------------------------------- : -
I0FWR4_SEQ32           : ------------------------------- : -
F7E9S4_SEQ33           : ------------------------------- : -
A0A096MM48_SEQ34       : ------------------------------- : -
A0A0D9RGK4_SEQ35       : ------------------------------- : -
F7ENM4_SEQ36           : ------------------------------- : -
M3VXS2_SEQ37           : ------------------------------- : -
M3YQS4_SEQ38           : ------------------------------- : -
G3TJE1_SEQ39           : ------------------------------- : -
G3U7Y6_SEQ40           : ------------------------------- : -
Q764N1_SEQ41           : ------------------------------- : -
S9XLT6_SEQ42           : TGSRT-------------------------- : 340
```

```
                          *         380        *
L8I7V9_SEQ43 : ------------------------------------- : -
Q7JFY1_SEQ44 : ------------------------------------- : -
Q29630_SEQ45 : ------------------------------------- : -
F6TGS3_SEQ46 : ------------------------------------- : -
Q9MXD5_SEQ47 : ------------------------------------- : -
G1SKK3_SEQ48 : ------------------------------------- : -
H0WQB3_SEQ49 : ------------------------------------- : -
L9KN01_SEQ50 : TQQALWAWVELHPCKVWAVGHEHSPCSGGSDTRK     : 375
I3MCR9_SEQ51 : ------------------------------------- : -
G3X0Q6_SEQ52 : ------------------------------------- : -
```

[Sequence alignment figure showing multiple protein sequences aligned from position 1 to 81, with P35_HUMAN_SEQ53 as the reference sequence: MDDQRDLISNNEQLPMLGRRPGAPESKCSRGALYTGFSILVTLLLAGQATTAYFLYQQQGRLDKLTVTSQNLQLENLRMKL, followed by aligned variants including P31_MOUSE_SEQ54, G3TJE1_SEQ55, M3VXS2_SEQ56, F6TGS3_SEQ57, S9XLT6_SEQ58, Q764N1_SEQ59, M3YQS4_SEQ60, I0FWR3_SEQ61, G7P8P8_SEQ62, A0A0D9RGK4_SEQ63, A0A096MM48_SEQ64, A5A6L4_SEQ65, G3R7S6_SEQ66, G1RHB8_SEQ67, Q5RFJ4_SEQ68, F7ENE8_SEQ69, G1QEN4_SEQ70, L5LQM9_SEQ71, L8I7V9_SEQ72, Q29630_SEQ73, S7N2W2_SEQ74, G5C391_SEQ75, A0A091E9W3_SEQ76, H0UZ94_SEQ77, G1SKK3_SEQ78, L5L1G3_SEQ79, P10247-2_SEQ80, L9KN01_SEQ81, I3MCR9_SEQ82, H0WQB3_SEQ83, G3X0Q6_SEQ84]

Figure 14

```
                              *         *        80         *
P35_HUMAN_SEQ85    : TAYFLYQQQGRLDKLTVTSQNLQLEN : 26
P31_MOUSE_SEQ86    : .........................S : 26
M3YQS4_SEQ87       : .......................... : 26
S7N2W2_SEQ88       : .......................... : 26
L5L1G3_SEQ89       : .......................... : 26
A0A091E9W3_SEQ90   : .......................... : 26
I3MCR9_SEQ91       : .......................... : 26
L8I7V9_SEQ92       : .......................... : 26
G5C391_SEQ93       : .......................... : 26
L5LQM9_SEQ94       : .......................... : 26
L9KN01_SEQ95       : ............Q.H........... : 26
G1QEN4_SEQ96       : .......................... : 26
P10247-2_SEQ97     : .......................... : 26
O29630_SEQ98       : .......................... : 26
H0WQB3_SEQ99       : .......................... : 26
H0UZ94_SEQ100      : .......................... : 26
F7ENE8_SEQ101      : .......................... : 26
G1RHB8_SEQ102      : .......................... : 26
G3R7S6_SEQ103      : .......................... : 26
Q5RFJ4_SEQ104      : .......................... : 26
A5A6L4_SEQ105      : .......................... : 26
I0FWR3_SEQ106      : .....................S.... : 26
G7P8P8_SEQ107      : .....................S.... : 26
A0A0D9RGK4_SEQ108  : .......................... : 26
A0A096MM48_SEQ109  : .......................... : 26
G3TJE1_SEQ110      : ..................A....... : 26
M3VXS2_SEQ111      : ..................A....... : 26
F6TGS3_SEQ112      : ..................A...K... : 26
Q764N1_SEQ113      : .........................S : 26
G1SKK3_SEQ114      : ............D............. : 26
G3X0Q6_SEQ115      : ...V.....................S : 26
S9XLT6_SEQ116      : .......................... : 26
```

FUSION PEPTIDES WITH ANTIGENS LINKED TO SHORT FRAGMENTS OF INVARIANT CHAIN(CD74)

REFERENCE TO SEQUENCE LISTING SUBMITTED VIA EFS-WEB

This application includes an electronically submitted sequence listing in .txt format. The .txt file contains a sequence listing entitled "2019-05-21_5979-0120PUS1_ST25.txt" created on May 21, 2019 and is 262,414 bytes in size. The sequence listing contained in this .txt file is part of the specification and is hereby incorporated by reference herein in its entirety.

The present application relates to polynucleotides encoding an antigenic sequence and a fragment of an invariant chain. The application also relates to fusion proteins encoded by said polynucleotides and to viral vectors comprising said polynucleotides.

BACKGROUND OF THE INVENTION

Infectious diseases are still a major threat to mankind. One way of preventing or treating infectious diseases is the artificial induction of an immune response by vaccination which is the administration of antigenic material to an individual such that an adaptive immune response against the respective antigen is developed. The antigenic material may be pathogens (e.g. microorganisms or viruses) which are structurally intact but inactivated (i.e. non-infective) or which are attenuated (i.e. with reduced infectivity), or purified components of the pathogen that have been found to be highly immunogenic. Another approach for inducing an immune response against a pathogen is the provision of expression systems comprising one or more vectors encoding immunogenic proteins of the pathogen. Such vectors may be in the form of naked plasmid DNA, or the immunogenic proteins may be delivered by using viral vectors, for example on the basis of modified vaccinia viruses (e.g. Modified Vaccinia Ankara; MVA) or adenoviral vectors. Such expression systems have the advantage of comprising well-characterized components having a low sensitivity against environmental conditions.

It is a particular aim when developing vector based expression systems that the application of these expression systems to a patient elicits an immune response which is protective against the infection by the respective pathogen. However, although inducing an immunogenic response against the pathogen, some expression systems are not able to elicit a strong immune response (for example, which is strong enough to fully protect against infections by the pathogen). Accordingly, there is still a need for improved expression systems which are capable of inducing a strong immune response against a pathogen.

Antigens are substances which induce an immune response in the body, especially the production of antibodies. Antigens can be presented on the surface of antigen presenting cells by MHC molecules. Antigens may be of foreign, i.e. pathogenic, origin or stem from the organism itself, the latter are referred to as self- or auto antigens. There are two classes of MHC molecules, MHC class I (MHC-I) and MHC-class-II (MHC-II). MHC-I molecules present fragments of peptides which are synthesized within the respective cell. MHC-II molecules present fragments of peptides which were taken up by phagocytosis and subsequently digested in the endosome. Typically, MHC-II molecules are only expressed by "professional" antigen presenting cells such as macrophages or dendritic cells. Antigens bound to MHC-II molecules are recognized by T-helper cells. The binding of the T-cell receptor of a T-helper cell to an antigen presented by a MHC-II molecule, together with cytokines secreted by the antigen-presenting cells, induces the maturation of an immature T-helper cell of the $Th_0$ phenotype into various types of effector cells.

The MHC-I molecules bind peptides generated mainly from degradation of cytosolic proteins by the proteasome. The MHC I:peptide complex is then inserted via the endoplasmic reticulum into the external plasma membrane of the cell. The epitope peptide is bound on extracellular parts of the class I MHC molecule. Thus, the function of the class I MHC is to display intracellular proteins to cytotoxic T cells (CTLs). However, class I MHC can also present peptides generated from exogenous proteins, in a process known as cross-presentation. A normal cell will display peptides from normal cellular protein turnover on its class I MHC, and CTLs will not be activated in response to them due to central and peripheral tolerance mechanisms. When a cell expresses foreign proteins, such as after viral infection, a fraction of the class I MHC will display these peptides on the cell surface. Consequently, CTLs specific for the MHC:peptide complex will recognize and kill presenting cells.

The MHC-II molecules are membrane-bound receptors which are synthesized in the endoplasmic reticulum and leave the endoplasmic reticulum in a MHC class II compartment. In order to prevent endogenous peptides, i.e. self-antigens, from binding to the MHC-II molecule, the nascent MHC-II molecule combines with another protein, the invariant chain, which blocks the peptide-binding cleft of the MHC-II molecule. When the MHC class II compartment fuses to a late endosome containing phagocytosed and degraded proteins, the invariant chain is cleaved to leave only the CLIP region bound to the MHC-II molecule. In a second step, CLIP is removed by an HLA-DM molecule leaving the MHC-II molecule free to bind fragments of the foreign antigen. Said fragments are presented on the surface of the antigen-presenting cell once the MHC class II compartment fuses with the plasma membrane, thus presenting the foreign antigens to other cells, primarily T-helper cells.

It is known that the immune response against an antigen is increased when an adenovirus expression system encoding a fusion of invariant chain and said antigen is used for vaccination (see WO2007/062656, which also published as US2011/0293704 and is incorporated by reference for the purpose of disclosing invariant chain sequences), i.e. the invariant chain enhances the immunogenicity of the antigen. Moreover, said adenoviral construct has proven useful for priming an immune response in the context of prime-boosting vaccination regimens (see WO2014/141176, which also published as US2016/0000904; and WO2010/057501, which also published as US2010/0278904 and is incorporated by reference for the purpose of disclosing invariant chain sequences and adenoviral vectors encoding invariant chain sequences).

SUMMARY OF THE INVENTION

The present inventors have surprisingly found that certain minor fragments of invariant chain are also capable of enhancing the immunogenicity of antigen. In particular embodiments, certain fragments of invariant chain have been found to provide substantially the same immunogenicity enhancement effect as that of full length invariant chain. In further particular embodiments, certain fragments of invariant chain have been found to provide a higher immunogenicity enhancement effect than that of full length invariant chain.

These fragments, while providing a level of immunogenicity enhancement, maintaining substantially the same immunogenicity enhancing effect as that of full length invariant chain or even providing an increased immunogenicity enhancement effect compared to full length invariant chain, have various advantages over full length invariant chain. For example, the fragments may have a lower risk of unintended immunological consequences such as possibly anaphylactic shock or antigen mimicry, which could trigger an anti-self immune response. Furthermore, many otherwise convenient host vectors may have limited insertion space, therefore the fragments of the invention represent a smaller invariant chain-derived insert which permits additional space for antigen or other components in the host vector.

Embodiments of the Present Invention May have One or More of the Following Advantages Compared to Related Approaches Disclosed in the Prior Art:
(i) increased immune response (such as CD4 T-cell and/or CD8 T-cell and/or antibody response),
(ii) broader immune response,
(iii) more sustained immune response,
(iv) reduced risk of harmful and/or unintended immune response,
(v) increased space available for further nucleic acid integration into a vector.

In one aspect of the invention, there is provided a fusion protein comprising a polypeptide wherein the polypeptide consists of a fragment of invariant chain which is operably linked to an antigenic sequence and wherein the fragment of invariant chain consists of:
(a) a portion of residues 17-97 of SEQ ID NO: 1, wherein the portion comprises at least 5 contiguous residues from residues 77-92 of SEQ ID NO: 1;
(b) 80 residues or fewer and comprises a sequence of at least 5 contiguous residues wherein the sequence shares at least 80% identity with at least 5 contiguous residues from residues 77-92 of SEQ ID NO: 1;
(c) residues 1-97 of SEQ ID NO: 1;
(d) 91 to 103 residues and shares at least 95% identity with residues 1-97 of SEQ ID NO: 1;
(e) residues 17-97 of SEQ ID NO: 1;
(f) 76 to 84 residues and shares at least 95% identity with residues 17-97 of SEQ ID NO: 1;
(g) residues 1-92 of SEQ ID NO: 1;
(h) 88 to 96 residues and shares at least 95% identity with residues 1-92 of SEQ ID NO: 1;
(i) residues 17-92 of SEQ ID NO: 1; or
(j) 71 to 79 residues and shares at least 95% identity with residues 17-92 of SEQ ID NO: 1.

In a further aspect of the invention, there is provided a polynucleotide encoding a fusion protein comprising a polypeptide wherein the polypeptide consists of a fragment of invariant chain which is operably linked to an antigenic sequence and wherein the fragment of invariant chain consists of:
(a) a portion of residues 17-97 of SEQ ID NO: 1, wherein the portion comprises at least 5 contiguous residues from residues 77-92 of SEQ ID NO: 1;
(b) 80 residues or fewer and comprises a sequence of at least 5 contiguous residues wherein the sequence shares at least 80% identity with at least 5 contiguous residues from residues 77-92 of SEQ ID NO: 1;
(c) residues 1-97 of SEQ ID NO: 1;
(d) 91 to 103 residues and shares at least 95% identity with residues 1-97 of SEQ ID NO: 1;
(e) residues 17-97 of SEQ ID NO: 1;
(f) 76 to 84 residues and shares at least 95% identity with residues 17-97 of SEQ ID NO: 1;
(g) residues 1-92 of SEQ ID NO: 1;
(h) 88 to 96 residues and shares at least 95% identity with residues 1-92 of SEQ ID NO: 1;
(i) residues 17-92 of SEQ ID NO: 1; or
(j) 71 to 79 residues and shares at least 95% identity with residues 17-92 of SEQ ID NO: 1.

In a further aspect of the invention, there is provided a viral vector comprising a polynucleotide encoding a fusion protein comprising a polypeptide wherein the polypeptide consists of a fragment of invariant chain which is operably linked to an antigenic sequence and wherein the fragment of invariant chain consists of:
(a) a portion of residues 17-97 of SEQ ID NO: 1, wherein the portion comprises at least 5 contiguous residues from residues 77-92 of SEQ ID NO: 1;
(b) 80 residues or fewer and comprises a sequence of at least 5 contiguous residues wherein the sequence shares at least 80% identity with at least 5 contiguous residues from residues 77-92 of SEQ ID NO: 1;
(c) residues 1-97 of SEQ ID NO: 1;
(d) 91 to 103 residues and shares at least 95% identity with residues 1-97 of SEQ ID NO: 1;
(e) residues 17-97 of SEQ ID NO: 1;
(f) 76 to 84 residues and shares at least 95% identity with residues 17-97 of SEQ ID NO: 1;
(g) residues 1-92 of SEQ ID NO: 1;
(h) 88 to 96 residues and shares at least 95% identity with residues 1-92 of SEQ ID NO: 1;
(i) residues 17-92 of SEQ ID NO: 1; or
(j) 71 to 79 residues and shares at least 95% identity with residues 17-92 of SEQ ID NO: 1.

BRIEF DESCRIPTION OF THE FIGURES

FIG. 12A-12J Alignment of the polypeptide sequence of invariant chain derived from various organisms.

FIG. 13 Alignment of fragments of invariant chain derived from various organisms which correspond to residues 1-97 of human p35 invariant chain.

FIG. 14 Alignment of fragments of invariant chain derived from various organisms which correspond to residues 67-92 of human p35 invariant chain.

BRIEF DESCRIPTION OF SEQUENCE IDENTIFIERS

Figure 1:
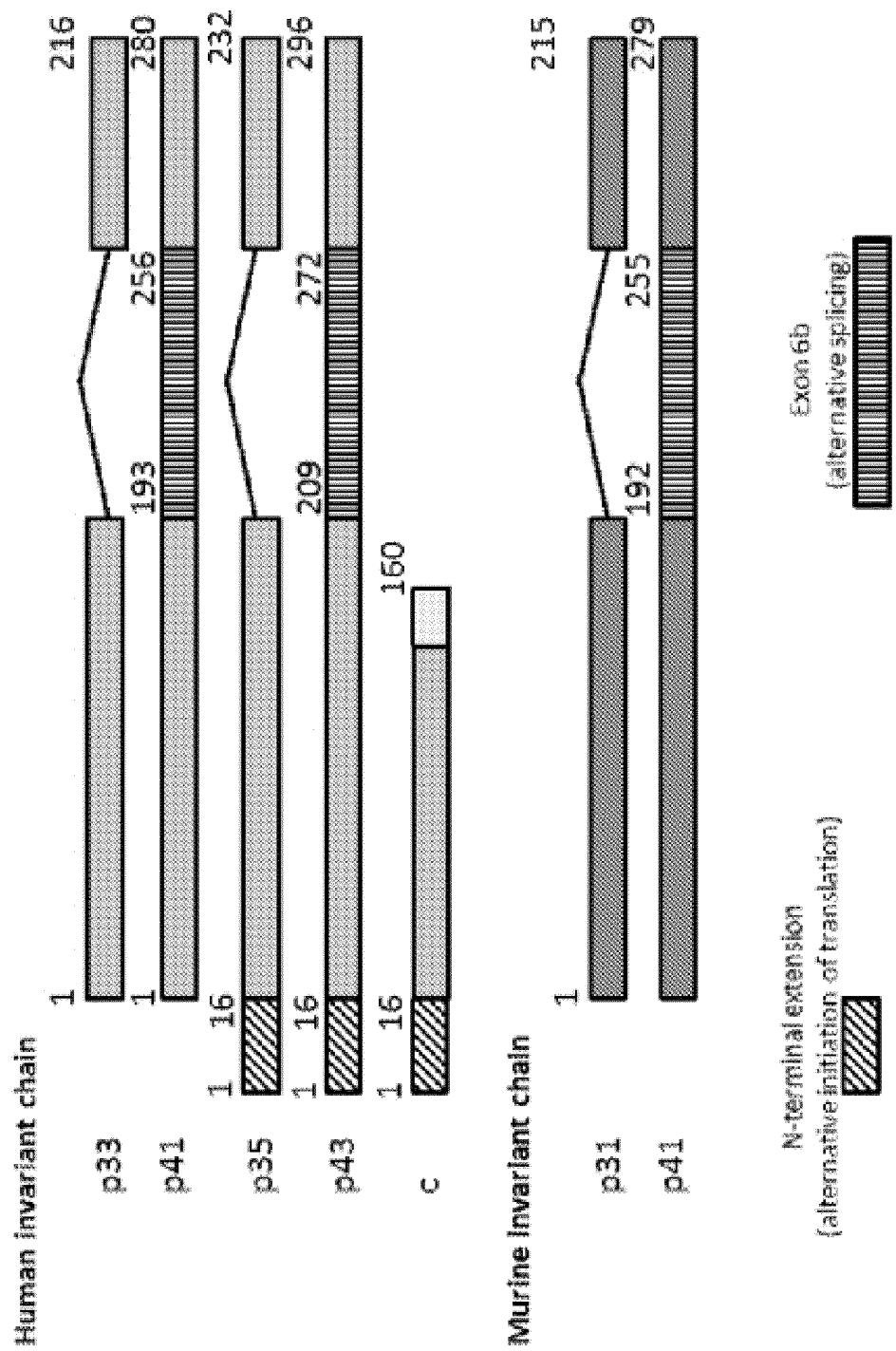
FIG. 1 Schematic diagram of murine li and human li isoforms.

SEQ ID No: 1 Amino acid sequence for human invariant chain isoform p35
SEQ ID No: 2 Nucleotide sequence encoding human invariant chain isoform p35
SEQ ID No: 3 Amino acid sequence for human invariant chain isoform p33
SEQ ID No: 4 Nucleotide sequence encoding the MAGE antigen
SEQ ID No: 5 Amino acid sequence for human invariant chain isoform p43
SEQ ID No: 6 Nucleotide sequence encoding human invariant chain isoform p43
SEQ ID No: 7 Amino acid sequence for human invariant chain isoform p41
SEQ ID No: 8 Nucleotide sequence encoding the OVA antigen
SEQ ID No: 9 Amino acid sequence for human invariant chain isoform c
SEQ ID No: 10 Nucleotide sequence encoding human invariant chain isoform c
SEQ ID No: 11 Amino acid sequence for murine invariant chain p31
SEQ ID No: 12 Nucleotide sequence encoding murine invariant chain p31
SEQ ID No: 13 Amino acid sequence for murine invariant chain p41
SEQ ID No: 14 Nucleotide sequence encoding murine invariant chain p41
SEQ ID No: 15 Amino acid sequence for *Cavia porcellus* invariant chain (UniProt accession number H0UZ94)
SEQ ID No: 16 Amino acid sequence for *Heterocephalus glaber* invariant chain (UniProt accession number G5C391)
SEQ ID No: 17 Amino acid sequence for *Fukomys damarensis* invariant chain (UniProt accession number A0A091E9W3)
SEQ ID No: 18 Amino acid sequence for *Rattus norvegicus* second isoform invariant chain (UniProt accession number P10247-2)
SEQ ID No: 19 Amino acid sequence for *Rattus norvegicus* first isoform invariant chain (UniProt accession number P10247)
SEQ ID No: 20 Amino acid sequence for *Myotis lucifugus* invariant chain (UniProt accession number G1QEN4)
SEQ ID No: 21 Amino acid sequence for *Myotis davidii* invariant chain (UniProt accession number L5LQM9)
SEQ ID No: 22 Amino acid sequence for *Myotis brandtii* invariant chain (UniProt accession number S7N2W2)
SEQ ID No: 23 Amino acid sequence for *Pteropus alecto* invariant chain (UniProt accession number L5L1G3)
SEQ ID No: 24 Amino acid sequence for *Pan troglodytes verus* invariant chain (UniProt accession number A5A6L4)
SEQ ID No: 25 Amino acid sequence for *Pongo abelii* invariant chain (UniProt accession number Q5RFJ4)
SEQ ID No: 26 Amino acid sequence for *Pan troglodytes* invariant chain (UniProt accession number H2QRT2)
SEQ ID No: 27 Amino acid sequence for *Gorilla gorilla gorilla* invariant chain (UniProt accession number G3R7S6)
SEQ ID No: 28 Amino acid sequence for *Nomascus leucogenys* invariant chain (UniProt accession number G1RHB8)
SEQ ID No: 29 Amino acid sequence for *Macaca mulatta* invariant chain (UniProt accession number I0FWR3)
SEQ ID No: 30 Amino acid sequence for *Macaca fascicularis* invariant chain (UniProt accession number G7P8P8)
SEQ ID No: 31 Amino acid sequence for *Macaca mulatta* invariant chain (UniProt accession number G7MVM5)
SEQ ID No: 32 Amino acid sequence for *Macaca mulatta* invariant chain (UniProt accession number I0FWR4)
SEQ ID No: 33 Amino acid sequence for *Macaca mulatta* invariant chain (UniProt accession number F7E9S4)
SEQ ID No: 34 Amino acid sequence for *Papio anubis* invariant chain (UniProt accession number A0A096MM48)
SEQ ID No: 35 Amino acid sequence for *Chlorocebus sabaeus* invariant chain (UniProt accession number A0A0D9RGK4)
SEQ ID No: 36 Amino acid sequence for *Callithrix jacchus* invariant chain (UniProt accession number F7ENM4)
SEQ ID No: 37 Amino acid sequence for *Felis catus* invariant chain (UniProt accession number M3VXS2)
SEQ ID No: 38 Amino acid sequence for *Mustela putorius* furo invariant chain (UniProt accession number M3YQS4)
SEQ ID No: 39 Amino acid sequence for *Loxodonta africana* invariant chain (UniProt accession number G3TJE1)
SEQ ID No: 40 Amino acid sequence for *Loxodonta africana* invariant chain (UniProt accession number G3U7Y6)

SEQ ID No: 41 Amino acid sequence for *Sus scrofa* invariant chain (UniProt accession number Q764N1)

SEQ ID No: 42 Amino acid sequence for *Camelus ferus* invariant chain (UniProt accession number S9XLT6)

SEQ ID No: 43 Amino acid sequence for *Bos mutus* invariant chain (UniProt accession number L8I7V9)

SEQ ID No: 44 Amino acid sequence for *Bos taurus* invariant chain (UniProt accession number Q7JFY1)

SEQ ID No: 45 Amino acid sequence for *Bos taurus* invariant chain (UniProt accession number Q29630)

SEQ ID No: 46 Amino acid sequence for *Equus caballus* invariant chain (UniProt accession number F6TGS3)

SEQ ID No: 47 Amino acid sequence for *Equus caballus* invariant chain (UniProt accession number Q9MXD5)

SEQ ID No: 48 Amino acid sequence for *Oryctolagus cuniculus* invariant chain (UniProt accession number G1SKK3)

SEQ ID No: 49 Amino acid sequence for *Otolemur gamettii* invariant chain (UniProt accession number H0WQB3)

SEQ ID No: 50 Amino acid sequence for *Tupaia chinensis* invariant chain (UniProt accession number L9KNO1)

SEQ ID No: 51 Amino acid sequence for *Ictidomys tridecemlineatus* invariant chain (UniProt accession number I3MCR9)

SEQ ID No: 52 Amino acid sequence for *Sarcophilus harrisii* invariant chain (UniProt accession number G3XOQ6)

SEQ ID No: 53 Amino acid sequence for residues 17-97 of human p35 invariant chain SEQ ID No: 54 Amino acid sequence for region of mouse p31 invariant chain corresponding to residues 17-97 of human p35 invariant chain SEQ ID No: 55 Amino acid sequence for region of *Loxodonta africana* invariant chain (UniProt accession number G3TJE1) corresponding to residues 17-97 of human p35 invariant chain SEQ ID No: 56 Amino acid sequence for region of *Felis catus* invariant chain (UniProt accession number M3VXS2) corresponding to residues 17-97 of human p35 invariant chain SEQ ID No: 57 Amino acid sequence for region of *Equus caballus* invariant chain (UniProt accession number F6TGS3) corresponding to residues 17-97 of human p35 invariant chain SEQ ID No: 58 Amino acid sequence for region of *Camelus ferus* invariant chain (UniProt accession number S9XLT6) corresponding to residues 17-97 of human p35 invariant chain SEQ ID No: 59 Amino acid sequence for region of *Sus scrofa* invariant chain (UniProt accession number Q764N1) corresponding to residues 17-97 of human p35 invariant chain SEQ ID No: 60 Amino acid sequence for region of *Mustela putorius furo* invariant chain (UniProt accession number M3YQS4) corresponding to residues 17-97 of human p35 invariant chain SEQ ID No: 61 Amino acid sequence for region of *Macaca mulatta* invariant chain (UniProt accession number I0FWR3) corresponding to residues 17-97 of human p35 invariant chain SEQ ID No: 62 Amino acid sequence for region of *Macaca fascicularis* invariant chain (UniProt accession number G7P8P8) corresponding to residues 17-97 of human p35 invariant chain SEQ ID No: 63 Amino acid sequence for region of *Chlorocebus sabaeus* invariant chain (UniProt accession number A0A0D9RGK4) corresponding to residues 17-97 of human p35 invariant chain SEQ ID No: 64 Amino acid sequence for region of *Papio anubis* invariant chain (UniProt accession number A0A096MM48) corresponding to residues 17-97 of human p35 invariant chain SEQ ID No: 65 Amino acid sequence for region of *Pan troglodytes verus* invariant chain (UniProt accession number A5A6L4) corresponding to residues 17-97 of human p35 invariant chain SEQ ID No: 66 Amino acid sequence for region of *Gorilla gorilla gorilla* invariant chain (UniProt accession number G3R7S6) corresponding to residues 17-97 of human p35 invariant chain SEQ ID No: 67 Amino acid sequence for region of *Nomascus leucogenys* invariant chain (UniProt accession number G1RHB8) corresponding to residues 17-97 of human p35 invariant chain SEQ ID No: 68 Amino acid sequence for region of *Pongo abelii* invariant chain (UniProt accession number Q5RFJ4) corresponding to residues 17-97 of human p35 invariant chain SEQ ID No: 69 Amino acid sequence for region of *Callithrix jacchus* invariant chain (UniProt accession number F7ENE8) corresponding to residues 17-97 of human p35 invariant chain SEQ ID No: 70 Amino acid sequence for region of *Myotis lucifugus* invariant chain (UniProt accession number G1QEN4) corresponding to residues 17-97 of human p35 invariant chain SEQ ID No: 71 Amino acid sequence for region of *Myotis davidii* invariant chain (UniProt accession number L5LQM9) corresponding to residues 17-97 of human p35 invariant chain SEQ ID No: 72 Amino acid sequence for region of *Bos mutus* invariant chain (UniProt accession number L8I7V9) corresponding to residues 17-97 of human p35 invariant chain SEQ ID No: 73 Amino acid sequence for region of *Bos taurus* invariant chain (UniProt accession number Q29630) corresponding to residues 17-97 of human p35 invariant chain SEQ ID No: 74 Amino acid sequence for region of *Myotis brandtii* invariant chain (UniProt accession number S7N2W2) corresponding to residues 17-97 of human p35 invariant chain SEQ ID No: 75 Amino acid sequence for region of *Heterocephalus glaber* invariant chain (UniProt accession number G5C391) corresponding to residues 17-97 of human p35 invariant chain SEQ ID No: 76 Amino acid sequence for region of *Fukomys damarensis* invariant chain (UniProt accession number A0A091E9W3) corresponding to residues 17-97 of human p35 invariant chain SEQ ID No: 77 Amino acid sequence for region of *Cavia porcellus* invariant chain (UniProt accession number H0UZ94) corresponding to residues 17-97 of human p35 invariant chain SEQ ID No: 78 Amino acid sequence for region of *Oryctolagus cuniculus* invariant chain (UniProt accession number G1SKK3) corresponding to residues 17-97 of human p35 invariant chain SEQ ID No: 79 Amino acid sequence for region of *Pteropus alecto* invariant chain (UniProt accession number L5L1G3) corresponding to residues 17-97 of human p35 invariant chain SEQ ID No: 80 Amino acid sequence for region of *Rattus norvegicus* second isoform invariant chain (UniProt accession number P10247-2) corresponding to residues 17-97 of human p35 invariant chain SEQ ID No: 81 Amino acid sequence for region of *Tupaia chinensis* invariant chain (UniProt accession number L9KNO1) corresponding to residues 17-97 of human p35 invariant chain SEQ ID No: 82 Amino acid sequence for region of *Ictidomys tridecemlineatus* invariant chain (UniProt accession number I3MCR9) corresponding to residues 17-97 of human p35 invariant chain SEQ ID No: 83 Amino acid sequence for region of *Otolemur gamettii* invariant chain (UniProt accession number H0WQB3) corresponding to residues 17-97 of human p35 invariant chain SEQ ID No: 84 Amino acid sequence for region of *Sarcophilus harrisii* invariant chain (UniProt accession number G3XOQ6) corresponding to residues 17-97 of human p35 invariant chain SEQ ID No: 85 Amino acid sequence for residues 67-92 of human p35 invariant chain SEQ ID No: 86 Amino acid sequence for region of mouse p31 invariant chain corresponding to residues 67-92 of human p35 invariant chain SEQ ID No: 87 Amino acid sequence for region of *Mustela putorius furo* invariant chain (UniProt accession number M3YQS4) corresponding to residues 67-92 of human p35 invariant chain SEQ ID No: 88 Amino acid sequence for region of *Myotis brandtii* invariant chain (UniProt accession number S7N2W2) corresponding to residues 67-92 of human p35 invariant chain SEQ ID No: 89 Amino acid sequence for region of *Pteropus alecto* invariant chain (UniProt accession number L5L1G3) corresponding to residues 67-92 of human p35 invariant chain SEQ ID No: 90 Amino acid sequence for region of *Fukomys damarensis* invariant chain (UniProt accession number A0A091E9W3) corresponding to residues 67-92 of human p35 invariant chain SEQ ID No: 91 Amino acid sequence for region of *Ictidomys tridecemlineatus* invariant chain (UniProt accession number I3MCR9) corresponding to residues 67-92 of human p35 invariant chain SEQ ID No: 92 Amino acid sequence for region of *Bos mutus* invariant chain (UniProt accession number L817V9) corresponding to residues 67-92 of human p35 invariant chain SEQ ID No: 93 Amino acid sequence for region of *Heterocephalus glaber* invariant chain (UniProt accession number G5C391) corresponding to residues 67-92 of human p35 invariant chain SEQ ID No: 94 Amino acid sequence for region of *Myotis davidii* invariant chain (UniProt accession number L5LQM9) corresponding to residues 67-92 of human p35 invariant chain SEQ ID No: 95 Amino acid sequence for region of *Tupaia chinensis* invariant chain (UniProt accession number L9KNO1) corresponding to residues 67-92 of human p35 invariant chain SEQ ID No: 96 Amino acid sequence for region of *Myotis lucifugus* invariant chain (UniProt accession number G1QEN4) corresponding to residues 67-92 of human p35 invariant chain SEQ ID No: 97 Amino acid sequence for region of *Rattus norvegicus* second isoform invariant chain (UniProt accession number P10247-2) corresponding to residues 67-92 of human p35 invariant chain SEQ ID No: 98 Amino acid sequence for region of *Bos taurus* invariant chain (UniProt accession number Q29630) corresponding to residues 67-92 of human p35 invariant chain SEQ ID No: 99 Amino acid sequence for region of *Otolemur gamettii* invariant chain (UniProt accession number H0WQB3) corresponding to residues 67-92 of human p35 invariant chain SEQ ID No: 100 Amino acid sequence for region of *Cavia porcellus* invariant chain (UniProt accession number H0UZ94) corresponding to residues 67-92 of human p35 invariant chain SEQ ID No: 101 Amino acid sequence for region of *Callithrix jacchus* invariant chain (UniProt accession number F7ENE8) corresponding to residues 67-92 of human p35 invariant chain SEQ ID No: 102 Amino acid sequence for region of *Nomascus leucogenys* invariant chain (UniProt accession number G1RHB8) corresponding to residues 67-92 of human p35 invariant chain SEQ ID No: 103 Amino acid sequence for region of *Gorilla gorilla gorilla* invariant chain (UniProt accession number G3R7S6) corresponding to residues 67-92 of human p35 invariant chain SEQ ID No: 104 Amino acid sequence for region of *Pongo abelii* invariant chain (UniProt accession number Q5RFJ4) corresponding to residues 67-92 of human p35 invariant chain SEQ ID No: 105 Amino acid sequence for region of *Pan troglodytes* verus invariant chain (UniProt accession number A5A6L4) corresponding to residues 67-92 of human p35 invariant chain SEQ ID No: 106 Amino acid sequence for region of *Macaca mulatta* invariant chain (UniProt accession number I0FWR3) corresponding to residues 67-92 of human p35 invariant chain SEQ ID No: 107 Amino acid sequence for region of *Macaca fascicularis* invariant chain (UniProt accession number G7P8P8) corresponding to residues 67-92 of human p35 invariant chain SEQ ID No: 108 Amino acid sequence for region of *Chlorocebus sabaeus* invariant chain (UniProt accession number A0A0D9RGK4) corresponding to residues 67-92 of human p35 invariant chain SEQ ID No: 109 Amino acid sequence for region of *Papio anubis* invariant chain (UniProt accession number A0A096MM48) corresponding to residues 67-92 of human p35 invariant chain SEQ ID No: 110 Amino acid sequence for region of *Loxodonta africana* invariant chain (UniProt accession number G3TJE1) corresponding to residues 67-92 of human p35 invariant chain SEQ ID No: 111 Amino acid sequence for region of *Felis catus* invariant chain (UniProt accession number M3VXS2) corresponding to residues 67-92 of human p35 invariant chain SEQ ID No: 112 Amino acid sequence for region of *Equus caballus* invariant chain (UniProt accession number F6TGS3) corresponding to residues 67-92 of human p35 invariant chain SEQ ID No: 113 Amino acid sequence for region of *Sus scrofa* invariant chain (UniProt accession number Q764N1) corresponding to residues 67-92 of human p35 invariant chain SEQ ID No: 114 Amino acid sequence for region of *Oryctolagus cuniculus* invariant chain (UniProt accession number G1SKK3) corresponding to residues 67-92 of human p35 invariant chain SEQ ID No: 115 Amino acid sequence for region of *Sarcophilus harrisii* invariant chain (UniProt accession number G3X0Q6) corresponding to residues 67-92 of human p35 invariant chain SEQ ID No: 116 Amino acid sequence for region of *Camelus ferus* invariant chain (UniProt accession number S9XLT6) corresponding to residues 67-92 of human p35 invariant chain SEQ ID No: 117 Nucleotide sequence encoding the HCV-NS antigen SEQ ID No: 118 OVA257-264 (SIINFEKL) peptide sequence SEQ ID No: 119 Amino acid sequence of the 'res' linker SEQ ID No: 120 Nucleotide sequence encoding the 'res' linker SEQ ID No: 121 Amino acid sequence of the HA tag SEQ ID No: 122 Nucleotide sequence encoding the HA tag SEQ ID No: 124 Human Ad5 penton protein sequence SEQ ID No: 125 Human Ad5 fiber protein sequence SEQ ID No: 126 Chimpanzee Adenovirus-ChAd 3 Hexon protein sequence SEQ ID No: 127 Chimpanzee Adenovirus-ChAd 3 Fiber protein sequence SEQ ID No: 128 Chimpanzee Adenovirus-ChAd 19 Hexon protein sequence SEQ ID No: 129 Chimpanzee Adenovirus-ChAd 19 Fiber protein sequence SEQ ID No: 130 Chimpanzee Adenovirus-ChAd 63 Hexon protein sequence SEQ ID No: 131 Chimpanzee Adenovirus-ChAd 63 Fiber protein sequence SEQ ID No: 132 Polypeptide sequence of ChAd155 hexon SEQ ID No: 133 Polypeptide sequence of ChAd155 penton SEQ ID No: 134 Polypeptide sequence of ChAd155 fiber SEQ ID No: 135 Polypeptide sequence of mli(full length) LLLmut SEQ ID No: 136 Polypeptide sequence of mli(full length) K63R SEQ ID No: 137 Polypeptide sequence of mli(1-75)K63R SEQ ID No: 138 Polypeptide sequence of mli(D+ER)

SEQ ID No: 139 Polypeptide sequence of mli(D-17) (i.e. N-terminal Met plus residues 18-215 of p31 mli)

SEQ ID No: 140 Polypeptide sequence of mli(50-215) (i.e. N-terminal Met plus residues 51-215 of p31 mli)

DETAILED DESCRIPTION OF THE INVENTION

As discussed above, the present inventors have surprisingly found that certain minor fragments of invariant chain are capable of enhancing the immunogenicity of an antigen. The invariant chain fragments disclosed herein are in particular devoid of the KEY, CLIP and trimerisation regions of invariant chain. Furthermore, in some embodiments, the invariant chain fragments disclosed herein are also devoid of the endolysosomal sorting sequence ("ESS").

The prior art discloses information on the immunogenicity-enhancing effect of full length invariant chain which includes the KEY, CLIP, trimerisation and ESS regions of invariant chain (see, for example, Holst et al. 2008). The prior art also discloses information on the immunogenicity-enhancing effect of the invariant chain KEY region itself (see, for example, (a) Holmes et al. 2008, which discloses a phase I trial of a fusion of the LRMK amino acids of the KEY region with the HER-2/neu peptide and (b) Kallinteris et al. 2006, which is directed at utilising specifically the KEY region for enhancement of vaccine potency). Regarding the trimerisation region, it is known that this region is important for its role as a MHC-II chaperone and MIF signaling receptor. Finally, regarding the ESS region, Walchli et al. 2014 disclose that invariant chain mediates its effect via co-localization in endosomal pathways. Invariant chain fragments lacking the ESS may therefore be expected to be unable to utilize this pathway, due to their inability to locate to endosomes.

Figure 7:
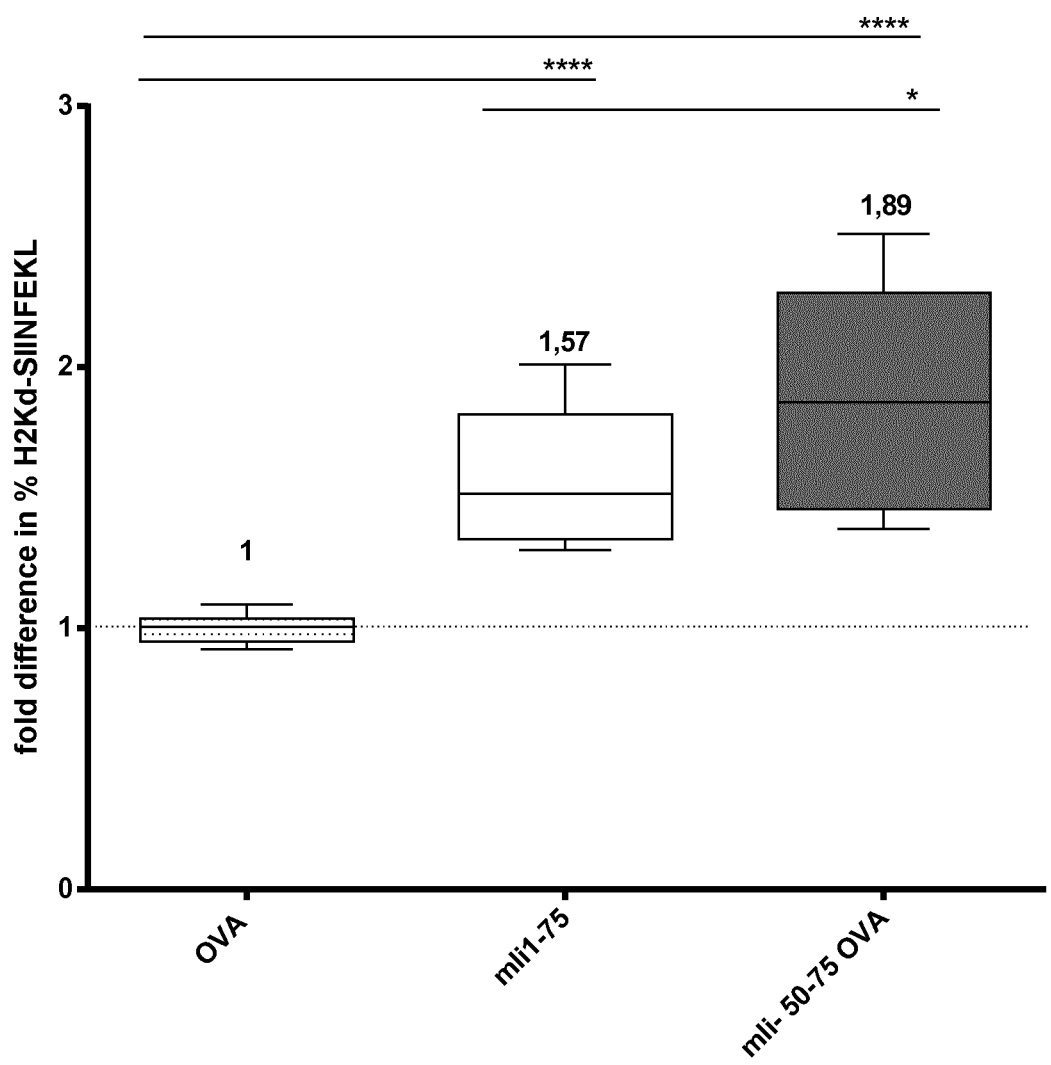
FIG. 7 Antigen presentation of ovalbumin peptide SIINFEKL in MHC class I 24 h after BMDC infection with Ad5 vectors encoding for mli short sequences 1-75 and 50-75 linked to OVA. Antigen presentation is expressed as the ratio of the % of $CD11^+/SIINFEKL^+$ cells after Ad5-mli and mli variants infection relative to Ad5-Ova control.

In WO2010057501 (referred to above) it is disclosed that adenovirus encoding a mouse invariant chain fragment of residues 51-118 fused to lymphocytic choriomeningitis virus glycoprotein (GP) antigen had a reduced immunogenicity relative to adenovirus encoding full length invariant chain fused to GP antigen (see WO2010057501, FIG. 7 and page 81, lines 33-34, where it is stated "thus when we tested a 51-118 variant (Ad-li51-118GP), a pronounced reduction in CD8$^+$ T cells stimulatory capacity was observed . . . ").

In light of the prior art therefore it is surprising that, as demonstrated in the examples provided herein, the mli1-80, mli1-75 and mli50-75 fragments, which are devoid of the KEY, CLIP and trimerisation regions (and in the case of mli50-75, the ESS) are nonetheless capable of increasing immunogenicity and/or antigen presentation to substantially the same level as full length mli or higher.

Furthermore, it is surprising that, as demonstrated in the examples provided herein, the mli55-75 and mli60-75 fragments, which are devoid of any known functional domains, are nonetheless capable of increasing immunogenicity and/or antigen presentation to substantially the same level as full length mli or higher.

In particular, it is surprising that residues 55-75 and 60-75 of mouse li, which are comprised within the 51-118 fragment disclosed in WO2010057501 above (and residues 50-75 of mouse li, which are comprised within the 51-118 fragment disclosed in WO2010057501 above but for one amino acid) provide substantially the same immunogenicity enhancing effect as that of full length invariant chain.

It may be expected that variants of the mli1-80, mli1-75 mli50-75, mli55-75 and mli60-75 fragments will share the same advantageous and surprising properties.

Unless defined otherwise, all technical and scientific terms used herein have the same meanings as commonly understood by one of ordinary skill in the art. For example, the terms used herein are defined as described in "A multilingual glossary of biotechnological terms: (IUPAC Recommendations)", Leuenberger, H. G. W, Nagel, B. and Klbl, 1995.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. Unless the context requires otherwise, the words "consists of" and variants such as "consisting of" will be understood to imply the inclusion of a stated integer or step or group of integers or steps and the exclusion of any further same or different integer or step or group of the same or different integers or steps, i.e. "consisting only of". Unless the context requires otherwise, the words "consists of at least" and variants such as "consisting of at least" will be understood to imply the inclusion of a stated integer or step or group of integers or steps as a minimum and also the inclusion of further instances of the same integer or step or group of integers or steps, but excluding any other different integer or step or group of different integers or steps.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention. All definitions provided herein in the context of one aspect of the invention also apply to the other aspects of the invention.

Proteins, Fusion Proteins and Polynucleotides

The terms "protein", "polypeptide" and "peptide" are used interchangeably herein and refer to any peptide-linked chain of amino acids, regardless of length, co-translational or post-translational modification. A fusion protein (or "chimeric protein") is a recombinant protein comprising two or more peptide-linked proteins. Fusion proteins are created through the joining of two or more genes that originally coded for the separate proteins. Translation of this fusion gene results in a single fusion protein.

The terms "polynucleotide" and "nucleic acid" are used interchangeably herein and refer to a polymeric macromolecule made from nucleotide monomers. Suitably the polynucleotides of the invention are recombinant. Recombinant means that the polynucleotide is the product of at least one of cloning, restriction or ligation steps, or other procedures that result in a polynucleotide that is distinct from a polynucleotide found in nature.

A heterologous sequence refers to any sequence that is not isolated from, derived from, or based upon a naturally occurring nucleic acid sequence found in the host organism. "Naturally occurring" means a sequence found in nature and not synthetically prepared or modified. A sequence is "derived" from a source when it is isolated from a source but modified (e.g., by deletion, substitution (mutation), insertion, or other modification), suitably so as not to disrupt the normal function of the source gene.

Suitably, the polynucleotides and polypeptides used in the present invention are isolated. An "isolated" polynucleotide (or polypeptide) is one that is removed from its original environment. For example, a naturally-occurring polynucleotide is isolated if it is separated from some or all of the coexisting materials in the natural system. A polynucleotide is considered to be isolated if, for example, it is cloned into a vector that is not a part of its natural environment or if it is comprised within cDNA.

Polypeptide and Polynucleotide Sequence Comparison

For the purposes of comparing two closely-related polypeptide or polynucleotide sequences, the "% sequence identity" between a first sequence and a second sequence may be calculated. Polypeptide or polynucleotide sequences are said to be the same as or identical to other polypeptide or polynucleotide sequences, if they share 100% sequence identity over their entire length. Residues in sequences are numbered from left to right, i.e. from N- to C-terminus for polypeptides; from 5' to 3' terminus for polynucleotides. The terms "identical" or percentage "identity", in the context of two or more polypeptide sequences, refer to two or more sequences or sub-sequences that are the same or have a specified percentage of amino acid residues that are the same (i.e., 70% identity, optionally 75%, 80%, 85%, 90%, 95%, 98% or 99% identity over a specified region), when compared and aligned for maximum correspondence over a comparison window, or designated region as measured using one of the following sequence comparison algorithms or by manual alignment and visual inspection. This definition also refers to the compliment of a test sequence. Optionally, the identity exists over a region that is at least 250 amino acids in length, such as 300 amino acids or 350 amino acids. Suitably, the comparison is performed over a window corresponding to the entire length of the reference sequence (as opposed to the derivative sequence).

For sequence comparison, one sequence acts as the reference sequence, to which the test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percentage sequence identities for the test sequences relative to the reference sequence, based on the program parameters.

A "comparison window", as used herein, refers to a segment in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman 1981, by the homology alignment algorithm of Needleman & Wunsch 1970, by the search for similarity method of Pearson & Lipman 1988, by computerised implementations of these algorithms (GAP, BEST-FIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al. 1995).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle 1987. The method used is similar to the method described by Higgins & Sharp 1989. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al. 1984).

Another example of algorithm that is suitable for determining percent sequence identity and sequence similarity are the BLAST and BLAST 2.0 algorithms, which are described in Altschul et al. 1977 and Altschul et al. 1990, respectively. Software for performing BLAST analyses is publicly available through the National Center for Biotechnology Information (website at www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighbourhood word score threshold (Altschul et al., supra). These initial neighbourhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff 1989) alignments (B) of 50, expectation (E) of 10, M=5, N=−4, and a comparison of both strands.

The BLAST algorithm also performs a statistical analysis of the similarity between two sequences (see, e.g., Karlin & Altschul 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

A "difference" between sequences refers to an insertion, deletion or substitution of a single residue in a position of the second sequence, compared to the first sequence. Two sequences can contain one, two or more such differences. Insertions, deletions or substitutions in a second sequence which is otherwise identical (100% sequence identity) to a first sequence result in reduced % sequence identity. For example, if the identical sequences are 9 residues long, one substitution in the second sequence results in a sequence identity of 88.9%. If the identical sequences are 17 amino acid residues long, two substitutions in the second sequence results in a sequence identity of 88.2%.

Alternatively, for the purposes of comparing a first, reference sequence to a second, comparison sequence, the number of additions, substitutions and/or deletions made to the first sequence to produce the second sequence may be ascertained. An addition is the addition of one residue into the first sequence (including addition at either terminus of the first sequence). A substitution is the substitution of one residue in the first sequence with one different residue. A deletion is the deletion of one residue from the first sequence (including deletion at either terminus of the first sequence).

Suitably, a substitution may be conservative. A 'conservative' substitution is an amino acid substitution in which an amino acid residue is replaced with another amino acid residue of similar chemical structure and which is expected to have little influence on the function, activity or other biological properties of the polypeptide. Such conservative substitutions suitably are substitutions in which one amino acid within the following groups is substituted by another amino acid residue from within the same group:

| Group | Amino acid residue |
| --- | --- |
| Non-polar aliphatic | Glycine |
| | Alanine |
| | Valine |
| | Leucine |
| | Isoleucine |
| Aromatic | Phenylalanine |
| | Tyrosine |
| | Tryptophan |
| Polar uncharged | Serine |
| | Methionine |
| | Cysteine |
| | Threonine |
| | Asparagine |
| | Glutamine |
| Negatively charged | Aspartate |
| | Glutamate |
| Positively charged | Lysine |
| | Arginine |
| | Histidine |

Invariant Chain and Fragments of Invariant Chain

The term "invariant chain", also known as "Ii" or "CD74" refers to a non-polymorphic type II integral membrane protein. The protein has multiple functions in lymphocyte maturation and adaptive immune responses; in particular Ii ensures the targeting of newly synthesized MHC II to the endocytic pathway, where the complex can meet antigenic peptides. (Pieters J. 1997). Additionally, Ii has been shown to function as an MHC class I chaperone (Morris et al. 2004) and, by its endosomal targeting sequence, to facilitate stimulation of $CD4^+$, but not $CD8^+$ T-cells directed against covalently linked antigen (Diebold et al. 2001).

For human invariant chain four different isoforms are known, generally termed p33, p35, p41 and p43 (Strubin et al. 1986). SEQ ID NO: 1 and SEQ ID NO: 2 correspond to the amino acid sequence and the nucleic acid sequence of human invariant chain p35 isoform, respectively. SEQ ID NO: 3 corresponds to the amino acid sequence of human invariant chain p33 isoform. SEQ ID NO: 5 and SEQ ID NO: 6 correspond to the amino acid sequence and the nucleic acid sequence of human invariant chain p43 isoform, respectively. SEQ ID NO: 7 corresponds to the amino acid sequence of human invariant chain p41 isoform. With respect to human p33 and p41 the human p35 and p43 isoforms contain an additional 16 residues at the N-terminus due to alternative initiation of translation. Compared to human p33 and p35 the human p41 and p43 isoforms comprise an additional domain (alternative splicing of exon 6b) inserted in frame in the C-terminal region of the invariant chain. The sequence of an additional human isoform c lacking two exons relative to human p33 and p35 is available in Genbank (Accession BCO24272). SEQ ID NO: 9 and SEQ ID NO: 10 correspond to the amino acid sequence and the nucleic acid sequence of human invariant chain c isoform, respectively. Suitably the fragment of invariant chain is derived from human p33, p35, p41, p43 or c isoforms of invariant chain.

TABLE 1

Variants of human invariant chain

| Isoform | 16 AA at N-terminus | Additional domain | Polypeptide SEQ ID NO | Polynucleotide SEQ ID NO |
|---------|---------------------|-------------------|----------------------|--------------------------|
| p35 | + | − | 1 | 2 |
| p33 | − | − | 3 | − |
| p43 | + | + | 5 | 6 |
| p41 | − | + | 7 | − |
| c | + | − | 9 | 10 |

A schematic overview of the different isoforms is shown in FIG. 1.

The invariant chain comprises several domains: a cytosolic domain which includes a sorting (targeting) peptide (also known as the "lysosomal targeting sequence", or "endolysosomal sorting sequence" ("ESS")) (positions 17 to 46 in human invariant chain SEQ ID NO: 1, positions 1 to 29 in the murine invariant chain SEQ ID NO: 11) preceded by an endoplasmic reticulum retention signal ("ERR" or "ER") in the human invariant chain p35 and p43 variants (positions 1 to 16 in human invariant chain SEQ ID NO: 1), a transmembrane domain ("TM", positions 47 to 72 in human invariant chain SEQ ID NO: 1, positions 30 to 55 in the murine invariant chain SEQ ID NO: 11), and a luminal domain which in itself comprises a KEY region (positions 93 to 96 in human invariant chain SEQ ID NO: 1, positions 76 to 79 in the murine invariant chain SEQ ID NO: 11), an adjacent CLIP region (positions 97 to 120 in human invariant chain SEQ ID NO 1, positions 80 to 103 in the murine invariant chain SEQ ID NO: 11). The CLIP region comprises a core CLIP peptide (positions 103 to 117 in human invariant chain SEQ ID NO: 1, positions 86 to 100 in the murine invariant chain SEQ ID NO: 11) and a trimerization domain (positions 134 to 208 in human invariant chain SEQ ID NO: 1, positions 117 to 191 in the murine invariant chain SEQ ID NO: 11; Mittendorf et al. 2009; Strumptner-Cuvelette and Benaroch 2002. The remainder of the luminal domain comprises two highly flexible regions situated between the transmembrane and KEY region (positions 73 to 92 in human invariant chain SEQ ID NO: 1, positions 56 to 75 in the murine invariant chain SEQ ID NO: 11) or downstream the trimerization domain (positions 209 to 232 in human invariant chain SEQ ID NO: 1, positions 192 to 215 in the murine invariant chain SEQ ID NO: 11).

Suitably the fusion protein does not comprise a full length invariant chain.

Figure 12A:
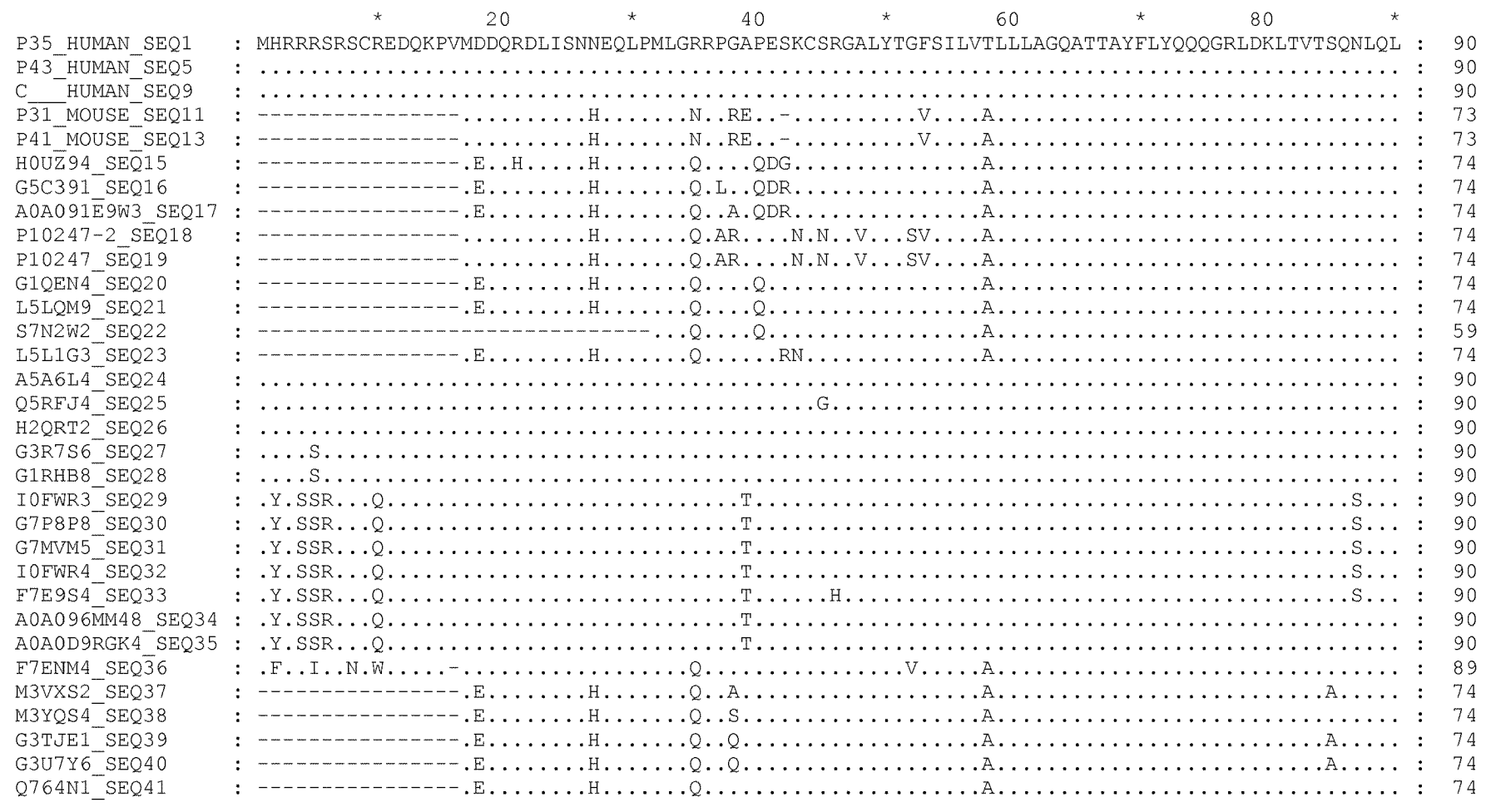
Figure 12C:
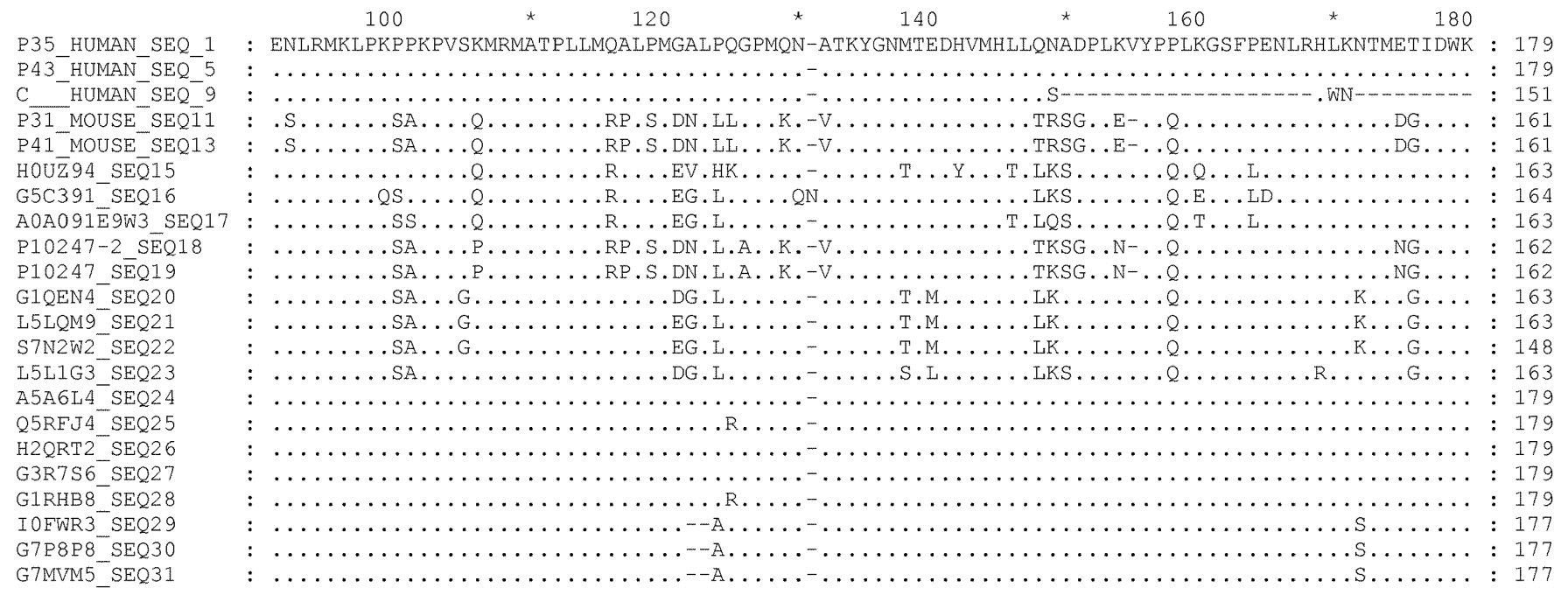
Figure 12D:
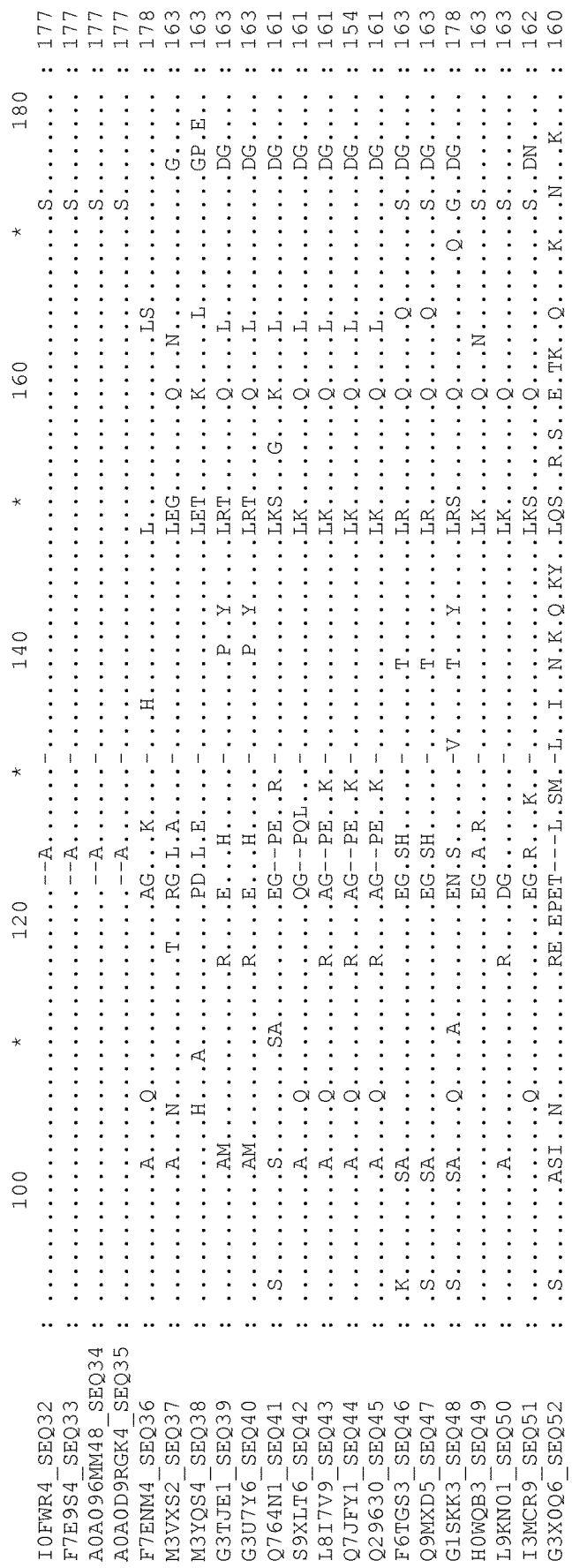

Invariant chain has been characterized in several organisms such as chicken, cow, dog, mouse, rat and human. The polypeptide sequence of invariant chain derived from various organisms is provided in FIG. 12, aligned relative to human p35 invariant chain (SEQ ID NO: 1). This figure also includes the human p43 and c isotypes and murine p31 and p41 isotypes. Each invariant chain sequence is labelled with its corresponding UniProt accession number and SEQ ID NO. The sequence identifier numbers of these invariant chain sequences are SEQ ID NOs: 1, 5, 9, 11, 13 and 15-52. Examples of fragments of invariant chain derived from various organisms which correspond to residues 17-97 of human p35 invariant chain are shown in FIG. 13, wherein the sequences are aligned relative to residues 17-97 of human p35 invariant chain (SEQ ID NO: 1). The sequence identifier numbers of these invariant chain fragment sequences are SEQ ID NOs: 53-84. Examples of portions of invariant chain derived from various organisms which correspond to residues 67-92 of human p35 invariant chain are shown in FIG. 14, wherein the sequences are aligned relative to residues 67-92 of human p35 invariant chain. The sequence identifier numbers of these invariant chain fragment sequences are SEQ ID NOs: 85-116.

Portions of Fragments of Invariant Chain Comprising Contiguous Residues from Residues 77-92 of SEQ ID NO: 1

In one embodiment, the fragment of invariant chain consists of a portion of residues 17-97 of SEQ ID NO: 1, wherein the portion comprises at least 5, more suitably at least 6, more suitably at least 7, more suitably at least 8, more suitably at least 9, more suitably at least 10, more suitably at least 11, more suitably at least 12, more suitably at least 13, more suitably at least 14, more suitably at least 15 contiguous residues from residues 77-92 of SEQ ID NO: 1. In a further embodiment, the portion comprises or more suitably consists of residues 77-92 of SEQ ID NO: 1.

In a further embodiment, the fragment of invariant chain consists of 80 residues or fewer and comprises a sequence of at least 5 contiguous residues wherein the sequence shares at least 80%, more suitably at least 90% identity with at least 5, more suitably at least 6, more suitably at least 7, more suitably at least 8, more suitably at least 9, more suitably at least 10, more suitably at least 11, more suitably at least 12, more suitably at least 13, more suitably at least 14, more suitably at least 15 contiguous residues from residues 77-92 of SEQ ID NO: 1. More suitably the fragment of invariant chain consists of 80 residues or fewer and comprises a sequence of at least 5, more suitably at least 6, more suitably at least 7, more suitably at least 8, more suitably at least 9, more suitably at least 10, more suitably at least 11, more suitably at least 12, more suitably at least 13, more suitably at least 14, more suitably at least 15 contiguous residues from residues 77-92 of SEQ ID NO: 1.

Alternatively, the fragment of invariant chain consists of 80 residues or fewer and comprises a sequence of at least 5 contiguous residues wherein the sequence comprises no more than 4, more suitably no more than 3, more suitably no more than 2, more suitably no more than 1 substitution, deletion or addition with respect to at least 5, more suitably at least 6, more suitably at least 7, more suitably at least 8, more suitably at least 9, more suitably at least 10, more suitably at least 11, more suitably at least 12, more suitably at least 13, more suitably at least 14, more suitably at least 15 contiguous residues from residues 77-92 of SEQ ID NO: 1.

Suitably the fragment of invariant chain comprises or consists of residues 77-81, 78-82, 79-83, 80-84, 81-85, 82-86, 83-87, 84-88, 85-89, 86-90 or 87-91 of SEQ ID NO: 1.

Suitably the fragment of invariant chain comprises or consists of residues 77-84, 78-85. 79-86, 80-87, 81-88, 82-89 or 83-90 of SEQ ID NO: 1.

Portions of Fragments of Invariant Chain Comprising Contiguous Residues from Residues 72-92 of SEQ ID NO: 1

In one embodiment, the fragment of invariant chain consists of a portion of residues 17-97 of SEQ ID NO: 1, wherein the portion comprises at least 5, more suitably at least 6, more suitably at least 7, more suitably at least 8, more suitably at least 9, more suitably at least 10, more suitably at least 11, more suitably at least 12, more suitably at least 13, more suitably at least 14, more suitably at least 15, more suitably at least 16, more suitably at least 17, more suitably at least 18, more suitably at least 19, more suitably at least 20 contiguous residues from residues 72-92 of SEQ ID NO: 1. In a further embodiment, the portion comprises or more suitably consists of residues 72-92 of SEQ ID NO: 1.

In a further embodiment, the fragment of invariant chain consists of 80 residues or fewer and comprises a sequence of at least 5 contiguous residues wherein the sequence shares at least 80%, more suitably at least 90% identity with at least 5, more suitably at least 6, more suitably at least 7, more suitably at least 8, more suitably at least 9, more suitably at least 10, more suitably at least 11, more suitably at least 12, more suitably at least 13, more suitably at least 14, more suitably at least 15, more suitably at least 16, more suitably at least 17, more suitably at least 18, more suitably at least 19, more suitably at least 20 contiguous residues from residues 72-92 of SEQ ID NO: 1.

More suitably the fragment of invariant chain consists of 80 residues or fewer and comprises a sequence of at least 5, more suitably at least 6, more suitably at least 7, more suitably at least 8, more suitably at least 9, more suitably at least 10, more suitably at least 11, more suitably at least 12, more suitably at least 13, more suitably at least 14, more suitably at least 15, more suitably at least 16, more suitably at least 17, more suitably at least 18, more suitably at least 19, more suitably at least 20 contiguous residues from residues 72-92 of SEQ ID NO: 1.

Alternatively, the fragment of invariant chain consists of 80 residues or fewer and comprises a sequence of at least 5 contiguous residues wherein the sequence comprises no more than 7, more suitably no more than 6, more suitably no more than 5, more suitably no more than 4, more suitably no more than 3, more suitably no more than 2, more suitably no more than 1 substitution, deletion or addition with respect to at least 5, more suitably at least 6, more suitably at least 7, more suitably at least 8, more suitably at least 9, more suitably at least 10, more suitably at least 11, more suitably at least 12, more suitably at least 13, more suitably at least 14, more suitably at least 15, more suitably at least 16, more suitably at least 17, more suitably at least 18, more suitably at least 19, more suitably at least 20 contiguous residues from residues 72-92 of SEQ ID NO: 1.

Portions of Fragments of Invariant Chain Comprising Contiguous Residues from Residues 67-92 of SEQ ID NO: 1

In one embodiment, the fragment of invariant chain consists of a portion of residues 17-97 of SEQ ID NO: 1, wherein the portion comprises at least 10, more suitably at least 15, more suitably at least 20 contiguous residues from residues 67-92 of SEQ ID NO: 1. In a further embodiment, the portion comprises or more suitably consists of residues 67-92 of SEQ ID NO: 1.

In a further embodiment, the fragment of invariant chain consists of 80 residues or fewer and comprises a sequence of at least 10 contiguous residues wherein the sequence shares at least 80%, more suitably at least 90% identity with at least 10 contiguous residues from residues 67-92 of SEQ ID NO: 1. More suitably the fragment of invariant chain consists of 80 residues or fewer and comprises a sequence of at least 10 contiguous residues wherein the sequence comprises at least 10 contiguous residues from residues 67-92 of SEQ ID NO: 1. Suitably the fragment of invariant chain comprises or consists of residues 67-76, 68-77, 69-78, 70-79, 71-80, 72-81, 73-82, 74-83, 75-84, 76-85, 77-86, 78-87, 79-88, 80-89, 81-90, 82-91 or 83-92 of SEQ ID NO: 1.

Suitably the fragment of invariant chain comprises at least 15 contiguous residues wherein the at least 15 contiguous residues share at least 80%, more suitably at least 90% identity with at least 15 contiguous residues from residues 67-92 of SEQ ID NO: 1. More suitably the fragment of invariant chain comprises at least 15 contiguous residues wherein the at least 15 contiguous residues comprise at least 15 contiguous residues from residues 67-92 of SEQ ID NO: 1. Suitably the fragment of invariant chain comprises or consists of residues 67-81, 68-82, 69-83, 70-84, 71-85, 72-86, 73-87, 74-88, 75-89, 76-90, 77-91 or 78-92 of SEQ ID NO: 1.

Suitably the fragment of invariant chain comprises at least 20 contiguous residues wherein the at least 20 contiguous residues share at least 80%, more suitably at least 90% identity with at least 20 contiguous residues from residues 67-92 of SEQ ID NO: 1. Suitably the fragment of invariant chain comprises at least 20 contiguous residues wherein the at least 20 contiguous residues comprise at least 20 contiguous residues from residues 67-92 of SEQ ID NO: 1. Suitably the fragment of invariant chain comprises or consists of residues 67-86, 68-87, 69-88, 70-89, 71-90, 72-91 or 73-92 of SEQ ID NO: 1.

Suitably the fragment of invariant chain comprises at least 25 contiguous residues wherein the at least 25 contiguous residues share at least 80%, more suitably at least 90% identity with at least 25 contiguous residues from residues 67-92 of SEQ ID NO: 1. Suitably the fragment of invariant chain comprises at least 25 contiguous residues wherein the at least 25 contiguous residues comprise at least 25 contiguous residues from residues 67-92 of SEQ ID NO: 1. Suitably the fragment of invariant chain comprises or consists of residues 67-91 or 68-92 of SEQ ID NO: 1.

Suitably the fragment of invariant chain comprises or more suitably consists of residues 70-92, 72-92, 73-92, 77-92, 79-92 or 85-92 of SEQ ID NO: 1. Alternatively, the fragment of invariant chain comprises or more suitably consists of residues 67-90, 67-87 or 67-82 of SEQ ID NO: 1. More suitably the fragment of invariant chain comprises or more suitably consists of residues 72-92 or 77-92 of SEQ ID NO: 1.

Suitably the fragment of invariant chain comprises or more suitably consists of a sequence selected from SEQ ID NOs: 85-116.

Suitably the fusion protein does not comprise a fragment of invariant chain operably linked to an antigenic sequence wherein the fragment of invariant chain comprises a greater number of contiguous residues of SEQ ID NO: 1 than residues 67-92 of SEQ ID NO: 1.

Fragments of Invariant Chain Consisting of Residues 1-97 of Human p35 Invariant Chain and Related Sequences In one embodiment, the fragment of invariant chain consists of residues 1-97 of SEQ ID NO: 1. In a further embodiment, the fragment of invariant chain consists of 91 to 103, more suitably 93 to 101, more suitably 95 to 99, more suitably 97 residues, and/or shares at least 95%, more suitably 97% identity with residues 1-97 of SEQ ID NO: 1. Suitably the fragment of invariant chain consists of residues 1-97 of SEQ ID NO: 1 or the residues of SEQ ID NOs: 5, 9, 11, 13 and 15-52 which correspond to residues 1-97 of SEQ ID NO: 1. More suitably the fragment of invariant chain consists of residues 1-97 of SEQ ID NO: 1.

Suitably the fusion protein does not comprise a fragment of invariant chain operably linked to an antigenic sequence wherein the fragment of invariant chain comprises a greater number of contiguous residues of SEQ ID NO: 1 than residues 1-97 of SEQ ID NO: 1.

Fragments of Invariant Chain Consisting of Residues 17-97 of Human p35 Invariant Chain and Related Sequences In one embodiment, the fragment of invariant chain consists of residues 17-97 of SEQ ID NO: 1. In a further embodiment, the fragment of invariant chain consists of 76 to 84, more suitably 78 to 82, more suitably 80 to 82, more suitably 81 residues, and/or shares at least 95%, more suitably 97% identity with residues 17-97 of SEQ ID NO: 1. Suitably the fragment of invariant chain consists of any one of more of SEQ ID NOs: 53-84. More suitably the fragment of invariant chain consists of SEQ ID NO: 53.

Suitably the fusion protein does not comprise a fragment of invariant chain operably linked to an antigenic sequence wherein the fragment of invariant chain comprises a greater number of contiguous residues of SEQ ID NO: 1 than residues 17-97 of SEQ ID NO: 1.

Fragments of Invariant Chain Consisting of Residues 1-92 of Human p35 Invariant Chain and Related Sequences In one embodiment, the fragment of invariant chain consists of residues 1-92 of SEQ ID NO: 1. In a further embodiment, the fragment of invariant chain consists of 88 to 96, more suitably 90 to 95, more suitably 91 to 93, more suitably 92 residues, and/or shares at least 95%, more suitably 97% identity with residues 1-92 of SEQ ID NO: 1. Suitably the fragment of invariant chain consists of residues 1-92 of SEQ ID NO: 1 or the residues of SEQ ID NOs: 5, 9, 11, 13 and 15-52 which correspond to residues 1-92 of SEQ ID NO: 1. More suitably the fragment of invariant chain consists of residues 1-92 of SEQ ID NO: 1.

Suitably the fusion protein does not comprise a fragment of invariant chain operably linked to an antigenic sequence wherein the fragment of invariant chain comprises a greater number of contiguous residues of SEQ ID NO: 1 than residues 1-92 of SEQ ID NO: 1.

Fragments of Invariant Chain Consisting of Residues 17-92 of Human p35 Invariant Chain and Related Sequences In one embodiment, the fragment of invariant chain consists of residues 17-92 of SEQ ID NO: 1. In a further embodiment, the fragment of invariant chain consists of 71 to 79, more suitably 74 to 78, more suitably 75 to 77, more suitably 76 residues, and/or shares at least 95%, more suitably 97% identity with residues 17-92 of SEQ ID NO: 1 or the residues of SEQ ID NOs: 5, 9, 11, 13 and 15-52 which correspond to residues 17-92 of SEQ ID NO: 1. More suitably the fragment of invariant chain consists of residues 17-92 of SEQ ID NO: 1.

Suitably the fusion protein does not comprise a fragment of invariant chain operably linked to an antigenic sequence wherein the fragment of invariant chain comprises a greater number of contiguous residues of SEQ ID NO: 1 than residues 17-92 of SEQ ID NO: 1.

Fragment Size, Fragment Location and Numbers of Fragments

Suitably the fragment of invariant chain consists of fewer than 30, more suitably fewer than 25, more suitably fewer than 20, more suitably fewer than 15, more suitably fewer than 10, more suitably fewer than 7 residues. Suitably the fragment of invariant chain consists of at least 25, more suitably at least 35, more suitably at least 45, more suitably at least 55 residues, more suitably at least 75 residues.

Suitably the fragment of invariant chain is linked to the antigenic sequence by the N-terminus or C-terminus of the fragment of invariant chain. Most suitably the fragment of invariant chain is linked to the antigenic sequence by the C-terminus of the fragment of invariant chain.

Suitably the fragment of invariant chain is at the N-terminus or C-terminus of the fusion protein. Most suitably the fragment of invariant chain is at the N-terminus of the fusion protein.

Suitably the fusion protein comprises multiple fragments of invariant chain. For example, two, three, four or more fragments of invariant chain. Suitably the fragment of invariant chain is internally encoded within the antigen.

The fusion protein according to the invention comprises a polypeptide wherein the polypeptide consists of a fragment of invariant chain which is operably linked to an antigenic sequence, wherein the fragment of invariant chain consists of certain defined sequences. By 'consists of', it is meant that although further residues may be present at either terminus of the invariant chain fragment, the additional further residues at either terminus of the invariant chain do not result in the fragment of invariant chain becoming a larger fragment of invariant chain than that which is defined (and do not result in the fragment of invariant chain becoming a full length invariant chain).

Suitably the fusion protein according to the invention is not a fusion protein disclosed in WO2010057501 (which is herein incorporated by reference, specifically for the purpose of disclaiming the fusions disclosed therein).

Invariant Chain Derived from Different Species

Suitably the fragment of invariant chain refers to a truncated version of an invariant chain derived from an animal, such as a vertebrate, such as a fish, bird or mammal. More suitably the fragment of invariant chain refers to a truncated version of an invariant chain derived from a mammal. More suitably the fragment of invariant chain refers to a truncated version of an invariant chain derived from a mammal selected from the list consisting of a chicken, cow, dog, mouse, rat, non-human primate or human. More suitably the fragment of invariant chain refers to a truncated version of an invariant chain derived from a human or mouse. More suitably the fragment of invariant chain refers to a truncated version of an invariant chain derived from a human.

Different invariant chain sequences from various species are provided in SEQ ID NOs: 1, 5, 9, 11, 13 and 15-52.

Invariant Chain Derived from Different Species: Murine Invariant Chain

For murine invariant chain only two isoforms (p31 and p41) are known corresponding to the human invariant chain isoforms p33 and p41, respectively. SEQ ID NO: 11 and SEQ ID NO: 12 correspond to the amino acid sequence and the nucleic acid sequence of murine invariant chain p31 isoform, respectively. SEQ ID NO: 13 and SEQ ID NO: 14 correspond to the amino acid sequence and the nucleic acid sequence of murine invariant chain p41 isoform, respectively. Suitably the fragment of invariant chain is derived from mouse p31 or p41 isoforms of invariant chain.

The present invention can be implemented using a fragment of murine invariant chain. Accordingly, the following aspects are provided.

A fusion protein comprising a polypeptide wherein the polypeptide consists of a fragment of invariant chain which is operably linked to an antigenic sequence and wherein the fragment of invariant chain consists of:
(a) a portion of residues 1-80 of SEQ ID NO: 11, wherein the portion comprises at least 5 contiguous residues from residues 60-75 of SEQ ID NO: 1;
(b) 80 residues or fewer and comprises a sequence of at least 5 contiguous residues wherein the sequence shares at least 80% identity with at least 5 contiguous residues from residues 60-75 of SEQ ID NO: 11;
(c) residues 1-80 of SEQ ID NO: 11;
(d) 91 to 103 residues and shares at least 95% identity with residues 1-80 of SEQ ID NO: 11; or
(e) residues 1-75 of SEQ ID NO: 11;

(f) 88 to 96 residues and shares at least 95% identity with residues 1-75 of SEQ ID NO: 11.

A polynucleotide encoding a fusion protein comprising a polypeptide wherein the polypeptide consists of a fragment of invariant chain which is operably linked to an antigenic sequence and wherein the fragment of invariant chain consists of:
(a) a portion of residues 1-80 of SEQ ID NO: 11, wherein the portion comprises at least 5 contiguous residues from residues 60-75 of SEQ ID NO: 1;
(b) 80 residues or fewer and comprises a sequence of at least 5 contiguous residues wherein the sequence shares at least 80% identity with at least 5 contiguous residues from residues 60-75 of SEQ ID NO: 11;
(c) residues 1-80 of SEQ ID NO: 11;
(d) 91 to 103 residues and shares at least 95% identity with residues 1-80 of SEQ ID NO: 11; or
(e) residues 1-75 of SEQ ID NO: 11;
(f) 88 to 96 residues and shares at least 95% identity with residues 1-75 of SEQ ID NO: 11.

A viral vector comprising a polynucleotide encoding a fusion protein comprising a polypeptide wherein the polypeptide consists of a fragment of invariant chain which is operably linked to an antigenic sequence and wherein the fragment of invariant chain consists of:
(a) a portion of residues 1-80 of SEQ ID NO: 11, wherein the portion comprises at least 5 contiguous residues from residues 60-75 of SEQ ID NO: 1;
(b) 80 residues or fewer and comprises a sequence of at least 5 contiguous residues wherein the sequence shares at least 80% identity with at least 5 contiguous residues from residues 60-75 of SEQ ID NO: 11;
(c) residues 1-80 of SEQ ID NO: 11;
(d) 91 to 103 residues and shares at least 95% identity with residues 1-80 of SEQ ID NO: 11; or
(e) residues 1-75 of SEQ ID NO: 11;
(f) 88 to 96 residues and shares at least 95% identity with residues 1-75 of SEQ ID NO: 11.

A fusion protein comprising a polypeptide wherein the polypeptide consists of a fragment of invariant chain which is operably linked to an antigenic sequence and wherein the fragment of invariant chain consists of:
(a) a portion of residues 1-80 of SEQ ID NO: 11, wherein the portion comprises at least 10 contiguous residues from residues 50-75 of SEQ ID NO: 1;
(b) 80 residues or fewer and comprises a sequence of at least 10 contiguous residues wherein the sequence shares at least 80% identity with at least 10 contiguous residues from residues 50-75 of SEQ ID NO: 11;
(c) residues 1-80 of SEQ ID NO: 11;
(d) 91 to 103 residues and shares at least 95% identity with residues 1-80 of SEQ ID NO: 11; or
(e) residues 1-75 of SEQ ID NO: 11;
(f) 88 to 96 residues and shares at least 95% identity with residues 1-75 of SEQ ID NO: 11.

A polynucleotide encoding a fusion protein comprising a polypeptide wherein the polypeptide consists of a fragment of invariant chain which is operably linked to an antigenic sequence and wherein the fragment of invariant chain consists of:
(a) a portion of residues 1-80 of SEQ ID NO: 11, wherein the portion comprises at least 10 contiguous residues from residues 50-75 of SEQ ID NO: 1;
(b) 80 residues or fewer and comprises a sequence of at least 10 contiguous residues wherein the sequence shares at least 80% identity with at least 10 contiguous residues from residues 50-75 of SEQ ID NO: 11;
(c) residues 1-80 of SEQ ID NO: 11;
(d) 91 to 103 residues and shares at least 95% identity with residues 1-80 of SEQ ID NO: 11; or
(e) residues 1-75 of SEQ ID NO: 11;
(f) 88 to 96 residues and shares at least 95% identity with residues 1-75 of SEQ ID NO: 11.

A viral vector comprising a polynucleotide encoding a fusion protein comprising a polypeptide wherein the polypeptide consists of a fragment of invariant chain which is operably linked to an antigenic sequence and wherein the fragment of invariant chain consists of:
(a) a portion of residues 1-80 of SEQ ID NO: 11, wherein the portion comprises at least 10 contiguous residues from residues 50-75 of SEQ ID NO: 1;
(b) 80 residues or fewer and comprises a sequence of at least 10 contiguous residues wherein the sequence shares at least 80% identity with at least 10 contiguous residues from residues 50-75 of SEQ ID NO: 11;
(c) residues 1-80 of SEQ ID NO: 11;
(d) 91 to 103 residues and shares at least 95% identity with residues 1-80 of SEQ ID NO: 11; or
(e) residues 1-75 of SEQ ID NO: 11;
(f) 88 to 96 residues and shares at least 95% identity with residues 1-75 of SEQ ID NO: 11.

In particular, the portion above may comprise or more suitably consist of residues 53-75, 55-75, 56-75, 60-75, 62-75 or 68-75 of SEQ ID NO: 11. Alternatively, the portion above may comprise or more suitably consist of residues 50-73, 50-70 or 50-65 of SEQ ID NO: 11.

More suitably, the portion above may comprise or more suitably consist of residues 55-75 or 60-75 of SEQ ID NO: 11.

Operative Link

According to the invention, the fragment of invariant chain is operably linked to an antigenic sequence. An operative link either refers to a direct link or to a sequence of amino acid residues or nucleotides that bind together the fragment of invariant chain and the antigenic sequence or the encoded fragment of invariant chain and antigenic sequence, such that on administration of the fusion protein, the invariant chain fragment increases the immunological response to the antigenic sequence substantially to the same extent as that of the invariant chain fragment directly linked to the antigenic sequence. A direct link is when the 3' end of the first polynucleotide is directly adjacent to the 5' end of the second sequence with no intervening nucleic acids. Alternatively, the ORFs may be indirectly linked such that there are intervening nucleic acids. For example, the intervening nucleic acids may be noncoding or may encode an amino acid sequence, for example a peptide linker. Operatively-linked nucleic acids may encode polypeptides that are directly linked, i.e., the carboxy-terminus ("C-terminus") of one encoded polypeptide is directly adjacent to the amino-terminus ("N-terminus") of a second encoded polypeptide. Alternatively, operatively-linked nucleic acids may encode indirectly linked polypeptides such that there are intervening amino acids between the encoded polypeptides. Such intervening amino acids are referred to herein as a peptide sequence or linker.

In one embodiment the fragment of invariant chain is directly linked to the antigenic sequence. In an alternative embodiment, the fragment of invariant chain is indirectly linked to the antigenic sequence. Suitably the fragment of invariant chain is indirectly linked to the antigenic sequence by a peptide sequence. Suitably the peptide sequence comprises or more suitably consists of glycine and serine, more suitably the peptide sequence comprises or more suitably consists of the sequence GlySer. Alternatively, the peptide sequence comprises or consists of the 'AscI' linker, which is a linker having the polypeptide sequence ArgArgAla, encoded by polynucleotide sequence AGGCGCGCC. Alternatively, the peptide sequence comprises or more suitably consists of the 'res' linker, which is a linker having the polypeptide sequence SerAspArgTyrLeuAsnArgArgAla (SEQ ID NO: 119), encoded by polynucleotide sequence AGCGATCGCTATTTAAATAGGCGCGCC (SEQ ID NO: 120). Alternatively, the peptide sequence comprises or more suitably consists of the human influenza hemagglutinin (HA) tag (polypeptide SEQ ID NO: 121, polynucleotide SEQ ID NO: 122).

Suitably the peptide sequence does not comprise a contiguous sequence of residues 98-100, more suitably residues 98-105, more suitably residues 98-110, more suitably residues 98-125, more suitably residues 98-150 of SEQ ID NO: 1. Suitably the peptide sequence does not comprise a contiguous sequence of more than 10, more suitably more than 7, more suitably more than 5, more suitably more than 3 contiguous residues from residues 98-232 of SEQ ID NO: 1.

Suitably the peptide sequence does not comprise a contiguous sequence of residues 93-100, more suitably residues 93-105, more suitably residues 93-110, more suitably residues 93-125, more suitably residues 93-150 of SEQ ID NO: 1.

Suitably the peptide sequence does not comprise a contiguous sequence of more than 10, more suitably more than 7, more suitably more than 5, more suitably more than 3 contiguous residues from residues 93-232 of SEQ ID NO: 1.

Throughout the specification, the phrase 'does not comprise a contiguous sequence of' means that the sequence in question does not comprise the whole contiguous sequence which is referred to.

Suitably the peptide sequence consists of 50 or fewer, more suitably 30 or fewer, more suitably 10 or fewer, more suitably 5 or fewer residues.

Antigenic Sequences

An antigenic sequence is a polypeptide which contains at least one epitope capable of eliciting an immune response. The terms antigenic sequence, antigenic protein, antigenic fragment, antigen and immunogen are used herein interchangeably. An epitope (also known as antigenic determinant) is that part of an antigenic sequence which is recognized by the immune system. Suitably, this recognition is mediated by the binding of antibodies, B cells, or T cells to the epitope in question. The epitopes bound by antibodies or B cells are referred to as B cell epitopes and the epitopes bound by T cells are referred to as T cell epitopes. Suitably binding is defined as binding with an association constant between the antibody or T cell receptor (TCR) and the respective epitope of $1\times10^5$ M$^{-1}$ or higher, or of $1\times10^6$ M$^{-1}$, $1\times10^7$ M$^{-1}$, $1\times10^8$ M$^{-1}$ or higher. The term "epitope" refers to conformational as well as non-conformational epitopes. Conformational and non-conformational epitopes are distinguished in that the binding to the former but not the latter is lost in the presence of denaturing solvents. T cell epitopes are non-conformational, i.e. they are linear, while B cell epitopes can be conformational or non-conformational. Linear B-cell epitopes typically vary between 5 to 20 amino acids in length.

Suitably the fusion protein comprises a plurality of antigenic sequences. Suitably the antigenic sequence is derived from a pathogen. An antigenic sequence is suitably derived from a pathogen selected from the group consisting of viruses, bacteria, protozoa and multicellular parasites. In an alternative embodiment the antigenic sequence is derived from a cancer cell.

Antigenic sequences induce a B-cell response or a T-cell response or a B-cell response and a T-cell response. Accordingly, antigenic proteins or antigenic fragments comprise at least one T cell epitope and/or at least one B cell epitope.

Suitably the polynucleotide sequence encoding the antigenic sequence comprises a sequence selected from the list consisting of SEQ ID NO: 4, SEQ ID NO: 8, or SEQ ID NO: 117.

The examples below in respect of murine invariant chain fragments demonstrate the effect of such fragments on ovalbumin (OVA) antigen immunogenicity and OVA antigen presentation when deployed in adenovirus type 5 (Ad5) vectors. OVA is a glycoprotein that is sufficiently large and complex to be mildly immunogenic. For this reason, OVA is a well-known model antigen frequently used in vaccination experiments, the findings in respect of which may be expected to apply equally to other antigens.

Vectors

In one embodiment, the polynucleotide of the invention is comprised in a vector.

Suitably, the vector is selected from one or more of the list consisting of a viral vector, a bacterial vector (such as *Salmonella* or *Listeria*) and a synthetic lipid nanoparticle (LNP) (such as a SAM®—a synthetic, self-amplifying mRNA, delivered by an LNP).

A viral vector is a virus comprising a heterologous nucleic acid which is capable of introducing the heterologous nucleic acid into a cell of an organism. In the context of the present invention it is contemplated that the antigen and the fragment of invariant chain encoded by the heterologous nucleic acid are expressed within said cell upon introduction by the viral vector.

A recombinant viral vector is a viral vector comprising a recombinant polynucleotide, including replicates of the original recombinant viral vector. Suitably the viral vector is selected from the group consisting of adenovirus vectors (also referred to herein as "adenoviral vectors" or simply "adenovirus"), adeno-associated virus (AAV) vectors (e.g., AAV type 5 and type 2), alphavirus vectors (e.g., Venezuelan equine encephalitis virus (VEE), sindbis virus (SIN), semliki forest virus (SFV), and VEE-SIN chimeras), herpes virus vectors (e.g. vectors derived from cytomegaloviruses, like rhesus cytomegalovirus (RhCMV), arena virus vectors (e.g. lymphocytic choriomeningitis virus (LCMV) vectors), measles virus vectors, poxvirus vectors, paramixovirus vector, baculovirus vector vesicular stomatitis virus vectors, retrovirus, lentivirus and viral like particles (VLPs).

In a particular embodiment, the viral vectors are adenoviral vectors. Adenovirus has been widely used for gene transfer applications due to its ability to achieve highly efficient gene transfer in a variety of target tissues and large transgene capacity. Adenoviral vectors of use in the present invention may be derived from a range of mammalian hosts. Over 100 distinct serotypes of adenovirus have been isolated which infect various mammalian species. These adenoviral serotypes have been categorised into six subgenera (A-F; B is subdivided into B1 and B2) according to sequence homology and on their ability to agglutinate red blood cells (Tatsis and Ertl 2004).

Suitably the adenoviral vector of use in the present invention is derived from a human adenovirus. Examples of human-derived adenoviruses are Ad1, Ad2, Ad4, Ad5, Ad6, Ad11, Ad19, Ad24, Ad34 and Ad35. Although Ad5-based vectors have been used extensively in a number of gene therapy trials, there may be limitations on the use of Ad5 and other human group C adenoviral vectors due to preexisting immunity in the general population due to natural infection. Ad5 and other human group C members tend to be among the most seroprevalent serotypes. Additionally, immunity to existing vectors may develop as a result of exposure to the vector during treatment. These types of preexisting or developed immunity to seroprevalent vectors may limit the effectiveness of gene therapy or vaccination efforts. Alternative adenovirus serotypes, thus constitute very important targets in the pursuit of gene delivery systems capable of evading the host immune response.

Suitably, the adenovirus comprises a hexon, penton and/or fiber protein wherein one or more of the hexon, penton and fiber proteins share at least 95% identity with, or more suitably at least 98% identity with, or more suitably is identical to, SEQ ID NO: 123, SEQ ID NO: 124 or SEQ ID NO: 125. These are the hexon, penton and fiber protein sequences of Ad5.

Alternatively the adenoviral vector of use in the present invention is derived from a non-human simian adenovirus. Numerous adenoviruses have been isolated from non-human simians such as chimpanzees, bonobos, rhesus macaques and gorillas, and vectors derived from these adenoviruses induce strong immune responses to transgenes encoded by these vectors (Colloca et al. 2012; Roy et al. 2004; Roy et al. 2010). Certain advantages of vectors based on non-human simian adenoviruses include the relative lack of cross-neutralising antibodies to these adenoviruses in the target population. For example, cross-reaction of certain chimpanzee adenoviruses with pre-existing neutralizing antibody responses is only present in 2% of the target population compared with 35% in the case of certain candidate human adenovirus vectors.

Suitably, the adenoviral vector is derived from a non-human simian adenovirus which is a chimpanzee adenovirus such as ChAd3, ChAd63, ChAd83, ChAd155, Pan 5, Pan 6, Pan 7 (also referred to as C7) or Pan 9. Examples of such strains are described in WO03/000283, WO2005/071093, WO2010/086189 and GB1510357.5 and are also available from the American Type Culture Collection, 10801 University Boulevard, Manassas, Va. 20110-2209, and other sources. Alternatively, adenoviral vectors may be derived from non-human simian adenoviruses isolated from bonobos, such as PanAd1, PanAd2 or PanAd3. Examples of such vectors described herein can be found for example in WO2005/071093 and WO2010/086189. Adenoviral vectors may also be derived from adenoviruses isolated from gorillas as described in WO2013/52799, WO2013/52811 and WO2013/52832.

Suitably, the adenovirus comprises a hexon and/or fiber protein wherein one or more of the hexon and fiber proteins share at least 95% identity with, or more suitably at least 98% identity with, or more suitably is identical to, SEQ ID NO: 126 or SEQ ID NO: 127, respectively. These are the hexon and fiber protein sequences of ChAd3.

Suitably, the adenovirus comprises a hexon and/or fiber protein wherein one or more of the hexon and fiber proteins share at least 95% identity with, or more suitably at least 98% identity with, or more suitably is identical to, SEQ ID NO: 128 or SEQ ID NO: 129, respectively. These are the hexon and fiber protein sequences of ChAd19.

Suitably, the adenovirus comprises a hexon and/or fiber protein wherein one or more of the hexon and fiber proteins share at least 95% identity with, or more suitably at least 98% identity with, or more suitably is identical to, SEQ ID NO: 130 or SEQ ID NO: 131, respectively. These are the hexon and fiber protein sequences of ChAd63.

Suitably, the adenovirus comprises a hexon, penton and/or fiber protein wherein one or more of the hexon, penton and fiber proteins share at least 95% identity with, or more suitably at least 98% identity with, or more suitably is identical to, SEQ ID NO: 132, SEQ ID NO: 133 or SEQ ID NO: 134, respectively. These are the hexon, penton and fiber protein sequences of ChAd155.

Adenoviruses have a characteristic morphology with an icosahedral capsid comprising three major proteins, hexon (II), penton base (III) and a knobbed fibre (IV), along with a number of other minor proteins, VI, VIII, IX, IIIa and IVa2. The virus genome is a linear, double-stranded DNA. The virus DNA is intimately associated with the highly basic protein VII and a small peptide pX (formerly termed mu). Another protein, V, is packaged with this DNA-protein complex and provides a structural link to the capsid via protein VI. The virus also contains a virus-encoded protease, which is necessary for processing of some of the structural proteins to produce mature infectious virus.

The adenoviral genome is well characterized. There is general conservation in the overall organization of the adenoviral genome with respect to specific open reading frames being similarly positioned, e.g. the location of the E1A, E1B, E2A, E2B, E3, E4, L1, L2, L3, L4 and L5 genes of each virus. Each extremity of the adenoviral genome comprises a sequence known as an inverted terminal repeat (ITR), which is necessary for viral replication. The virus also comprises a virus-encoded protease, which is necessary for processing some of the structural proteins required to produce infectious virions. The structure of the adenoviral genome is described on the basis of the order in which the viral genes are expressed following host cell transduction. More specifically, the viral genes are referred to as early (E) or late (L) genes according to whether transcription occurs prior to or after onset of DNA replication. In the early phase of transduction, the E1A, E1B, E2A, E2B, E3 and E4 genes of adenovirus are expressed to prepare the host cell for viral replication. During the late phase of infection, expression of the late genes L1-L5, which encode the structural components of the virus particles, is activated.

A replication-competent adenovirus is an adenovirus which can replicate in a host cell in the absence of any recombinant helper proteins comprised in the cell. Suitably, a replication-competent adenovirus comprises the following intact or functional essential early genes: E1A, E1B, E2A, E2B, E3 and E4. Wild type adenoviruses isolated from a particular animal will be replication competent in that animal.

A replication-incompetent or replication-defective adenovirus is an adenovirus which is incapable of replication because it has been engineered to comprise at least a functional deletion (or "loss-of-function" mutation), i.e. a deletion or mutation which impairs the function of a gene without removing it entirely, e.g. introduction of artificial stop codons, deletion or mutation of active sites or interaction domains, mutation or deletion of a regulatory sequence of a gene etc, or a complete removal of a gene encoding a gene product that is essential for viral replication, such as one or more of the adenoviral genes selected from E1A, E1B, E2A, E2B, E3 and E4 (such as E3 ORF1, E3 ORF2, E3 ORF3, E3 ORF4, E3 ORF5, E3 ORF6, E3 ORF7, E3 ORF8, E3 ORF9, E4 ORF7, E4 ORF6, E4 ORF5, E4 ORF4, E4 ORF3, E4 ORF2 and/or E4 ORF1). Suitably the E1 and E3 genes are deleted. More suitably the E1, E3 and E4 genes are deleted. Suitably when using an Ad5 vector, the E1, E3 and E4 genes are deleted with Ad5 E4 ORF6 reinserted. Suitably when using a PanAd3 vector, the E1 and E4 genes are deleted with Ad5 E4 ORF6 inserted. Suitably when using a ChAd3 vector, the E1, E3, and E4 genes are deleted with Ad5 E4 ORF6 inserted.

In the construction of adenovirus vectors for delivery of a gene to a mammalian (such as human) cell, a range of modified adenovirus nucleic acid sequences can be employed in the vectors. For example, all or a portion of the adenovirus delayed early gene E3 may be eliminated from the adenovirus sequence which forms a part of the recombinant virus. The function of E3 is believed to be irrelevant to the function and production of the recombinant virus particle. Adenovirus vectors may also be constructed having a deletion of at least the ORF6 region of the E4 gene, and more desirably because of the redundancy in the function of this region, the entire E4 region. Still another vector of the invention contains a deletion in the delayed early gene E2A. Deletions may also be made in any of the late genes L1 to L5 of the adenovirus genome. Similarly, deletions in the intermediate genes IX and IVa2 may be useful for some purposes. Other deletions may be made in the other structural or non-structural adenovirus genes. The above discussed deletions may be used individually, i.e., an adenovirus sequence for use as described herein may contain deletions in only a single region. Alternatively, deletions of entire genes or portions thereof effective to destroy their biological activity may be used in any combination.

An adenovirus lacking one or more essential adenoviral sequences (e.g., E1A, E1B, E2A, E2B, E4 ORF6, L1, L2, L3, L4 and L5) may be cultured in the presence of the missing adenoviral gene products which are required for viral infectivity and propagation of an adenoviral particle. These helper functions may be provided by culturing the adenovirus in the presence of one or more helper constructs (e.g., a plasmid or virus) or a packaging host cell.

Suitably the viral vector is a poxviral vector. The family poxviridae is characterised by a genome consisting of double-stranded DNA. Suitably, the poxviral vector belongs to the subfamily chordopoxvirinae, more preferably to a genus in said subfamily selected from the group consisting of orthopox, parapox, yatapox, avipox (preferably canarypox (ALVAC) or fowlpox (FPV)) and molluscipox. Even more preferably, the poxviral vector belongs to the orthopox and is selected from the group consisting of vaccinia virus, NYVAC (derived from the Copenhagen strain of vaccinia), modified vaccinia Ankara (MVA), cowpoxvirus and monkeypox virus. Most preferably, the poxviral vector is MVA.

A description of MVA can be found in Mayr A, Stickl H, Müller H K, Danner K, Singer H. 1978 and in Mayr, A., Hochstein-Mintzel, V. & Stickl, H. 1975.

MVA is a highly attenuated strain of vaccinia virus that underwent multiple, fully characterised deletions during more than 570 passages in chick embryo fibroblast cells. These included host range genes and genes encoding cytokine receptors. The virus is unable to replicate efficiently in human and most other mammalian cells but the replication defect occurs at a late stage of virion assembly such that viral and recombinant gene expression is unimpaired making MVA an efficient single round expression vector incapable of causing infection in mammals. In one embodiment, MVA is derived from the virus seed batch 460 MG obtained from 571th passage of Vaccinia Virus on CEF cells. In another embodiment, MVA is derived from the virus seed batch MVA 476 MG/14/78. In a further embodiment, MVA is derived or produced prior to 31 Dec. 1978 and is free of prion contamination.

In addition to the polynucleotide encoding the fusion protein, the vector may also include conventional control elements which are operably linked to the encoding polynucleotide in a manner that permits its transcription, translation and/or expression in a cell transfected with the vector.

Expression control sequences include appropriate transcription initiation, termination, promoter and enhancer sequences; efficient RNA processing signals such as splicing and polyadenylation (poly A) signals including rabbit beta-globin polyA; sequences that stabilize cytoplasmic mRNA; sequences that enhance translation efficiency (e.g., Kozak consensus sequence); sequences that enhance protein stability; and when desired, sequences that enhance secretion of the encoded product. Among other sequences, chimeric introns may be used.

A promoter is a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and mammals (including humans). A great number of expression control sequences, including promoters which are internal, native, constitutive, inducible and/or tissue-specific, are known in the art and may be utilized.

Examples of constitutive promoters include, the TBG promoter, the retroviral Rous sarcoma virus (RSV) LTR promoter (optionally with the RSV enhancer), the cytomegalovirus (CMV) promoter (optionally with the CMV enhancer, see, e.g., Boshart et al. 1985), the CASI promoter, the SV40 promoter, the dihydrofolate reductase promoter, the β-actin promoter, the phosphoglycerol kinase (PGK) promoter, and the EF1a promoter (Invitrogen). Suitably the promoter is an HCV promoter or variant thereof, more suitably a human CMV (HCMV) promoter or variant thereof.

The examples below in respect of murine invariant chain fragments demonstrate the effect of such fragments on OVA antigen immunogenicity and OVA antigen presentation when deployed in adenovirus type 5 (Ad5) vectors. Ad5 has been shown to be an effective vaccine vector (see, for example, Tatsis and Hildegund 2004). It may be expected that findings in respect of the Ad5 vector provided in the examples herein will apply equally to other vectors, such as bacterial vectors and synthetic lipid nanoparticles. In the case of bacterial vectors, the invariant chain fragments disclosed herein may be expected to favorably impact, in particular, the $CD8^+$ T cell response driven by such vectors.

Pharmaceutical Compositions and Adjuvants

The fusion protein, polynucleotide or vector of the present invention may be comprised within a pharmaceutical composition. Suitably a pharmaceutical composition will include a pharmaceutically acceptable carrier. A vaccine is a pharmaceutical composition that provides acquired immunity to a particular disease. The present invention provides vaccines comprising a fusion protein, polynucleotide or vector of the invention.

The vector may be prepared for administration by being suspended or dissolved in a pharmaceutically or physiologically acceptable carrier such as isotonic saline or other isotonic salts solution. The appropriate carrier will be evident to those skilled in the art and will depend in large part upon the route of administration. The compositions described herein may be administered to in a sustained release formulation, suitably using a biodegradable biocompatible polymer, or by on-site delivery using micelles, gels and liposomes.

The term "carrier", as used herein, refers to a pharmacologically inactive substance such as but not limited to a diluent, excipient, or vehicle with which the therapeutically active ingredient is administered. Such pharmaceutical carriers can be liquid or solid. Liquid carrier include but are not limited to sterile liquids, such as saline solutions in water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. A saline solution is one preferred carrier when the pharmaceutical composition is administered intravenously or intranasally by a nebulizer.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E. W. Martin.

The term "adjuvant" refers to agents that augment, stimulate, activate, potentiate, or modulate the immune response to the active ingredient of the composition at either the cellular or humoral level, e.g. immunologic adjuvants stimulate the response of the immune system to the actual antigen, but have no immunological effect themselves. Suitably the pharmaceutical composition of the invention comprises an adjuvant.

Examples of such adjuvants include but are not limited to inorganic adjuvants (e.g. inorganic metal salts such as aluminium phosphate or aluminium hydroxide), organic adjuvants (e.g. saponins, such as QS21, or squalene), oil-based adjuvants (e.g. Freund's complete adjuvant and Freund's incomplete adjuvant), cytokines (e.g. IL-1β, IL-2, IL-7, IL-12, IL-18, GM-CFS, and INF-γ) particulate adjuvants (e.g. immuno-stimulatory complexes (ISCOMS), liposomes, or biodegradable microspheres), virosomes, bacterial adjuvants (e.g. monophosphoryl lipid A, such as 3-de-O-acylated monophosphoryl lipid A (3D-MPL), or muramyl peptides), synthetic adjuvants (e.g. non-ionic block copolymers, muramyl peptide analogues, or synthetic lipid A), synthetic polynucleotides adjuvants (e.g polyarginine or polylysine) and immunostimulatory oligonucleotides containing unmethylated CpG dinucleotides ("CpG").

One suitable adjuvant is monophosphoryl lipid A (MPL), in particular 3-de-O-acylated monophosphoryl lipid A (3D-MPL). Chemically it is often supplied as a mixture of 3-de-O-acylated monophosphoryl lipid A with either 4, 5, or 6 acylated chains. It can be purified and prepared by the methods taught in GB 2122204B, which reference also discloses the preparation of diphosphoryl lipid A, and 3-O-deacylated variants thereof. Other purified and synthetic lipopolysaccharides have been described (U.S. Pat. No. 6,005,099 and EP 0 729 473 B1; Hilgers et al. 1986; Hilgers et al. 1987; and EP 0 549 074 B1).

Saponins are also suitable adjuvants (see Lacaille-Dubois, M and Wagner, H 1996). For example, the saponin Quil A (derived from the bark of the South American tree Quillaja Saponaria Molina), and fractions thereof, are described in U.S. Pat. No. 5,057,540 and Kensil 1996; and EP 0 362 279 B1. Purified fractions of Quil A are also known as immunostimulants, such as QS21 and QS17; methods of their production is disclosed in U.S. Pat. No. 5,057,540 and EP 0 362 279 B1. Also described in these references is QS7 (a non-haemolytic fraction of Quil-A). Use of QS21 is further described in Kensil et al 1991). Combinations of QS21 and polysorbate or cyclodextrin are also known (WO 99/10008). Particulate adjuvant systems comprising fractions of QuilA, such as QS21 and QS7 are described in WO 96/33739 and WO 96/11711.

Another adjuvant is an immunostimulatory oligonucleotide containing unmethylated CpG dinucleotides ("CpG") (Krieg 1995). CpG is an abbreviation for cytosine-guanosine dinucleotide motifs present in DNA. CpG is known as an adjuvant when administered by both systemic and mucosal routes (WO 96/02555, EP 468520, Davis et al 1998; McCluskie and Davis 1998). CpG, when formulated into vaccines, may be administered in free solution together with free antigen (WO 96/02555) or covalently conjugated to an antigen (WO 98/16247), or formulated with a carrier such as aluminium hydroxide (Brazolot-Millan et al. 1998).

Adjuvants such as those described above may be formulated together with carriers, such as liposomes, oil in water emulsions, and/or metallic salts (including aluminum salts such as aluminum hydroxide). For example, 3D-MPL may be formulated with aluminum hydroxide (EP 0 689 454) or oil in water emulsions (WO 95/17210); QS21 may be formulated with cholesterol containing liposomes (WO 96/33739), oil in water emulsions (WO 95/17210) or alum (WO 98/15287); CpG may be formulated with alum (Brazolot-Millan, supra) or with other cationic carriers.

Combinations of adjuvants may be utilized in the present invention, in particular a combination of a monophosphoryl lipid A and a saponin derivative (see, e.g., WO 94/00153; WO 95/17210; WO 96/33739; WO 98/56414; WO 99/12565; WO 99/11241), more particularly the combination of QS21 and 3D-MPL as disclosed in WO 94/00153, or a composition where the QS21 is quenched in cholesterol-containing liposomes (DQ) as disclosed in WO 96/33739. Alternatively, a combination of CpG plus a saponin such as QS21 is an adjuvant suitable for use in the present invention. A potent adjuvant formulation involving QS21, 3D-MPL & tocopherol in an oil in water emulsion is described in WO 95/17210 and is another formulation for use in the present invention. Saponin adjuvants may be formulated in a liposome and combined with an immunostimulatory oligonucleotide. Thus, suitable adjuvant systems include, for example, a combination of monophosphoryl lipid A, preferably 3D-MPL, together with an aluminium salt (e.g. as described in WO00/23105). A further exemplary adjuvant comprises QS21 and/or MPL and/or CpG. QS21 may be quenched in cholesterol-containing liposomes as disclosed in WO 96/33739.

Other suitable adjuvants include alkyl glucosaminide phosphates (AGPs) such as those disclosed in WO9850399 or U.S. Pat. No. 6,303,347 (processes for preparation of AGPs are also disclosed), or pharmaceutically acceptable salts of AGPs as disclosed in U.S. Pat. No. 6,764,840. Some AGPs are TLR4 agonists, and some are TLR4 antagonists. Both are thought to be useful as adjuvants.

In one embodiment, there is provided the fusion protein, polynucleotide, viral vector or pharmaceutical composition according to the invention, for use as a medicament. Suitably the fusion protein, polynucleotide, viral vector or pharmaceutical composition is for use in the treatment or prevention of hepatitis B viral infection or hepatitis C viral infection. Also provided is the use of a fusion protein, polynucleotide, viral vector or pharmaceutical composition according to the invention in the manufacture of a medicament for the prevention or treatment of hepatitis B viral infection or hepatitis C viral infection. Also provided is a method of treating or preventing hepatitis B viral infection or hepatitis C viral infection, comprising administering to a person in need thereof an effective amount of the fusion protein, polynucleotide, viral vector or pharmaceutical composition according to the invention.

Administration

In one embodiment, the vector is administered via intranasal, intramuscular, subcutaneous, intradermal, intragastric, oral, rectal or topical routes.

An intranasal administration is the administration of the vector to the mucosa of the complete respiratory tract including the lung. More particularly, the composition is administered to the mucosa of the nose. In one embodiment, an intranasal administration is achieved by means of spray or aerosol. In a further embodiment, said administration does not involve perforation of the mucosa by mechanical means such as a needle. Intramuscular administration refers to the injection of a vector into any muscle of an individual. Exemplary intramuscular injections are administered into the deltoid, vastus lateralis or the ventrogluteal and dorsogluteal areas. Subcutaneous administration refers to the injection of the vector into the hypodermis. Intradermal administration refers to the injection of a vector into the dermis between the layers of the skin. Intragastric administration refers to the administration of the vector directly to the stomach. Oral administration refers to the administration of the vector via the mouth to the gastric system. Topical administration is the administration of the vector to any part of the skin or mucosa without penetrating the skin with a needle or a comparable device. The vector may be administered topically to the mucosa of the mouth, nose, genital region and/or rectum. Topical administration includes administration means such as sublingual and/or buccal administration. Sublingual administration is the administration of the vector under the tongue (for example, using an oral thin film (OTF)). Buccal administration is the administration of the vector via the buccal mucosa of the cheek.

The fusion protein, polynucleotide or vector of the invention may be used for priming an immune response. The term "priming an immune response" refers to the first encounter of the immune system with the antigenic sequence and the subsequent induction of an antigen-specific immune response within a defined period of time. In one embodiment, encounters of the individual's immune system with the antigenic sequence which do not induce an antigen-specific immune response are not considered as "priming an immune response". For example, encounters of the individual's immune system with the antigenic sequence which do not induce immunity are not considered as "priming an immune response" according to the present invention. In a further embodiment, the induction of immunity is mediated by the generation of memory B cells and/or memory T cells. In the case of cancer, for example, a specific antigen may be expressed by the cancer cells without eliciting an immune response. The mere presence of this antigen is not a "priming of an immune response" against said antigen. In one embodiment, the individual has not been deliberately immunised with the antigenic sequence or a vector comprising polynucleotide encoding such a sequence with the aim of treating or preventing a disease in the period of time given before.

The individual to be immunised with a polynucleotide according to the present invention is, for example, a mammal or a bird, more specifically a primate, mouse, rat, sheep, goat, cow, pig, horse, goose, chicken, duck or turkey and, most specifically, a human. Suitably the fusion protein, polynucleotide, viral vector or pharmaceutical composition is for administration to a mammal, more suitably a human.

The polynucleotide of the invention may be used in a prime-boost vaccination regimen. In many cases, a single administration of a vaccine is not sufficient to generate the number of long-lasting immune cells which is required for effective protection in case of future infection of the pathogen in question, protect against diseases or for therapeutically treating a disease. Consequently, repeated challenge with a biological preparation specific for a specific pathogen or disease may be required in order to establish lasting and protective immunity against said pathogen or disease or to cure a given disease. An administration regimen comprising the repeated administration of a vaccine directed against the same pathogen or disease is referred to as a "prime-boost vaccination regimen". In one embodiment, a prime-boost vaccination regimen involves at least two administrations of a vaccine directed against a specific pathogen, group of pathogens or diseases. The first administration of the vaccine is referred to as "priming" and any subsequent administration of the same vaccine or a vaccine directed against the same pathogen as the first vaccine is referred to as "boosting". Thus, in a further embodiment of the present invention the prime-boosting vaccination regimen involves one administration of the vaccine for priming the immune response and at least one subsequent administration for boosting the immune response. It is to be understood that 2, 3, 4 or even 5 administrations for boosting the immune response are also contemplated. The period of time between prime and boost is, optionally, 1 week, 2 weeks, 4 weeks, 6 weeks or 8 weeks. More particularly, it is 4 weeks or 8 weeks. If more than one boost is performed, the subsequent boost is administered 1 week, 2 weeks, 4 weeks, 6 weeks or 8 weeks after the preceding boost. For example, the interval between any two boosts is 4 weeks or 8 weeks.

Prime-boost vaccination regimens may be homologous or heterologous. In homologous prime-boost regimens both the priming and the at least one boosting is performed using the same means of administration of the antigenic protein or antigenic fragment thereof, i.e. priming and boosting are performed using a polypeptide or priming and boosting are performed using a polynucleotide comprised by the same vector. In the context of the present invention a homologous prime-boost vaccination regimen would comprise the use of the vector of the invention both for priming as well as for boosting the immune response. A heterologous prime-boosting regimen involves the use of different means for priming and for boosting the immune response. A heterologous prime-boosting regimen would comprise a vector of the invention for the priming of an immune response and a different vector or a peptide vaccine for the boosting of the immune response.

Alternatively, a heterologous prime-boosting regimen would comprise a different vector or a peptide vaccine for the priming of an immune response and a vector of the invention for the boosting of the immune response. In one embodiment of the present invention the prime-boosting vaccination regimen is homologous. In another embodiment of the present invention the prime-boosting vaccination regimen is heterologous. In one heterologous prime boosting regimen the vector is used for the boosting of the immune response and a different vector or a peptide vaccine is used for the priming of the immune response. In another embodiment, heterologous prime boosting regimen, the vector is used for the priming of the immune response and a different vector or a peptide vaccine is used for the boosting of the immune response. Suitably the antigenic sequence used for boosting the immune response is immunologically identical to the antigenic sequence used for priming the immune response. Two or more antigenic sequences are "immunologically identical" if they are recognized by the same antibody, T-cell or B-cell. The recognition of two or more immunogenic sequences by the same antibody, T-cell or B-cell is also known as "cross reactivity" of said antibody, T-cell or B-cell. In one embodiment, the recognition of two or more immunologically identical sequences by the same antibody, T-cell or B-cell is due to the presence of identical or similar epitopes in all sequences. Similar epitopes share enough structural and/or charge characteristics to be bound by the Fab region of the same antibody or B-cell receptor or by the V region of the same T-cell receptor. The binding characteristics of an antibody, T-cell receptor or B-cell receptor are, for example, defined by the binding affinity of the receptor to the epitope in question. Suitably two immunogenic polypeptides are immunologically identical if the affinity constant of polypeptide with the lower affinity constant is at least 30%, at least 40%, at least 50%, at least 60%, at least 70%, at least 80%, at least 90%, at least 95% or at least 98% of the affinity constant of the polypeptide with the higher affinity constant. Suitably two or more immunologically identical polypeptides comprise at least one identical epitope. The strongest vaccination effects can usually be obtained, if the immunogenic polypeptides comprise identical epitopes or if they have an identical amino acid sequence. In one embodiment, the use of the vector for the priming or boosting of an immune response will establish protective immunity against a pathogen or disease or will lead to eradication of the disease. In one embodiment, the use of the vector for the priming or boosting of an immune response will increase the antigen-specific $CD8^+$ T cell response as compared to the same regimen without the fragment of invariant chain. In one embodiment, the use of the vector for the priming or boosting of an immune response will increase the antigen-specific $CD4^+$ T cell response as compared to the same regimen without the fragment of invariant chain.

In one embodiment of the invention the vaccine is used in a prime-boost vaccination regimen. In a first embodiment of this prime-boost vaccination regimen the vector is used for priming the immune response. In another embodiment of the prime-boost vaccination regimen, the vector is used for boosting the immune response.

In an embodiment of the present invention, the immune response is primed by intranasal administration and the immune response is boosted by at least one intramuscular administration; the immune response is primed by intranasal administration and the immune response is boosted by at least one subcutaneous administration; the immune response is primed by intranasal administration and the immune response is boosted by at least one intradermal administration; the immune response is primed by intranasal administration and the immune response is boosted by at least one intragastric administration; the immune response is primed by intranasal administration and the immune response is boosted by at least one oral administration; the immune response is primed by intranasal administration and the immune response is boosted by at least one topical administration; the immune response is primed by intranasal administration and the immune response is boosted by at least one intranasal administration; the immune response is primed by intramuscular administration and the immune response is boosted by at least one intramuscular administration; the immune response is primed by intramuscular administration and the immune response is boosted by at least one subcutaneous administration; the immune response is primed by intramuscular administration and the immune response is boosted by at least one intradermal administration; the immune response is primed by intramuscular administration and the immune response is boosted by at least one intragastric administration; the immune response is primed by intramuscular administration and the immune response is boosted by at least one oral administration; the immune response is primed by intramuscular administration and the immune response is boosted by at least one topical administration; the immune response is primed by intramuscular administration and the immune response is boosted by at least one intranasal administration; the immune response is primed by subcutaneous administration and the immune response is boosted by at least one intramuscular administration; the immune response is primed by subcutaneous administration and the immune response is boosted by at least one subcutaneous administration; the immune response is primed by subcutaneous administration and the immune response is boosted by at least one intradermal administration; the immune response is primed by subcutaneous administration and the immune response is boosted by at least one intragastric administration; the immune response is primed by subcutaneous administration and the immune response is boosted by at least one oral administration; the immune response is primed by subcutaneous administration and the immune response is boosted by at least one topical administration; the immune response is primed by subcutaneous administration and the immune response is boosted by at least one intranasal administration; the immune response is primed by intradermal administration and the immune response is boosted by at least one intramuscular administration; the immune response is primed by intradermal administration and the immune response is boosted by at least one subcutaneous administration; the immune response is primed by intradermal administration and the immune response is boosted by at least one intradermal administration; the immune response is primed by intradermal administration and the immune response is boosted by at least one intragastric administration; the immune response is primed by intradermal administration and the immune response is boosted by at least one oral administration; the immune response is primed by intradermal administration and the immune response is boosted by at least one topical administration; the immune response is primed by intradermal administration and the immune response is boosted by at least one intranasal administration; the immune response is primed by intragastric administration and the immune response is boosted by at least one intramuscular administration; the immune response is primed by intragastric administration and the immune response is boosted by at least one subcutaneous administration; the immune response is primed by intragastric administration and the immune response is boosted by at least one intradermal administration; the immune response is primed by intragastric administration and the immune response is boosted by at least one intragastric administration; the immune response is primed by intragastric administration and the immune response is boosted by at least one oral administration; the immune response is primed by intragastric administration and the immune response is boosted by at least one topical administration; the immune response is primed by intragastric administration and the immune response is boosted by at least one intranasal administration; the immune response is primed by oral administration and the immune response is boosted by at least one intramuscular administration; the immune response is primed by oral administration and the immune response is boosted by at least one subcutaneous administration; the immune response is primed by oral administration and the immune response is boosted by at least one intradermal administration; the immune response is primed by oral administration and the immune response is boosted by at least one intragastric administration; the immune response is primed by oral administration and the immune response is boosted by at least one oral administration; the immune response is primed by oral administration and the immune response is boosted by at least one topical administration; the immune response is primed by oral administration and the immune response is boosted by at least one intranasal administration; the immune response is primed by topical administration and the immune response is boosted by at least one intramuscular administration; the immune response is primed by topical administration and the immune response is boosted by at least one subcutaneous administration; the immune response is primed by topical administration and the immune response is boosted by at least one intradermal administration; the immune response is primed by topical administration and the immune response is boosted by at least one intragastric administration; the immune response is primed by topical administration and the immune response is boosted by at least one oral administration; the immune response is primed by topical administration and the immune response is boosted by at least one topical administration; the immune response is primed by topical administration and the immune response is boosted by at least one intranasal administration. In one embodiment, the immune response is primed by intranasal administration and the immune response is boosted by at least one intramuscular administration. In yet another embodiment, the immune response is primed by intranasal administration and the immune response is boosted by at least one intranasal administration. In yet another embodiment, the immune response is primed by intramuscular administration and the immune response is boosted by at least one intramuscular administration.

If the vector of the invention is administered in a therapeutic regimen which involves co-administration with a further component, each formulated in different compositions, they are favourably administered co-locationally at or near the same site. For example, the components can be administered (e.g. via an administration route selected from intramuscular, transdermal, intradermal, sub-cutaneous) to the same side or extremity ("co-lateral" administration) or to opposite sides or extremities ("contra-lateral" administration).

Dosage

Dosages of the vector will depend primarily on factors such as the condition being treated, the age, weight and health of the patient, and may thus vary among patients. For example, a therapeutically effective adult human or veterinary dosage of the viral vector generally contains $1\times10^5$ to $1\times10^{15}$ viral particles, such as from $1\times10^9$ to $1\times10^{12}$ (e.g., $1\times10^9$, $5\times10^9$, $1\times10^9$, $5\times10^9$, $1\times10^{10}$, $2.5\times10^{10}$, $5\times10^{10}$, $1\times10^{11}$ $5\times10^{11}$ or $1\times10^{12}$ particles). Alternatively, a viral vector can be administered at a dose that is typically from $1\times10^5$ to $1\times10^{19}$ plaque forming units (PFU), such as $1\times10^5$ PFU, $5\times10^5$ PFU, $1\times10^6$ PFU, $5\times10^6$ PFU, $1\times10^7$ PFU, $5\times10^7$ PFU, $1\times10^8$ PFU, $5\times10^8$ PFU, $1\times10^9$ PFU, $5\times10^9$ PFU, or $1\times10^{10}$ PFU. Dosages will vary depending upon the size of the animal and the route of administration. For example, a suitable human or veterinary dosage (for about an 80 kg animal) for intramuscular injection is in the range of about $1\times10^9$ to about $5\times10^{12}$ particles per mL, for a single site. Optionally, multiple sites of administration may be used. In another example, a suitable human or veterinary dosage may be in the range of about $1\times10^{11}$ to about $1\times10^{15}$ particles for an oral formulation.

An immunologically effective amount of a nucleic acid may suitably be between 1 ng and 100 mg. For example, a suitable amount can be from 1 μg to 100 mg. An appropriate amount of the particular nucleic acid can readily be determined by those of skill in the art. Exemplary effective amounts of a nucleic acid component can be between 1 ng and 100 μg, such as between 1 ng and 1 μg (e.g., 100 ng-1 μg), or between 1 μg and 100 μg, such as 10 ng, 50 ng, 100 ng, 150 ng, 200 ng, 250 ng, 500 ng, 750 ng, or 1 μg. Effective amounts of a nucleic acid can also include from 1 μg to 500 μg, such as between 1 μg and 200 μg, such as between 10 and 100 μg, for example 1 μg, 2 μg, 5 μg, 10 μg, 20 μg, 50 μg, 75 μg, 100 μg, 150 μg, or 200 μg. Alternatively, an exemplary effective amount of a nucleic acid can be between 100 μg and 1 mg, such as from 100 μg to 500 μg, for example, 100 μg, 150 μg, 200 μg, 250 μg, 300 μg, 400 μg, 500 μg, 600 μg, 700 μg, 800 μg, 900 μg or 1 mg.

Generally a human dose will be in a volume of between 0.5 ml and 2 ml. Thus the composition described herein can be formulated in a volume of, for example 0.5, 1.0, 1.5 or 2.0 ml human dose per individual or combined immunogenic components.

One of skill in the art may adjust these doses, depending on the route of administration and the therapeutic or vaccine application for which the recombinant vector is employed. The levels of expression of the antigenic sequence can be monitored to determine the frequency of dosage administration.

EXAMPLES

Figure 2:
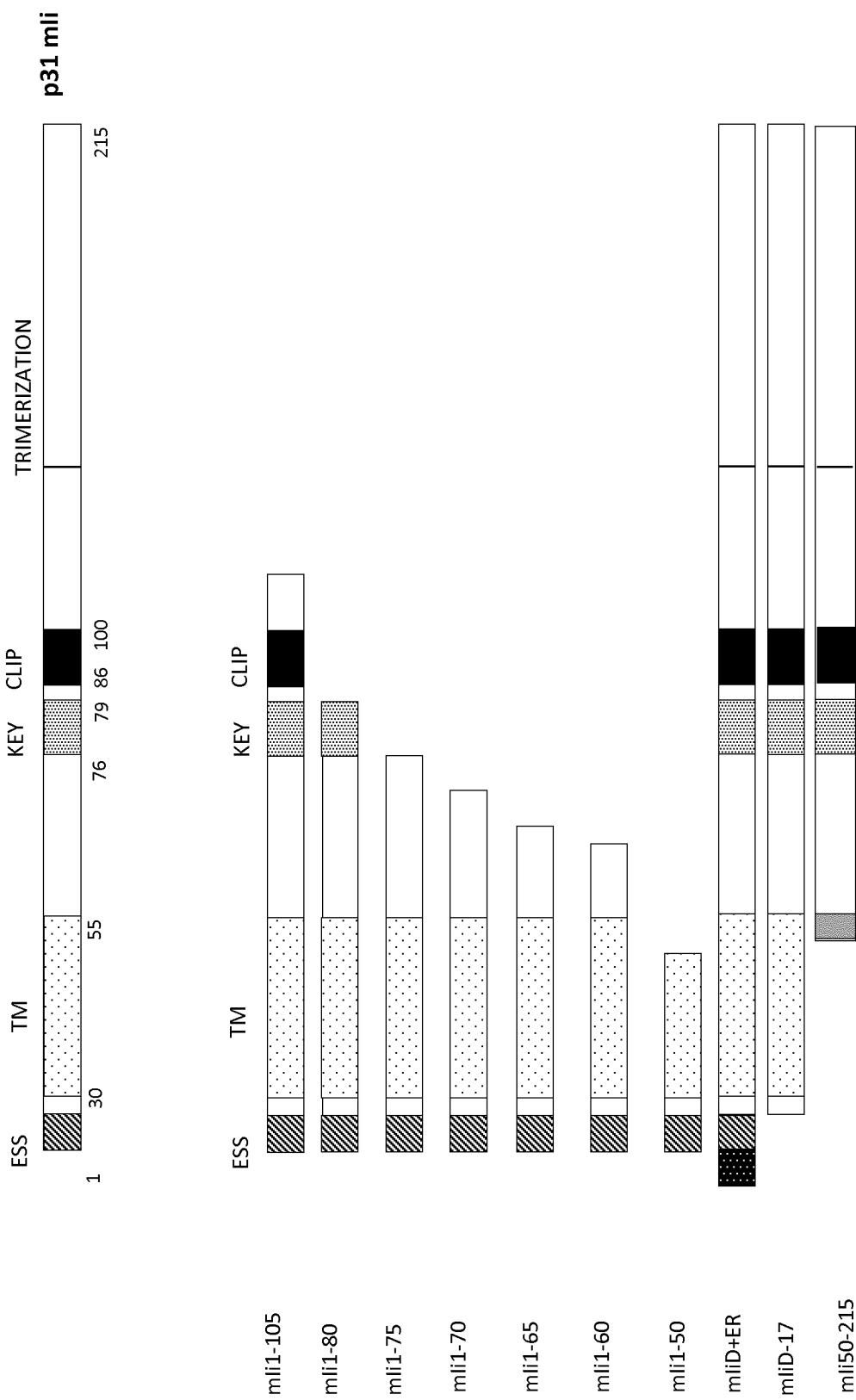
FIG. 2 Schematic diagram of murine li fragments fused to OVA (ovalbumin) comprised in Ad5 constructs.
Figure 3:
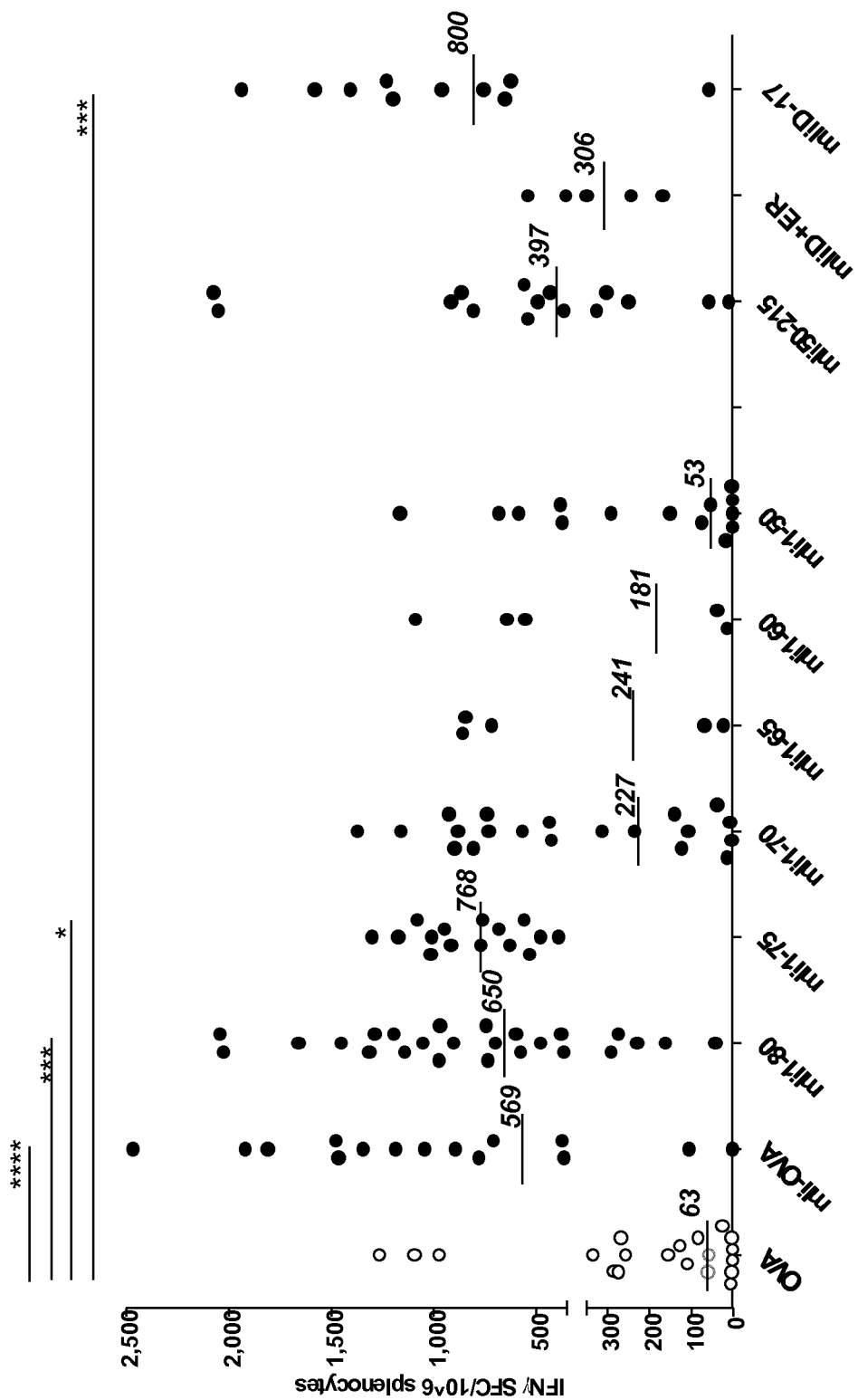
FIG. 3 Immune response (number of T cells producing IFN-γ per million splenocytes) elicited by murine li fragments fused to OVA comprised in Ad5 constructs in mice.

Example 1: Preparation and In Vivo Immunogenicity Testing of a Range of Murine Li Fragments Fused to OVA E1E3 deleted Ad5 constructs comprising the ovalbumin antigen ("OVA", SEQ ID NO: 8) were produced wherein OVA was fused via a human influenza hemagglutinin (HA) tag (SEQ ID NO: 121) to the C-terminus of fragments of murine li sequences (mli), isoform p31. The mli fragments tested are illustrated in FIG. 2, wherein numbering indicates amino acid position in the fragment with respect to mli p31 (see SEQ ID NO: 11), "D+ER", indicates addition of the endoplasmic reticulum retention sequence and "D-17" indicates removal of the endolysosomal sorting sequence (ESS). Ad5 constructs comprising the following were produced:

1. OVA only (not shown in FIG. 2)
2. mli(full length)-OVA
3. mli(1-105)-OVA
4. mli(1-80)-OVA
5. mli(1-75)-OVA
6. mli(1-70)-OVA
7. mli(1-65)-OVA
8. mli(1-60)-OVA
9. mli(1-50)-OVA
10. mli(D+ER)-OVA
11. mli(D-17)-OVA
12. mli(50-215)-OVA The polypeptide sequence of mli(D+ER) is given in SEQ ID NO: 138. The polypeptide sequence of mli(D-17) (N-terminal Met plus residues 18-215 of p31 mli) is given in SEQ ID NO: 139. The polypeptide sequence of mli(50-215) (N-terminal Met plus residues 51-215 of p31 mli) is given in SEQ ID NO: 140. Note that, contrary to the label, mli(50-215) does not contain residues 50-215 of p31, but residues 51-215, instead.

mliThe promoter used for all constructs in this example and all those provided below was the HCMV promoter or variants thereof (e.g. pacCMV). Co-transfection of viruses was performed using HCMV promoter, a Sv40polyA sequence and pJM17, as described in Becker et al. 1994. The immunological potency of the different constructs was evaluated by injecting C57BL/6 mice with a single intramuscular dose of $3\times10^6$ viral particles (vp). Splenocytes were collected two weeks after injection and tested by IFN-γ ELISpot using as antigen the OVA 257-264 dominant CD8 peptide SIINFEKL (SEQ ID NO: 118, previously identified and mapped in C57BL/6 mice). The results are shown in FIG. 3, with responses expressed as number of T cells producing IFNγ per million splenocytes. The statistical test applied was the One-way ANOVA (Dunnett's multiple comparison test) wherein: $*p<0.05$; $p<0.01$; $*p<0.001$; $****p<0,0001$.

As expected, the mli(full length)-OVA construct provided a mean higher response compared to OVA only (see FIG. 3, 'mli-OVA' and 'OVA', respectively). Similarly, the prior art art-based constructs mli(D+ER)-OVA, mli(D-17)-OVA and mli(50-215)-OVA provided mean higher responses compared to OVA only. The comparison between mli(full length)-OVA and the analogous constructs comprising mli fragments revealed that, from amongst the mli fragments tested, the mli(1-75) sequence was the minimal sequence which maintained the full adjuvant effect of full length mli. In fact, mli(1-75) demonstrated an even higher mean level of immunogenicity enhancement than full length mli. These are surprising observations, as mli(1-75) lacks not only the trimerisation region, (which is important for its role as a MHC-II chaperone and MIF signalling receptor) but also lacks the KEY and CLIP regions previously thought to be of importance for the adjuvant effect of li. In contrast, further truncation to the mli(1-70) fragment resulted in a substantial loss of immunogenicity. Data is not shown in respect of mli(1-105)-OVA. mli(1-105)-OVA provided responses which were similar to mli(full length)-OVA.

Example 2: In Vitro Tests of Antigen Presentation with Murine Li1-50, Li1-75, Li1-80, Li50-215 or Murine Li(Full Length) Fused to OVA The activity of truncated mli was also evaluated in vitro in terms of impact on MHC-I antigen presentation. The in vitro tests consisted of infection of bone marrow derived dendritic cells (BMDC) with Ad5 comprising OVA and individual mli fragments fused via an HA tag to OVA (mli(1-50)-OVA, mli(1-75)-OVA, mli(1-80)-OVA, mli(50-215)-OVA and mli(full length)-OVA), in the same orientation as outlined in Example 1.

Figure 4:
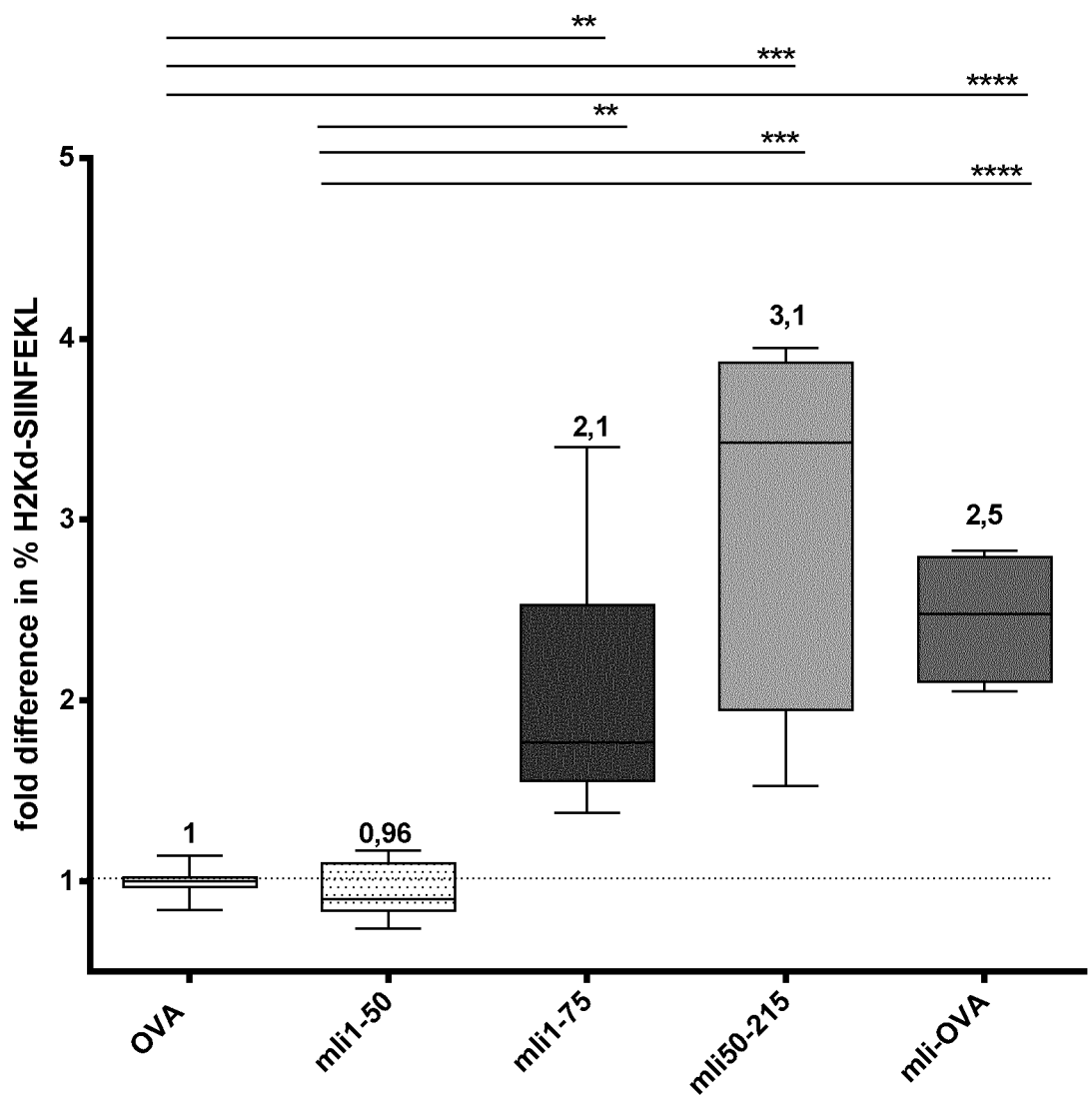
FIG. 4 Antigen presentation of ovalbumin peptide SIINFEKL in MHC class I 24 h after BMDC infection with Ad5 vectors encoding for mli full length or short sequences 1-50, 1-75 and 50-215 linked to OVA. Antigen presentation is expressed as the ratio of the % of $CD11^+/SIINFEKL^+$ cells after Ad5-mli and mli variants infection relative to Ad5-Ova control.
Figure 5:
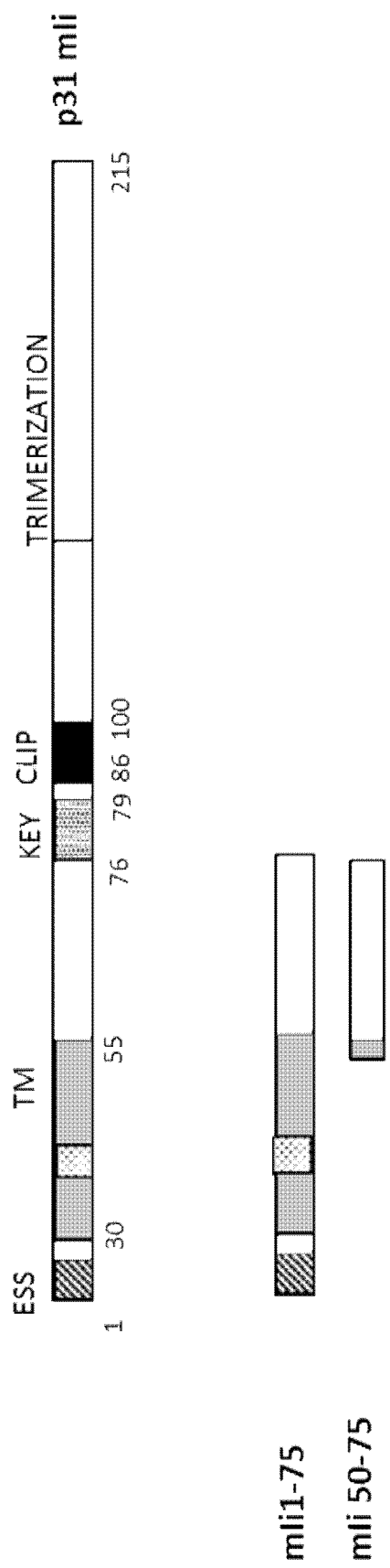
FIG. 5 Schematic diagram of mli(1-75) and mli(50-75) fused to OVA comprised in Ad5 constructs.

24 h post infection, cells were stained with a fluorescent monoclonal antibody recognizing the ovalbumin-derived peptide SIINFEKL (SEQ ID NO: 118) bound to H-2Kb of MHC-I and the level of antigen presentation was established by measuring the % of CD11$^+$/SIINFEKL$^+$ cells after infection with Ad5-mli(full length)-OVA and Ad5-mli(truncated)-OVA relative to Ad5-OVA control as shown in FIG. 4. The antibody specifically reacts with OVA-derived peptide SIINFEKL bound to H-2Kb of MHC class I, but not with unbound H-2Kb or H-2Kb bound with an irrelevant peptide. FIG. 4 therefore illustrates the fold difference of OVA presentation for mli(full length)-OVA or variants, compared with OVA. Statistical significance was determined by two-tailed unpaired parametric Student's t-test ($*p<0.05$, $p<0.01$, $*p<0.001$, $****p<0.001$). It was found that mli(1-75) and mli(50-215) both increased antigen presentation to a similar level to that of full length mli (labelled in FIG. 4 as "mli-OVA"). In contrast, mli(1-50) resulted in a lower level of antigen presentation, similar to that of OVA alone (labelled in FIG. 5 as "OVA"). Data is not shown in respect of mli(1-80)-OVA. mli(1-80)-OVA provided responses which were similar to mli(full length)-OVA.

Example 3: Preparation, In Vivo Immunogenicity and In Vitro Testing of Antigen Presentation of Murine Lit-75 or Li50-75 Fused to OVA Ad5 constructs comprising OVA were produced wherein OVA was fused to the C-terminus of fragments of murine p31 li sequences via an HA tag. The Ad5 constructs were E1E3E4 deleted with Ad5 E4ORF6 reinserted and included a variant of the HCMV promoter and a bovine growth hormone polyadenylation signal (BGHpolyA). Ad5 constructs comprising mli(1-75)-OVA and mli(50-75)-OVA were produced (see schematic diagram in FIG. 5).

Figure 6:
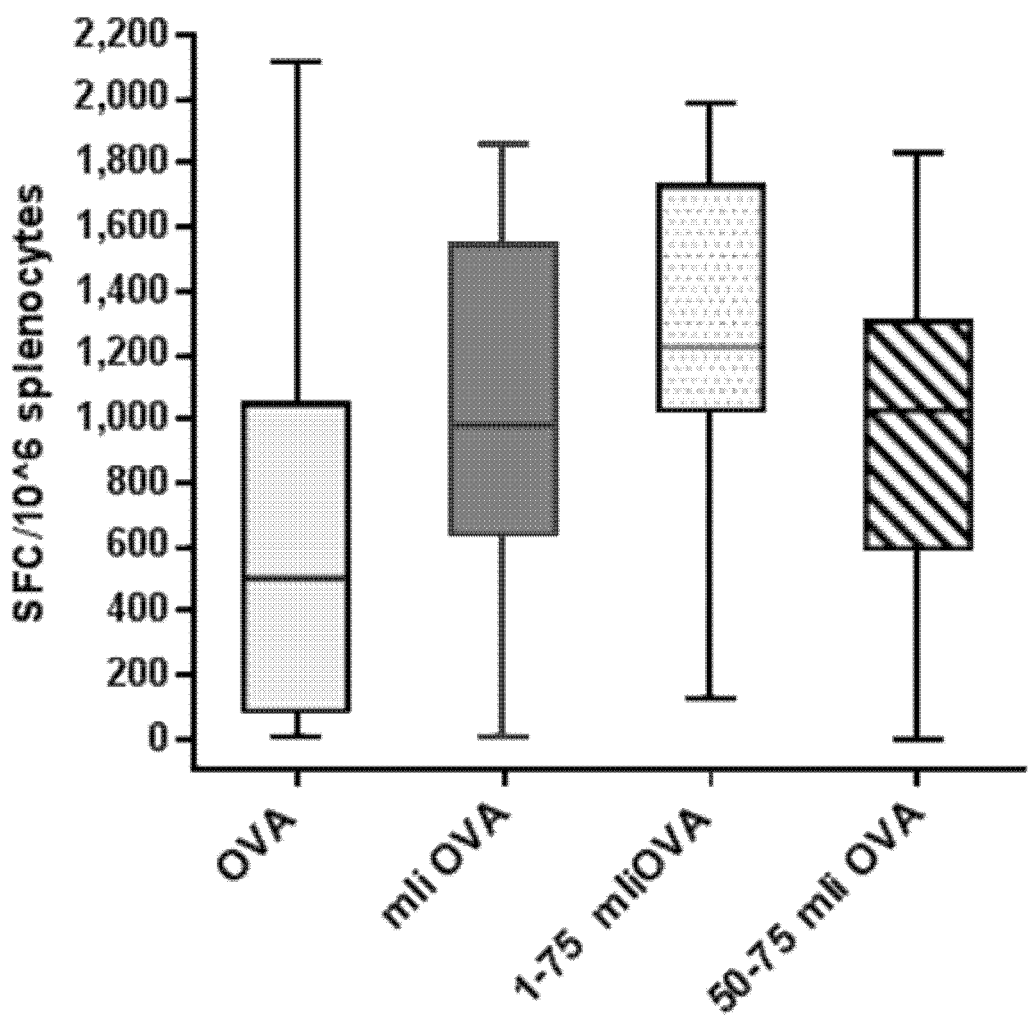
FIG. 6 Immune response (number of T cells producing IFN-γ per million splenocytes) elicited by murine li fragments 1-75 and 50-75 fused to OVA comprised in Ad5 constructs.

The immunological potency of the different constructs was evaluated by injecting female C57BL/6 mice with a single intramuscular dose of $10^6$ vp. Splenocytes were collected two weeks after injection and tested by IFN-γ ELISpot using as antigen the OVA 257-264 dominant CD8 peptide of SEQ ID NO: 118 (SIINFEKL, previously identified and mapped in C57BL/6 mice). The results are shown in FIG. 6, with responses expressed as number of T cells producing IFN-γ per million splenocytes. Boxes represent the distribution of data (first and third quartile), the lines within the boxes are the medians and the two whiskers for each box are the minimum and maximum values of the data.

The linkage of the mli full length sequence and mli1-75 to OVA antigen provided higher responses compared to unlinked Ad5-OVA, confirming the findings of Example 1. These data demonstrate that mli(50-75) is capable of increasing immunological responses to a level similar to that of full length mli and mli(1-75). mli(1-75) demonstrated the highest average response level.

The activity of truncated mli 50-75 was also evaluated in vitro in terms of impact on MHC-I antigen presentation as described before in Example 2. Bone marrow derived dendritic cells (BMDC) were infected with Ad5 comprising OVA and individual mli fragments fused via an HA tag to OVA (mli(1-75)-OVA and mli(50-75)-OVA). 24 h post infection, cells were stained with a fluorescent monoclonal antibody recognizing the ovalbumin-derived peptide SIINFEKL (SEQ ID NO: 118) bound to H-2Kb of MHC-I and the level of antigen presentation is shown in FIG. 7 as % of CD11$^+$/SIINFEKL$^+$ relative to Ad5-OVA control.

FIG. 7 therefore illustrates the fold difference of OVA presentation for mli(1-75)-OVA or mli(50-75)-OVA variants, compared with OVA. Statistical significance was determined by two-tailed unpaired Student's t-test ($*p<0.05$, $****p<0,0001$). It was found that mli(1-75) and mli(50-75) increased antigen presentation relative to that of OVA alone (labelled as "OVA").

The observations in respect of mli(50-75) made in this example by in vivo and in vitro testing are surprising, as mli(50-75) (which corresponds to hli(67-92)) is a particularly short fragment of invariant chain, not only lacking the trimerisation region, the KEY and the CLIP regions of li (as is the case for mli(1-75)), but also lacking all residues N-terminal to residue 50, which includes the endolysosomal sorting sequence ("ESS").

Example 4: Preparation and In Vivo Testing of Immunogenicity in a Range of Human Li Fragments Fused to MAGE A3

PanAd3 constructs comprising melanoma-associated antigen 3 ("MAGE A3", SEQ ID NO: 4) alone and comprising fusions of hli(full length)-MAGE A3, hli(1-97)-MAGE A3 and hli(17-97)-MAGE A3 were produced wherein MAGE A3 was fused to the C-terminus of the full length human p35 li (hli) or fragment thereof. The PanAd3 constructs were E1E4 deleted with Ad5 E4ORF6 inserted. hli(17-97) is the region of hli which is analogous to mli(1-80), while hli(1-97) further comprises an additional 16 residues (an ER retention sequence) at the N-terminus due to an alternative initiation of translation (see FIGS. 1 and 12).

Figure 8:
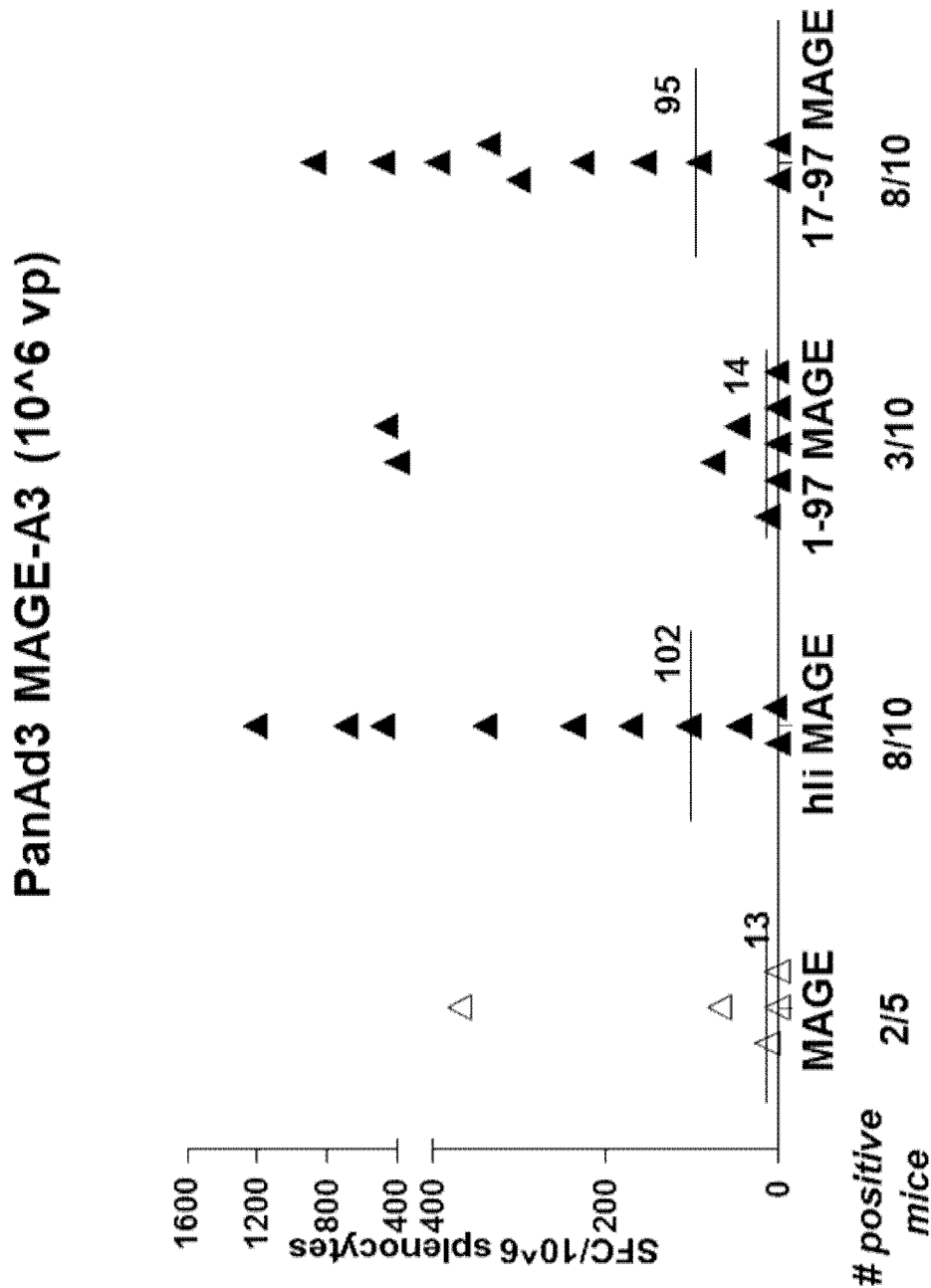
FIG. 8 Immune response (number of T cells producing IFN-γ per million splenocytes) elicited by PanAd3 constructs comprising MAGE A3 alone and comprising fusions of hli(full length)-MAGE A3, hli(1-97)-MAGE A3 and hli(17-97)-MAGE A3.

Immunogenicity of these constructs was evaluated in CB6F1 mice after a single intramuscular immunisation at a dose of $10^6$ vp. Splenocytes were collected two weeks after immunisation and tested by IFN-γ ELISpot using as antigen the MAGE A3 dominant CD8 peptide. The results are shown in FIG. 8, wherein immunisation with PanAd3 comprising MAGE A3 alone is labelled "MAGE", PanAd3 comprising full length hli fused to MAGE A3 is labelled 'hli MAGE' and PanAd3 comprising hli fragments fused to MAGE A3 are labelled "1-97 MAGE and 17-97 MAGE". Responses are expressed as number of T cells producing IFN-γ per millions of splenocytes.

It can be seen from FIG. 8 that hli(1-97) (which contains the ER retention sequence) provided a lower adjuvant effect than that of full length hli, but hli(17-97) induced a T cell response comparable to full length hli. The findings in respect of hli(17-97) were further confirmed in an independent repeat experiment (not shown).

Example 5: Preparation and In Vivo Testing of Immunogenicity in a Range of Human Li Fragments Fused to HCV-NS ChAd3 constructs comprising hepatitis C virus non-structural protein ("HCV-NS", SEQ ID NO: 117) alone and comprising fusions of hli(full length)-HCV-NS, hli(1-97)-HCV-NS and hli(17-97)-HCV-NS were produced, wherein HCV-NS was fused to the C-terminus of the full length human p35 li (hli) or fragment thereof. The ChAd3 constructs were E1 E3E4 deleted with Ad5 E4ORF6 inserted.

Immunogenicity of these constructs was evaluated in outbred CD1 mice after a single intramuscular immunization at dose of $10^8$ vp. Splenocytes were collected two weeks after immunisation and tested by IFN-γ ELISpot using as antigen peptide pools covering the entire NS sequence (FIG. 9).

Figure 9:
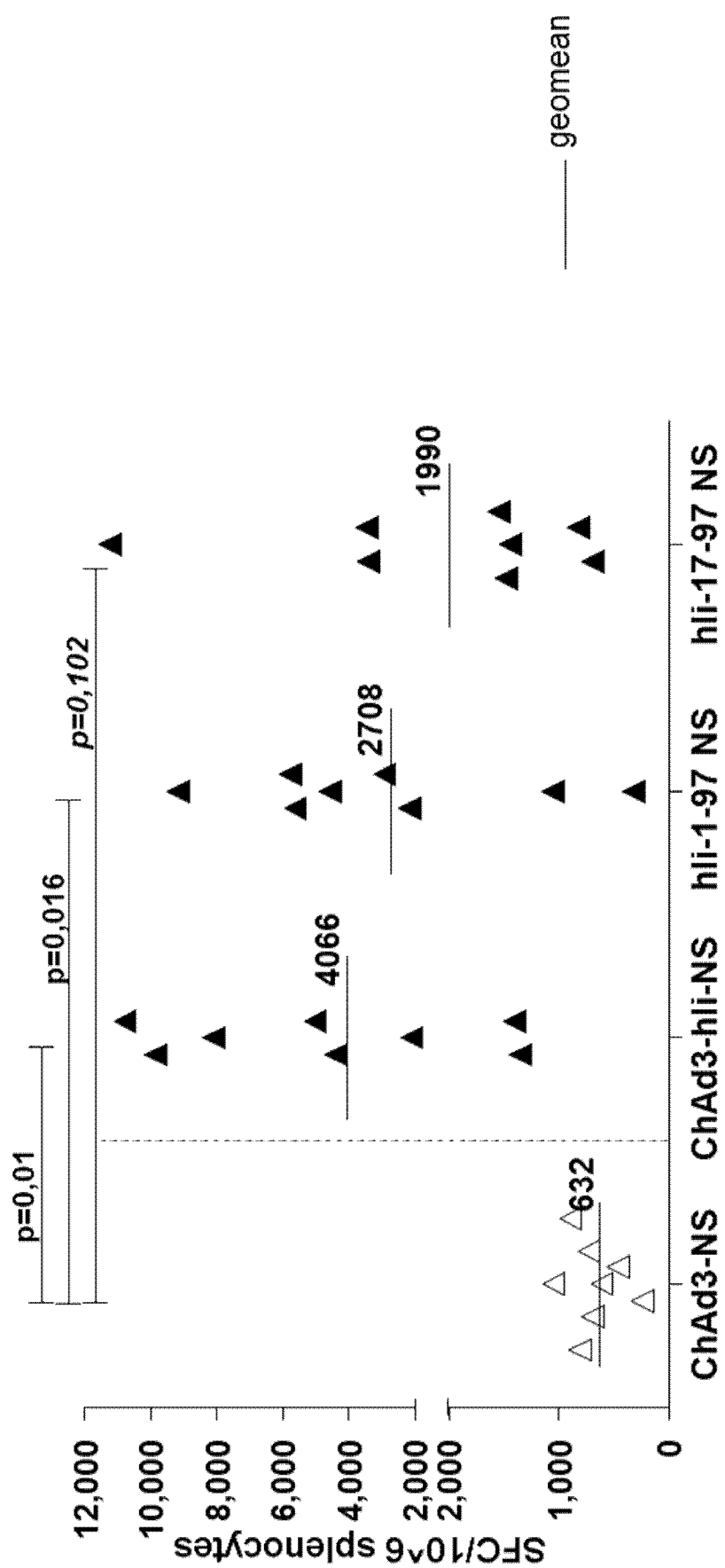
FIG. 9 Immune response (number of T cells producing IFN-γ per million splenocytes) elicited by ChAd3 constructs comprising HCV-NS alone and comprising fusions of hli (full length)-HCV-NS, hli(1-97)-HCV-NS and hli(17-97)-HCV-NS.

It can be seen from FIG. 9 that hli(full length)-HCV-NS, hli(1-97)-HCV-NS and hli(17-97)-HCV-NS all produced higher average responses than HCV-NS.

Example 6: Targeting of the Li-Antigen to the Proteasome Via the Ubiquitin Signal In order to characterize the molecular mechanism/pathway of li responsible of augmented antigen presentation, the effect of li linkage on antigen processing in the presence of the proteasome inhibitor MG-132 was investigated. Protein degradation through the proteasome, a key step for the class I antigen processing, is a highly specific process which requires as a crucial event the covalent attachment of one or more ubiquitin molecules to the protein to be degraded.

To address whether ubiquitination facilitates li-OVA degradation via the proteasome, two experiments were carried out. In the first experiment, HeLa cells were transiently transfected with a plasmid expressing ubiquitin and then infected with 50 MOI of Ad5-mli(full length)-OVA, Ad5-mli(1-75)-OVA and Ad5-mli(1-50)-OVA in the absence or presence of 10 uM MG-132. Cell extracts were immunoprecipitated with an anti-Lys48 antibody followed by western blot with anti-HA tag antibody. A mock sample corresponding to uninfected cells was used as control. In the second experiment, the same procedure was carried out but using Ad5-OVA, Ad5-mli(full length)-OVA, Ad5-mli(1-75)-OVA and Ad5-mli(50-75)-OVA.

Figure 10A:
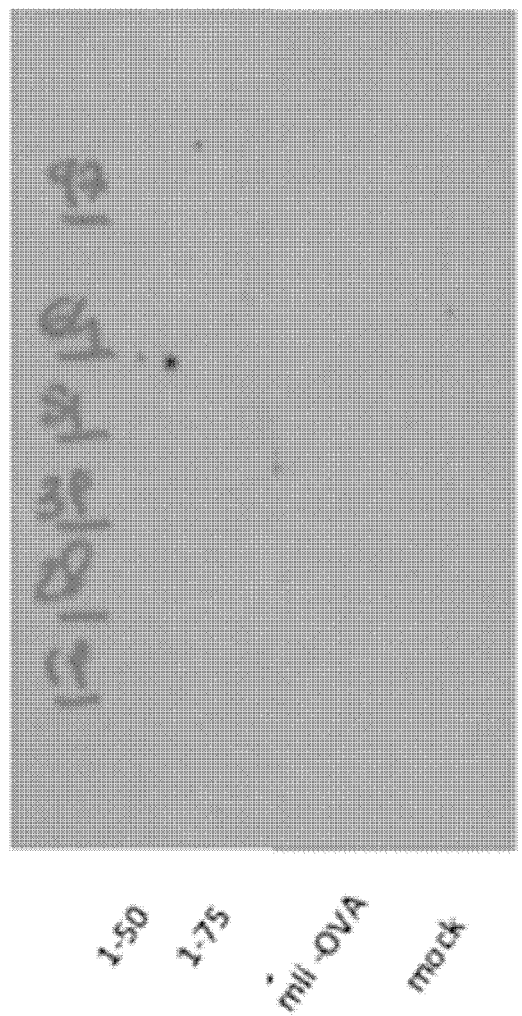
FIG. 10A-10B Western blots demonstrating targeting of the li-antigen to the proteasome via the ubiquitin signal using mli sequences 1-75 and 1-50 linked to OVA comprised in Ad5 constructs.
Figure 10B:
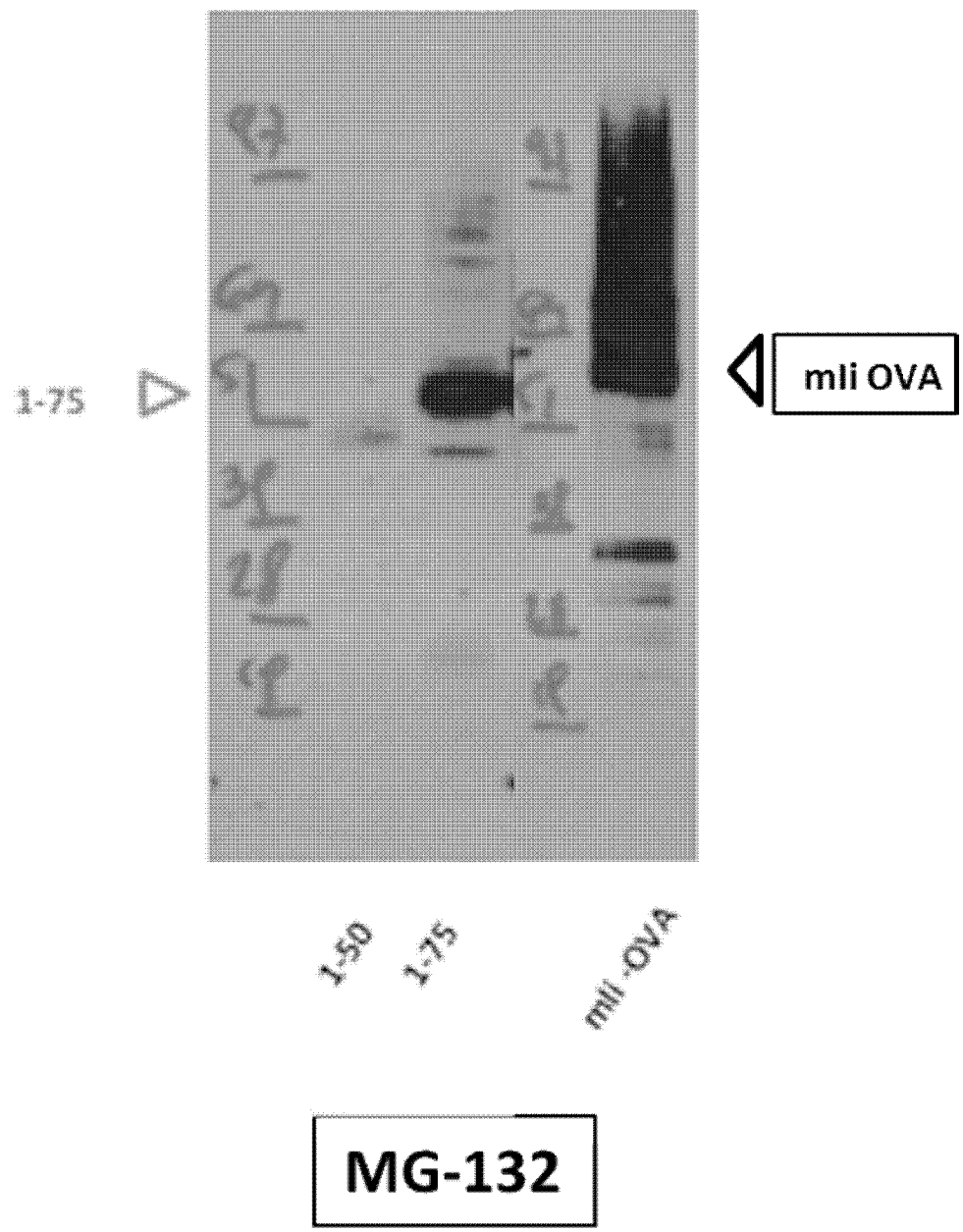
Figure 11:
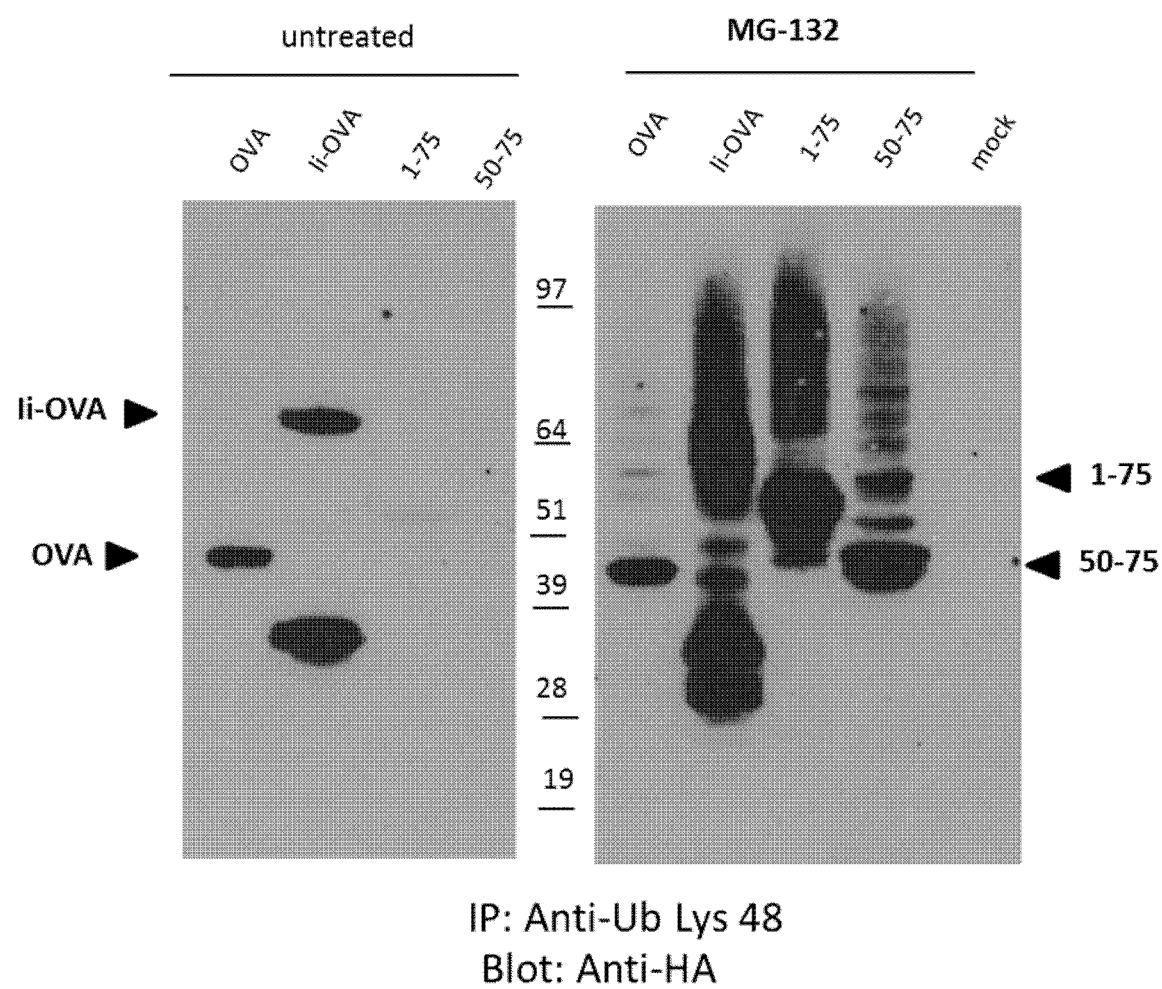
FIG. 11 Western blots demonstrating targeting of the li-antigen to the proteasome via the ubiquitin signal using mli full length or short sequences 1-75 and 50-75 linked to OVA comprised in Ad5 constructs.

The results of the first experiment are shown in FIG. 10 and the results of the second experiment are shown in FIG. 11. The results revealed the presence and accumulation of poly-ubiquitinated li-OVA post proteasome inhibition for Ad5-mli(full length)-OVA, Ad5-mli(1-75)-OVA and Ad5-mli(50-75)-OVA (FIG. 11). Thus, linkage of this antigen to full length mli, mli(1-75) and mli(50-75) causes poly-ubiquitination of the antigen that can be detected by blocking the proteasome. This poly-ubiquitination phenomenon does not occur with mli(1-50) (FIG. 10).

These results suggest that in the presence of full length mli, mli(1-75) and mli(50-75), the antigen is more efficiently processed through the proteasome generating a larger amount of antigenic peptides that are proficiently presented by MHC class I on dendritic cells. These same fragments are highly effective in enhancing antigen immunogenicity in vivo. However, this effect was not observed with the mli(1-50) fragment (i.e. an li fragment which is ineffective in enhancing antigen immunogenicity in vivo).

Example 7: Preparation and In Vivo Immunogenicity Testing of Smaller Murine Li Fragments Fused to OVA It was established in Example 3 that the mli(50-75) fragment (which corresponds to hli(67-92)) is capable of increasing immunological responses to a level similar to that of full length mli and mli(1-75). In this example, Ad5 vectors encoding further trimmed fragments of murine p31 li (mli) fused to ovalbumin antigen (OVA) were generated and their immunogenicity was tested in mice after a single immunization.

Ad5 constructs comprising the following were generated: mli(28-75)-OVA, mli(55-75)-OVA and mli(60-75)-OVA. The mli(28-75)-OVA construct was included to investigate the effect of including the transmembrane domain (TM). These new constructs were compared with Ad5 constructs comprising OVA alone, mli(full length)-OVA and mli(50-75)-OVA (FIG. 15, OVA alone and mli(full length)-OVA not shown). The Ad5 constructs used in this example were as described in Example 3 (E1E3E4 deleted with Ad5 E4ORF6 reinserted and included a variant of the HCMV promoter and a bovine growth hormone polyadenylation signal (BGH-polyA)).

The immunological potency of the different constructs was evaluated in C57BL/6 mice after a single intramuscular dose of $10^6$ viral particles (vp). Splenocytes were collected two weeks after injection and tested by IFN-γ ELISpot using as antigen the OVA 257-264 dominant CD8 peptide SIN- FEKL (SEQ ID NO: 118, previously identified and mapped in C57BL/6 mice). The median ELISpot responses are shown in Table 2.

TABLE 2 median ELISpot responses

| | OVA | mli | mli (50-75) | mli (28-75) | mli (55-75) | mli (60-75) |
|---|---|---|---|---|---|---|
| median | 451 | 1379 | 1604 | 1938 | 1392 | 1898 |

Figure 16:
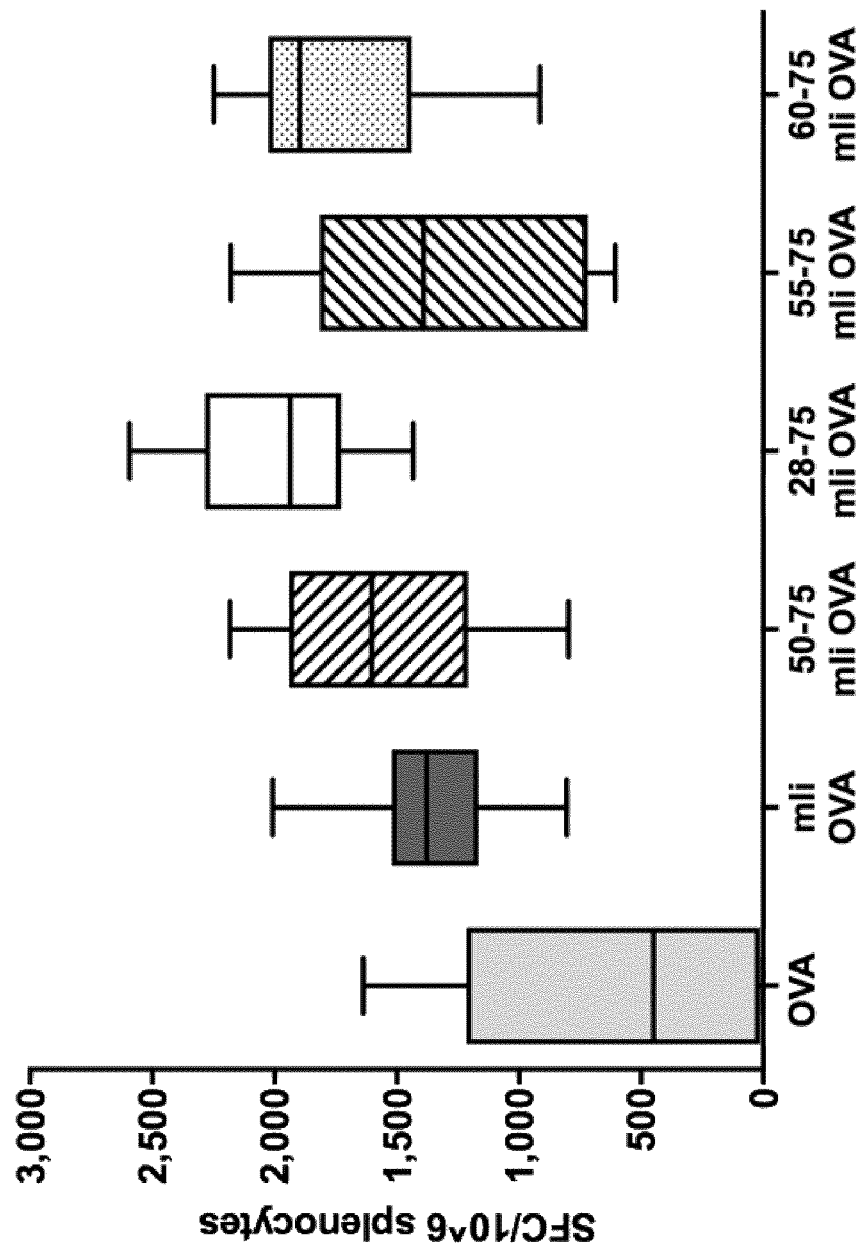
FIG. 16 Immune response (number of T cells producing IFN-γ per million splenocytes) elicited by mli(50-75), mli (28-75), mli(55-75) and mli(60-75) fused to OVA comprised in Ad5 constructs.

It was found that the linkage of these mli fragments (28-75, 55-75 and 60-75) to OVA antigen provided significantly ($p<0.05$) higher responses in comparison to the unlinked OVA vector. In particular, it is noteworthy that even the 16 amino acid long fragment mli-60-75 appears to be capable of providing adjuvant effect comparable to, or even higher than, that of mli(full length) or mli(50-75) (FIG. 16). Boxes represent the distribution of data (first and third quartile), the lines within the boxes are the medians and the two whiskers for each box are the minimum and maximum values of the data.

mli55-75 corresponds to hli(72-92) and mli60-75 corresponds to hli(77-92).

Figure 15:
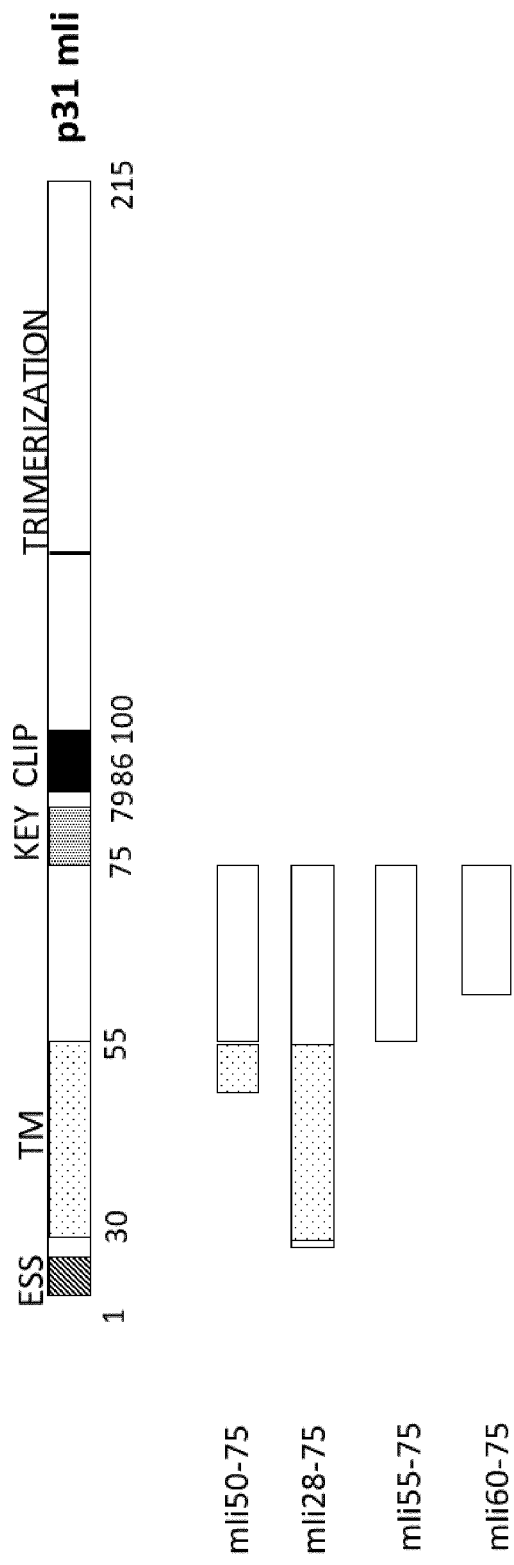
FIG. 15 Schematic diagram of mli(50-75), mli(28-75), mli(55-75) and mli(60-75) fused to OVA comprised in Ad5 constructs.

As also discussed under Examples 1 and 2, the immunogenicity enhancement provided by mli(55-75) and mli(60-75) is particularly surprising given that these short regions of invariant chain contain no known functional domains (see FIG. 15).

Example 8: Preparation and In Vivo Immunogenicity Testing of Mutated Murine Li and Murine Li Fragments Fused to OVA Ad5 constructs comprising the following mutated murine li and murine li fragments were generated: mli(full length) LLLmut-OVA, mli(full length)K63R-OVA and mli(1-75) K63R-OVA.

In mli(full length)LLLmut (SEQ ID NO: 135), the three amino acids LLL in positions 42, 43 and 44 of full length p31 mli were each mutated to A while in each of mli(full length)K63R (SEQ ID NO: 136) and mli(1-75)K63R (SEQ ID NO: 137), K at position 63 of full length p31 mli was mutated to R. These new constructs were compared with Ad5 constructs comprising OVA alone, mli(full length)-OVA and mli(1-75)-OVA. The Ad5 constructs used in this example were as described in Example 3 (E1 E3E4 deleted with Ad5 E4ORF6 reinserted and included a variant of the HCMV promoter and a bovine growth hormone polyadenylation signal (BGHpolyA)).

The immunological potency of the different Ad5-mli mutated constructs was evaluated in C57BL/6 mice after a single intramuscular dose of $10^6$ viral particles. Splenocytes were collected two weeks after injection and tested by IFN-γ ELISpot using as antigen the OVA 257-264 dominant CD8 peptide SIINFEKL (SEQ ID NO: 118, previously identified and mapped in C57BL/6 mice).

Figure 17:
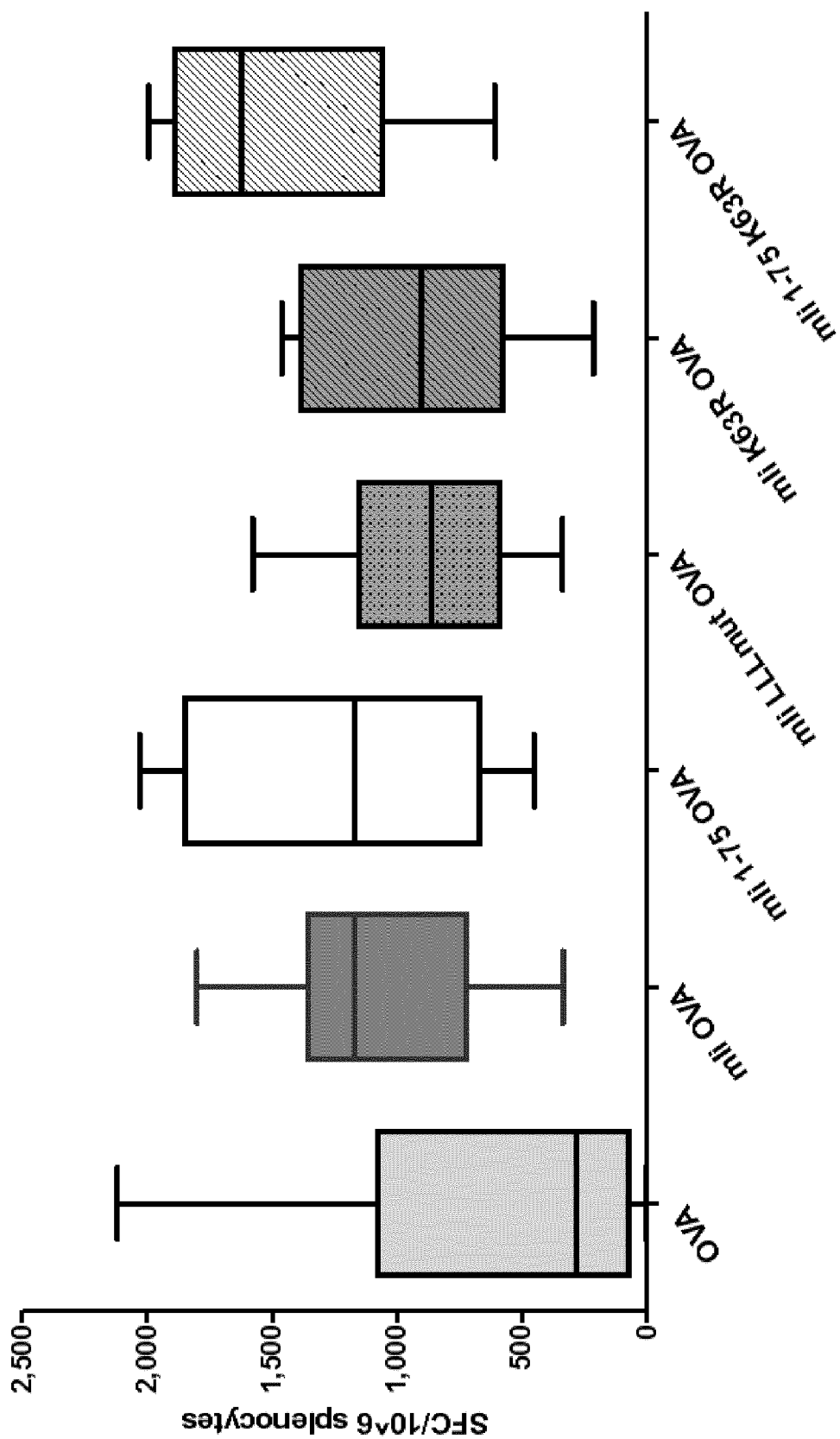
FIG. 17 Immune response (number of T cells producing IFN-γ per million splenocytes) elicited by mutated full length and mutated fragments of invariant chain fused to OVA comprised in Ad5 constructs.

The results are shown in FIG. 17. Boxes represent the distribution of data (first and third quartile), the lines within the boxes are the medians and the two whiskers for each box are the minimum and maximum values of the data. It was found that mutation of 63K to 63R did not substantially affect the adjuvant activity of either full length li nor the 1-75 li fragment. Similarly, no impact was seen due to the mutation of LLL at positions 42, 43 and 44 to AAA.

REFERENCES

Altschul et al., *Nuc. Acids Res.* 25:3389-3402 (1977)
Altschul et al., *J. Mol. Biol.* 215:403-410 (1990)
Ausubel et al., *Current Protocols in Molecular Biology* eds. 1995 supplement
Becker et al., *Methods Cell Biol.* 43(A):161-189 (1994)
Brazolot-Millan et al., *Proc. Natl. Acad. Sci., USA*, 95:15553-8 (1998)
Boshart et al., *Cell*, 41:521-530 (1985)
Colloca et al., *Sci. Transl. Med.* 4:1-9 (2012)
Davis et al., *J. Immunol*, 160:870-876 (1998)
Devereaux et al., *Nuc. Acids Res.* 12:387-395 (1984)
Diebold et al., *Gene Ther.* 8: 487-493 (2001)
Feng & Doolittle, *J. Mol. Evol.* 35:351-360 (1987)
Henikoff & Henikoff, *Proc. Natl. Acad. Sci. USA* 89:10915 (1989)
Higgins & Sharp, *CABIOS* 5:151-153 (1989)
Hilgers et al., *Int. Arch. Allergy. Immunol.* 79(4):392-6 (1986)
Hilgers et al., *Immunology*, 60(1):141-6 (1987)
Holmes et al., *Journal of Clinical Oncology* 26(20):3426-3433 (2008)
Holst et al., *Journal of Immunology* 180(5):3339-3346 (2008)
Kallinteris et al., *Expert Opinion Biol Ther* 6(12):1311-1321 (2006)
Karlin & Altschul, *Proc. Nat'l. Acad. Sci. USA* 90:5873-5787 (1993)
Leuenberger, H. G. W, Nagel, B. and Klbl, H. eds. (1995), Helvetica Chimica Acta, CH-4010 Basel, Switzerland
Kensil et al., *J. Immunology*, 146:431-437 (1991)
Kensil, *Crit. Rev. Ther. Drug Carrier Syst.*, 12:1-55 (1996)
Krieg, *Nature* 374:546-549 (1995)
Lacaille-Dubois, M and Wagner H, *Phytomedicine* 2:363-386 (1996)
Martin, E. W. "Remington's Pharmaceutical Sciences"
Mayr, A., Hochstein-Mintzel, V. & Stickl, H. *Infection* 3, 6-14 (1975)
Mayr A, Stickl H, Müller H K, Danner K, Singer H. Zentralbl Bakteriol B. 167(5-6):375-90 (1978)
McCluskie and Davis, *J. Immunol.*, 161:4463-4466 (1998)
Mittendorf et al., *Expert Opin. Biol. Ther.*, 9:71-78 (2009)
Morris et al., *Immunol. Res.*, 30: 171-179 (2004)
Needleman & Wunsch, *J. Mol. Biol.* 48:443 (1970)
Pearson & Lipman, *Proc. Nat'l. Acad. Sci. USA* 85:2444 (1988)
Pieters *J. Curr. Opin. Immunol.*, 9: 8996 (1997)
Roy et al., *Virol.* 324:361-372 (2004)
Roy et al., *J. of Gene Med.* 13:17-25 (2010)
Smith & Waterman, *Adv. Appl. Math.* 2:482-489 (1981)
Strubin et al., *EMBO Journal*, 5:3483-3488 (1986)
Strumptner-Cuvelette and Benaroch, *Biochem. Biophys. Acta*, 1542:1-13 (2002)
Tatsis and Ertl *Molecular Therapy* 10:616-629 (2004)
Tatsis and Hildegund, *Molecular Therapy* 10:616-629 (2004)
Walchli et al., *Eur J Immunol.* 44(3):774-784 (2014)

The invention claimed is:

1. A fusion protein, comprising a polypeptide, wherein the polypeptide consists of a fragment of an invariant chain which is operably linked to an antigenic sequence, and wherein the fragment of invariant chain consists of:
   (a) a portion of residues 17-97 of SEQ ID NO: 1, wherein the portion must have at least 5 contiguous residues from residues 77-92 of SEQ ID NO: 1;
   (b) a sequence of 80 residues or fewer and wherein at least 5 contiguous residues of the sequence share at least 80% identity with at least 5 contiguous residues from residues 77-92 of SEQ ID NO: 1;
   (c) residues 1-97 of SEQ ID NO: 1;
   (d) 91 to 103 residues and shares at least 95% identity with residues 1-97 of SEQ ID NO: 1;
   (e) residues 17-97 of SEQ ID NO: 1;
   (f) 76 to 84 residues and shares at least 95% identity with residues 17-97 of SEQ ID NO: 1;
   (g) residues 1-92 of SEQ ID NO: 1;
   (h) 88 to 96 residues and shares at least 95% identity with residues 1-92 of SEQ ID NO: 1;
   (i) residues 17-92 of SEQ ID NO: 1; or
   (j) 71 to 79 residues and shares at least 95% identity with residues 17-92 of SEQ ID NO: 1.

2. A polynucleotide encoding a fusion protein, which comprises a polypeptide, wherein the polypeptide consists of a fragment of an invariant chain which is operably linked to an antigenic sequence, and wherein the fragment of invariant chain consists of:
   (a) a portion of residues 17-97 of SEQ ID NO: 1, wherein the portion must have at least 5 contiguous residues from residues 77-92 of SEQ ID NO: 1;
   (b) a sequence of 80 residues or fewer and wherein at least 5 contiguous residues of the sequence share at least 80% identity with at least 5 contiguous residues from residues 77-92 of SEQ ID NO: 1;
   (c) residues 1-97 of SEQ ID NO: 1;
   (d) 91 to 103 residues and shares at least 95% identity with residues 1-97 of SEQ ID NO: 1;
   (e) residues 17-97 of SEQ ID NO: 1;
   (f) 76 to 84 residues and shares at least 95% identity with residues 17-97 of SEQ ID NO: 1;
   (g) residues 1-92 of SEQ ID NO: 1;
   (h) 88 to 96 residues and shares at least 95% identity with residues 1-92 of SEQ ID NO: 1;
   (i) residues 17-92 of SEQ ID NO: 1; or
   (j) 71 to 79 residues and shares at least 95% identity with residues 17-92 of SEQ ID NO: 1.

3. A viral vector, comprising a polynucleotide encoding a fusion protein, which comprises a polypeptide, wherein the polypeptide consists of a fragment of invariant chain which is operably linked to an antigenic sequence and wherein the fragment of invariant chain consists of:
   (a) a portion of residues 17-97 of SEQ ID NO: 1, wherein the portion must have at least 5 contiguous residues from residues 77-92 of SEQ ID NO: 1;
   (b) a sequence of 80 residues or fewer and wherein at least 5 contiguous residues of the sequence share at least 80% identity with at least 5 contiguous residues from residues 77-92 of SEQ ID NO: 1;
   (c) residues 1-97 of SEQ ID NO: 1;
   (d) 91 to 103 residues and shares at least 95% identity with residues 1-97 of SEQ ID NO: 1;
   (e) residues 17-97 of SEQ ID NO: 1;
   (f) 76 to 84 residues and shares at least 95% identity with residues 17-97 of SEQ ID NO: 1;
   (g) residues 1-92 of SEQ ID NO: 1;
   (h) 88 to 96 residues and shares at least 95% identity with residues 1-92 of SEQ ID NO: 1;
   (i) residues 17-92 of SEQ ID NO: 1; or
   (j) 71 to 79 residues and shares at least 95% identity with residues 17-92 of SEQ ID NO: 1.

4. The viral vector according to claim 3, wherein the fragment of invariant chain consists of a portion of residues 17-97 of SEQ ID NO: 1, wherein the portion must have at least 5 contiguous residues from residues 77-92 of SEQ ID NO: 1.

5. The viral vector according to claim 4, wherein the portion must have at least 8 contiguous residues from residues 77-92 of SEQ ID NO: 1.

6. The viral vector according to claim 5, wherein the portion must have at least 12 contiguous residues from residues 77-92 of SEQ ID NO: 1.

7. The viral vector according to claim 3, wherein the fragment of invariant chain consists of a sequence of 80 residues or fewer and, wherein at least 5 contiguous residues of the sequence share at least 80% identity with at least 5 contiguous residues from residues 77-92 of SEQ ID NO: 1.

8. The viral vector according claim 7, wherein the fragment of invariant chain consists of a sequence of 80 residues or fewer and, wherein at least 5 contiguous residues of the sequence are from residues 77-92 of SEQ ID NO: 1.

9. The viral vector according to claim 3, wherein the fragment of invariant chain must have at least 7 contiguous residues which share at least 80% identity with at least 7 contiguous residues from residues 77-92 of SEQ ID NO: 1.

10. The viral vector according to claim 9, wherein the fragment of invariant chain must have at least 7 contiguous residues which share at least 90% identity with at least 7 contiguous residues from residues 77-92 of SEQ ID NO: 1.

11. The viral vector according to claim 10, wherein the fragment of invariant chain must have at least 7 contiguous residues from residues 77-92 of SEQ ID NO: 1.

12. The viral vector according to claim 3, wherein the fragment of invariant chain must have at least 9 contiguous residues which share at least 80% identity with at least 9 contiguous residues from residues 77-92 of SEQ ID NO: 1.

13. The viral vector according to claim 12, wherein the fragment of invariant chain must have at least 9 contiguous residues which share at least 90% identity with at least 9 contiguous residues from residues 77-92 of SEQ ID NO: 1.

14. The viral vector according to claim 13, wherein the fragment of invariant chain must have at least 9 contiguous residues from residues 77-92 of SEQ ID NO: 1.

15. The fusion protein according to claim 1, wherein the polypeptide consists of a fragment of invariant chain which is operably linked to an antigenic sequence, and wherein the fragment of invariant chain consists of:
 (a) a portion of residues 17-97 of SEQ ID NO: 1, wherein the portion must have at least 10 contiguous residues from residues 67-92 of SEQ ID NO: 1;
 (b) a sequence of 80 residues or fewer and wherein at least 10 contiguous residues of the sequence share at least 80% identity with at least 10 contiguous residues from residues 67-92 of SEQ ID NO: 1;
 (c) residues 1-97 of SEQ ID NO: 1;
 (d) 91 to 103 residues and shares at least 95% identity with residues 1-97 of SEQ ID NO: 1;
 (e) residues 17-97 of SEQ ID NO: 1;
 (f) 76 to 84 residues and shares at least 95% identity with residues 17-97 of SEQ ID NO: 1;
 (g) residues 1-92 of SEQ ID NO: 1;
 (h) 88 to 96 residues and shares at least 95% identity with residues 1-92 of SEQ ID NO: 1;
 (i) residues 17-92 of SEQ ID NO: 1; or
 (j) 71 to 79 residues and shares at least 95% identity with residues 17-92 of SEQ ID NO: 1.

16. The polynucleotide according to claim 2, wherein the polypeptide consists of a fragment of invariant chain which is operably linked to an antigenic sequence, and wherein the fragment of invariant chain consists of:
 (a) a portion of residues 17-97 of SEQ ID NO: 1, wherein the portion must have at least 10 contiguous residues from residues 67-92 of SEQ ID NO: 1;
 (b) a sequence of 80 residues or fewer and wherein at least 10 contiguous residues of the sequence share at least 80% identity with at least 10 contiguous residues from residues 67-92 of SEQ ID NO: 1;
 (c) residues 1-97 of SEQ ID NO: 1;
 (d) 91 to 103 residues and shares at least 95% identity with residues 1-97 of SEQ ID NO: 1;
 (e) residues 17-97 of SEQ ID NO: 1;
 (f) 76 to 84 residues and shares at least 95% identity with residues 17-97 of SEQ ID NO: 1;
 (g) residues 1-92 of SEQ ID NO: 1;
 (h) 88 to 96 residues and shares at least 95% identity with residues 1-92 of SEQ ID NO: 1;
 (i) residues 17-92 of SEQ ID NO: 1; or
 (j) 71 to 79 residues and shares at least 95% identity with residues 17-92 of SEQ ID NO: 1.

17. The viral vector according to claim 3, wherein the polypeptide consists of a fragment of invariant chain which is operably linked to an antigenic sequence, and wherein the fragment of invariant chain consists of:
 (a) a portion of residues 17-97 of SEQ ID NO: 1, wherein the portion must have at least 10 contiguous residues from residues 67-92 of SEQ ID NO: 1;
 (b) a sequence of 80 residues or fewer and wherein at least 10 contiguous residues of the sequence share at least 80% identity with at least 10 contiguous residues from residues 67-92 of SEQ ID NO: 1;
 (c) residues 1-97 of SEQ ID NO: 1;
 (d) 91 to 103 residues and shares at least 95% identity with residues 1-97 of SEQ ID NO: 1;
 (e) residues 17-97 of SEQ ID NO: 1;
 (f) 76 to 84 residues and shares at least 95% identity with residues 17-97 of SEQ ID NO: 1;
 (g) residues 1-92 of SEQ ID NO: 1;
 (h) 88 to 96 residues and shares at least 95% identity with residues 1-92 of SEQ ID NO: 1;
 (i) residues 17-92 of SEQ ID NO: 1; or
 (j) 71 to 79 residues and shares at least 95% identity with residues 17-92 of SEQ ID NO: 1.

18. The viral vector according to claim 3, wherein the antigenic sequence is an antigen derived from a hepatitis B or hepatitis C virus protein.

19. A method of treating or preventing hepatitis B viral infection or hepatitis C viral infection, comprising administering to a person in need thereof an effective amount of the viral vector according to claim 3.

* * * * *

SEQUENCE LISTING

<160> NUMBER OF SEQ ID NOS: 140

<210> SEQ ID NO 1
<211> LENGTH: 232
<212> TYPE: PRT
<213> ORGANISM: Homo sapiens
<220> FEATURE:
<221> NAME/KEY: Misc_feature
<223> OTHER INFORMATION: Amino acid sequence for human invariant chain
      isoform p35

<400> SEQUENCE: 1

Met His Arg Arg Arg Ser Arg Ser Cys Arg Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Ala Pro Glu Ser Lys Cys Ser Arg Gly Ala
        35                  40                  45

Leu Tyr Thr Gly Phe Ser Ile Leu Val Thr Leu Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Ser Gln Asn Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Leu Pro Gln Gly Pro Met
        115                 120                 125

Gln Asn Ala Thr Lys Tyr Gly Asn Met Thr Glu Asp His Val Met His
    130                 135                 140

Leu Leu Gln Asn Ala Asp Pro Leu Lys Val Tyr Pro Pro Leu Lys Gly
145                 150                 155                 160

Ser Phe Pro Glu Asn Leu Arg His Leu Lys Asn Thr Met Glu Thr Ile
                165                 170                 175

Asp Trp Lys Val Phe Glu Ser Trp Met His His Trp Leu Leu Phe Glu
            180                 185                 190

Met Ser Arg His Ser Leu Glu Gln Lys Pro Thr Asp Ala Pro Pro Lys
        195                 200                 205

Glu Ser Leu Glu Leu Glu Asp Pro Ser Ser Gly Leu Gly Val Thr Lys
    210                 215                 220

Gln Asp Leu Gly Pro Val Pro Met
225                 230

<210> SEQ ID NO 2
<211> LENGTH: 699
<212> TYPE: DNA
<213> ORGANISM: Homo sapiens
<220> FEATURE:
<221> NAME/KEY: Misc_feature
<223> OTHER INFORMATION: Nucleotide sequence encoding human invariant
      chain isoform p35

<400> SEQUENCE: 2
atgcacagga ggagaagcag gagctgtcgg gaagatcaga agccagtcat ggatgaccag     60
cgcgacctta tctccaacaa tgagcaactg cccatgctgg gccggcgccc tggggccccg    120
gagagcaagt gcagccgcgg agccctgtac acaggctttt ccatcctggt gactctgctc    180
ctcgctggcc aggccaccac cgcctacttc ctgtaccagc agcagggccg gctggacaaa    240

```
ctgacagtca cctcccagaa cctgcagctg gagaacctgc gcatgaagct tcccaagcct    300
cccaagcctg tgagcaagat gcgcatggcc accccgctgc tgatgcaggc gctgcccatg    360
ggagccctgc cccaggggcc catgcagaat gccaccaagt atggcaacat gacagaggac    420
catgtgatgc acctgctcca gaatgctgac cccctgaagg tgtacccgcc actgaagggg    480
agcttcccgg agaacctgag acaccttaag aacaccatgg agaccataga ctggaaggtc    540
tttgagagct ggatgcacca ttggctcctg tttgaaatga gcaggcactc cttggagcaa    600
aagcccactg acgctccacc gaaagagtca ctggaactgg aggaccgtc ttctgggctg    660 ggtgtgacca agcaggatct gggcccagtc cccatgtga                          699
```

```
<210> SEQ ID NO 3
<211> LENGTH: 216
<212> TYPE: PRT
<213> ORGANISM: Homo sapiens
<220> FEATURE:
<221> NAME/KEY: Misc_feature
<223> OTHER INFORMATION: Amino acid sequence for human invariant chain
      isoform p33

<400> SEQUENCE: 3
```

```
Met Asp Asp Gln Arg Asp Leu Ile Ser Asn Asn Glu Gln Leu Pro Met
1               5                   10                  15

Leu Gly Arg Arg Pro Gly Ala Pro Glu Ser Lys Cys Ser Arg Gly Ala
            20                  25                  30

Leu Tyr Thr Gly Phe Ser Ile Leu Val Thr Leu Leu Leu Ala Gly Gln
        35                  40                  45

Ala Thr Thr Ala Tyr Phe Leu Tyr Gln Gln Gln Gly Arg Leu Asp Lys
    50                  55                  60

Leu Thr Val Thr Ser Gln Asn Leu Gln Leu Glu Asn Leu Arg Met Lys
65                  70                  75                  80

Leu Pro Lys Pro Pro Lys Pro Val Ser Lys Met Arg Met Ala Thr Pro
                85                  90                  95

Leu Leu Met Gln Ala Leu Pro Met Gly Ala Leu Pro Gln Gly Pro Met
            100                 105                 110

Gln Asn Ala Thr Lys Tyr Gly Asn Met Thr Glu Asp His Val Met His
        115                 120                 125

Leu Leu Gln Asn Ala Asp Pro Leu Lys Val Tyr Pro Pro Leu Lys Gly
    130                 135                 140

Ser Phe Pro Glu Asn Leu Arg His Leu Lys Asn Thr Met Glu Thr Ile
145                 150                 155                 160

Asp Trp Lys Val Phe Glu Ser Trp Met His His Trp Leu Leu Phe Glu
                165                 170                 175

Met Ser Arg His Ser Leu Glu Gln Lys Pro Thr Asp Ala Pro Pro Lys
            180                 185                 190

Glu Ser Leu Glu Leu Glu Asp Pro Ser Ser Gly Leu Gly Val Thr Lys
        195                 200                 205

Gln Asp Leu Gly Pro Val Pro Met
    210                 215
```

```
<210> SEQ ID NO 4
<211> LENGTH: 951
<212> TYPE: DNA
<213> ORGANISM: Homo sapiens
<220> FEATURE:
<221> NAME/KEY: Misc_feature
<223> OTHER INFORMATION: Nucleotide sequence encoding the MAGE antigen
```

<400> SEQUENCE: 4

```
atgccctgg aacagcggag ccagcactgc aagcccgagg aaggcctgga agccagaggc    60
gaggctctgg gactcgtggg agcacaggcc cctgccaccg aggaacagga agccgccagc   120
agcagctcca ccctggtgga agtgaccctg ggcgaagtgc ctgccgccga gagccctgat   180
cctccccagt ctcctcaggg cgccagcagc ctgcccacca ccatgaacta cccctgtgg   240
tcccagagct acgaggacag cagcaaccag gaagaggaag ccccagcac cttccccgac   300
ctggaaagcg agttccaggc cgccctgagc cggaaggtgg ccgagctggt gcacttcctg   360
ctgctgaagt accgggccag agaacccgtg accaaggccg agatgctggg cagcgtcgtg   420
ggcaactggc agtacttctt ccccgtgatc ttctccaagg ccagcagctc cctgcagctg   480
gtgttcggca tcgagctgat ggaagtggac cccatcggcc acctgtacat cttcgccacc   540
tgtctgggcc tgagctacga cggcctgctg ggcgacaacc agatcatgcc caaggccggc   600
ctgctgatca tcgtgctggc catcattgcc cgcgagggcg actgcgcccc tgaggaaaag   660
atctgggagg aactgagcgt gctggaagtg ttcgagggca gagaggacag catcctgggc   720
gaccccaaga gctgctgac ccagcacttc gtgcaggaaa actacctcga gtacagacag   780
gtgcccggca gcgaccccgc tgctacgag tttctgtggg cccccagggc tctggtggaa   840
accagctacg tgaaggtgct gcaccacatg gtcaagatca gcggcggacc ccacatcagc   900
taccccccac tgcacgagtg ggtgctgcgg gaaggcgagg aatgatgatg a            951
```

<210> SEQ ID NO 5
<211> LENGTH: 296
<212> TYPE: PRT
<213> ORGANISM: Homo sapiens
<220> FEATURE:
<221> NAME/KEY: Misc_feature
<223> OTHER INFORMATION: Amino acid sequence for human invariant chain
      isoform p43

<400> SEQUENCE: 5

```
Met His Arg Arg Arg Ser Arg Ser Cys Arg Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Ala Pro Glu Ser Lys Cys Ser Arg Gly Ala
        35                  40                  45

Leu Tyr Thr Gly Phe Ser Ile Leu Val Thr Leu Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Ser Gln Asn Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Leu Pro Gln Gly Pro Met
        115                 120                 125

Gln Asn Ala Thr Lys Tyr Gly Asn Met Thr Glu Asp His Val Met His
    130                 135                 140

Leu Leu Gln Asn Ala Asp Pro Leu Lys Val Tyr Pro Pro Leu Lys Gly
145                 150                 155                 160

Ser Phe Pro Glu Asn Leu Arg His Leu Lys Asn Thr Met Glu Thr Ile
                165                 170                 175
```

Asp Trp Lys Val Phe Glu Ser Trp Met His His Trp Leu Leu Phe Glu
            180                 185                 190

Met Ser Arg His Ser Leu Glu Gln Lys Pro Thr Asp Ala Pro Pro Lys
            195                 200                 205

Val Leu Thr Lys Cys Gln Glu Glu Val Ser His Ile Pro Ala Val His
210                 215                 220

Pro Gly Ser Phe Arg Pro Lys Cys Asp Glu Asn Gly Asn Tyr Leu Pro
225                 230                 235                 240

Leu Gln Cys Tyr Gly Ser Ile Gly Tyr Cys Trp Cys Val Phe Pro Asn
                245                 250                 255

Gly Thr Glu Val Pro Asn Thr Arg Ser Arg Gly His His Asn Cys Ser
            260                 265                 270

Glu Ser Leu Glu Leu Glu Asp Pro Ser Ser Gly Leu Gly Val Thr Lys
            275                 280                 285

Gln Asp Leu Gly Pro Val Pro Met
            290                 295

```
<210> SEQ ID NO 6
<211> LENGTH: 891
<212> TYPE: DNA
<213> ORGANISM: Homo sapiens
<220> FEATURE:
<221> NAME/KEY: Misc_feature
<223> OTHER INFORMATION: Nucleotide sequence encoding human invariant
      chain isoform p43

<400> SEQUENCE: 6
atgcacagga ggagaagcag gagctgtcgg gaagatcaga agccagtcat ggatgaccag      60
cgcgacctta tctccaacaa tgagcaactg cccatgctgg gccggcgccc tggggccccg     120
gagagcaagt gcagccgcgg agccctgtac acaggctttt ccatcctggt gactctgctc     180
ctcgctggcc aggccaccac cgcctacttc ctgtaccagc agcagggccg gctggacaaa     240
ctgacagtca cctcccagaa cctgcagctg agaaacctgc gcatgaagct tcccaagcct     300
cccaagcctg tgagcaagat gcgcatggcc accccgctgc tgatgcaggc gctgcccatg     360
ggagccctgc cccaggggcc catgcagaat gccaccaagt atggcaacat gacagaggac     420
catgtgatgc acctgctcca gaatgctgac cccctgaagg tgtacccgcc actgaagggg     480
agcttcccgg agaacctgag acaccttaag aacaccatgg agaccataga ctggaaggtc     540
tttgagagct ggatgcacca ttggctcctg tttgaaatga gcaggcactc cttggagcaa     600
aagcccactg acgctccacc gaaagtactg accaagtgcc aggaagaggt cagccacatc     660
cctgctgtcc acccgggttc attcaggccc aagtgcgacg agaacggcaa ctatctgcca     720
ctccagtgct atgggagcat cggctactgc tggtgtgtct tccccaacgg cacgaggtc     780 cccaacacca agcgcggg gcaccataac tgcagtgagt cactggaact ggaggacccg     840
tcttctgggc tgggtgtgac caagcaggat ctgggcccag tccccatgtg a             891

<210> SEQ ID NO 7
<211> LENGTH: 280
<212> TYPE: PRT
<213> ORGANISM: Homo sapiens
<220> FEATURE:
<221> NAME/KEY: Misc_feature
<223> OTHER INFORMATION: Amino acid sequence for human invariant chain
      isoform p41

<400> SEQUENCE: 7
```

Met Asp Asp Gln Arg Asp Leu Ile Ser Asn Asn Glu Gln Leu Pro Met

-continued

```
1               5                   10                  15
Leu Gly Arg Arg Pro Gly Ala Pro Glu Ser Lys Cys Ser Arg Gly Ala
                20                  25                  30
Leu Tyr Thr Gly Phe Ser Ile Leu Val Thr Leu Leu Leu Ala Gly Gln
                35                  40                  45
Ala Thr Thr Ala Tyr Phe Leu Tyr Gln Gln Gln Gly Arg Leu Asp Lys
                50                  55                  60
Leu Thr Val Thr Ser Gln Asn Leu Gln Leu Glu Asn Leu Arg Met Lys
65                  70                  75                  80
Leu Pro Lys Pro Pro Lys Pro Val Ser Lys Met Arg Met Ala Thr Pro
                85                  90                  95
Leu Leu Met Gln Ala Leu Pro Met Gly Ala Leu Pro Gln Gly Pro Met
                100                 105                 110
Gln Asn Ala Thr Lys Tyr Gly Asn Met Thr Glu Asp His Val Met His
                115                 120                 125
Leu Leu Gln Asn Ala Asp Pro Leu Lys Val Tyr Pro Pro Leu Lys Gly
                130                 135                 140
Ser Phe Pro Glu Asn Leu Arg His Leu Lys Asn Thr Met Glu Thr Ile
145                 150                 155                 160
Asp Trp Lys Val Phe Glu Ser Trp Met His His Trp Leu Leu Phe Glu
                165                 170                 175
Met Ser Arg His Ser Leu Glu Gln Lys Pro Thr Asp Ala Pro Pro Lys
                180                 185                 190
Val Leu Thr Lys Cys Gln Glu Glu Val Ser His Ile Pro Ala Val His
                195                 200                 205
Pro Gly Ser Phe Arg Pro Lys Cys Asp Glu Asn Gly Asn Tyr Leu Pro
                210                 215                 220
Leu Gln Cys Tyr Gly Ser Ile Gly Tyr Cys Trp Cys Val Phe Pro Asn
225                 230                 235                 240
Gly Thr Glu Val Pro Asn Thr Arg Ser Arg Gly His His Asn Cys Ser
                245                 250                 255
Glu Ser Leu Glu Leu Glu Asp Pro Ser Ser Gly Leu Gly Val Thr Lys
                260                 265                 270
Gln Asp Leu Gly Pro Val Pro Met
                275                 280
```

```
<210> SEQ ID NO 8
<211> LENGTH: 1185
<212> TYPE: DNA
<213> ORGANISM: Gallus gallus
<220> FEATURE:
<221> NAME/KEY: Misc_feature
<223> OTHER INFORMATION: Nucleotide sequence encoding the OVA antigen

<400> SEQUENCE: 8
atgggctcca tcggcgcagc aagcatggaa ttttgttttg atgtattcaa ggagctcaaa      60
gtccaccatg ccaatgagaa catcttctac tgccccattg ccatcatgtc agctctagcc     120
atggtatacc tgggtgcaaa agacagcacc aggacacaga taaataaggt tgttcgcttt     180
gataaacttc caggattcgg agacagtatt gaagctcagt gtggcacatc tgtaaacgtt     240
cactcttcac ttagagacat cctcaaccaa atcaccaaac caatgatgt ttattcgttc     300 agccttgcca gtagacttta tgctgaagag atacccaa tcctgccaga atacttgcag     360
tgtgtgaagg aactgtatag aggaggcttg aacctatca actttcaaac agctgcagat     420
caagccagag agctcatcaa ttcctgggta gaaagtcaga caaatggaat tatcagaaat     480
```

```
gtccttcagc caagctccgt ggattctcaa actgcaatgg ttctggttaa tgccattgtc    540
ttcaaaggac tgtgggagaa acatttaag gatgaagaca cacaagcaat gcctttcaga    600
gtgactgagc aagaaagcaa acctgtgcag atgatgtacc agattggttt atttagagtg    660
gcatcaatgg cttctgagaa aatgaagatc ctggagcttc catttgccag tgggacaatg    720
agcatgttgg tgctgttgcc tgatgaagtc tcaggccttg agcagcttga gagtataatc    780
aactttgaaa aactgactga atggaccagt tctaatgtta tggaagagag gaagatcaaa    840
gtgtacttac ctcgcatgaa gatggaggaa aaatacaacc tcacatctgt cttaatggct    900
atgggcatta ctgacgtgtt tagctcttca gccaatctgt ctggcatctc ctcagcagag    960
agcctgaaga tatctcaagc tgtccatgca gcacatgcag aaatcaatga agcaggcaga   1020
gaggtggtag ggtcagcaga ggctggagtg gatgctgcaa gcgtctctga agaatttagg   1080
gctgaccatc cattcctctt ctgtatcaag cacatcgcaa ccaacgccgt tctcttcttt   1140
ggcagatgtg tttcccctca tcaccatcac catcactgat aatag               1185
```

<210> SEQ ID NO 9
<211> LENGTH: 160
<212> TYPE: PRT
<213> ORGANISM: Homo sapiens
<220> FEATURE:
<221> NAME/KEY: Misc_feature
<223> OTHER INFORMATION: Amino acid sequence for human invariant chain
      isoform c

<400> SEQUENCE: 9

```
Met His Arg Arg Arg Ser Arg Ser Cys Arg Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Ala Pro Glu Ser Lys Cys Ser Arg Gly Ala
        35                  40                  45

Leu Tyr Thr Gly Phe Ser Ile Leu Val Thr Leu Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Ser Gln Asn Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Leu Pro Gln Gly Pro Met
        115                 120                 125

Gln Asn Ala Thr Lys Tyr Gly Asn Met Thr Glu Asp His Val Met His
    130                 135                 140

Leu Leu Gln Ser His Trp Asn Trp Arg Thr Arg Leu Leu Gly Trp Val
145                 150                 155                 160
```

<210> SEQ ID NO 10
<211> LENGTH: 483
<212> TYPE: DNA
<213> ORGANISM: Homo sapiens
<220> FEATURE:
<221> NAME/KEY: Misc_feature
<223> OTHER INFORMATION: Nucleotide sequence encoding human invariant
      chain isoform c

<400> SEQUENCE: 10

```
atgcacagga ggagaagcag gagctgtcgg gaagatcaga agccagtcat ggatgaccag    60
cgcgacctta tctccaacaa tgagcaactg cccatgctgg ccggcgccc tggggccccg    120 gagagcaagt gcagccgcgg agccctgtac acaggctttt ccatcctggt gactctgctc    180
ctcgctggcc aggccaccac cgcctacttc ctgtaccagc agcagggccg gctggacaaa    240
ctgacagtca cctcccagaa cctgcagctg agaacctgc gcatgaagct tcccaagcct    300
cccaagcctg tgagcaagat cgcatggcc accccgctgc tgatgcaggc gctgcccatg    360
ggagccctgc cccaggggcc catgcagaat gccaccaagt atggcaacat gacagaggac    420
catgtgatgc acctgctcca gagtcactgg aactggagga cccgtcttct gggctgggtg    480
tga                                                                  483
```

<210> SEQ ID NO 11
<211> LENGTH: 215
<212> TYPE: PRT
<213> ORGANISM: Homo sapiens
<220> FEATURE:
<221> NAME/KEY: Misc_feature
<223> OTHER INFORMATION: Amino acid sequence for murine invariant chain
      p31

<400> SEQUENCE: 11

```
Met Asp Asp Gln Arg Asp Leu Ile Ser Asn His Glu Gln Leu Pro Ile
1               5                   10                  15

Leu Gly Asn Arg Pro Arg Glu Pro Glu Arg Cys Ser Arg Gly Ala Leu
            20                  25                  30

Tyr Thr Gly Val Ser Val Leu Val Ala Leu Leu Leu Ala Gly Gln Ala
        35                  40                  45

Thr Thr Ala Tyr Phe Leu Tyr Gln Gln Gln Gly Arg Leu Asp Lys Leu
    50                  55                  60

Thr Ile Thr Ser Gln Asn Leu Gln Leu Glu Ser Leu Arg Met Lys Leu
65                  70                  75                  80

Pro Lys Ser Ala Lys Pro Val Ser Gln Met Arg Met Ala Thr Pro Leu
                85                  90                  95

Leu Met Arg Pro Met Ser Met Asp Asn Met Leu Leu Gly Pro Val Lys
            100                 105                 110

Asn Val Thr Lys Tyr Gly Asn Met Thr Gln Asp His Val Met His Leu
        115                 120                 125

Leu Thr Arg Ser Gly Pro Leu Glu Tyr Pro Gln Leu Lys Gly Thr Phe
    130                 135                 140

Pro Glu Asn Leu Lys His Leu Lys Asn Ser Met Asp Gly Val Asn Trp
145                 150                 155                 160

Lys Ile Phe Glu Ser Trp Met Lys Gln Trp Leu Leu Phe Glu Met Ser
                165                 170                 175

Lys Asn Ser Leu Glu Glu Lys Lys Pro Thr Glu Ala Pro Pro Lys Glu
            180                 185                 190

Pro Leu Asp Met Glu Asp Leu Ser Ser Gly Leu Gly Val Thr Arg Gln
        195                 200                 205

Glu Leu Gly Gln Val Thr Leu
    210                 215
```

<210> SEQ ID NO 12
<211> LENGTH: 648
<212> TYPE: DNA
<213> ORGANISM: Homo sapiens
<220> FEATURE:
<221> NAME/KEY: Misc_feature
<223> OTHER INFORMATION: Nucleotide sequence encoding murine invariant
      chain p31

<400> SEQUENCE: 12

```
atggatgacc aacgcgacct catctctaac catgaacagt tgcccatact gggcaaccgc      60
cctagagagc cagaaaggtg cagccgtgga gctctgtaca ccggtgtctc tgtcctggtg     120
gctctgctct tggctgggca ggccaccact gcttacttcc tgtaccagca cagggccgc     180
ctagacaagc tgaccatcac ctcccagaac ctgcaactgg agagccttcg catgaagctt     240
ccgaaatctg ccaaacctgt gagccagatg cggatggcta ctcccttgct gatgcgtcca     300
atgtccatgg ataacatgct ccttgggcct gtgaagaacg ttaccaagta cggcaacatg     360
acccaggacc atgtgatgca tctgctcacg aggtctggac ccctggagta cccgcagctg     420
aaggggacct tcccagagaa tctgaagcat cttaagaact ccatggatgg cgtgaactgg     480
aagatcttcg agagctggat gaagcagtgg ctcttgtttg agatgagcaa gaactccctg     540
gaggagaaga gcccaccgga ggctccacct aaagagccac tggacatgga agacctatct     600
tctggcctgg gagtgaccag gcaggaactg ggtcaagtca ccctgtga                 648
```

<210> SEQ ID NO 13
<211> LENGTH: 279
<212> TYPE: PRT
<213> ORGANISM: Homo sapiens
<220> FEATURE:
<221> NAME/KEY: Misc_feature
<223> OTHER INFORMATION: Amino acid sequence for murine invariant chain
      p41

<400> SEQUENCE: 13

```
Met Asp Asp Gln Arg Asp Leu Ile Ser Asn His Glu Gln Leu Pro Ile
1               5                   10                  15

Leu Gly Asn Arg Pro Arg Glu Pro Glu Arg Cys Ser Arg Gly Ala Leu
            20                  25                  30

Tyr Thr Gly Val Ser Val Leu Val Ala Leu Leu Leu Ala Gly Gln Ala
        35                  40                  45

Thr Thr Ala Tyr Phe Leu Tyr Gln Gln Gln Gly Arg Leu Asp Lys Leu
    50                  55                  60

Thr Ile Thr Ser Gln Asn Leu Gln Leu Glu Ser Leu Arg Met Lys Leu
65                  70                  75                  80

Pro Lys Ser Ala Lys Pro Val Ser Gln Met Arg Met Ala Thr Pro Leu
                85                  90                  95

Leu Met Arg Pro Met Ser Met Asp Asn Met Leu Leu Gly Pro Val Lys
            100                 105                 110

Asn Val Thr Lys Tyr Gly Asn Met Thr Gln Asp His Val Met His Leu
        115                 120                 125

Leu Thr Arg Ser Gly Pro Leu Glu Tyr Pro Gln Leu Lys Gly Thr Phe
    130                 135                 140

Pro Glu Asn Leu Lys His Leu Lys Asn Ser Met Asp Gly Val Asn Trp
145                 150                 155                 160

Lys Ile Phe Glu Ser Trp Met Lys Gln Trp Leu Leu Phe Glu Met Ser
                165                 170                 175

Lys Asn Ser Leu Glu Glu Lys Lys Pro Thr Glu Ala Pro Pro Lys Val
            180                 185                 190

Leu Thr Lys Cys Gln Glu Glu Val Ser His Ile Pro Ala Val Tyr Pro
        195                 200                 205

Gly Ala Phe Arg Pro Lys Cys Asp Glu Asn Gly Asn Tyr Leu Pro Leu
```

Gln Cys His Gly Ser Thr Gly Tyr Cys Trp Cys Val Phe Pro Asn Gly
225                 230                 235                 240

Thr Glu Val Pro His Thr Lys Ser Arg Gly Arg His Asn Cys Ser Glu
            245                 250                 255

Pro Leu Asp Met Glu Asp Leu Ser Ser Gly Leu Gly Val Thr Arg Gln
            260                 265                 270

Glu Leu Gly Gln Val Thr Leu
        275

<210> SEQ ID NO 14
<211> LENGTH: 840
<212> TYPE: DNA
<213> ORGANISM: Homo sapiens
<220> FEATURE:
<221> NAME/KEY: Misc_feature
<223> OTHER INFORMATION: Nucleotide sequence encoding murine invariant
      chain p41

<400> SEQUENCE: 14

```
atggatgacc aacgcgacct catctctaac catgaacagt tgcccatact gggcaaccgc      60
cctagagagc agaaaggtg cagccgtgga gctctgtaca ccggtgtctc tgtcctggtg     120
gctctgctct tggctgggca ggccaccact gcttacttcc tgtaccagca acagggccgc    180
ctagacaagc tgaccatcac ctcccagaac ctgcaactgg agagccttcg catgaagctt    240
ccgaaatctg ccaaacctgt gagccagatg cggatggcta ctcccttgct gatgcgtcca    300
atgtccatgg ataacatgct ccttgggcct gtgaagaacg ttaccaagta cggcaacatg    360
acccaggacc atgtgatgca tctgctcacg aggtctggac ccctggagta cccgcagctg    420
aagggggacct tcccagagaa tctgaagcat cttaagaact ccatggatgg cgtgaactgg    480
aagatcttcg agagctggat gaagcagtgg ctcttgtttg agatgagcaa gaactccctg    540
gaggagaaga agcccaccga ggctccacct aaagtactga ccaagtgcca ggaagaagtc    600
agccacatcc ctgccgtcta cccgggtgcg ttccgtccca agtgcgacga gaacggtaac    660
tatttgccac tccagtgcca cgggagcact ggctactgct ggtgtgtgtt ccccaacggc    720
actgaggttc ctcacaccaa gagccgcggg cgccataact gcagtgagcc actggacatg    780
gaagacctat cttctggcct gggagtgacc aggcaggaac tgggtcaagt cacccctgtga    840
```

<210> SEQ ID NO 15
<211> LENGTH: 280
<212> TYPE: PRT
<213> ORGANISM: Cavia porcellus
<220> FEATURE:
<221> NAME/KEY: Misc_feature
<223> OTHER INFORMATION: Amino acid sequence for Cavia porcellus
      invariant chain (UniProt accession number H0UZ94)

<400> SEQUENCE: 15

Met Glu Asp Gln His Asp Leu Ile Ser Asn His Glu Gln Leu Pro Met
1               5                   10                  15

Leu Gly Gln Arg Pro Gly Ala Gln Asp Gly Lys Cys Ser Arg Gly Ala
            20                  25                  30

Leu Tyr Thr Gly Phe Ser Val Leu Ala Leu Leu Leu Ala Gly Gln
        35                  40                  45

Ala Thr Thr Ala Tyr Phe Leu Tyr Gln Gln Gln Gly Arg Leu Asp Lys
    50                  55                  60

Leu Thr Val Thr Ser Gln Asn Leu Gln Leu Glu Asn Leu Arg Met Lys

```
                65                  70                  75                  80
Met Pro Lys Pro Pro Lys Pro Val Ser Gln Met Arg Met Ala Thr Pro
                        85                  90                  95

Leu Leu Met Arg Ala Leu Pro Met Glu Val Met His Lys Gly Pro Val
                100                 105                 110

Gln Asn Ala Thr Lys Tyr Gly Asn Thr Thr Gln Asp Tyr Val Met His
                115                 120                 125

Thr Leu Leu Lys Ser Asp Pro Leu Lys Val Tyr Pro Gln Leu Gln Gly
130                 135                 140

Ser Phe Leu Glu Asn Leu Lys His Leu Lys Asn Thr Met Glu Ser Leu
145                 150                 155                 160

Asp Trp Lys Val Phe Glu Ser Trp Met His His Trp Leu Leu Phe Glu
                165                 170                 175

Met Ser Arg Asn Ser Pro Glu Glu Lys Pro Thr Glu Ala Pro Pro Lys
                180                 185                 190

Val Leu Ser Lys Cys Gln Glu Glu Val Ser His Ile Pro Ala Val His
                195                 200                 205

Pro Gly Thr Phe Arg Pro Gln Cys Asp Glu Asn Gly Asn Tyr Met Pro
                210                 215                 220

Leu Gln Cys His Gly Ser Thr Gly Tyr Cys Trp Cys Val Phe Pro Asn
225                 230                 235                 240

Gly Thr Glu Val Pro His Thr Arg Ser His Gly His His Asn Cys Ser
                245                 250                 255

Glu Pro Leu Glu Ala Glu Asp Leu Ser Ser Gly Leu Gly Val Thr Lys
                260                 265                 270

Gln Glu Leu Gly Gln Ala Ser Leu
            275                 280

<210> SEQ ID NO 16
<211> LENGTH: 329
<212> TYPE: PRT
<213> ORGANISM: Heterocephalus glaber
<220> FEATURE:
<221> NAME/KEY: Misc_feature
<223> OTHER INFORMATION: Amino acid sequence for Heterocephalus glaber
      invariant chain (UniProt accession number G5C391)

<400> SEQUENCE: 16

Met Glu Asp Gln Arg Asp Leu Ile Ser Asn His Glu Gln Leu Pro Met
1               5                   10                  15

Leu Gly Gln Arg Leu Gly Ala Gln Asp Arg Lys Cys Ser Arg Gly Ala
                20                  25                  30

Leu Tyr Thr Gly Phe Ser Val Leu Val Ala Leu Leu Leu Ala Gly Gln
                35                  40                  45

Ala Thr Thr Ala Tyr Phe Leu Tyr Gln Gln Gln Gly Arg Leu Asp Lys
            50                  55                  60

Leu Thr Val Thr Ser Gln Asn Leu Gln Leu Glu Asn Leu Arg Met Lys
65                  70                  75                  80

Met Pro Gln Ser Pro Lys Pro Val Ser Gln Met Arg Val Ala Thr Pro
                        85                  90                  95

Leu Leu Met Arg Ala Leu Pro Met Glu Gly Leu Leu Gln Gly Pro Met
                100                 105                 110

Gln Gln Asn Ala Thr Lys Tyr Gly Asn Met Thr Gln Asp His Val Met
                115                 120                 125

His Met Leu Leu Lys Ser Asp Pro Leu Lys Val Tyr Pro Gln Leu Glu
            130                 135                 140
```

-continued

```
Gly Ser Phe Leu Asp Asn Leu Lys His Leu Lys Asn Thr Met Glu Ser
145                 150                 155                 160

Leu Asp Trp Lys Val Phe Glu Ser Trp Met His His Trp Leu Leu Phe
                165                 170                 175

Glu Met Ser Arg Asn Ser Pro Gly Glu Lys Pro Thr Glu Ala Pro Pro
            180                 185                 190

Lys Val Leu Ser Lys Cys Gln Glu Val Ser His Ile Pro Ala Val
        195                 200                 205

His Pro Gly Thr Phe Arg Pro Gln Cys Asp Glu Asn Gly Asn Tyr Met
    210                 215                 220

Pro Leu Gln Cys His Gly Ser Thr Gly Tyr Cys Trp Cys Val Phe Pro
225                 230                 235                 240

Asn Gly Thr Glu Val Pro Gln Thr Arg Ser Arg Gly His His Asn Cys
                245                 250                 255

Ser Glu Pro Leu Glu Ala Glu Asp Leu Ser Ser Gly Leu Gly Met Thr
            260                 265                 270

Lys Gln Glu Leu Gly Pro Ala His Leu Ala Ala Arg Ala Lys Asp Ser
        275                 280                 285

Ser Val Arg Lys Arg Thr Cys Thr Arg Cys Leu Gly Leu Ser His Arg
    290                 295                 300

Leu Leu Cys Arg Leu Leu Leu Gly Glu Lys Gly Asp Arg Leu Trp
305                 310                 315                 320

Ser Leu Leu Phe Leu Ser Ile Ala Ala
                325

<210> SEQ ID NO 17
<211> LENGTH: 298
<212> TYPE: PRT
<213> ORGANISM: Fukomys damarensis
<220> FEATURE:
<221> NAME/KEY: Misc_feature
<223> OTHER INFORMATION: Amino acid sequence for Fukomys damarensis
      invariant chain (UniProt accession number A0A091E9W3)

<400> SEQUENCE: 17

Met Glu Asp Gln Arg Asp Leu Ile Ser Asn His Glu Gln Leu Pro Met
1               5                   10                  15

Leu Gly Gln Arg Pro Ala Ala Gln Asp Arg Lys Cys Ser Arg Gly Ala
            20                  25                  30

Leu Tyr Thr Gly Phe Ser Ile Leu Val Ala Leu Leu Ala Gly Gln
        35                  40                  45

Ala Thr Thr Ala Tyr Phe Leu Tyr Gln Gln Gln Gly Arg Leu Asp Lys
    50                  55                  60

Leu Thr Val Thr Ser Gln Asn Leu Gln Leu Glu Asn Leu Arg Met Lys
65                  70                  75                  80

Met Pro Lys Ser Ser Lys Pro Met Thr Gln Met Arg Val Ala Thr Pro
                85                  90                  95

Met Leu Met Arg Ala Leu Pro Met Glu Gly Leu Leu Gln Gly Pro Met
            100                 105                 110

Gln Asn Ala Thr Lys Tyr Gly Asn Met Thr Gln Asp His Val Met His
        115                 120                 125

Thr Leu Leu Gln Ser Asp Pro Leu Lys Val Tyr Pro Gln Leu Thr Gly
    130                 135                 140

Ser Phe Leu Glu Asn Leu Lys His Leu Lys Asn Thr Met Gln Ser Leu
145                 150                 155                 160
```

```
Asp Trp Lys Val Phe Glu Ser Trp Met His His Trp Leu Leu Phe Glu
            165                 170                 175
Met Ser Arg Asn Ser Pro Glu Lys Pro Thr Glu Ala Pro Pro Lys Val
        180                 185                 190
Leu Ser Lys Cys Gln Glu Val Ser His Ile Pro Ala Val His Pro
    195                 200                 205
Gly Thr Phe Arg Pro Gln Cys Asp Glu Asn Gly Asn Tyr Met Pro Leu
210                 215                 220
Gln Cys His Gly Ser Thr Gly Tyr Cys Trp Cys Val Phe Pro Asn Gly
225                 230                 235                 240
Thr Glu Val Pro His Thr Arg Ser Arg Gly His His Asn Cys Ser Asp
                245                 250                 255
Pro Leu Glu Ala Glu Asp Leu Ser Ser Gly Leu Gly Val Thr Lys Gln
            260                 265                 270
Glu Leu Gly Pro Gly Leu Cys Leu Ala Lys Leu Val Ile Ser Ser Gln
        275                 280                 285
Gly Arg Gly Ser Trp Lys Asn Lys Arg Gly
    290                 295
```

<210> SEQ ID NO 18
<211> LENGTH: 216
<212> TYPE: PRT
<213> ORGANISM: Rattus norvegicus
<220> FEATURE:
<221> NAME/KEY: Misc_feature
<223> OTHER INFORMATION: Amino acid sequence for Rattus norvegicus
      second isoform invariant chain (UniProt accession number P10247-2)

<400> SEQUENCE: 18

```
Met Asp Asp Gln Arg Asp Leu Ile Ser Asn His Glu Gln Leu Pro Ile
1               5                   10                  15
Leu Gly Gln Arg Ala Arg Ala Pro Glu Ser Asn Cys Asn Arg Gly Val
            20                  25                  30
Leu Tyr Thr Ser Val Ser Val Leu Val Ala Leu Leu Ala Gly Gln
        35                  40                  45
Ala Thr Thr Ala Tyr Phe Leu Tyr Gln Gln Gln Gly Arg Leu Asp Lys
50                  55                  60
Leu Thr Val Thr Ser Gln Asn Leu Gln Leu Glu Asn Leu Arg Met Lys
65                  70                  75                  80
Leu Pro Lys Ser Ala Lys Pro Val Ser Pro Met Arg Met Ala Thr Pro
                85                  90                  95
Leu Leu Met Arg Pro Leu Ser Met Asp Asn Met Leu Gln Ala Pro Val
            100                 105                 110
Lys Asn Val Thr Lys Tyr Gly Asn Met Thr Gln Asp His Val Met His
        115                 120                 125
Leu Leu Thr Lys Ser Gly Pro Val Asn Tyr Pro Gln Leu Lys Gly Ser
    130                 135                 140
Phe Pro Glu Asn Leu Lys His Leu Lys Asn Ser Met Asn Gly Leu Asp
145                 150                 155                 160
Trp Lys Val Phe Glu Ser Trp Met Lys Gln Trp Leu Leu Phe Glu Met
                165                 170                 175
Ser Lys Asn Ser Leu Glu Glu Lys Gln Pro Thr Gln Thr Pro Pro Lys
            180                 185                 190
Glu Pro Leu Asp Met Glu Asp Pro Ser Ser Gly Leu Gly Val Thr Lys
        195                 200                 205
Gln Asp Met Gly Gln Met Phe Leu
```

<210> SEQ ID NO 19
<211> LENGTH: 280
<212> TYPE: PRT
<213> ORGANISM: Rattus norvegicus
<220> FEATURE:
<221> NAME/KEY: Misc_feature
<223> OTHER INFORMATION: Amino acid sequence for Rattus norvegicus first
      isoform invariant chain (UniProt accession number P10247)

<400> SEQUENCE: 19

Met Asp Asp Gln Arg Asp Leu Ile Ser Asn His Glu Gln Leu Pro Ile
1               5                   10                  15

Leu Gly Gln Arg Ala Arg Ala Pro Glu Ser Asn Cys Asn Arg Gly Val
            20                  25                  30

Leu Tyr Thr Ser Val Ser Val Leu Val Ala Leu Leu Leu Ala Gly Gln
        35                  40                  45

Ala Thr Thr Ala Tyr Phe Leu Tyr Gln Gln Gln Gly Arg Leu Asp Lys
    50                  55                  60

Leu Thr Val Thr Ser Gln Asn Leu Gln Leu Glu Asn Leu Arg Met Lys
65                  70                  75                  80

Leu Pro Lys Ser Ala Lys Pro Val Ser Pro Met Arg Met Ala Thr Pro
                85                  90                  95

Leu Leu Met Arg Pro Leu Ser Met Asp Asn Met Leu Gln Ala Pro Val
            100                 105                 110

Lys Asn Val Thr Lys Tyr Gly Asn Met Thr Gln Asp His Val Met His
        115                 120                 125

Leu Leu Thr Lys Ser Gly Pro Val Asn Tyr Pro Gln Leu Lys Gly Ser
    130                 135                 140

Phe Pro Glu Asn Leu Lys His Leu Lys Asn Ser Met Asn Gly Leu Asp
145                 150                 155                 160

Trp Lys Val Phe Glu Ser Trp Met Lys Gln Trp Leu Leu Phe Glu Met
                165                 170                 175

Ser Lys Asn Ser Leu Glu Glu Lys Gln Pro Thr Gln Thr Pro Pro Lys
            180                 185                 190

Val Leu Thr Lys Cys Gln Glu Glu Val Ser His Ile Pro Asp Val His
        195                 200                 205

Pro Gly Ala Phe Arg Pro Lys Cys Asp Glu Asn Gly Asn Tyr Met Pro
    210                 215                 220

Leu Gln Cys His Gly Ser Thr Gly Tyr Cys Trp Cys Val Phe Pro Asn
225                 230                 235                 240

Gly Thr Glu Val Pro His Thr Lys Ser Arg Gly Arg His Asn Cys Ser
                245                 250                 255

Glu Pro Leu Asp Met Glu Asp Pro Ser Ser Gly Leu Gly Val Thr Lys
            260                 265                 270

Gln Asp Met Gly Gln Met Phe Leu
        275                 280

<210> SEQ ID NO 20
<211> LENGTH: 280
<212> TYPE: PRT
<213> ORGANISM: Myotis lucifugus
<220> FEATURE:
<221> NAME/KEY: Misc_feature
<223> OTHER INFORMATION: Amino acid sequence for Myotis lucifugus
      invariant chain (UniProt accession number G1QEN4)

<400> SEQUENCE: 20

Met Glu Asp Gln Arg Asp Leu Ile Ser Asn His Glu Gln Leu Pro Met
1               5                  10                  15

Leu Gly Gln Arg Pro Gly Ala Gln Glu Ser Lys Cys Ser Arg Gly Ala
            20                  25                  30

Leu Tyr Thr Gly Phe Ser Val Leu Val Ala Leu Leu Leu Ala Gly Gln
        35                  40                  45

Ala Thr Thr Ala Tyr Phe Leu Tyr Gln Gln Gln Gly Arg Leu Asp Lys
    50                  55                  60

Leu Thr Val Thr Ser Gln Asn Leu Gln Leu Glu Asn Met Arg Met Lys
65                  70                  75                  80

Leu Pro Lys Ser Ala Lys Pro Val Gly Lys Met Arg Val Ala Thr Pro
                85                  90                  95

Met Leu Met Gln Ala Leu Pro Met Asp Gly Leu Leu Gln Gly Pro Met
            100                 105                 110

Gln Asn Ala Thr Lys Tyr Gly Asn Thr Thr Met Asp His Val Met His
        115                 120                 125

Leu Leu Leu Lys Ala Asp Pro Leu Lys Val Tyr Pro Gln Met Lys Gly
    130                 135                 140

Ser Phe Pro Glu Asn Leu Lys His Leu Lys Lys Thr Met Glu Gly Leu
145                 150                 155                 160

Asp Trp Lys Ile Phe Glu Ser Trp Met His Gln Trp Leu Leu Phe Glu
                165                 170                 175

Met Ser Lys Asn Ser Leu Gly Glu Lys Leu Thr Glu Gly Ser Pro Lys
            180                 185                 190

Val Leu Thr Lys Cys Leu Glu Glu Ala Ser Arg Ile Pro Ala Ile His
        195                 200                 205

Pro Gly Arg Phe Lys Pro Gln Cys Asp Glu Asn Gly Asn Tyr Met Pro
    210                 215                 220

Leu Gln Cys Phe Gly Ser Ile Gly Tyr Cys Trp Cys Val Phe Pro Asn
225                 230                 235                 240

Gly Thr Glu Val Pro His Thr Arg Ser Arg Gly Arg His Asn Cys Ser
                245                 250                 255

Glu Pro Leu Asp Met Glu Asp Leu Ser Ser Gly Leu Gly Val Thr Lys
            260                 265                 270

Gln Asp Leu Val Gln Ala Thr Met
        275                 280

<210> SEQ ID NO 21
<211> LENGTH: 323
<212> TYPE: PRT
<213> ORGANISM: Myotis davidii
<220> FEATURE:
<221> NAME/KEY: Misc_feature
<223> OTHER INFORMATION: Amino acid sequence for Myotis davidii
      invariant chain (UniProt accession number L5LQM9)

<400> SEQUENCE: 21

Met Glu Asp Gln Arg Asp Leu Ile Ser Asn His Glu Gln Leu Pro Met
1               5                  10                  15

Leu Gly Gln Arg Pro Gly Ala Gln Glu Ser Lys Cys Ser Arg Gly Ala
            20                  25                  30

Leu Tyr Thr Gly Phe Ser Val Leu Val Ala Leu Leu Leu Ala Gly Gln
        35                  40                  45

Ala Thr Thr Ala Tyr Phe Leu Tyr Gln Gln Gln Gly Arg Leu Asp Lys
    50                  55                  60

Leu Thr Val Thr Ser Gln Asn Leu Gln Leu Glu Asn Leu Arg Met Lys
65                  70                  75                  80

Leu Pro Lys Ser Ala Lys Pro Val Gly Lys Met Arg Val Ala Thr Pro
            85                  90                  95

Met Leu Met Gln Ala Leu Pro Met Glu Gly Leu Leu Gln Gly Pro Met
        100                 105                 110

Gln Asn Ala Thr Lys Tyr Gly Asn Thr Thr Met Asp His Val Met His
        115                 120                 125

Leu Leu Leu Lys Ala Asp Pro Leu Lys Val Tyr Pro Gln Met Lys Gly
    130                 135                 140

Ser Phe Pro Glu Asn Leu Lys His Leu Lys Lys Thr Met Glu Gly Leu
145                 150                 155                 160

Asp Trp Lys Ile Phe Glu Ser Trp Met His Gln Trp Leu Leu Phe Glu
                165                 170                 175

Met Ser Lys Asn Ser Leu Gly Glu Lys Leu Thr Glu Gly Ser Pro Lys
            180                 185                 190

Val Leu Thr Gln Cys Leu Glu Glu Ala Ser Arg Ile Pro Ala Ile His
        195                 200                 205

Pro Gly Arg Phe Lys Pro Gln Cys Asp Glu Asn Gly Asn Tyr Met Pro
    210                 215                 220

Leu Gln Cys Phe Gly Ser Ile Gly Tyr Cys Trp Cys Val Phe Pro Asn
225                 230                 235                 240

Gly Thr Glu Val Pro His Thr Arg Ser Arg Gly Arg His Asn Cys Ser
                245                 250                 255

Glu Pro Leu Asp Met Glu Asp Leu Ser Ser Gly Leu Gly Val Thr Lys
            260                 265                 270

Gln Asp Leu Val Gln Ala Ile Glu Asp Thr Ser Thr Gln Ser Ala Leu
        275                 280                 285

His Gly His Ser Phe Leu Ala Leu Phe Arg Pro Pro Asn Leu Ala Thr
    290                 295                 300

Tyr Phe Ser Pro Leu His Ala Leu Leu Pro Pro Ser Pro Thr Leu His
305                 310                 315                 320

Leu Ile Ser

<210> SEQ ID NO 22
<211> LENGTH: 295
<212> TYPE: PRT
<213> ORGANISM: Myotis brandtii
<220> FEATURE:
<221> NAME/KEY: Misc_feature
<223> OTHER INFORMATION: Amino acid sequence for Myotis brandtii
      invariant chain (UniProt accession number S7N2W2)

<400> SEQUENCE: 22

Met Leu Gly Gln Arg Pro Gly Ala Gln Glu Ser Lys Cys Ser Arg Gly
1               5                   10                  15

Ala Leu Tyr Thr Gly Phe Ser Val Leu Val Ala Leu Leu Leu Ala Gly
            20                  25                  30

Gln Ala Thr Thr Ala Tyr Phe Leu Tyr Gln Gln Gln Gly Arg Leu Asp
        35                  40                  45

Lys Leu Thr Val Thr Ser Gln Asn Leu Gln Leu Glu Asn Leu Arg Met
    50                  55                  60

Lys Leu Pro Lys Ser Ala Lys Pro Val Gly Lys Met Arg Val Ala Thr
65                  70                  75                  80

Pro Met Leu Met Gln Ala Leu Pro Met Glu Gly Leu Leu Gln Gly Pro
            85                  90                  95

Met Gln Asn Ala Thr Lys Tyr Gly Asn Thr Thr Met Asp His Val Met
                100                 105                 110

His Leu Leu Leu Lys Ala Asp Pro Leu Lys Val Tyr Pro Gln Met Lys
            115                 120                 125

Gly Ser Phe Pro Glu Asn Leu Lys His Leu Lys Lys Thr Met Glu Gly
        130                 135                 140

Leu Asp Trp Lys Ile Phe Glu Ser Trp Met His Gln Trp Leu Leu Phe
145                 150                 155                 160

Glu Met Ser Lys Asn Ser Leu Gly Glu Lys Leu Thr Glu Gly Ser Pro
                165                 170                 175

Lys Val Leu Thr Lys Cys Leu Glu Glu Ala Ser Arg Ile Pro Ala Ile
            180                 185                 190

His Pro Gly Arg Phe Lys Pro Gln Cys Asp Glu Asn Gly Asn Tyr Met
        195                 200                 205

Pro Leu Gln Cys Phe Gly Ser Ile Gly Tyr Cys Trp Cys Val Phe Pro
210                 215                 220

Asn Gly Thr Glu Val Pro His Thr Arg Ser Arg Gly Arg His Asn Cys
225                 230                 235                 240

Ser Glu Pro Leu Asp Met Glu Asp Leu Ser Ser Gly Leu Gly Val Thr
                245                 250                 255

Lys Gln Asp Leu Val Gln Glu Ile Thr Ser Glu Gln Gln Ile Arg Arg
            260                 265                 270

Ala Leu Leu Pro Lys Pro Pro Ser Ile Ser Arg His Thr Arg Pro Lys
        275                 280                 285

Glu Leu Asp His Glu Leu Gly
    290                 295

<210> SEQ ID NO 23
<211> LENGTH: 299
<212> TYPE: PRT
<213> ORGANISM: Pteropus alecto
<220> FEATURE:
<221> NAME/KEY: Misc_feature
<223> OTHER INFORMATION: Amino acid sequence for Pteropus alecto
      invariant chain (UniProt accession number L5L1G3)

<400> SEQUENCE: 23

Met Glu Asp Gln Arg Asp Leu Ile Ser Asn His Glu Gln Leu Pro Met
1               5                   10                  15

Leu Gly Gln Arg Pro Gly Ala Pro Glu Arg Asn Cys Ser Arg Gly Ala
            20                  25                  30

Leu Tyr Thr Gly Phe Ser Val Leu Val Ala Leu Leu Leu Ala Gly Gln
        35                  40                  45

Ala Thr Thr Ala Tyr Phe Leu Tyr Gln Gln Gly Arg Leu Asp Lys
50                  55                  60

Leu Thr Val Thr Ser Gln Asn Leu Gln Leu Glu Asn Leu Arg Met Lys
65                  70                  75                  80

Leu Pro Lys Ser Ala Lys Pro Val Ser Lys Met Arg Val Ala Thr Pro
                85                  90                  95

Met Leu Met Gln Ala Leu Pro Met Asp Gly Val Leu Gln Gly Pro Met
            100                 105                 110

Gln Asn Ala Thr Lys Tyr Gly Asn Ser Thr Leu Asp His Val Met His
        115                 120                 125

Leu Leu Leu Lys Ser Asp Pro Leu Lys Val Tyr Pro Gln Leu Lys Gly
    130                 135                 140

```
Ser Phe Pro Glu Asn Leu Lys Arg Leu Arg Asn Thr Met Glu Gly Leu
145                 150                 155                 160

Asp Trp Lys Ala Phe Glu Asn Trp Met His Gln Trp Leu Leu Phe Glu
            165                 170                 175

Met Ser Lys Asn Ser Leu Glu Glu Lys Pro Lys Pro Thr Gln Val Pro
        180                 185                 190

Thr Lys Val Leu Thr Lys Cys Leu Glu Glu Val Ser Arg Ile Pro Ala
    195                 200                 205

Ile His Pro Gly Met Phe Lys Pro Lys Cys Asp Glu Asn Gly Asn Tyr
210                 215                 220

Met Pro Leu Gln Cys Tyr Gly Ser Ile Gly Tyr Cys Trp Cys Val Phe
225                 230                 235                 240

Pro Asn Gly Thr Glu Val Pro His Thr Arg Ser Arg Lys Arg Ser Asn
                245                 250                 255

Cys Ser Glu Pro Val Asp Met Glu Asp Leu Ser Ser Gly Leu Gly Val
                260                 265                 270

Thr Lys Gln Asp Leu Ser Gln Gly Lys Gly Ala Cys Arg Gly Asp Ala
    275                 280                 285

Gln His Gly Thr Thr Leu Val His Ser Pro Thr
290                 295

<210> SEQ ID NO 24
<211> LENGTH: 232
<212> TYPE: PRT
<213> ORGANISM: Pan troglodytes
<220> FEATURE:
<221> NAME/KEY: Misc_feature
<223> OTHER INFORMATION: Amino acid sequence for Pan troglodytes verus
      invariant chain (UniProt accession number A5A6L4)

<400> SEQUENCE: 24

Met His Arg Arg Arg Ser Arg Ser Cys Arg Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Ala Pro Glu Ser Lys Cys Ser Arg Gly Ala
        35                  40                  45

Leu Tyr Thr Gly Phe Ser Ile Leu Val Thr Leu Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Ser Gln Asn Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Leu Pro Gln Gly Pro Met
        115                 120                 125

Gln Asn Ala Thr Lys Tyr Gly Asn Met Thr Glu Asp His Val Met His
    130                 135                 140

Leu Leu Gln Asn Ala Asp Pro Leu Lys Val Tyr Pro Pro Leu Lys Gly
145                 150                 155                 160

Ser Phe Pro Glu Asn Leu Arg His Leu Lys Asn Thr Met Glu Thr Ile
                165                 170                 175

Asp Trp Lys Val Phe Glu Ser Trp Met His His Trp Leu Leu Phe Glu
            180                 185                 190

Met Ser Arg His Ser Leu Glu Gln Lys Pro Thr Glu Ala Pro Pro Lys
```

```
                195                 200                 205
Glu Ser Leu Glu Leu Glu Asp Pro Ser Ser Gly Leu Gly Val Thr Lys
    210                 215                 220

Gln Asp Leu Gly Pro Val Pro Met
225                 230

<210> SEQ ID NO 25
<211> LENGTH: 232
<212> TYPE: PRT
<213> ORGANISM: Pongo abelii
<220> FEATURE:
<221> NAME/KEY: Misc_feature
<223> OTHER INFORMATION: Amino acid sequence for Pongo abelii invariant
      chain (UniProt accession number Q5RFJ4)

<400> SEQUENCE: 25

Met His Arg Arg Arg Ser Arg Ser Cys Arg Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Ala Pro Glu Ser Lys Cys Gly Arg Gly Ala
        35                  40                  45

Leu Tyr Thr Gly Phe Ser Ile Leu Val Thr Leu Leu Leu Ala Gly Gln
    50                  55                  60

Ala Thr Thr Ala Tyr Phe Leu Tyr Gln Gln Gly Arg Leu Asp Lys
65                  70                  75                  80

Leu Thr Val Thr Ser Gln Asn Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Leu Pro Arg Gly Pro Met
        115                 120                 125

Gln Asn Ala Thr Lys Tyr Gly Asn Met Thr Glu Asp His Val Met His
    130                 135                 140

Leu Leu Gln Asn Ala Asp Pro Leu Lys Val Tyr Pro Pro Leu Lys Gly
145                 150                 155                 160

Ser Phe Pro Glu Asn Leu Arg His Leu Lys Asn Thr Met Glu Thr Ile
                165                 170                 175

Asp Trp Lys Val Phe Glu Ser Trp Met His His Trp Leu Leu Phe Glu
            180                 185                 190

Met Ser Arg His Ser Leu Glu Gln Lys Pro Thr Glu Ala Pro Pro Lys
        195                 200                 205

Glu Ser Leu Glu Leu Glu Asp Pro Ser Ser Gly Leu Gly Val Thr Lys
    210                 215                 220

Gln Asp Leu Gly Pro Val Pro Met
225                 230

<210> SEQ ID NO 26
<211> LENGTH: 232
<212> TYPE: PRT
<213> ORGANISM: Pan troglodytes
<220> FEATURE:
<221> NAME/KEY: Misc_feature
<223> OTHER INFORMATION: Amino acid sequence for Pan troglodytes
      invariant chain (UniProt accession number H2QRT2)

<400> SEQUENCE: 26

Met His Arg Arg Arg Ser Arg Ser Cys Arg Glu Asp Gln Lys Pro Val
1               5                   10                  15
```

Met Asp Asp Gln Arg Asp Leu Ile Ser Asn Asn Glu Gln Leu Pro Met
            20                  25                  30

Leu Gly Arg Arg Pro Gly Ala Pro Glu Ser Lys Cys Ser Arg Gly Ala
        35                  40                  45

Leu Tyr Thr Gly Phe Ser Ile Leu Val Thr Leu Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Ser Gln Asn Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Leu Pro Gln Gly Pro Met
        115                 120                 125

Gln Asn Ala Thr Lys Tyr Gly Asn Met Thr Glu Asp His Val Met His
130                 135                 140

Leu Leu Gln Asn Ala Asp Pro Leu Lys Val Tyr Pro Pro Leu Lys Gly
145                 150                 155                 160

Ser Phe Pro Glu Asn Leu Arg His Leu Lys Asn Thr Met Glu Thr Ile
                165                 170                 175

Asp Trp Lys Val Phe Glu Ser Trp Met His His Trp Leu Leu Phe Glu
            180                 185                 190

Met Ser Arg His Ser Leu Glu Gln Lys Pro Thr Glu Ala Pro Pro Lys
        195                 200                 205

Glu Ser Leu Glu Leu Glu Asp Pro Ser Ser Gly Leu Gly Val Thr Lys
    210                 215                 220

Gln Asp Leu Gly Pro Ala Pro Leu
225                 230

<210> SEQ ID NO 27
<211> LENGTH: 296
<212> TYPE: PRT
<213> ORGANISM: Gorilla gorilla gorilla
<220> FEATURE:
<221> NAME/KEY: Misc_feature
<223> OTHER INFORMATION: Amino acid sequence for Gorilla gorilla gorilla
      invariant chain (UniProt accession number G3R7S6)

<400> SEQUENCE: 27

Met His Arg Arg Ser Ser Arg Ser Cys Arg Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Ala Pro Glu Ser Lys Cys Ser Arg Gly Ala
        35                  40                  45

Leu Tyr Thr Gly Phe Ser Ile Leu Val Thr Leu Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Ser Gln Asn Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Leu Pro Gln Gly Pro Met
        115                 120                 125

```
Gln Asn Ala Thr Lys Tyr Gly Asn Met Thr Glu Asp His Val Met His
            130                 135                 140

Leu Leu Gln Asn Ala Asp Pro Leu Lys Val Tyr Pro Pro Leu Lys Gly
145                 150                 155                 160

Ser Phe Pro Glu Asn Leu Arg His Leu Lys Asn Thr Met Glu Thr Ile
                165                 170                 175

Asp Trp Lys Val Phe Glu Ser Trp Met His His Trp Leu Leu Phe Glu
            180                 185                 190

Met Ser Arg His Ser Leu Glu Gln Lys Pro Thr Glu Ala Pro Pro Lys
            195                 200                 205

Val Leu Thr Lys Cys Gln Glu Val Ser His Ile Pro Ala Val His
210                 215                 220

Pro Gly Ser Phe Arg Pro Thr Cys Asp Glu Asn Gly Asn Tyr Leu Pro
225                 230                 235                 240

Leu Gln Cys Tyr Gly Ser Ile Gly Tyr Cys Trp Cys Val Phe Pro Asn
                245                 250                 255

Gly Thr Glu Val Pro Asn Thr Arg Ser Arg Gly His His Asn Cys Ser
            260                 265                 270

Glu Ser Leu Glu Leu Glu Asp Pro Ser Gly Leu Gly Val Thr Lys
            275                 280                 285

Gln Asp Leu Ser Pro Val Pro Met
290                 295

<210> SEQ ID NO 28
<211> LENGTH: 296
<212> TYPE: PRT
<213> ORGANISM: Nomascus leucogenys
<220> FEATURE:
<221> NAME/KEY: Misc_feature
<223> OTHER INFORMATION: Amino acid sequence for Nomascus leucogenys
      invariant chain (UniProt accession number G1RHB8)

<400> SEQUENCE: 28

Met His Arg Arg Ser Ser Arg Ser Cys Arg Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Ala Pro Glu Ser Lys Cys Ser Arg Gly Ala
        35                  40                  45

Leu Tyr Thr Gly Phe Ser Ile Leu Val Thr Leu Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Ser Gln Asn Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Leu Pro Arg Gly Pro Met
        115                 120                 125

Gln Asn Ala Thr Lys Tyr Gly Asn Met Thr Glu Asp His Val Met His
    130                 135                 140

Leu Leu Gln Asn Ala Asp Pro Leu Lys Val Tyr Pro Pro Leu Lys Gly
145                 150                 155                 160

Ser Phe Pro Glu Asn Leu Arg His Leu Lys Asn Thr Met Glu Thr Ile
                165                 170                 175

Asp Trp Lys Val Phe Glu Ser Trp Met His His Trp Leu Leu Phe Glu
```

```
                    180                 185                 190
Met Ser Arg His Ser Leu Glu Gln Lys Pro Thr Glu Ala Pro Pro Lys
                195                 200                 205

Val Leu Thr Lys Cys Gln Glu Val Ser His Ile Pro Ala Val His
            210                 215                 220

Pro Gly Ser Phe Arg Pro Lys Cys Asp Glu Asn Gly Asn Tyr Leu Pro
225                 230                 235                 240

Leu Gln Cys Tyr Gly Ser Ile Gly Tyr Cys Trp Cys Val Phe Pro Asn
                245                 250                 255

Gly Thr Glu Val Pro Asn Thr Arg Ser Arg Gly His His Asn Cys Ser
            260                 265                 270

Glu Ser Leu Glu Leu Glu Asp Pro Ser Ser Gly Leu Gly Val Thr Lys
                275                 280                 285

Gln Asp Leu Gly Pro Val Pro Ile
                290                 295

<210> SEQ ID NO 29
<211> LENGTH: 230
<212> TYPE: PRT
<213> ORGANISM: Macaca mulatta
<220> FEATURE:
<221> NAME/KEY: Misc_feature
<223> OTHER INFORMATION: Amino acid sequence for Macaca mulatta
      invariant chain (UniProt accession number I0FWR3)

<400> SEQUENCE: 29

Met Tyr Arg Ser Ser Arg Arg Ser Cys Gln Glu Asp Gln Lys Pro Val
1               5                   10                  15

Met Asp Asp Gln Arg Asp Leu Ile Ser Asn Asn Glu Gln Leu Pro Met
                20                  25                  30

Leu Gly Arg Arg Pro Gly Thr Pro Glu Ser Lys Cys Ser Arg Gly Ala
            35                  40                  45

Leu Tyr Thr Gly Phe Ser Ile Leu Val Thr Leu Leu Leu Ala Gly Gln
        50                  55                  60

Ala Thr Thr Ala Tyr Phe Leu Tyr Gln Gln Gln Gly Arg Leu Asp Lys
65                  70                  75                  80

Leu Thr Val Thr Thr Gln Ser Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Gln Gly Pro Met Gln Asn
        115                 120                 125

Ala Thr Lys Tyr Gly Asn Met Thr Glu Asp His Val Met His Leu Leu
130                 135                 140

Gln Asn Ala Asp Pro Leu Lys Val Tyr Pro Pro Leu Lys Gly Ser Phe
145                 150                 155                 160

Pro Glu Asn Leu Arg His Leu Lys Ser Thr Met Glu Thr Leu Asp Trp
                165                 170                 175

Lys Val Phe Glu Ser Trp Met His His Trp Leu Leu Phe Glu Met Ser
            180                 185                 190

Lys His Ser Leu Glu Gln Lys Pro Thr Glu Ala Pro Pro Lys Glu Ser
        195                 200                 205

Leu Glu Leu Glu Asp Pro Ser Ser Gly Leu Gly Val Thr Lys Gln Asp
210                 215                 220

Leu Gly Pro Val Pro Met
225                 230
```

<210> SEQ ID NO 30
<211> LENGTH: 346
<212> TYPE: PRT
<213> ORGANISM: Macaca fascicularis
<220> FEATURE:
<221> NAME/KEY: Misc_feature
<223> OTHER INFORMATION: Amino acid sequence for Macaca fascicularis invariant chain (UniProt accession number G7P8P8)

<400> SEQUENCE: 30

Met Tyr Arg Ser Ser Arg Arg Ser Cys Gln Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Thr Pro Glu Ser Lys Cys Ser Arg Gly Ala
        35                  40                  45

Leu Tyr Thr Gly Phe Ser Ile Leu Val Thr Leu Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Thr Gln Ser Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Gln Gly Pro Met Gln Asn
        115                 120                 125

Ala Thr Lys Tyr Gly Asn Met Thr Glu Asp His Val Met His Leu Leu
    130                 135                 140

Gln Asn Ala Asp Pro Leu Lys Val Tyr Pro Pro Leu Lys Gly Ser Phe
145                 150                 155                 160

Pro Glu Asn Leu Arg His Leu Lys Ser Thr Met Glu Thr Leu Asp Trp
                165                 170                 175

Lys Val Phe Glu Ser Trp Met His His Trp Leu Leu Phe Glu Met Ser
            180                 185                 190

Lys His Ser Leu Glu Gln Lys Pro Thr Glu Ala Pro Pro Lys Val Leu
        195                 200                 205

Thr Lys Cys Gln Glu Glu Val Ser Arg Ile Pro Ala Val His Pro Gly
    210                 215                 220

Ser Phe Arg Pro Lys Cys Asp Glu Asn Gly Asn Tyr Leu Pro Leu Gln
225                 230                 235                 240

Cys Tyr Gly Ser Thr Gly Tyr Cys Trp Cys Val Phe Pro Asn Gly Thr
                245                 250                 255

Glu Val Pro Asn Thr Arg Ser Arg Gly His Gln Asn Cys Ser Glu Ser
            260                 265                 270

Leu Glu Leu Glu Asp Pro Ser Ser Gly Leu Gly Val Thr Lys Gln Asp
        275                 280                 285

Leu Gly Pro Val His Thr Gln Asp Ile Ile Leu Ser Phe Met Phe Ile
    290                 295                 300

His Phe Leu Pro Ser Pro Gln Asn His Gly Glu Leu Asp Val Arg
305                 310                 315                 320

Gly Asn Ser Leu Leu Thr Phe Leu Asp Leu Leu Cys Leu Pro Gln Leu
                325                 330                 335

Phe Thr Met His Leu Gln Gly Ala Cys Pro
            340                 345

<210> SEQ ID NO 31
<211> LENGTH: 346
<212> TYPE: PRT
<213> ORGANISM: Macaca mulatta
<220> FEATURE:
<221> NAME/KEY: Misc_feature
<223> OTHER INFORMATION: Amino acid sequence for Macaca mulatta invariant chain (UniProt accession number G7MVM5)

<400> SEQUENCE: 31

```
Met Tyr Arg Ser Ser Arg Arg Ser Cys Gln Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Thr Pro Glu Ser Lys Cys Ser Arg Gly Ala
        35                  40                  45

Leu Tyr Thr Gly Phe Ser Ile Leu Val Thr Leu Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Thr Gln Ser Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Gln Gly Pro Met Gln Asn
        115                 120                 125

Ala Thr Lys Tyr Gly Asn Met Thr Glu Asp His Val Met His Leu Leu
    130                 135                 140

Gln Asn Ala Asp Pro Leu Lys Val Tyr Pro Pro Leu Lys Gly Ser Phe
145                 150                 155                 160

Pro Glu Asn Leu Arg His Leu Lys Ser Thr Met Glu Thr Leu Asp Trp
                165                 170                 175

Lys Val Phe Glu Ser Trp Met His His Trp Leu Leu Phe Glu Met Ser
            180                 185                 190

Lys His Ser Leu Glu Gln Lys Pro Thr Glu Ala Pro Pro Lys Val Leu
        195                 200                 205

Thr Lys Cys Gln Glu Glu Val Ser Arg Ile Pro Ala Val His Pro Gly
    210                 215                 220

Ser Phe Arg Pro Lys Cys Asp Glu Asn Gly Asn Tyr Leu Pro Leu Gln
225                 230                 235                 240

Cys Tyr Gly Ser Thr Gly Tyr Cys Trp Cys Val Phe Pro Asn Gly Thr
                245                 250                 255

Glu Val Pro Asn Thr Arg Ser Arg Gly His Gln Asn Cys Ser Glu Ser
            260                 265                 270

Leu Glu Leu Glu Asp Pro Ser Ser Gly Leu Gly Val Thr Lys Gln Asp
        275                 280                 285

Leu Gly Pro Val His Thr Gln Asp Ile Ile Leu Ser Phe Met Phe Ile
    290                 295                 300

His Phe Leu Pro Ser Pro Pro Gln Asn His Gly Glu Leu Asp Val Arg
305                 310                 315                 320

Gly Asn Ser Leu Leu Thr Phe Leu Asp Leu Leu Cys Leu Pro Gln Leu
                325                 330                 335

Phe Thr Met His Leu Gln Gly Ala Cys Pro
            340                 345
```

<210> SEQ ID NO 32
<211> LENGTH: 294
<212> TYPE: PRT
<213> ORGANISM: Macaca mulatta
<220> FEATURE:
<221> NAME/KEY: Misc_feature
<223> OTHER INFORMATION: Amino acid sequence for Macaca mulatta
      invariant chain (UniProt accession number I0FWR4)

<400> SEQUENCE: 32

Met Tyr Arg Ser Ser Arg Arg Ser Cys Gln Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Thr Pro Glu Ser Lys Cys Ser Arg Gly Ala
        35                  40                  45

Leu Tyr Thr Gly Phe Ser Ile Leu Val Thr Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Thr Gln Ser Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Gly Pro Met Gln Asn
        115                 120                 125

Ala Thr Lys Tyr Gly Asn Met Thr Glu Asp His Val Met His Leu Leu
    130                 135                 140

Gln Asn Ala Asp Pro Leu Lys Val Tyr Pro Pro Leu Lys Gly Ser Phe
145                 150                 155                 160

Pro Glu Asn Leu Arg His Leu Lys Ser Thr Met Glu Thr Leu Asp Trp
                165                 170                 175

Lys Val Phe Glu Ser Trp Met His His Trp Leu Leu Phe Glu Met Ser
            180                 185                 190

Lys His Ser Leu Glu Gln Lys Pro Thr Glu Ala Pro Pro Lys Val Leu
        195                 200                 205

Thr Lys Cys Gln Glu Glu Val Ser Arg Ile Pro Ala Val His Pro Gly
    210                 215                 220

Ser Phe Arg Pro Lys Cys Asp Glu Asn Gly Asn Tyr Leu Pro Leu Gln
225                 230                 235                 240

Cys Tyr Gly Ser Thr Gly Tyr Cys Trp Cys Val Phe Pro Asn Gly Thr
                245                 250                 255

Glu Val Pro Asn Thr Arg Ser Arg Gly His Gln Asn Cys Ser Glu Ser
            260                 265                 270

Leu Glu Leu Glu Asp Pro Ser Ser Gly Leu Gly Val Thr Lys Gln Asp
        275                 280                 285

Leu Gly Pro Val Pro Met
    290

<210> SEQ ID NO 33
<211> LENGTH: 270
<212> TYPE: PRT
<213> ORGANISM: Macaca mulatta
<220> FEATURE:
<221> NAME/KEY: Misc_feature
<223> OTHER INFORMATION: Amino acid sequence for Macaca mulatta
      invariant chain (UniProt accession number F7E9S4)

<400> SEQUENCE: 33

```
Met Tyr Arg Ser Ser Arg Arg Ser Cys Gln Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Thr Pro Glu Ser Lys Cys Ser His Gly Ala
            35                  40                  45

Leu Tyr Thr Gly Phe Ser Ile Leu Val Thr Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Thr Gln Ser Leu Gln Leu Glu Asn Leu Arg Met Lys
                85                  90                  95

Leu Pro Lys Pro Pro Lys Pro Val Ser Lys Met Arg Met Ala Thr Pro
                100                 105                 110

Leu Leu Met Gln Ala Leu Pro Met Gly Ala Gln Gly Pro Met Gln Asn
            115                 120                 125

Ala Thr Lys Tyr Gly Asn Met Thr Glu Asp His Val Met His Leu Leu
130                 135                 140

Gln Asn Ala Asp Pro Leu Lys Val Tyr Pro Pro Leu Lys Gly Ser Phe
145                 150                 155                 160

Pro Glu Asn Leu Arg His Leu Lys Ser Thr Met Glu Thr Leu Asp Trp
                165                 170                 175

Lys Val Phe Glu Ser Trp Met His His Trp Leu Leu Phe Glu Met Ser
                180                 185                 190

Lys His Ser Leu Glu Gln Lys Pro Thr Glu Ala Pro Lys Val Leu
                195                 200                 205

Thr Lys Cys Gln Glu Glu Val Ser Arg Ile Pro Ala Val His Pro Gly
210                 215                 220

Ser Phe Arg Pro Lys Cys Asp Glu Asn Gly Asn Tyr Leu Pro Leu Gln
225                 230                 235                 240

Cys Tyr Gly Ser Thr Gly Tyr Cys Trp Cys Val Phe Pro Asn Gly Thr
                245                 250                 255

Glu Val Pro Asn Thr Arg Ser Arg Gly His Gln Asn Cys Ser
                260                 265                 270

<210> SEQ ID NO 34
<211> LENGTH: 294
<212> TYPE: PRT
<213> ORGANISM: Papio anubis
<220> FEATURE:
<221> NAME/KEY: Misc_feature
<223> OTHER INFORMATION: Amino acid sequence for Papio anubis invariant
      chain (UniProt accession number A0A096MM48)

<400> SEQUENCE: 34

Met Tyr Arg Ser Ser Arg Arg Ser Cys Gln Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Thr Pro Glu Ser Lys Cys Ser Arg Gly Ala
            35                  40                  45

Leu Tyr Thr Gly Phe Ser Ile Leu Val Thr Leu Leu Ala Gly Gln
    50                  55                  60

Ala Thr Thr Ala Tyr Phe Leu Tyr Gln Gln Gln Gly Arg Leu Asp Lys
65                  70                  75                  80
```

```
Leu Thr Val Thr Thr Gln Asn Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Gln Gly Pro Met Gln Asn
            115                 120                 125

Ala Thr Lys Tyr Gly Asn Met Thr Glu Asp His Val Met His Leu Leu
            130                 135                 140

Gln Asn Ala Asp Pro Leu Lys Val Tyr Pro Pro Leu Lys Gly Ser Phe
145                 150                 155                 160

Pro Glu Asn Leu Arg His Leu Lys Ser Thr Met Glu Thr Leu Asp Trp
                165                 170                 175

Lys Val Phe Glu Ser Trp Met His His Trp Leu Leu Phe Glu Met Ser
                180                 185                 190

Lys His Ser Leu Glu Gln Lys Pro Thr Glu Ala Pro Pro Lys Val Leu
                195                 200                 205

Thr Lys Cys Gln Glu Glu Val Ser Arg Ile Pro Ala Val His Pro Gly
            210                 215                 220

Ser Phe Arg Pro Lys Cys Asp Glu Asn Gly Asn Tyr Leu Pro Leu Gln
225                 230                 235                 240

Cys Tyr Gly Ser Thr Gly Tyr Cys Trp Cys Val Phe Pro Asn Gly Thr
                245                 250                 255

Glu Val Pro Asn Thr Arg Ser Arg Gly His Gln Asn Cys Ser Glu Ser
                260                 265                 270

Leu Glu Leu Glu Asp Pro Ser Ser Gly Leu Gly Val Thr Lys Gln Asp
                275                 280                 285

Leu Gly Pro Val Pro Met
            290

<210> SEQ ID NO 35
<211> LENGTH: 294
<212> TYPE: PRT
<213> ORGANISM: Chlorocebus sabaeus
<220> FEATURE:
<221> NAME/KEY: Misc_feature
<223> OTHER INFORMATION: Amino acid sequence for Chlorocebus sabaeus
      invariant chain (UniProt accession number A0A0D9RGK4)

<400> SEQUENCE: 35

Met Tyr Arg Ser Ser Arg Arg Ser Cys Gln Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Thr Pro Glu Ser Lys Cys Ser Arg Gly Ala
            35                  40                  45

Leu Tyr Thr Gly Phe Ser Ile Leu Val Thr Leu Leu Leu Ala Gly Gln
        50                  55                  60

Ala Thr Thr Ala Tyr Phe Leu Tyr Gln Gln Gln Gly Arg Leu Asp Lys
65                  70                  75                  80

Leu Thr Val Thr Thr Gln Asn Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Gln Gly Pro Met Gln Asn
            115                 120                 125

Ala Thr Lys Tyr Gly Asn Met Thr Glu Asp His Val Met His Leu Leu
```

```
                130             135             140
Gln Asn Ala Asp Pro Leu Lys Val Tyr Pro Leu Lys Gly Ser Phe
145                 150                 155                 160

Pro Glu Asn Leu Arg His Leu Lys Ser Thr Met Glu Thr Leu Asp Trp
                165                 170                 175

Lys Val Phe Glu Ser Trp Met His His Trp Leu Leu Phe Glu Met Ser
            180                 185                 190

Lys His Ser Leu Glu Gln Lys Pro Thr Glu Ala Pro Pro Lys Val Leu
            195                 200                 205

Thr Lys Cys Gln Glu Glu Val Ser Arg Ile Pro Ala Val His Pro Gly
        210                 215                 220

Thr Phe Arg Pro Lys Cys Asp Glu Asn Gly Asn Tyr Leu Pro Leu Gln
225                 230                 235                 240

Cys Tyr Gly Ser Thr Gly Tyr Cys Trp Cys Val Phe Pro Asn Gly Thr
                245                 250                 255

Glu Val Pro Asn Thr Arg Ser Arg Gly His Gln Asn Cys Ser Glu Ser
            260                 265                 270

Leu Glu Leu Glu Asp Pro Ser Ser Gly Leu Gly Val Thr Lys Gln Asp
        275                 280                 285

Leu Gly Pro Val Pro Met
        290
```

<210> SEQ ID NO 36
<211> LENGTH: 295
<212> TYPE: PRT
<213> ORGANISM: Callithrix jacchus
<220> FEATURE:
<221> NAME/KEY: Misc_feature
<223> OTHER INFORMATION: Amino acid sequence for Callithrix jacchus
      invariant chain (UniProt accession number F7ENM4)

<400> SEQUENCE: 36

```
Val Phe Arg Arg Ile Ser Arg Asn Cys Trp Glu Asp Gln Lys Pro Met
1               5                   10                  15

Asp Asp Gln Arg Asp Leu Ile Ser Asn Asn Glu Gln Leu Pro Met Leu
            20                  25                  30

Gly Gln Arg Pro Gly Ala Pro Glu Ser Lys Cys Ser Arg Gly Ala Val
        35                  40                  45

Tyr Thr Val Phe Ser Ile Leu Val Ala Leu Leu Leu Ala Gly Gln Ala
    50                  55                  60

Thr Thr Ala Tyr Phe Leu Tyr Gln Gln Gln Gly Arg Leu Asp Lys Leu
65                  70                  75                  80

Thr Val Thr Ser Gln Asn Leu Gln Leu Glu Asn Leu Arg Met Lys Leu
                85                  90                  95

Pro Lys Pro Ala Lys Pro Leu Ser Gln Met Arg Met Ala Thr Pro Leu
            100                 105                 110

Leu Met Gln Ala Leu Pro Met Ala Gly Leu Pro Gln Lys Pro Met Gln
        115                 120                 125

Asn Ala Thr Lys His Gly Asn Met Thr Glu Asp His Val Met His Leu
    130                 135                 140

Leu Leu Asn Ala Asp Pro Leu Lys Val Tyr Pro Pro Leu Lys Gly Ser
145                 150                 155                 160

Leu Ser Glu Asn Leu Lys His Leu Lys Asn Thr Met Glu Thr Met Asp
                165                 170                 175

Trp Lys Val Phe Glu Ser Trp Leu His His Trp Leu Leu Phe Glu Met
            180                 185                 190
```

```
Ser Lys His Ser Leu Glu Gln Lys Pro Thr Glu Ala Pro Pro Lys Ala
        195                 200                 205

Leu Thr Lys Cys Gln Glu Glu Val Ser His Ile Pro Asp Val His Pro
210                 215                 220

Gly Ser Phe Arg Pro Lys Cys Asp Glu Asn Gly Asn Tyr Leu Pro Leu
225                 230                 235                 240

Gln Cys Tyr Gly Ser Ile Gly Tyr Cys Trp Cys Val Phe Pro Asn Gly
                245                 250                 255

Thr Glu Val Pro Asn Thr Arg Ser Arg Gly His His Asn Cys Ser Glu
                260                 265                 270

Ser Leu Glu Leu Glu Asp Pro Ser Ser Gly Leu Gly Val Thr Lys Gln
                275                 280                 285

Asp Leu Gly Pro Ala Pro Leu
                290                 295

<210> SEQ ID NO 37
<211> LENGTH: 280
<212> TYPE: PRT
<213> ORGANISM: Felis catus
<220> FEATURE:
<221> NAME/KEY: Misc_feature
<223> OTHER INFORMATION: Amino acid sequence for Felis catus invariant
      chain (UniProt accession number M3VXS2)

<400> SEQUENCE: 37

Met Glu Asp Gln Arg Asp Leu Ile Ser Asn His Glu Gln Leu Pro Ile
1               5                   10                  15

Leu Gly Gln Arg Pro Ala Ala Pro Glu Ser Lys Cys Ser Arg Gly Ala
                20                  25                  30

Leu Tyr Thr Gly Phe Ser Val Leu Val Ala Leu Leu Leu Ala Gly Gln
                35                  40                  45

Ala Thr Thr Ala Tyr Phe Leu Tyr Gln Gln Gln Gly Arg Leu Asp Lys
        50                  55                  60

Leu Thr Val Thr Ala Gln Asn Leu Gln Leu Glu Asn Leu Arg Met Lys
65                  70                  75                  80

Leu Pro Lys Pro Ala Lys Pro Leu Asn Lys Leu Arg Val Ala Thr Pro
                85                  90                  95

Met Leu Met Gln Thr Met Pro Val Arg Gly Leu Leu Gln Ala Pro Met
                100                 105                 110

Gln Asn Ala Thr Lys Tyr Gly Asn Met Thr Gln Asp His Val Met His
        115                 120                 125

Met Leu Leu Glu Gly Asp Pro Leu Lys Val Tyr Pro Gln Leu Lys Gly
    130                 135                 140

Asn Phe Pro Glu Asn Leu Lys His Leu Lys Asn Thr Met Gly Thr Leu
145                 150                 155                 160

Asp Trp Lys Val Phe Glu Asn Trp Met Tyr Gln Trp Leu Leu Phe Glu
                165                 170                 175

Met Ser Lys Asn Ser Leu Glu Lys His Pro Ala Asp Ile Pro Leu Lys
                180                 185                 190

Val Leu Thr Lys Cys Gln Glu Glu Val Ser Arg Ile Pro Ala Val His
        195                 200                 205

Pro Gly Thr Phe Arg Pro Gln Cys Asp Glu Asn Gly Asn Tyr Lys Pro
        210                 215                 220

Leu Gln Cys Tyr Gly Ser Thr Gly Tyr Cys Trp Cys Val Phe Pro Asn
225                 230                 235                 240
```

```
Gly Thr Glu Val Pro His Ser Arg Ser His Gly His Arg Asn Cys Ser
                    245                 250                 255

Glu Ser Val Asp Val Glu Asp Leu Ser Ser Gly Leu Gly Met Thr Lys
                260                 265                 270

Pro Asp Leu Gly Gln Ala Pro Leu
        275                 280

<210> SEQ ID NO 38
<211> LENGTH: 279
<212> TYPE: PRT
<213> ORGANISM: Mustela putorius furo
<220> FEATURE:
<221> NAME/KEY: Misc_feature
<223> OTHER INFORMATION: Amino acid sequence for Mustela putorius furo
      invariant chain (UniProt accession number M3YQS4)

<400> SEQUENCE: 38

Met Glu Asp Gln Arg Asp Leu Ile Ser Asn His Glu Gln Leu Pro Met
1               5                   10                  15

Leu Gly Gln Arg Pro Ser Ala Pro Glu Ser Lys Cys Ser Arg Gly Ala
                20                  25                  30

Leu Tyr Thr Gly Phe Ser Val Leu Val Ala Leu Leu Leu Ala Gly Gln
            35                  40                  45

Ala Thr Thr Ala Tyr Phe Leu Tyr Gln Gln Gln Gly Arg Leu Asp Lys
        50                  55                  60

Leu Thr Val Thr Ser Gln Asn Leu Gln Leu Glu Asn Leu Arg Met Lys
65                  70                  75                  80

Leu Pro Lys Pro Pro Lys Pro Leu His Lys Met Arg Ala Ala Thr Pro
                85                  90                  95

Met Leu Met Gln Ala Leu Pro Met Pro Asp Leu Leu Gln Glu Pro Leu
            100                 105                 110

Gln Asn Ala Thr Lys Tyr Gly Asn Met Thr Gln Asp His Val Met His
        115                 120                 125

Val Leu Leu Glu Thr Asp Pro Leu Lys Val Tyr Pro Lys Leu Lys Gly
    130                 135                 140

Ser Phe Leu Glu Asn Leu Lys His Leu Lys Asn Thr Met Gly Pro Leu
145                 150                 155                 160

Glu Trp Lys Val Phe Glu Ser Trp Met Tyr Gln Trp Leu Leu Phe Glu
                165                 170                 175

Met Ser Lys Asn Ser Leu Glu Asn Lys Pro Glu Val Pro Leu Lys Ala
            180                 185                 190

Leu Thr Gln Cys Gln Glu Glu Val Ser Arg Val Pro Ala Val His Pro
        195                 200                 205

Gly Thr Phe Arg Pro Gln Cys Asp Glu Asn Gly Asn Tyr Lys Pro Leu
    210                 215                 220

Gln Cys Tyr Gly Ser Thr Gly Tyr Cys Trp Cys Val Phe Pro Asn Gly
225                 230                 235                 240

Thr Glu Val Pro His Thr Arg Ser Arg Gly His His Asn Cys Arg Glu
                245                 250                 255

Pro Leu Asp Met Glu Asp Leu Ser Ser Gly Leu Gly Met Thr Lys Gln
            260                 265                 270

Asp Leu Gly Gln Val Ala Val
        275

<210> SEQ ID NO 39
<211> LENGTH: 280
<212> TYPE: PRT
```

```
<213> ORGANISM: Loxodonta africana
<220> FEATURE:
<221> NAME/KEY: Misc_feature
<223> OTHER INFORMATION: Amino acid sequence for Loxodonta africana
      invariant chain (UniProt accession number G3TJE1)

<400> SEQUENCE: 39

Met Glu Asp Gln Arg Asp Leu Ile Ser Asn His Glu Gln Leu Pro Ile
1               5                   10                  15

Leu Gly Gln Arg Pro Gln Ala Pro Glu Ser Lys Cys Ser Arg Gly Ala
            20                  25                  30

Leu Tyr Thr Gly Phe Ser Val Leu Val Ala Leu Leu Leu Ala Gly Gln
        35                  40                  45

Ala Thr Thr Ala Tyr Phe Leu Tyr Gln Gln Gln Gly Arg Leu Asp Lys
    50                  55                  60

Leu Thr Val Thr Ala Gln Asn Leu Gln Leu Glu Asn Leu Arg Met Lys
65                  70                  75                  80

Leu Pro Lys Pro Ala Met Pro Met Ser Lys Met Arg Met Ala Thr Pro
                85                  90                  95

Leu Leu Met Arg Ala Leu Pro Met Glu Ala Leu Pro His Gly Pro Met
            100                 105                 110

Gln Asn Ala Thr Lys Tyr Gly Asn Met Pro Gln Asp Tyr Val Met His
        115                 120                 125

Met Leu Leu Arg Thr Asp Pro Leu Lys Val Tyr Pro Gln Leu Lys Gly
    130                 135                 140

Thr Leu Pro Glu Asn Leu Lys His Leu Lys Asn Thr Met Asp Gly Leu
145                 150                 155                 160

Asp Trp Lys Ala Phe Glu Asn Trp Met His Gln Trp Leu Leu Phe Glu
                165                 170                 175

Met Ser Lys Asn Ser Val Glu Glu Lys Pro Thr Glu Ala Pro Thr Lys
            180                 185                 190

Ala Leu Thr Lys Cys Gln Glu Val Ser Arg Ile Pro Ala Ile His
        195                 200                 205

Pro Gly Val Tyr Arg Pro Lys Cys Asp Glu Asn Gly Asn Tyr Leu Pro
    210                 215                 220

Leu Gln Cys Tyr Gly Ser Thr Gly Tyr Cys Trp Cys Val Phe Pro Asn
225                 230                 235                 240

Gly Thr Glu Val Pro His Thr Arg Ser Arg Gly His His Asn Cys Ser
                245                 250                 255

Glu Pro Leu Glu Leu Glu Asp Leu Ser Ser Gly Val Asp Met Thr Lys
            260                 265                 270

Gln Gly Val Gly Glu Glu Thr Leu
        275                 280

<210> SEQ ID NO 40
<211> LENGTH: 280
<212> TYPE: PRT
<213> ORGANISM: Loxodonta africana
<220> FEATURE:
<221> NAME/KEY: Misc_feature
<223> OTHER INFORMATION: Amino acid sequence for Loxodonta africana
      invariant chain (UniProt accession number G3U7Y6)

<400> SEQUENCE: 40

Met Glu Asp Gln Arg Asp Leu Ile Ser Asn His Glu Gln Leu Pro Ile
1               5                   10                  15

Leu Gly Gln Arg Pro Gln Ala Pro Glu Ser Lys Cys Ser Arg Gly Ala
            20                  25                  30
```

Leu Tyr Thr Gly Phe Ser Val Leu Val Ala Leu Leu Ala Gly Gln
        35                  40                  45

Ala Thr Thr Ala Tyr Phe Leu Tyr Gln Gln Gln Gly Arg Leu Asp Lys
 50                  55                  60

Leu Thr Val Thr Ala Gln Asn Leu Gln Leu Glu Asn Leu Arg Met Lys
 65                  70                  75                  80

Leu Pro Lys Pro Ala Met Pro Met Ser Lys Met Arg Met Ala Thr Pro
                 85                  90                  95

Leu Leu Met Arg Ala Leu Pro Met Glu Ala Leu Pro His Gly Pro Met
             100                 105                 110

Gln Asn Ala Thr Lys Tyr Gly Asn Met Pro Gln Asp Tyr Val Met His
             115                 120                 125

Met Leu Leu Arg Thr Asp Pro Leu Lys Val Tyr Pro Gln Leu Lys Gly
         130                 135                 140

Thr Leu Pro Glu Asn Leu Lys His Leu Lys Asn Thr Met Asp Gly Leu
145                 150                 155                 160

Asp Trp Lys Ala Phe Glu Asn Trp Met His Gln Trp Leu Leu Phe Glu
                 165                 170                 175

Met Ser Lys Asn Ser Val Glu Glu Lys Pro Thr Glu Ala Pro Thr Lys
             180                 185                 190

Ala Leu Thr Lys Cys Gln Glu Glu Val Ser Arg Ile Pro Ala Ile His
         195                 200                 205

Pro Gly Val Tyr Arg Pro Lys Cys Asp Glu Asn Gly Asn Tyr Leu Pro
     210                 215                 220

Leu Gln Cys Tyr Gly Ser Thr Gly Tyr Cys Trp Cys Val Phe Pro Asn
225                 230                 235                 240

Gly Thr Glu Val Pro His Thr Arg Ser Arg Gly His His Asn Cys Ser
                 245                 250                 255

Glu Pro Leu Glu Leu Glu Asp Leu Ser Ser Gly Val Asp Met Thr Lys
             260                 265                 270

Gln Gly Val Gly Glu Gly Leu Leu
         275                 280

<210> SEQ ID NO 41
<211> LENGTH: 214
<212> TYPE: PRT
<213> ORGANISM: Sus scrofa
<220> FEATURE:
<221> NAME/KEY: Misc_feature
<223> OTHER INFORMATION: Amino acid sequence for Sus scrofa invariant
      chain (UniProt accession number Q764N1)

<400> SEQUENCE: 41

Met Glu Asp Gln Arg Asp Leu Ile Ser Asn His Glu Gln Leu Pro Met
 1               5                  10                  15

Leu Gly Gln Arg Pro Gly Ala Pro Glu Ser Lys Cys Ser Arg Gly Ala
             20                  25                  30

Leu Tyr Thr Gly Phe Ser Val Leu Val Ala Leu Leu Ala Gly Gln
         35                  40                  45

Ala Thr Thr Ala Tyr Phe Leu Tyr Gln Gln Gln Gly Arg Leu Asp Lys
 50                  55                  60

Leu Thr Val Thr Ser Gln Asn Leu Gln Leu Glu Ser Leu Arg Met Lys
 65                  70                  75                  80

Leu Pro Lys Pro Ser Lys Pro Leu Ser Lys Met Arg Val Ser Ala Pro
                 85                  90                  95

Met Leu Met Gln Ala Leu Pro Met Glu Gly Pro Glu Pro Met Arg Asn
                100                 105                 110

Ala Thr Lys Tyr Gly Asn Met Thr Gln Asp His Val Met His Leu Leu
            115                 120                 125

Leu Lys Ser Asp Pro Leu Gly Val Tyr Pro Lys Leu Lys Gly Ser Leu
        130                 135                 140

Pro Glu Asn Leu Lys His Leu Lys Asn Thr Met Asp Gly Val Asn Trp
145                 150                 155                 160

Lys Leu Phe Glu Asn Trp Leu Arg Gln Trp Leu Leu Phe Glu Met Ser
                165                 170                 175

Lys Asn Ser Leu Glu Glu Thr Pro Phe Glu Val Pro Pro Lys Asp Pro
            180                 185                 190

Leu Glu Thr Glu Asp Leu Ser Ser Gly Leu Gly Val Thr Lys Gln Asp
        195                 200                 205

Leu Gly Gln Val Ile Leu
        210

<210> SEQ ID NO 42
<211> LENGTH: 340
<212> TYPE: PRT
<213> ORGANISM: Camelus ferus
<220> FEATURE:
<221> NAME/KEY: Misc_feature
<223> OTHER INFORMATION: Amino acid sequence for Camelus ferus invariant
      chain (UniProt accession number S9XLT6)

<400> SEQUENCE: 42

Met Glu Asp Gln Arg Asp Leu Ile Ser Asn His Glu Gln Leu Pro Ile
1               5                   10                  15

Leu Gly Gln Arg Pro Ala Ala Pro Glu Ser Lys Cys Ser Arg Gly Ala
            20                  25                  30

Leu Tyr Thr Gly Phe Ser Val Leu Met Ala Leu Leu Leu Ala Gly Gln
        35                  40                  45

Ala Thr Thr Ala Tyr Phe Leu Tyr Gln Gln Gln Gly Arg Leu Asp Lys
    50                  55                  60

Leu Thr Ile Thr Ser Gln Asn Leu Gln Leu Glu Asn Leu Arg Met Lys
65                  70                  75                  80

Leu Pro Lys Pro Ala Lys Pro Leu Ser Gln Met Arg Met Ala Thr Pro
                85                  90                  95

Met Leu Met Gln Ala Leu Pro Met Gln Gly Pro Gln Leu Met Gln Asn
                100                 105                 110

Ala Thr Lys Tyr Gly Asn Met Thr Gln Asp His Val Met His Leu Leu
            115                 120                 125

Leu Lys Ala Asp Pro Leu Lys Val Tyr Pro Gln Leu Lys Gly Ser Leu
        130                 135                 140

Pro Glu Asn Leu Lys His Leu Lys Asn Thr Met Asp Gly Met Asn Trp
145                 150                 155                 160

Lys Leu Phe Glu Asn Trp Met His Tyr Trp Leu Leu Phe Glu Met Ser
                165                 170                 175

Lys Asn Ser Gln Glu Glu Gln Pro Phe Glu Val Pro Thr Lys Ala Leu
            180                 185                 190

Thr Lys Cys Gln Glu Glu Val Ser Arg Ile Pro Ala Ile His Pro Gly
        195                 200                 205

Thr Phe Arg Pro Lys Cys Asp Glu Asn Gly Asn Tyr Met Pro Leu Gln
        210                 215                 220

Cys Tyr Gly Ser Ile Gly Tyr Cys Trp Cys Val Phe Pro Asn Gly Thr

```
                225                 230                 235                 240

Glu Val Pro His Thr Arg Ser Arg Gly His His Asn Cys Ser Asp Pro
                245                 250                 255

Leu Glu Met Glu Asp Leu Ser Ser Gly Leu Gly Val Thr Lys Pro Asp
                260                 265                 270

Leu Gly Gln Gly Pro Thr His Glu Ala Leu Ser Ser Ser Leu Gly Pro
                275                 280                 285

Arg Gln Met Leu Glu Leu Pro Ser Cys Pro Pro Arg Val Val Asn Asp
                290                 295                 300

Gln Gln Gly Phe Gln Thr Gln Glu Ala Tyr Leu Pro Pro Gly Val Leu
305                 310                 315                 320

Gln Thr Val Cys Ser Ala Val Phe Phe Cys Glu Arg Gly Met Thr
                325                 330                 335

Gly Ser Arg Thr
                340

<210> SEQ ID NO 43
<211> LENGTH: 268
<212> TYPE: PRT
<213> ORGANISM: Bos
<220> FEATURE:
<221> NAME/KEY: Misc_feature
<223> OTHER INFORMATION: Amino acid sequence for Bos mutus invariant
      chain (UniProt accession number L8I7V9)

<400> SEQUENCE: 43

Met Glu Asp Gln Arg Asp Leu Ile Ser Asn His Glu Gln Leu Pro Met
1               5                   10                  15

Leu Gly Gln Arg Pro Gly Ala Gln Glu Ser Lys Cys Ser Arg Gly Ala
                20                  25                  30

Leu Tyr Thr Gly Phe Ser Val Leu Val Ala Leu Leu Leu Ala Gly Gln
                35                  40                  45

Ala Thr Thr Ala Tyr Phe Leu Tyr Gln Gln Gln Gly Arg Leu Asp Lys
            50                  55                  60

Leu Thr Val Thr Ser Gln Asn Leu Gln Leu Glu Asn Leu Arg Met Lys
65                  70                  75                  80

Leu Pro Lys Pro Ala Lys Pro Met Ser Gln Met Arg Met Ala Thr Pro
                85                  90                  95

Met Leu Met Arg Ala Leu Pro Met Ala Gly Pro Glu Pro Met Lys Asn
                100                 105                 110

Ala Thr Lys Tyr Gly Asn Met Thr Gln Asp His Val Met His Leu Leu
                115                 120                 125

Leu Lys Ala Asp Pro Leu Lys Val Tyr Pro Gln Leu Lys Gly Ser Leu
            130                 135                 140

Pro Glu Asn Leu Lys His Leu Lys Asp Ser Met Asp Gly Leu Asp Trp
145                 150                 155                 160

Lys Leu Phe Glu Ser Trp Leu His Gln Trp Leu Leu Phe Glu Met Ser
                165                 170                 175

Lys Asn Ser Leu Glu Glu Lys Pro Phe Glu Gly Pro Pro Lys Val Leu
                180                 185                 190

Thr Gln Cys Gln Glu Glu Val Ser Arg Ile Pro Ala Ile His Pro Gly
                195                 200                 205

Val Phe Lys Pro Asn Cys Asp Glu Asn Gly Asn Tyr Met Pro Leu Gln
            210                 215                 220

Cys Tyr Gly Ser Ile Gly Tyr Cys Trp Cys Val Phe Pro Asn Gly Thr
225                 230                 235                 240
```

```
Glu Val Pro His Thr Arg Ser Arg Gly His Arg Asn Cys Ser Asp Pro
            245                 250                 255

Met Glu Met Glu Tyr Pro Ser Ser Gly Leu Gly Val
            260                 265

<210> SEQ ID NO 44
<211> LENGTH: 190
<212> TYPE: PRT
<213> ORGANISM: Bos taurus
<220> FEATURE:
<221> NAME/KEY: Misc_feature
<223> OTHER INFORMATION: Amino acid sequence for Bos taurus invariant
      chain (UniProt accession number Q7JFY1)

<400> SEQUENCE: 44

Ile Ser Asn His Glu Gln Leu Pro Met Leu Gly Gln Arg Pro Gly Ala
1               5                   10                  15

Gln Glu Ser Lys Cys Ser Arg Gly Ala Leu Tyr Thr Gly Phe Ser Val
            20                  25                  30

Leu Val Ala Leu Leu Leu Ala Gly Gln Ala Thr Thr Ala Tyr Phe Leu
        35                  40                  45

Tyr Gln Gln Gln Gly Arg Leu Asp Lys Leu Thr Val Thr Ser Gln Asn
50                  55                  60

Leu Gln Leu Glu Asn Leu Arg Met Lys Leu Pro Lys Pro Ala Lys Pro
65                  70                  75                  80

Met Ser Gln Met Arg Met Ala Thr Pro Met Leu Met Arg Ala Leu Pro
                85                  90                  95

Met Ala Gly Pro Glu Pro Met Lys Asn Ala Thr Lys Tyr Gly Asn Met
            100                 105                 110

Thr Gln Asp His Val Met His Leu Leu Leu Lys Ala Asp Pro Leu Lys
        115                 120                 125

Val Tyr Pro Gln Leu Lys Gly Ser Leu Pro Glu Asn Leu Lys His Leu
    130                 135                 140

Lys Asp Ser Met Asp Gly Leu Asp Trp Lys Leu Phe Glu Ser Trp Leu
145                 150                 155                 160

His Gln Trp Leu Leu Phe Glu Met Ser Lys Asn Ser Leu Glu Glu Lys
                165                 170                 175

Pro Phe Glu Gly Pro Pro Lys Asp Pro Met Glu Met Glu Tyr
            180                 185                 190

<210> SEQ ID NO 45
<211> LENGTH: 204
<212> TYPE: PRT
<213> ORGANISM: Bos taurus
<220> FEATURE:
<221> NAME/KEY: Misc_feature
<223> OTHER INFORMATION: Amino acid sequence for Bos taurus invariant
      chain (UniProt accession number Q29630)

<400> SEQUENCE: 45

Met Glu Asp Gln Arg Asp Leu Ile Ser Asn His Glu Gln Leu Pro Met
1               5                   10                  15

Leu Gly Gln Arg Pro Gly Ala Gln Glu Ser Lys Cys Ser Arg Gly Ala
            20                  25                  30

Leu Tyr Thr Gly Phe Ser Val Leu Val Ala Leu Leu Leu Ala Gly Gln
        35                  40                  45

Ala Thr Thr Ala Tyr Phe Leu Tyr Gln Gln Gln Gly Arg Leu Asp Lys
    50                  55                  60
```

Leu Thr Val Thr Ser Gln Asn Leu Gln Leu Glu Asn Leu Arg Met Lys
65                  70                  75                  80

Leu Pro Lys Pro Ala Lys Pro Met Ser Gln Met Arg Met Ala Thr Pro
                85                  90                  95

Met Leu Met Arg Ala Leu Pro Met Ala Gly Pro Glu Pro Met Lys Asn
            100                 105                 110

Ala Thr Lys Tyr Gly Asn Met Thr Gln Asp His Val Met His Leu Leu
        115                 120                 125

Leu Lys Ala Asp Pro Leu Lys Val Tyr Pro Gln Leu Lys Gly Ser Leu
    130                 135                 140

Pro Glu Asn Leu Lys His Leu Lys Asp Ser Met Asp Gly Leu Asp Trp
145                 150                 155                 160

Lys Leu Phe Glu Ser Trp Leu His Gln Trp Leu Leu Phe Glu Met Ser
                165                 170                 175

Lys Asn Ser Leu Glu Glu Lys Pro Phe Glu Gly Pro Pro Lys Asp Pro
            180                 185                 190

Met Glu Met Glu Tyr Pro Ser Ser Gly Leu Gly Val
        195                 200

<210> SEQ ID NO 46
<211> LENGTH: 208
<212> TYPE: PRT
<213> ORGANISM: Equus caballus
<220> FEATURE:
<221> NAME/KEY: Misc_feature
<223> OTHER INFORMATION: Amino acid sequence for Equus caballus
      invariant chain (UniProt accession number F6TGS3)

<400> SEQUENCE: 46

Met Glu Asp Gln Arg Asp Leu Ile Ser Asn His Glu Gln Val Pro Ile
1               5                   10                  15

Leu Gly Gln Arg Pro Ala Ala Pro Glu Arg Lys Cys Ser Arg Gly Ala
                20                  25                  30

Leu Tyr Thr Gly Phe Ser Val Leu Val Ala Leu Leu Ala Gly Gln
            35                  40                  45

Ala Thr Thr Ala Tyr Phe Leu Phe Gln Gln Gln Gly Arg Leu Asp Lys
        50                  55                  60

Leu Thr Val Thr Ala Gln Asn Leu Gln Leu Glu Lys Leu Arg Met Lys
65                  70                  75                  80

Leu Pro Lys Ser Ala Lys Pro Val Ser Lys Ile Arg Val Ala Thr Pro
                85                  90                  95

Met Leu Met Gln Ala Leu Pro Met Glu Gly Leu Ser His Gly Pro Met
            100                 105                 110

Gln Asn Ala Thr Lys Tyr Gly Asn Thr Thr Gln Asp His Val Met His
        115                 120                 125

Leu Leu Leu Arg Ala Asp Pro Leu Lys Val Tyr Pro Gln Leu Lys Gly
    130                 135                 140

Ser Phe Gln Glu Asn Leu Lys His Leu Lys Ser Thr Met Asp Gly Leu
145                 150                 155                 160

Asp Trp Lys Val Phe Glu Asn Trp Met His Gln Trp Leu Leu Phe Glu
                165                 170                 175

Met Ser Arg Asn Ser Leu Glu Glu Lys Pro Thr Gln Gly Pro Thr Lys
            180                 185                 190

Glu Pro Leu Glu Ile Glu Asp Leu Ser Ser Gly Val Gly Met Ala Lys
        195                 200                 205

-continued

```
<210> SEQ ID NO 47
<211> LENGTH: 208
<212> TYPE: PRT
<213> ORGANISM: Equus caballus
<220> FEATURE:
<221> NAME/KEY: Misc_feature
<223> OTHER INFORMATION: Amino acid sequence for Equus caballus
      invariant chain (UniProt accession number Q9MXD5)

<400> SEQUENCE: 47
```

Met Glu Asp Gln Arg Asp Leu Ile Ser Asn His Glu Gln Val Pro Ile
1               5                   10                  15

Leu Gly Gln Arg Pro Ala Ala Pro Glu Arg Lys Cys Ser Arg Gly Ala
                20                  25                  30

Leu Tyr Thr Gly Phe Ser Val Leu Val Ala Leu Leu Leu Ala Gly Gln
            35                  40                  45

Ala Thr Thr Ala Tyr Phe Leu Phe Gln Gln Gln Gly Arg Pro Asp Lys
        50                  55                  60

Leu Thr Val Thr Ala Gln Asn Leu Gln Leu Glu Ser Leu Arg Met Lys
65                  70                  75                  80

Leu Pro Lys Ser Ala Lys Pro Val Ser Lys Ile Arg Val Ala Thr Pro
                85                  90                  95

Met Leu Met Gln Ala Leu Pro Met Glu Gly Leu Ser His Gly Pro Met
            100                 105                 110

Gln Asn Ala Thr Lys Tyr Gly Asn Thr Thr Gln Asp His Val Met His
        115                 120                 125

Leu Leu Leu Arg Ala Asp Pro Leu Lys Val Tyr Pro Gln Leu Lys Gly
    130                 135                 140

Ser Phe Gln Glu Asn Leu Lys His Leu Lys Ser Thr Met Asp Gly Leu
145                 150                 155                 160

Asp Trp Lys Val Phe Glu Asn Trp Met His Gln Trp Leu Leu Phe Glu
                165                 170                 175

Met Ser Arg Asn Ser Leu Glu Glu Lys Pro Thr Gln Gly Pro Thr Lys
            180                 185                 190

Glu Pro Leu Glu Ile Glu Asp Leu Ser Ser Gly Val Gly Met Ala Lys
        195                 200                 205

```
<210> SEQ ID NO 48
<211> LENGTH: 292
<212> TYPE: PRT
<213> ORGANISM: Oryctolagus cuniculus
<220> FEATURE:
<221> NAME/KEY: Misc_feature
<223> OTHER INFORMATION: Amino acid sequence for Oryctolagus cuniculus
      invariant chain (UniProt accession number G1SKK3)

<400> SEQUENCE: 48
```

Phe Arg Ser Gln Thr Arg Lys Leu Lys Thr Ser Glu Ala Arg Ala Met
1               5                   10                  15

Asp Asp Gln Arg Asp Leu Ile Ser Asn His Glu Gln Met Pro Met Leu
                20                  25                  30

Gly Gln Arg Pro Gly Ala Gln Glu Arg Lys Cys Ser Arg Gly Ala Leu
            35                  40                  45

Tyr Thr Gly Phe Ser Val Leu Val Ala Leu Leu Leu Ala Gly Gln Ala
        50                  55                  60

Thr Thr Ala Tyr Phe Leu Tyr Gln Gln Gln Asp Arg Leu Asp Lys Leu
65                  70                  75                  80

Thr Val Thr Ser Gln Asn Leu Gln Leu Glu Ser Leu Arg Met Lys Leu
                85                  90                  95

```
Pro Lys Ser Ala Lys Pro Met Ser Gln Met Arg Met Ala Ala Pro Met
            100                 105                 110

Met Met Gln Ala Leu Pro Met Glu Asn Leu Ser Gln Gly Pro Val Gln
            115                 120                 125

Asn Val Thr Lys Tyr Gly Asn Thr Thr Gln Asp Tyr Val Met His Leu
130                 135                 140

Leu Leu Arg Ser Asp Pro Leu Lys Val Tyr Pro Gln Leu Lys Gly Ser
145                 150                 155                 160

Phe Pro Glu Asn Leu Lys Gln Leu Lys Gly Thr Met Asp Gly Leu Asn
                165                 170                 175

Trp Lys Val Phe Glu Ser Trp Leu His Gln Trp Leu Leu Phe Glu Met
            180                 185                 190

Ser Lys Asn Ser Leu Glu Glu Lys Pro Thr Glu Ala Pro Thr Lys Val
                195                 200                 205

Leu Ser Lys Cys Leu Glu Glu Ala Ser His Val Pro Asp Val His Pro
210                 215                 220

Gly Arg Phe Lys Pro Gln Cys Asp Glu Asn Gly Asn Tyr Met Pro Leu
225                 230                 235                 240

Gln Cys His Gly Ser Ile Gly Tyr Cys Trp Cys Val Phe Pro Asn Gly
                245                 250                 255

Thr Glu Val Pro His Thr Arg Ser Arg Gly His His Asn Cys Ser Glu
                260                 265                 270

Pro Met Glu Phe Glu Tyr Pro Ser Ser Gly Leu Asp Met Ala Arg Pro
            275                 280                 285

Glu Met Gly Lys
    290

<210> SEQ ID NO 49
<211> LENGTH: 282
<212> TYPE: PRT
<213> ORGANISM: Otolemur garnettii
<220> FEATURE:
<221> NAME/KEY: Misc_feature
<223> OTHER INFORMATION: Amino acid sequence for Otolemur garnettii
      invariant chain (UniProt accession number H0WQB3)

<400> SEQUENCE: 49

Met Glu Asp Gln Arg Asp Leu Ile Ser Asn His Glu Gln Thr Pro Ile
1               5                   10                  15

Leu Ser Gln Arg Ala Gly Ala Pro Glu Arg Gln Cys Ser Arg Gly Ala
            20                  25                  30

Leu Tyr Thr Gly Phe Ser Val Leu Val Ala Leu Leu Leu Ala Gly Gln
            35                  40                  45

Ala Thr Thr Ala Tyr Phe Leu Tyr Gln Gln Gln Gly Arg Leu Asp Lys
50                  55                  60

Leu Thr Val Thr Ser Gln Asn Leu Gln Leu Glu Asn Leu Arg Met Lys
65                  70                  75                  80

Leu Pro Lys Pro Pro Lys Pro Met Ser Lys Met Arg Met Ala Thr Pro
                85                  90                  95

Leu Met Met Gln Ala Leu Pro Met Glu Gly Leu Ala Gln Arg Pro Val
            100                 105                 110

Gln Asn Ala Thr Lys Tyr Gly Asn Met Thr Gln Asp His Val Met His
            115                 120                 125

Leu Leu Leu Lys Ala Asp Pro Leu Lys Val Tyr Pro Gln Met Lys Gly
130                 135                 140
```

Asn Phe Pro Glu Asn Leu Lys His Leu Lys Ser Thr Met Glu Thr Leu
145                 150                 155                 160

Asp Trp Lys Val Phe Glu Ser Trp Met His Gln Trp Leu Leu Phe Glu
                165                 170                 175

Met Ser Lys Asn Ser Gly Glu Glu Lys Pro Thr Glu Ala Pro Pro Lys
            180                 185                 190

Val Leu Thr Lys Cys Gln Glu Glu Phe Ser Arg Val Pro Ala Ile His
        195                 200                 205

Pro Gly Thr Phe Arg Pro Lys Cys Asp Glu Asn Gly Asn Tyr Met Pro
    210                 215                 220

Leu Gln Cys His Gly Ser Ile Gly Tyr Cys Trp Cys Val Phe Pro Asn
225                 230                 235                 240

Gly Thr Glu Val Pro His Thr Arg Ser Arg Gly Gln His Asn Cys Ser
                245                 250                 255

Glu Pro Gln Asp Leu Glu Asp Pro Ser Ser Gly Leu Gly Phe Thr Lys
                260                 265                 270

Gln Glu Pro Gly Ile Gly Lys Gly Pro Val
            275                 280

<210> SEQ ID NO 50
<211> LENGTH: 375
<212> TYPE: PRT
<213> ORGANISM: Tupaia chinensis
<220> FEATURE:
<221> NAME/KEY: Misc_feature
<223> OTHER INFORMATION: Amino acid sequence for Tupaia chinensis
      invariant chain (UniProt accession number L9KN01)

<400> SEQUENCE: 50

Met Asp Asp Gln Arg Asp Leu Ile Ser Asn His Glu Gln Val Pro Ile
1               5                   10                  15

Leu Gly Gln Arg Pro Arg Glu Ala Glu Ser Lys Cys Gly Arg Gly Ala
                20                  25                  30

Leu Tyr Thr Gly Phe Ser Val Leu Val Ala Leu Leu Ala Gly Gln
            35                  40                  45

Ala Thr Thr Ala Tyr Phe Leu Tyr Gln Gln Gln Gly Gln Leu His Lys
50                  55                  60

Leu Thr Val Thr Ser Gln Asn Leu Gln Leu Glu Asn Leu Arg Met Lys
65                  70                  75                  80

Leu Pro Lys Pro Ala Lys Pro Leu Ser Lys Met Arg Met Ala Thr Pro
                85                  90                  95

Leu Leu Met Arg Ala Leu Pro Met Asp Gly Leu Pro Gln Gly Pro Val
            100                 105                 110

Gln Asn Ala Thr Lys Tyr Gly Asn Met Thr Gln Asp His Val Met His
        115                 120                 125

Leu Leu Leu Lys Ala Asp Pro Leu Lys Val Tyr Pro Gln Leu Lys Gly
    130                 135                 140

Ser Phe Pro Glu Asn Leu Lys His Leu Lys Ser Thr Met Glu Thr Met
145                 150                 155                 160

Asp Trp Lys Val Phe Glu Ser Trp Met His Gln Trp Leu Leu Phe Glu
                165                 170                 175

Met Ser Lys Asn Ser Met Glu Glu Lys Pro Thr Glu Pro Thr Lys
            180                 185                 190

Ala Leu Thr Lys Cys Gln Glu Glu Val Ser Arg Ile Pro Ala Val His
        195                 200                 205

Pro Gly Thr Phe Arg Pro Lys Cys Asp Glu Asn Gly Asn Tyr Met Pro

```
                  210                 215                 220
Leu Gln Cys His Gly Ser Ile Gly Tyr Cys Trp Cys Val Phe Pro Asn
225                 230                 235                 240

Gly Thr Glu Val Pro His Thr Arg Ser Arg Gly His His Asn Cys Ser
                245                 250                 255

Gly Pro Thr Cys Leu Ala Leu Trp Asp His Leu Asp Ala Arg Ala Ala
                260                 265                 270

Leu Leu Gln Glu Ala Tyr Leu Gly Leu Val Pro Val Ala Leu Arg Arg
                275                 280                 285

Ser Val Pro Leu Ser Ser Val Gly Glu Lys Tyr Glu Arg Leu Leu
        290                 295                 300

Lys Leu Leu Trp Pro Pro Glu Gln Ile Leu Gly Leu Gln Gly Cys Leu
305                 310                 315                 320

Arg Ala Gly Gln Gly Ser Ala Ser Cys Thr Leu Gln Glu Gly Ala Arg
                325                 330                 335

Gly Ser Ala Leu Ile Thr Gln Gln Ala Leu Trp Ala Trp Val Glu Leu
                340                 345                 350

His Pro Cys Lys Val Trp Ala Val Gly His Glu His Ser Pro Cys Ser
                355                 360                 365

Gly Gly Ser Asp Thr Arg Lys
        370                 375

<210> SEQ ID NO 51
<211> LENGTH: 279
<212> TYPE: PRT
<213> ORGANISM: Ictidomys tridecemlineatus
<220> FEATURE:
<221> NAME/KEY: Misc_feature
<223> OTHER INFORMATION: Amino acid sequence for Ictidomys
      tridecemlineatus invariant chain (UniProt accession number I3MCR9)

<400> SEQUENCE: 51

Met Glu Asp Gln Arg Asp Leu Ile Ser Asn His Glu Gln Leu Pro Ile
1               5                   10                  15

Leu Gly Gln Arg Pro Arg Glu Gln Glu Arg Cys Ser Arg Gly Thr Leu
                20                  25                  30

Tyr Thr Gly Phe Ser Val Leu Val Ala Leu Leu Ala Gly Gln Ala
            35                  40                  45

Thr Thr Ala Tyr Phe Leu Tyr Gln Gln Gln Gly Arg Leu Asp Lys Leu
        50                  55                  60

Thr Val Thr Ser Gln Asn Leu Gln Leu Glu Asn Leu Arg Met Lys Leu
65                  70                  75                  80

Pro Lys Pro Pro Lys Pro Val Ser Gln Leu Arg Met Ala Thr Pro Leu
                85                  90                  95

Leu Met Gln Ala Leu Pro Met Glu Gly Leu Arg Gln Gly Pro Lys Gln
                100                 105                 110

Asn Ala Thr Lys Tyr Gly Asn Met Thr Gln Asp His Val Met His Leu
            115                 120                 125

Leu Leu Lys Ser Asn Pro Leu Lys Val Tyr Pro Gln Leu Lys Gly Ser
        130                 135                 140

Phe Pro Glu Asn Leu Lys His Leu Lys Ser Thr Met Asp Asn Leu Asp
145                 150                 155                 160

Trp Lys Ile Phe Glu Asn Trp Leu His Gln Trp Leu Leu Phe Glu Met
                165                 170                 175

Ser Lys Asn Ser Leu Glu Glu Lys Pro Thr Glu Ala Pro Thr Arg Val
                180                 185                 190
```

```
Leu Thr Lys Cys Gln Glu Val Ser His Ile Pro Ala Val His Pro
            195                 200                 205

Gly Ala Phe Arg Pro Lys Cys Asp Glu Asn Gly Asn Tyr Met Pro Leu
210                 215                 220

Gln Cys His Gly Ser Ile Gly Tyr Cys Trp Cys Val Phe Pro Asn Gly
225                 230                 235                 240

Thr Glu Val Pro His Thr Arg Ser Arg Gly Arg His Asp Cys Ser Glu
            245                 250                 255

Pro Leu Glu Leu Glu Asp Val Ser Ser Gly Leu Gly Val Thr Lys Gln
            260                 265                 270

Asp Leu Gly Gln Val Ile Met
            275

<210> SEQ ID NO 52
<211> LENGTH: 209
<212> TYPE: PRT
<213> ORGANISM: Sarcophilus harrisii
<220> FEATURE:
<221> NAME/KEY: Misc_feature
<223> OTHER INFORMATION: Amino acid sequence for Sarcophilus harrisii
      invariant chain (UniProt accession number G3X0Q6

<400> SEQUENCE: 52

Met Glu Asp Gln Arg Asp Leu Ile Ser Asn His Glu Gln Gln Pro Met
1               5                   10                  15

Leu Gly Gly Ser Ala Gly Gly Gln His Arg Ser Cys Asn Gln Gly Ala
            20                  25                  30

Phe Tyr Thr Gly Phe Ser Val Leu Val Ala Leu Leu Ile Ala Gly Gln
        35                  40                  45

Ala Ala Thr Val Tyr Phe Val Tyr Gln Gln Gly Arg Leu Asp Lys
50                  55                  60

Leu Thr Val Thr Ser Gln Asn Leu Gln Leu Glu Ser Leu Lys Met Lys
65                  70                  75                  80

Leu Pro Lys Ala Ser Ile Pro Met Asn Lys Leu Arg Leu Ala Thr Pro
                85                  90                  95

Met Leu Met Arg Glu Leu Glu Pro Glu Thr Leu Pro Ser Met Asp Leu
            100                 105                 110

Thr Lys Ile Gly Asn Asn Thr Lys Asp Gln Val Lys Tyr Leu Leu Leu
        115                 120                 125

Gln Ser Asp Pro Arg Arg Ser Phe Pro Glu Leu Thr Lys Ser Phe Gln
130                 135                 140

Glu Asn Met Lys Lys Leu Lys Asn Asn Met Glu Thr Lys Asn Trp Lys
145                 150                 155                 160

Asn Phe Glu Asn Trp Met His Gln Trp Leu Leu Phe Glu Met Ser Lys
                165                 170                 175

Lys Pro Asn Glu Glu Asn Val Glu Lys Lys Thr Glu Pro Leu Gln Lys
            180                 185                 190

Gly Leu Leu Asp Glu Glu Met Phe Ser Ser Gly Leu Gly Phe Pro Lys
        195                 200                 205

Gln

<210> SEQ ID NO 53
<211> LENGTH: 81
<212> TYPE: PRT
<213> ORGANISM: Homo sapiens
<220> FEATURE:
<221> NAME/KEY: Misc_feature
```

<223> OTHER INFORMATION: Amino acid sequence for residues 17-97 of human
p35 invariant chain

<400> SEQUENCE: 53

Met Asp Asp Gln Arg Asp Leu Ile Ser Asn Asn Glu Gln Leu Pro Met
1               5                   10                  15

Leu Gly Arg Arg Pro Gly Ala Pro Glu Ser Lys Cys Ser Arg Gly Ala
            20                  25                  30

Leu Tyr Thr Gly Phe Ser Ile Leu Val Thr Leu Leu Leu Ala Gly Gln
        35                  40                  45

Ala Thr Thr Ala Tyr Phe Leu Tyr Gln Gln Gln Gly Arg Leu Asp Lys
    50                  55                  60

Leu Thr Val Thr Ser Gln Asn Leu Gln Leu Glu Asn Leu Arg Met Lys
65                  70                  75                  80

Leu

<210> SEQ ID NO 54
<211> LENGTH: 80
<212> TYPE: PRT
<213> ORGANISM: Mus musculus
<220> FEATURE:
<221> NAME/KEY: Misc_feature
<223> OTHER INFORMATION: Amino acid sequence for region of mouse p31
invariant chain corresponding to residues 17-97 of human p35
invariant chain

<400> SEQUENCE: 54

Met Asp Asp Gln Arg Asp Leu Ile Ser Asn His Glu Gln Leu Pro Ile
1               5                   10                  15

Leu Gly Asn Arg Pro Arg Glu Pro Glu Arg Cys Ser Arg Gly Ala Leu
            20                  25                  30

Tyr Thr Gly Val Ser Val Leu Val Ala Leu Leu Leu Ala Gly Gln Ala
        35                  40                  45

Thr Thr Ala Tyr Phe Leu Tyr Gln Gln Gln Gly Arg Leu Asp Lys Leu
    50                  55                  60

Thr Ile Thr Ser Gln Asn Leu Gln Leu Glu Ser Leu Arg Met Lys Leu
65                  70                  75                  80

<210> SEQ ID NO 55
<211> LENGTH: 81
<212> TYPE: PRT
<213> ORGANISM: Loxodonta africana
<220> FEATURE:
<221> NAME/KEY: Misc_feature
<223> OTHER INFORMATION: Amino acid sequence for region of Loxodonta
africana invariant chain (UniProt accession number G3TJE1)
corresponding to residues 17-97 of human p35 invariant chain

<400> SEQUENCE: 55

Met Glu Asp Gln Arg Asp Leu Ile Ser Asn His Glu Gln Leu Pro Ile
1               5                   10                  15

Leu Gly Gln Arg Pro Gln Ala Pro Glu Ser Lys Cys Ser Arg Gly Ala
            20                  25                  30

Leu Tyr Thr Gly Phe Ser Val Leu Val Ala Leu Leu Leu Ala Gly Gln
        35                  40                  45

Ala Thr Thr Ala Tyr Phe Leu Tyr Gln Gln Gln Gly Arg Leu Asp Lys
    50                  55                  60

Leu Thr Val Thr Ala Gln Asn Leu Gln Leu Glu Asn Leu Arg Met Lys
65                  70                  75                  80

Leu

```
<210> SEQ ID NO 56
<211> LENGTH: 81
<212> TYPE: PRT
<213> ORGANISM: Felis catus
<220> FEATURE:
<221> NAME/KEY: Misc_feature
<223> OTHER INFORMATION: Amino acid sequence for region of Felis catus
      invariant chain (UniProt accession number M3VXS2) corresponding to
      residues 17-97 of human p35 invariant chain

<400> SEQUENCE: 56

Met Glu Asp Gln Arg Asp Leu Ile Ser Asn His Glu Gln Leu Pro Ile
1               5                   10                  15

Leu Gly Gln Arg Pro Ala Ala Pro Glu Ser Lys Cys Ser Arg Gly Ala
            20                  25                  30

Leu Tyr Thr Gly Phe Ser Val Leu Val Ala Leu Leu Ala Gly Gln
        35                  40                  45

Ala Thr Thr Ala Tyr Phe Leu Tyr Gln Gln Gln Gly Arg Leu Asp Lys
    50                  55                  60

Leu Thr Val Thr Ala Gln Asn Leu Gln Leu Glu Asn Leu Arg Met Lys
65                  70                  75                  80

Leu

<210> SEQ ID NO 57
<211> LENGTH: 81
<212> TYPE: PRT
<213> ORGANISM: Equus caballus
<220> FEATURE:
<221> NAME/KEY: Misc_feature
<223> OTHER INFORMATION: Amino acid sequence for region of Equus
      caballus invariant chain (UniProt accession number F6TGS3)
      corresponding to residues 17-97 of human p35 invariant chain

<400> SEQUENCE: 57

Met Glu Asp Gln Arg Asp Leu Ile Ser Asn His Glu Gln Val Pro Ile
1               5                   10                  15

Leu Gly Gln Arg Pro Ala Ala Pro Glu Arg Lys Cys Ser Arg Gly Ala
            20                  25                  30

Leu Tyr Thr Gly Phe Ser Val Leu Val Ala Leu Leu Leu Ala Gly Gln
        35                  40                  45

Ala Thr Thr Ala Tyr Phe Leu Phe Gln Gln Gln Gly Arg Leu Asp Lys
    50                  55                  60

Leu Thr Val Thr Ala Gln Asn Leu Gln Leu Glu Lys Leu Arg Met Lys
65                  70                  75                  80

Leu

<210> SEQ ID NO 58
<211> LENGTH: 81
<212> TYPE: PRT
<213> ORGANISM: Camelus ferus
<220> FEATURE:
<221> NAME/KEY: Misc_feature
<223> OTHER INFORMATION: Amino acid sequence for region of Camelus ferus
      invariant chain (UniProt accession number S9XLT6) corresponding to
      residues 17-97 of human p35 invariant chain

<400> SEQUENCE: 58

Met Glu Asp Gln Arg Asp Leu Ile Ser Asn His Glu Gln Leu Pro Ile
1               5                   10                  15

Leu Gly Gln Arg Pro Ala Ala Pro Glu Ser Lys Cys Ser Arg Gly Ala
            20                  25                  30
```

```
Leu Tyr Thr Gly Phe Ser Val Leu Met Ala Leu Leu Leu Ala Gly Gln
        35                  40                  45

Ala Thr Thr Ala Tyr Phe Leu Tyr Gln Gln Gln Gly Arg Leu Asp Lys
 50                  55                  60

Leu Thr Ile Thr Ser Gln Asn Leu Gln Leu Glu Asn Leu Arg Met Lys
 65                  70                  75                  80

Leu

<210> SEQ ID NO 59
<211> LENGTH: 81
<212> TYPE: PRT
<213> ORGANISM: Sus scrofa
<220> FEATURE:
<221> NAME/KEY: Misc_feature
<223> OTHER INFORMATION: Amino acid sequence for region of Sus scrofa
      invariant chain (UniProt accession number Q764N1) corresponding to
      residues 17-97 of human p35 invariant chain

<400> SEQUENCE: 59

Met Glu Asp Gln Arg Asp Leu Ile Ser Asn His Glu Gln Leu Pro Met
 1               5                  10                  15

Leu Gly Gln Arg Pro Gly Ala Pro Glu Ser Lys Cys Ser Arg Gly Ala
                20                  25                  30

Leu Tyr Thr Gly Phe Ser Val Leu Val Ala Leu Leu Leu Ala Gly Gln
        35                  40                  45

Ala Thr Thr Ala Tyr Phe Leu Tyr Gln Gln Gln Gly Arg Leu Asp Lys
 50                  55                  60

Leu Thr Val Thr Ser Gln Asn Leu Gln Leu Glu Ser Leu Arg Met Lys
 65                  70                  75                  80

Leu

<210> SEQ ID NO 60
<211> LENGTH: 81
<212> TYPE: PRT
<213> ORGANISM: Mustela putorius furo
<220> FEATURE:
<221> NAME/KEY: Misc_feature
<223> OTHER INFORMATION: Amino acid sequence for region of Mustela
      putorius furo invariant chain (UniProt accession number M3YQS4)
      corresponding to residues 17-97 of human p35 invariant chain

<400> SEQUENCE: 60

Met Glu Asp Gln Arg Asp Leu Ile Ser Asn His Glu Gln Leu Pro Met
 1               5                  10                  15

Leu Gly Gln Arg Pro Ser Ala Pro Glu Ser Lys Cys Ser Arg Gly Ala
                20                  25                  30

Leu Tyr Thr Gly Phe Ser Val Leu Val Ala Leu Leu Leu Ala Gly Gln
        35                  40                  45

Ala Thr Thr Ala Tyr Phe Leu Tyr Gln Gln Gln Gly Arg Leu Asp Lys
 50                  55                  60

Leu Thr Val Thr Ser Gln Asn Leu Gln Leu Glu Asn Leu Arg Met Lys
 65                  70                  75                  80

Leu

<210> SEQ ID NO 61
<211> LENGTH: 81
<212> TYPE: PRT
<213> ORGANISM: Macaca mulatta
<220> FEATURE:
<221> NAME/KEY: Misc_feature
```

<223> OTHER INFORMATION: Amino acid sequence for region of Macaca
mulatta invariant chain (UniProt accession number I0FWR3)
corresponding to residues 17-97 of human p35 invariant chain

<400> SEQUENCE: 61

Met Asp Asp Gln Arg Asp Leu Ile Ser Asn Asn Glu Gln Leu Pro Met
1               5                   10                  15

Leu Gly Arg Arg Pro Gly Thr Pro Glu Ser Lys Cys Ser Arg Gly Ala
            20                  25                  30

Leu Tyr Thr Gly Phe Ser Ile Leu Val Thr Leu Leu Leu Ala Gly Gln
        35                  40                  45

Ala Thr Thr Ala Tyr Phe Leu Tyr Gln Gln Gln Gly Arg Leu Asp Lys
    50                  55                  60

Leu Thr Val Thr Thr Gln Ser Leu Gln Leu Glu Asn Leu Arg Met Lys
65                  70                  75                  80

Leu

<210> SEQ ID NO 62
<211> LENGTH: 81
<212> TYPE: PRT
<213> ORGANISM: Macaca fascicularis
<220> FEATURE:
<221> NAME/KEY: Misc_feature
<223> OTHER INFORMATION: Amino acid sequence for region of Macaca
fascicularis invariant chain (UniProt accession number G7P8P8)
corresponding to residues 17-97 of human p35 invariant chain

<400> SEQUENCE: 62

Met Asp Asp Gln Arg Asp Leu Ile Ser Asn Asn Glu Gln Leu Pro Met
1               5                   10                  15

Leu Gly Arg Arg Pro Gly Thr Pro Glu Ser Lys Cys Ser Arg Gly Ala
            20                  25                  30

Leu Tyr Thr Gly Phe Ser Ile Leu Val Thr Leu Leu Leu Ala Gly Gln
        35                  40                  45

Ala Thr Thr Ala Tyr Phe Leu Tyr Gln Gln Gln Gly Arg Leu Asp Lys
    50                  55                  60

Leu Thr Val Thr Thr Gln Ser Leu Gln Leu Glu Asn Leu Arg Met Lys
65                  70                  75                  80

Leu

<210> SEQ ID NO 63
<211> LENGTH: 81
<212> TYPE: PRT
<213> ORGANISM: Chlorocebus sabaeus
<220> FEATURE:
<221> NAME/KEY: Misc_feature
<223> OTHER INFORMATION: Amino acid sequence for region of Chlorocebus
sabaeus invariant chain (UniProt accession number A0A0D9RGK4)
corresponding to residues 17-97 of human p35 invariant chain

<400> SEQUENCE: 63

Met Asp Asp Gln Arg Asp Leu Ile Ser Asn Asn Glu Gln Leu Pro Met
1               5                   10                  15

Leu Gly Arg Arg Pro Gly Thr Pro Glu Ser Lys Cys Ser Arg Gly Ala
            20                  25                  30

Leu Tyr Thr Gly Phe Ser Ile Leu Val Thr Leu Leu Leu Ala Gly Gln
        35                  40                  45

Ala Thr Thr Ala Tyr Phe Leu Tyr Gln Gln Gln Gly Arg Leu Asp Lys
    50                  55                  60

Leu Thr Val Thr Thr Gln Asn Leu Gln Leu Glu Asn Leu Arg Met Lys

```
                65                  70                  75                  80
Leu

<210> SEQ ID NO 64
<211> LENGTH: 81
<212> TYPE: PRT
<213> ORGANISM: Papio anubis
<220> FEATURE:
<221> NAME/KEY: Misc_feature
<223> OTHER INFORMATION: Amino acid sequence for region of Papio anubis
      invariant chain (UniProt accession number A0A096MM48)
      corresponding to residues 17-97 of human p35 invariant chain

<400> SEQUENCE: 64

Met Asp Asp Gln Arg Asp Leu Ile Ser Asn Asn Glu Gln Leu Pro Met
1               5                   10                  15

Leu Gly Arg Arg Pro Gly Thr Pro Glu Ser Lys Cys Ser Arg Gly Ala
            20                  25                  30

Leu Tyr Thr Gly Phe Ser Ile Leu Val Thr Leu Leu Leu Ala Gly Gln
        35                  40                  45

Ala Thr Thr Ala Tyr Phe Leu Tyr Gln Gln Gln Gly Arg Leu Asp Lys
    50                  55                  60

Leu Thr Val Thr Thr Gln Asn Leu Gln Leu Glu Asn Leu Arg Met Lys
65                  70                  75                  80

Leu

<210> SEQ ID NO 65
<211> LENGTH: 81
<212> TYPE: PRT
<213> ORGANISM: Pan troglodytes
<220> FEATURE:
<221> NAME/KEY: Misc_feature
<223> OTHER INFORMATION: Amino acid sequence for region of Pan
      troglodytes verus invariant chain (UniProt accession number
      A5A6L4) corresponding to residues 17-97 of human p35 invariant
      chain

<400> SEQUENCE: 65

Met Asp Asp Gln Arg Asp Leu Ile Ser Asn Asn Glu Gln Leu Pro Met
1               5                   10                  15

Leu Gly Arg Arg Pro Gly Ala Pro Glu Ser Lys Cys Ser Arg Gly Ala
            20                  25                  30

Leu Tyr Thr Gly Phe Ser Ile Leu Val Thr Leu Leu Leu Ala Gly Gln
        35                  40                  45

Ala Thr Thr Ala Tyr Phe Leu Tyr Gln Gln Gln Gly Arg Leu Asp Lys
    50                  55                  60

Leu Thr Val Thr Ser Gln Asn Leu Gln Leu Glu Asn Leu Arg Met Lys
65                  70                  75                  80

Leu

<210> SEQ ID NO 66
<211> LENGTH: 81
<212> TYPE: PRT
<213> ORGANISM: Gorilla gorilla gorilla
<220> FEATURE:
<221> NAME/KEY: Misc_feature
<223> OTHER INFORMATION: Amino acid sequence for region of Gorilla
      gorilla gorilla invariant chain (UniProt accession number G3R7S6)
      corresponding to residues 17-97 of human p35 invariant chain

<400> SEQUENCE: 66

Met Asp Asp Gln Arg Asp Leu Ile Ser Asn Asn Glu Gln Leu Pro Met
```

```
                1               5                  10                 15
Leu Gly Arg Arg Pro Gly Ala Pro Glu Ser Lys Cys Ser Arg Gly Ala
            20                  25                 30

Leu Tyr Thr Gly Phe Ser Ile Leu Val Thr Leu Leu Leu Ala Gly Gln
        35                  40                 45

Ala Thr Thr Ala Tyr Phe Leu Tyr Gln Gln Gln Gly Arg Leu Asp Lys
    50                  55                 60

Leu Thr Val Thr Ser Gln Asn Leu Gln Leu Glu Asn Leu Arg Met Lys
65                  70                  75                 80

Leu

<210> SEQ ID NO 67
<211> LENGTH: 81
<212> TYPE: PRT
<213> ORGANISM: Nomascus leucogenys
<220> FEATURE:
<221> NAME/KEY: Misc_feature
<223> OTHER INFORMATION: Amino acid sequence for region of Nomascus
      leucogenys invariant chain (UniProt accession number G1RHB8)
      corresponding to residues 17-97 of human p35 invariant chain

<400> SEQUENCE: 67

Met Asp Asp Gln Arg Asp Leu Ile Ser Asn Asn Glu Gln Leu Pro Met
1               5                   10                 15

Leu Gly Arg Arg Pro Gly Ala Pro Glu Ser Lys Cys Ser Arg Gly Ala
            20                  25                 30

Leu Tyr Thr Gly Phe Ser Ile Leu Val Thr Leu Leu Leu Ala Gly Gln
        35                  40                 45

Ala Thr Thr Ala Tyr Phe Leu Tyr Gln Gln Gln Gly Arg Leu Asp Lys
    50                  55                 60

Leu Thr Val Thr Ser Gln Asn Leu Gln Leu Glu Asn Leu Arg Met Lys
65                  70                  75                 80

Leu

<210> SEQ ID NO 68
<211> LENGTH: 81
<212> TYPE: PRT
<213> ORGANISM: Pongo abelii
<220> FEATURE:
<221> NAME/KEY: Misc_feature
<223> OTHER INFORMATION: Amino acid sequence for region of Pongo abelii
      invariant chain (UniProt accession number Q5RFJ4) corresponding to
      residues 17-97 of human p35 invariant chain

<400> SEQUENCE: 68

Met Asp Asp Gln Arg Asp Leu Ile Ser Asn Asn Glu Gln Leu Pro Met
1               5                   10                 15

Leu Gly Arg Arg Pro Gly Ala Pro Glu Ser Lys Cys Gly Arg Gly Ala
            20                  25                 30

Leu Tyr Thr Gly Phe Ser Ile Leu Val Thr Leu Leu Leu Ala Gly Gln
        35                  40                 45

Ala Thr Thr Ala Tyr Phe Leu Tyr Gln Gln Gln Gly Arg Leu Asp Lys
    50                  55                 60

Leu Thr Val Thr Ser Gln Asn Leu Gln Leu Glu Asn Leu Arg Met Lys
65                  70                  75                 80

Leu

<210> SEQ ID NO 69
<211> LENGTH: 81
```

```
<212> TYPE: PRT
<213> ORGANISM: Callithrix jacchus
<220> FEATURE:
<221> NAME/KEY: Misc_feature
<223> OTHER INFORMATION: Amino acid sequence for region of Callithrix
      jacchus invariant chain (UniProt accession number F7ENE8)
      corresponding to residues 17-97 of human p35 invariant chain

<400> SEQUENCE: 69

Met Asp Asp Gln Arg Asp Leu Ile Ser Asn Asn Glu Gln Leu Pro Met
1               5                   10                  15

Leu Gly Gln Arg Pro Gly Ala Pro Glu Ser Lys Cys Ser Arg Gly Ala
            20                  25                  30

Val Tyr Thr Val Phe Ser Ile Leu Val Ala Leu Leu Leu Ala Gly Gln
        35                  40                  45

Ala Thr Thr Ala Tyr Phe Leu Tyr Gln Gln Gln Gly Arg Leu Asp Lys
    50                  55                  60

Leu Thr Val Thr Ser Gln Asn Leu Gln Leu Glu Asn Leu Arg Met Lys
65                  70                  75                  80

Leu

<210> SEQ ID NO 70
<211> LENGTH: 81
<212> TYPE: PRT
<213> ORGANISM: Myotis lucifugus
<220> FEATURE:
<221> NAME/KEY: Misc_feature
<223> OTHER INFORMATION: Amino acid sequence for region of Myotis
      lucifugus invariant chain (UniProt accession number G1QEN4)
      corresponding to residues 17-97 of human p35 invariant chain

<400> SEQUENCE: 70

Met Glu Asp Gln Arg Asp Leu Ile Ser Asn His Glu Gln Leu Pro Met
1               5                   10                  15

Leu Gly Gln Arg Pro Gly Ala Gln Glu Ser Lys Cys Ser Arg Gly Ala
            20                  25                  30

Leu Tyr Thr Gly Phe Ser Val Leu Val Ala Leu Leu Leu Ala Gly Gln
        35                  40                  45

Ala Thr Thr Ala Tyr Phe Leu Tyr Gln Gln Gln Gly Arg Leu Asp Lys
    50                  55                  60

Leu Thr Val Thr Ser Gln Asn Leu Gln Leu Glu Asn Met Arg Met Lys
65                  70                  75                  80

Leu

<210> SEQ ID NO 71
<211> LENGTH: 81
<212> TYPE: PRT
<213> ORGANISM: Myotis davidii
<220> FEATURE:
<221> NAME/KEY: Misc_feature
<223> OTHER INFORMATION: Amino acid sequence for region of Myotis
      davidii invariant chain (UniProt accession number L5LQM9)
      corresponding to residues 17-97 of human p35 invariant chain

<400> SEQUENCE: 71

Met Glu Asp Gln Arg Asp Leu Ile Ser Asn His Glu Gln Leu Pro Met
1               5                   10                  15

Leu Gly Gln Arg Pro Gly Ala Gln Glu Ser Lys Cys Ser Arg Gly Ala
            20                  25                  30

Leu Tyr Thr Gly Phe Ser Val Leu Val Ala Leu Leu Leu Ala Gly Gln
        35                  40                  45
```

```
Ala Thr Thr Ala Tyr Phe Leu Tyr Gln Gln Gln Gly Arg Leu Asp Lys
    50                  55                  60

Leu Thr Val Thr Ser Gln Asn Leu Gln Leu Glu Asn Leu Arg Met Lys
65                  70                  75                  80

Leu

<210> SEQ ID NO 72
<211> LENGTH: 81
<212> TYPE: PRT
<213> ORGANISM: Bos
<220> FEATURE:
<221> NAME/KEY: Misc_feature
<223> OTHER INFORMATION: Amino acid sequence for region of Bos mutus
      invariant chain (UniProt accession number L8I7V9) corresponding to
      residues 17-97 of human p35 invariant chain

<400> SEQUENCE: 72

Met Glu Asp Gln Arg Asp Leu Ile Ser Asn His Glu Gln Leu Pro Met
1               5                   10                  15

Leu Gly Gln Arg Pro Gly Ala Gln Glu Ser Lys Cys Ser Arg Gly Ala
            20                  25                  30

Leu Tyr Thr Gly Phe Ser Val Leu Val Ala Leu Leu Leu Ala Gly Gln
        35                  40                  45

Ala Thr Thr Ala Tyr Phe Leu Tyr Gln Gln Gln Gly Arg Leu Asp Lys
    50                  55                  60

Leu Thr Val Thr Ser Gln Asn Leu Gln Leu Glu Asn Leu Arg Met Lys
65                  70                  75                  80

Leu

<210> SEQ ID NO 73
<211> LENGTH: 81
<212> TYPE: PRT
<213> ORGANISM: Bos taurus
<220> FEATURE:
<221> NAME/KEY: Misc_feature
<223> OTHER INFORMATION: Amino acid sequence for region of Bos taurus
      invariant chain (UniProt accession number Q29630) corresponding to
      residues 17-97 of human p35 invariant chain

<400> SEQUENCE: 73

Met Glu Asp Gln Arg Asp Leu Ile Ser Asn His Glu Gln Leu Pro Met
1               5                   10                  15

Leu Gly Gln Arg Pro Gly Ala Gln Glu Ser Lys Cys Ser Arg Gly Ala
            20                  25                  30

Leu Tyr Thr Gly Phe Ser Val Leu Val Ala Leu Leu Leu Ala Gly Gln
        35                  40                  45

Ala Thr Thr Ala Tyr Phe Leu Tyr Gln Gln Gln Gly Arg Leu Asp Lys
    50                  55                  60

Leu Thr Val Thr Ser Gln Asn Leu Gln Leu Glu Asn Leu Arg Met Lys
65                  70                  75                  80

Leu

<210> SEQ ID NO 74
<211> LENGTH: 66
<212> TYPE: PRT
<213> ORGANISM: Myotis brandtii
<220> FEATURE:
<221> NAME/KEY: Misc_feature
<223> OTHER INFORMATION: Amino acid sequence for region of Myotis
      brandtii invariant chain (UniProt accession number S7N2W2)
      corresponding to residues 17-97 of human p35 invariant chain
```

<400> SEQUENCE: 74

```
Met Leu Gly Gln Arg Pro Gly Ala Gln Glu Ser Lys Cys Ser Arg Gly
1               5                   10                  15

Ala Leu Tyr Thr Gly Phe Ser Val Leu Val Ala Leu Leu Leu Ala Gly
            20                  25                  30

Gln Ala Thr Thr Ala Tyr Phe Leu Tyr Gln Gln Gln Gly Arg Leu Asp
        35                  40                  45

Lys Leu Thr Val Thr Ser Gln Asn Leu Gln Leu Glu Asn Leu Arg Met
50                  55                  60

Lys Leu
65
```

<210> SEQ ID NO 75
<211> LENGTH: 81
<212> TYPE: PRT
<213> ORGANISM: Heterocephalus glaber
<220> FEATURE:
<221> NAME/KEY: Misc_feature
<223> OTHER INFORMATION: Amino acid sequence for region of
    Heterocephalus glaber invariant chain (UniProt accession number
    G5C391) corresponding to residues 17-97 of human p35 invariant
    chain

<400> SEQUENCE: 75

```
Met Glu Asp Gln Arg Asp Leu Ile Ser Asn His Glu Gln Leu Pro Met
1               5                   10                  15

Leu Gly Gln Arg Leu Gly Ala Gln Asp Arg Lys Cys Ser Arg Gly Ala
            20                  25                  30

Leu Tyr Thr Gly Phe Ser Val Leu Val Ala Leu Leu Leu Ala Gly Gln
        35                  40                  45

Ala Thr Thr Ala Tyr Phe Leu Tyr Gln Gln Gln Gly Arg Leu Asp Lys
    50                  55                  60

Leu Thr Val Thr Ser Gln Asn Leu Gln Leu Glu Asn Leu Arg Met Lys
65                  70                  75                  80

Met
```

<210> SEQ ID NO 76
<211> LENGTH: 81
<212> TYPE: PRT
<213> ORGANISM: Fukomys damarensis
<220> FEATURE:
<221> NAME/KEY: Misc_feature
<223> OTHER INFORMATION: Amino acid sequence for region of Fukomys
    damarensis invariant chain (UniProt accession number A0A091E9W3)
    corresponding to residues 17-97 of human p35 invariant chain

<400> SEQUENCE: 76

```
Met Glu Asp Gln Arg Asp Leu Ile Ser Asn His Glu Gln Leu Pro Met
1               5                   10                  15

Leu Gly Gln Arg Pro Ala Ala Gln Asp Arg Lys Cys Ser Arg Gly Ala
            20                  25                  30

Leu Tyr Thr Gly Phe Ser Ile Leu Val Ala Leu Leu Leu Ala Gly Gln
        35                  40                  45

Ala Thr Thr Ala Tyr Phe Leu Tyr Gln Gln Gln Gly Arg Leu Asp Lys
    50                  55                  60

Leu Thr Val Thr Ser Gln Asn Leu Gln Leu Glu Asn Leu Arg Met Lys
65                  70                  75                  80

Met
```

```
<210> SEQ ID NO 77
<211> LENGTH: 81
<212> TYPE: PRT
<213> ORGANISM: Cavia porcellus
<220> FEATURE:
<221> NAME/KEY: Misc_feature
<223> OTHER INFORMATION: Amino acid sequence for region of Cavia
      porcellus invariant chain (UniProt accession number H0UZ94)
      corresponding to residues 17-97 of human p35 invariant chain

<400> SEQUENCE: 77

Met Glu Asp Gln His Asp Leu Ile Ser Asn His Glu Gln Leu Pro Met
1               5                   10                  15

Leu Gly Gln Arg Pro Gly Ala Gln Asp Gly Lys Cys Ser Arg Gly Ala
            20                  25                  30

Leu Tyr Thr Gly Phe Ser Val Leu Val Ala Leu Leu Leu Ala Gly Gln
        35                  40                  45

Ala Thr Thr Ala Tyr Phe Leu Tyr Gln Gln Gln Gly Arg Leu Asp Lys
    50                  55                  60

Leu Thr Val Thr Ser Gln Asn Leu Gln Leu Glu Asn Leu Arg Met Lys
65                  70                  75                  80

Met

<210> SEQ ID NO 78
<211> LENGTH: 81
<212> TYPE: PRT
<213> ORGANISM: Oryctolagus cuniculus
<220> FEATURE:
<221> NAME/KEY: Misc_feature
<223> OTHER INFORMATION: Amino acid sequence for region of Oryctolagus
      cuniculus invariant chain (UniProt accession number G1SKK3)
      corresponding to residues 17-97 of human p35 invariant chain

<400> SEQUENCE: 78

Met Asp Asp Gln Arg Asp Leu Ile Ser Asn His Glu Gln Met Pro Met
1               5                   10                  15

Leu Gly Gln Arg Pro Gly Ala Gln Glu Arg Lys Cys Ser Arg Gly Ala
            20                  25                  30

Leu Tyr Thr Gly Phe Ser Val Leu Val Ala Leu Leu Leu Ala Gly Gln
        35                  40                  45

Ala Thr Thr Ala Tyr Phe Leu Tyr Gln Gln Gln Asp Arg Leu Asp Lys
    50                  55                  60

Leu Thr Val Thr Ser Gln Asn Leu Gln Leu Glu Ser Leu Arg Met Lys
65                  70                  75                  80

Leu

<210> SEQ ID NO 79
<211> LENGTH: 81
<212> TYPE: PRT
<213> ORGANISM: Pteropus alecto
<220> FEATURE:
<221> NAME/KEY: Misc_feature
<223> OTHER INFORMATION: Amino acid sequence for region of Pteropus
      alecto invariant chain (UniProt accession number L5L1G3)
      corresponding to residues 17-97 of human p35 invariant chain

<400> SEQUENCE: 79

Met Glu Asp Gln Arg Asp Leu Ile Ser Asn His Glu Gln Leu Pro Met
1               5                   10                  15

Leu Gly Gln Arg Pro Gly Ala Pro Glu Arg Asn Cys Ser Arg Gly Ala
            20                  25                  30

Leu Tyr Thr Gly Phe Ser Val Leu Val Ala Leu Leu Leu Ala Gly Gln
```

```
                    35                  40                  45

Ala Thr Thr Ala Tyr Phe Leu Tyr Gln Gln Gln Gly Arg Leu Asp Lys
        50                  55                  60

Leu Thr Val Thr Ser Gln Asn Leu Gln Leu Glu Asn Leu Arg Met Lys
65                  70                  75                  80

Leu

<210> SEQ ID NO 80
<211> LENGTH: 81
<212> TYPE: PRT
<213> ORGANISM: Rattus norvegicus
<220> FEATURE:
<221> NAME/KEY: Misc_feature
<223> OTHER INFORMATION: Amino acid sequence for region of Rattus
      norvegicus second isoform invariant chain (UniProt accession
      number P10247-2) corresponding to residues 17-97 of human p35
      invariant chain

<400> SEQUENCE: 80

Met Asp Asp Gln Arg Asp Leu Ile Ser Asn His Glu Gln Leu Pro Ile
1               5                   10                  15

Leu Gly Gln Arg Ala Arg Ala Pro Glu Ser Asn Cys Asn Arg Gly Val
            20                  25                  30

Leu Tyr Thr Ser Val Ser Val Leu Val Ala Leu Leu Leu Ala Gly Gln
        35                  40                  45

Ala Thr Thr Ala Tyr Phe Leu Tyr Gln Gln Gln Gly Arg Leu Asp Lys
    50                  55                  60

Leu Thr Val Thr Ser Gln Asn Leu Gln Leu Glu Asn Leu Arg Met Lys
65                  70                  75                  80

Leu

<210> SEQ ID NO 81
<211> LENGTH: 81
<212> TYPE: PRT
<213> ORGANISM: Tupaia chinensis
<220> FEATURE:
<221> NAME/KEY: Misc_feature
<223> OTHER INFORMATION: Amino acid sequence for region of Tupaia
      chinensis invariant chain (UniProt accession number L9KN01)
      corresponding to residues 17-97 of human p35 invariant chain

<400> SEQUENCE: 81

Met Asp Asp Gln Arg Asp Leu Ile Ser Asn His Glu Gln Val Pro Ile
1               5                   10                  15

Leu Gly Gln Arg Pro Arg Glu Ala Glu Ser Lys Cys Gly Arg Gly Ala
            20                  25                  30

Leu Tyr Thr Gly Phe Ser Val Leu Val Ala Leu Leu Leu Ala Gly Gln
        35                  40                  45

Ala Thr Thr Ala Tyr Phe Leu Tyr Gln Gln Gln Gly Gln Leu His Lys
    50                  55                  60

Leu Thr Val Thr Ser Gln Asn Leu Gln Leu Glu Asn Leu Arg Met Lys
65                  70                  75                  80

Leu

<210> SEQ ID NO 82
<211> LENGTH: 80
<212> TYPE: PRT
<213> ORGANISM: Ictidomys tridecemlineatus
<220> FEATURE:
<221> NAME/KEY: Misc_feature
<223> OTHER INFORMATION: Amino acid sequence for region of Ictidomys
``` tridecemlineatus invariant chain (UniProt accession number I3MCR9)
corresponding to residues 17-97 of human p35 invariant chain

<400> SEQUENCE: 82

Met Glu Asp Gln Arg Asp Leu Ile Ser Asn His Glu Gln Leu Pro Ile
1               5                   10                  15

Leu Gly Gln Arg Pro Arg Glu Gln Glu Arg Cys Ser Arg Gly Thr Leu
            20                  25                  30

Tyr Thr Gly Phe Ser Val Leu Val Ala Leu Leu Leu Ala Gly Gln Ala
        35                  40                  45

Thr Thr Ala Tyr Phe Leu Tyr Gln Gln Gln Gly Arg Leu Asp Lys Leu
    50                  55                  60

Thr Val Thr Ser Gln Asn Leu Gln Leu Glu Asn Leu Arg Met Lys Leu
65                  70                  75                  80

<210> SEQ ID NO 83
<211> LENGTH: 81
<212> TYPE: PRT
<213> ORGANISM: Otolemur garnettii
<220> FEATURE:
<221> NAME/KEY: Misc_feature
<223> OTHER INFORMATION: Amino acid sequence for region of Otolemur
      garnettii invariant chain (UniProt accession number H0WQB3)
      corresponding to residues 17-97 of human p35 invariant chain

<400> SEQUENCE: 83

Met Glu Asp Gln Arg Asp Leu Ile Ser Asn His Glu Gln Thr Pro Ile
1               5                   10                  15

Leu Ser Gln Arg Ala Gly Ala Pro Glu Arg Gln Cys Ser Arg Gly Ala
            20                  25                  30

Leu Tyr Thr Gly Phe Ser Val Leu Val Ala Leu Leu Leu Ala Gly Gln
        35                  40                  45

Ala Thr Thr Ala Tyr Phe Leu Tyr Gln Gln Gln Gly Arg Leu Asp Lys
    50                  55                  60

Leu Thr Val Thr Ser Gln Asn Leu Gln Leu Glu Asn Leu Arg Met Lys
65                  70                  75                  80

Leu

<210> SEQ ID NO 84
<211> LENGTH: 81
<212> TYPE: PRT
<213> ORGANISM: Sarcophilus harrisii
<220> FEATURE:
<221> NAME/KEY: Misc_feature
<223> OTHER INFORMATION: Amino acid sequence for region of Sarcophilus
      harrisii invariant chain (UniProt accession number G3X0Q6)
      corresponding to residues 17-97 of human p35 invariant chain

<400> SEQUENCE: 84

Met Glu Asp Gln Arg Asp Leu Ile Ser Asn His Glu Gln Gln Pro Met
1               5                   10                  15

Leu Gly Gly Ser Ala Gly Gly Gln His Arg Ser Cys Asn Gln Gly Ala
            20                  25                  30

Phe Tyr Thr Gly Phe Ser Val Leu Val Ala Leu Leu Ile Ala Gly Gln
        35                  40                  45

Ala Ala Thr Val Tyr Phe Val Tyr Gln Gln Gln Gly Arg Leu Asp Lys
    50                  55                  60

Leu Thr Val Thr Ser Gln Asn Leu Gln Leu Glu Ser Leu Lys Met Lys
65                  70                  75                  80

Leu

```
<210> SEQ ID NO 85
<211> LENGTH: 26
<212> TYPE: PRT
<213> ORGANISM: Homo sapiens
<220> FEATURE:
<221> NAME/KEY: Misc_feature
<223> OTHER INFORMATION: Amino acid sequence for residues 67-92 of human
      p35 invariant chain

<400> SEQUENCE: 85

Thr Ala Tyr Phe Leu Tyr Gln Gln Gln Gly Arg Leu Asp Lys Leu Thr
1               5                   10                  15

Val Thr Ser Gln Asn Leu Gln Leu Glu Asn
            20                  25

<210> SEQ ID NO 86
<211> LENGTH: 26
<212> TYPE: PRT
<213> ORGANISM: Mus musculus
<220> FEATURE:
<221> NAME/KEY: Misc_feature
<223> OTHER INFORMATION: Amino acid sequence for region of mouse p31
      invariant chain corresponding to residues 67-92 of human p35
      invariant chain

<400> SEQUENCE: 86

Thr Ala Tyr Phe Leu Tyr Gln Gln Gln Gly Arg Leu Asp Lys Leu Thr
1               5                   10                  15

Ile Thr Ser Gln Asn Leu Gln Leu Glu Ser
            20                  25

<210> SEQ ID NO 87
<211> LENGTH: 26
<212> TYPE: PRT
<213> ORGANISM: Mustela putorius furo
<220> FEATURE:
<221> NAME/KEY: Misc_feature
<223> OTHER INFORMATION: Amino acid sequence for region of Mustela
      putorius furo invariant chain (UniProt accession number M3YQS4)
      corresponding to residues 67-92 of human p35 invariant chain

<400> SEQUENCE: 87

Thr Ala Tyr Phe Leu Tyr Gln Gln Gln Gly Arg Leu Asp Lys Leu Thr
1               5                   10                  15

Val Thr Ser Gln Asn Leu Gln Leu Glu Asn
            20                  25

<210> SEQ ID NO 88
<211> LENGTH: 26
<212> TYPE: PRT
<213> ORGANISM: Myotis brandtii
<220> FEATURE:
<221> NAME/KEY: Misc_feature
<223> OTHER INFORMATION: Amino acid sequence for region of Myotis
      brandtii invariant chain (UniProt accession number S7N2W2)
      corresponding to residues 67-92 of human p35 invariant chain

<400> SEQUENCE: 88

Thr Ala Tyr Phe Leu Tyr Gln Gln Gln Gly Arg Leu Asp Lys Leu Thr
1               5                   10                  15

Val Thr Ser Gln Asn Leu Gln Leu Glu Asn
            20                  25

<210> SEQ ID NO 89
<211> LENGTH: 26
```

```
<212> TYPE: PRT
<213> ORGANISM: Pteropus alecto
<220> FEATURE:
<221> NAME/KEY: Misc_feature
<223> OTHER INFORMATION: Amino acid sequence for region of Pteropus
      alecto invariant chain (UniProt accession number L5L1G3)
      corresponding to residues 67-92 of human p35 invariant chain

<400> SEQUENCE: 89

Thr Ala Tyr Phe Leu Tyr Gln Gln Gln Gly Arg Leu Asp Lys Leu Thr
1               5                   10                  15

Val Thr Ser Gln Asn Leu Gln Leu Glu Asn
            20                  25

<210> SEQ ID NO 90
<211> LENGTH: 26
<212> TYPE: PRT
<213> ORGANISM: Fukomys damarensis
<220> FEATURE:
<221> NAME/KEY: Misc_feature
<223> OTHER INFORMATION: Amino acid sequence for region of Fukomys
      damarensis invariant chain (UniProt accession number A0A091E9W3)
      corresponding to residues 67-92 of human p35 invariant chain

<400> SEQUENCE: 90

Thr Ala Tyr Phe Leu Tyr Gln Gln Gln Gly Arg Leu Asp Lys Leu Thr
1               5                   10                  15

Val Thr Ser Gln Asn Leu Gln Leu Glu Asn
            20                  25

<210> SEQ ID NO 91
<211> LENGTH: 26
<212> TYPE: PRT
<213> ORGANISM: Ictidomys tridecemlineatus
<220> FEATURE:
<221> NAME/KEY: Misc_feature
<223> OTHER INFORMATION: Amino acid sequence for region of Ictidomys
      tridecemlineatus invariant chain (UniProt accession number I3MCR9)
      corresponding to residues 67-92 of human p35 invariant chain

<400> SEQUENCE: 91

Thr Ala Tyr Phe Leu Tyr Gln Gln Gln Gly Arg Leu Asp Lys Leu Thr
1               5                   10                  15

Val Thr Ser Gln Asn Leu Gln Leu Glu Asn
            20                  25

<210> SEQ ID NO 92
<211> LENGTH: 26
<212> TYPE: PRT
<213> ORGANISM: Bos
<220> FEATURE:
<221> NAME/KEY: Misc_feature
<223> OTHER INFORMATION: Amino acid sequence for region of Bos mutus
      invariant chain (UniProt accession number L8I7V9) corresponding to
      residues 67-92 of human p35 invariant chain

<400> SEQUENCE: 92

Thr Ala Tyr Phe Leu Tyr Gln Gln Gln Gly Arg Leu Asp Lys Leu Thr
1               5                   10                  15

Val Thr Ser Gln Asn Leu Gln Leu Glu Asn
            20                  25

<210> SEQ ID NO 93
<211> LENGTH: 26
<212> TYPE: PRT
<213> ORGANISM: Heterocephalus glaber
<220> FEATURE:
```

```
<221> NAME/KEY: Misc_feature
<223> OTHER INFORMATION: Amino acid sequence for region of
      Heterocephalus glaber invariant chain (UniProt accession number
      G5C391) corresponding to residues 67-92 of human p35 invariant
      chain

<400> SEQUENCE: 93

Thr Ala Tyr Phe Leu Tyr Gln Gln Gln Gly Arg Leu Asp Lys Leu Thr
1               5                  10                  15

Val Thr Ser Gln Asn Leu Gln Leu Glu Asn
            20                  25

<210> SEQ ID NO 94
<211> LENGTH: 26
<212> TYPE: PRT
<213> ORGANISM: Myotis davidii
<220> FEATURE:
<221> NAME/KEY: Misc_feature
<223> OTHER INFORMATION: Amino acid sequence for region of Myotis
      davidii invariant chain (UniProt accession number L5LQM9)
      corresponding to residues 67-92 of human p35 invariant chain

<400> SEQUENCE: 94

Thr Ala Tyr Phe Leu Tyr Gln Gln Gln Gly Arg Leu Asp Lys Leu Thr
1               5                  10                  15

Val Thr Ser Gln Asn Leu Gln Leu Glu Asn
            20                  25

<210> SEQ ID NO 95
<211> LENGTH: 26
<212> TYPE: PRT
<213> ORGANISM: Tupaia chinensis
<220> FEATURE:
<221> NAME/KEY: Misc_feature
<223> OTHER INFORMATION: Amino acid sequence for region of Tupaia
      chinensis invariant chain (UniProt accession number L9KN01)
      corresponding to residues 67-92 of human p35 invariant chain

<400> SEQUENCE: 95

Thr Ala Tyr Phe Leu Tyr Gln Gln Gln Gly Gln Leu His Lys Leu Thr
1               5                  10                  15

Val Thr Ser Gln Asn Leu Gln Leu Glu Asn
            20                  25

<210> SEQ ID NO 96
<211> LENGTH: 26
<212> TYPE: PRT
<213> ORGANISM: Myotis lucifugus
<220> FEATURE:
<221> NAME/KEY: Misc_feature
<223> OTHER INFORMATION: Amino acid sequence for region of Myotis
      lucifugus invariant chain (UniProt accession number G1QEN4)
      corresponding to residues 67-92 of human p35 invariant chain

<400> SEQUENCE: 96

Thr Ala Tyr Phe Leu Tyr Gln Gln Gln Gly Arg Leu Asp Lys Leu Thr
1               5                  10                  15

Val Thr Ser Gln Asn Leu Gln Leu Glu Asn
            20                  25

<210> SEQ ID NO 97
<211> LENGTH: 26
<212> TYPE: PRT
<213> ORGANISM: Rattus norvegicus
<220> FEATURE:
<221> NAME/KEY: Misc_feature
<223> OTHER INFORMATION: Amino acid sequence for region of Rattus
``` norvegicus second isoform invariant chain (UniProt accession
number P10247-2) corresponding to residues 67-92 of human p35
invariant chain

<400> SEQUENCE: 97

Thr Ala Tyr Phe Leu Tyr Gln Gln Gln Gly Arg Leu Asp Lys Leu Thr
1               5                   10                  15

Val Thr Ser Gln Asn Leu Gln Leu Glu Asn
            20                  25

<210> SEQ ID NO 98
<211> LENGTH: 26
<212> TYPE: PRT
<213> ORGANISM: Bos taurus
<220> FEATURE:
<221> NAME/KEY: Misc_feature
<223> OTHER INFORMATION: Amino acid sequence for region of Bos taurus
      invariant chain (UniProt accession number Q29630) corresponding to
      residues 67-92 of human p35 invariant chain

<400> SEQUENCE: 98

Thr Ala Tyr Phe Leu Tyr Gln Gln Gln Gly Arg Leu Asp Lys Leu Thr
1               5                   10                  15

Val Thr Ser Gln Asn Leu Gln Leu Glu Asn
            20                  25

<210> SEQ ID NO 99
<211> LENGTH: 26
<212> TYPE: PRT
<213> ORGANISM: Otolemur garnettii
<220> FEATURE:
<221> NAME/KEY: Misc_feature
<223> OTHER INFORMATION: Amino acid sequence for region of Otolemur
      garnettii invariant chain (UniProt accession number H0WQB3)
      corresponding to residues 67-92 of human p35 invariant chain

<400> SEQUENCE: 99

Thr Ala Tyr Phe Leu Tyr Gln Gln Gln Gly Arg Leu Asp Lys Leu Thr
1               5                   10                  15

Val Thr Ser Gln Asn Leu Gln Leu Glu Asn
            20                  25

<210> SEQ ID NO 100
<211> LENGTH: 26
<212> TYPE: PRT
<213> ORGANISM: Cavia porcellus
<220> FEATURE:
<221> NAME/KEY: Misc_feature
<223> OTHER INFORMATION: Amino acid sequence for region of Cavia
      porcellus invariant chain (UniProt accession number H0UZ94)
      corresponding to residues 67-92 of human p35 invariant chain

<400> SEQUENCE: 100

Thr Ala Tyr Phe Leu Tyr Gln Gln Gln Gly Arg Leu Asp Lys Leu Thr
1               5                   10                  15

Val Thr Ser Gln Asn Leu Gln Leu Glu Asn
            20                  25

<210> SEQ ID NO 101
<211> LENGTH: 26
<212> TYPE: PRT
<213> ORGANISM: Callithrix jacchus
<220> FEATURE:
<221> NAME/KEY: Misc_feature
<223> OTHER INFORMATION: Amino acid sequence for region of Callithrix
      jacchus invariant chain (UniProt accession number F7ENE8)
      corresponding to residues 67-92 of human p35 invariant chain

<400> SEQUENCE: 101

Thr Ala Tyr Phe Leu Tyr Gln Gln Gln Gly Arg Leu Asp Lys Leu Thr
1               5                   10                  15

Val Thr Ser Gln Asn Leu Gln Leu Glu Asn
            20                  25

<210> SEQ ID NO 102
<211> LENGTH: 26
<212> TYPE: PRT
<213> ORGANISM: Callithrix jacchus
<220> FEATURE:
<221> NAME/KEY: Misc_feature
<223> OTHER INFORMATION: Amino acid sequence for region of Nomascus
      leucogenys invariant chain (UniProt accession number G1RHB8)
      corresponding to residues 67-92 of human p35 invariant chain

<400> SEQUENCE: 102

Thr Ala Tyr Phe Leu Tyr Gln Gln Gln Gly Arg Leu Asp Lys Leu Thr
1               5                   10                  15

Val Thr Ser Gln Asn Leu Gln Leu Glu Asn
            20                  25

<210> SEQ ID NO 103
<211> LENGTH: 26
<212> TYPE: PRT
<213> ORGANISM: Gorilla gorilla gorilla
<220> FEATURE:
<221> NAME/KEY: Misc_feature
<223> OTHER INFORMATION: Amino acid sequence for region of Gorilla
      gorilla gorilla invariant chain (UniProt accession number G3R7S6)
      corresponding to residues 67-92 of human p35 invariant chain

<400> SEQUENCE: 103

Thr Ala Tyr Phe Leu Tyr Gln Gln Gln Gly Arg Leu Asp Lys Leu Thr
1               5                   10                  15

Val Thr Ser Gln Asn Leu Gln Leu Glu Asn
            20                  25

<210> SEQ ID NO 104
<211> LENGTH: 26
<212> TYPE: PRT
<213> ORGANISM: Pongo abelii
<220> FEATURE:
<221> NAME/KEY: Misc_feature
<223> OTHER INFORMATION: Amino acid sequence for region of Pongo abelii
      invariant chain (UniProt accession number Q5RFJ4) corresponding to
      residues 67-92 of human p35 invariant chain

<400> SEQUENCE: 104

Thr Ala Tyr Phe Leu Tyr Gln Gln Gln Gly Arg Leu Asp Lys Leu Thr
1               5                   10                  15

Val Thr Ser Gln Asn Leu Gln Leu Glu Asn
            20                  25

<210> SEQ ID NO 105
<211> LENGTH: 26
<212> TYPE: PRT
<213> ORGANISM: Pan troglodytes
<220> FEATURE:
<221> NAME/KEY: Misc_feature
<223> OTHER INFORMATION: Amino acid sequence for region of Pan
      troglodytes verus invariant chain (UniProt accession number
      A5A6L4) corresponding to residues 67-92 of human p35 invariant
      chain

<400> SEQUENCE: 105

Thr Ala Tyr Phe Leu Tyr Gln Gln Gln Gly Arg Leu Asp Lys Leu Thr
1               5                   10                  15

Val Thr Ser Gln Asn Leu Gln Leu Glu Asn
            20                  25

<210> SEQ ID NO 106
<211> LENGTH: 26
<212> TYPE: PRT
<213> ORGANISM: Macaca mulatta
<220> FEATURE:
<221> NAME/KEY: Misc_feature
<223> OTHER INFORMATION: Amino acid sequence for region of Macaca
      mulatta invariant chain (UniProt accession number I0FWR3)
      corresponding to residues 67-92 of human p35 invariant chain

<400> SEQUENCE: 106

Thr Ala Tyr Phe Leu Tyr Gln Gln Gln Gly Arg Leu Asp Lys Leu Thr
1               5                   10                  15

Val Thr Thr Gln Ser Leu Gln Leu Glu Asn
            20                  25

<210> SEQ ID NO 107
<211> LENGTH: 26
<212> TYPE: PRT
<213> ORGANISM: Macaca fascicularis
<220> FEATURE:
<221> NAME/KEY: Misc_feature
<223> OTHER INFORMATION: Amino acid sequence for region of Macaca
      fascicularis invariant chain (UniProt accession number G7P8P8)
      corresponding to residues 67-92 of human p35 invariant chain

<400> SEQUENCE: 107

Thr Ala Tyr Phe Leu Tyr Gln Gln Gln Gly Arg Leu Asp Lys Leu Thr
1               5                   10                  15

Val Thr Thr Gln Ser Leu Gln Leu Glu Asn
            20                  25

<210> SEQ ID NO 108
<211> LENGTH: 26
<212> TYPE: PRT
<213> ORGANISM: Chlorocebus sabaeus
<220> FEATURE:
<221> NAME/KEY: Misc_feature
<223> OTHER INFORMATION: Amino acid sequence for region of Chlorocebus
      sabaeus invariant chain (UniProt accession number A0A0D9RGK4)
      corresponding to residues 67-92 of human p35 invariant chain

<400> SEQUENCE: 108

Thr Ala Tyr Phe Leu Tyr Gln Gln Gln Gly Arg Leu Asp Lys Leu Thr
1               5                   10                  15

Val Thr Thr Gln Asn Leu Gln Leu Glu Asn
            20                  25

<210> SEQ ID NO 109
<211> LENGTH: 26
<212> TYPE: PRT
<213> ORGANISM: Papio anubis
<220> FEATURE:
<221> NAME/KEY: Misc_feature
<223> OTHER INFORMATION: Amino acid sequence for region of Papio anubis
      invariant chain (UniProt accession number A0A096MM48)
      corresponding to residues 67-92 of human p35 invariant chain

<400> SEQUENCE: 109

Thr Ala Tyr Phe Leu Tyr Gln Gln Gln Gly Arg Leu Asp Lys Leu Thr
1               5                   10                  15

Val Thr Thr Gln Asn Leu Gln Leu Glu Asn
        20                  25

<210> SEQ ID NO 110
<211> LENGTH: 26
<212> TYPE: PRT
<213> ORGANISM: Loxodonta africana
<220> FEATURE:
<221> NAME/KEY: Misc_feature
<223> OTHER INFORMATION: Amino acid sequence for region of Loxodonta
      africana invariant chain (UniProt accession number G3TJE1)
      corresponding to residues 67-92 of human p35 invariant chain

<400> SEQUENCE: 110

Thr Ala Tyr Phe Leu Tyr Gln Gln Gln Gly Arg Leu Asp Lys Leu Thr
1               5                   10                  15

Val Thr Ala Gln Asn Leu Gln Leu Glu Asn
        20                  25

<210> SEQ ID NO 111
<211> LENGTH: 26
<212> TYPE: PRT
<213> ORGANISM: Felis catus
<220> FEATURE:
<221> NAME/KEY: Misc_feature
<223> OTHER INFORMATION: Amino acid sequence for region of Felis catus
      invariant chain (UniProt accession number M3VXS2) corresponding to
      residues 67-92 of human p35 invariant chain

<400> SEQUENCE: 111

Thr Ala Tyr Phe Leu Tyr Gln Gln Gln Gly Arg Leu Asp Lys Leu Thr
1               5                   10                  15

Val Thr Ala Gln Asn Leu Gln Leu Glu Asn
        20                  25

<210> SEQ ID NO 112
<211> LENGTH: 26
<212> TYPE: PRT
<213> ORGANISM: Equus caballus
<220> FEATURE:
<221> NAME/KEY: Misc_feature
<223> OTHER INFORMATION: Amino acid sequence for region of Equus
      caballus invariant chain (UniProt accession number F6TGS3)
      corresponding to residues 67-92 of human p35 invariant chain

<400> SEQUENCE: 112

Thr Ala Tyr Phe Leu Phe Gln Gln Gln Gly Arg Leu Asp Lys Leu Thr
1               5                   10                  15

Val Thr Ala Gln Asn Leu Gln Leu Glu Lys
        20                  25

<210> SEQ ID NO 113
<211> LENGTH: 26
<212> TYPE: PRT
<213> ORGANISM: Sus scrofa
<220> FEATURE:
<221> NAME/KEY: Misc_feature
<223> OTHER INFORMATION: Amino acid sequence for region of Sus scrofa
      invariant chain (UniProt accession number Q764N1) corresponding to
      residues 67-92 of human p35 invariant chain

<400> SEQUENCE: 113

Thr Ala Tyr Phe Leu Tyr Gln Gln Gln Gly Arg Leu Asp Lys Leu Thr
1               5                   10                  15

Val Thr Ser Gln Asn Leu Gln Leu Glu Ser
        20                  25

```
<210> SEQ ID NO 114
<211> LENGTH: 26
<212> TYPE: PRT
<213> ORGANISM: Oryctolagus cuniculus
<220> FEATURE:
<221> NAME/KEY: Misc_feature
<223> OTHER INFORMATION: Amino acid sequence for region of Oryctolagus
      cuniculus invariant chain (UniProt accession number G1SKK3)
      corresponding to residues 67-92 of human p35 invariant chain

<400> SEQUENCE: 114

Thr Ala Tyr Phe Leu Tyr Gln Gln Gln Asp Arg Leu Asp Lys Leu Thr
1               5                   10                  15

Val Thr Ser Gln Asn Leu Gln Leu Glu Ser
            20                  25

<210> SEQ ID NO 115
<211> LENGTH: 26
<212> TYPE: PRT
<213> ORGANISM: Sarcophilus harrisii
<220> FEATURE:
<221> NAME/KEY: Misc_feature
<223> OTHER INFORMATION: Amino acid sequence for region of Sarcophilus
      harrisii invariant chain (UniProt accession number G3X0Q6)
      corresponding to residues 67-92 of human p35 invariant chain

<400> SEQUENCE: 115

Thr Val Tyr Phe Val Tyr Gln Gln Gln Gly Arg Leu Asp Lys Leu Thr
1               5                   10                  15

Val Thr Ser Gln Asn Leu Gln Leu Glu Ser
            20                  25

<210> SEQ ID NO 116
<211> LENGTH: 26
<212> TYPE: PRT
<213> ORGANISM: Camelus ferus
<220> FEATURE:
<221> NAME/KEY: Misc_feature
<223> OTHER INFORMATION: Amino acid sequence for region of Camelus ferus
      invariant chain (UniProt accession number S9XLT6) corresponding to
      residues 67-92 of human p35 invariant chain

<400> SEQUENCE: 116

Thr Ala Tyr Phe Leu Tyr Gln Gln Gln Gly Arg Leu Asp Lys Leu Thr
1               5                   10                  15

Ile Thr Ser Gln Asn Leu Gln Leu Glu Asn
            20                  25

<210> SEQ ID NO 117
<211> LENGTH: 5922
<212> TYPE: DNA
<213> ORGANISM: Hepatitis C virus
<220> FEATURE:
<221> NAME/KEY: Misc_feature
<223> OTHER INFORMATION: Nucleotide sequence encoding the HCV-NS antigen

<400> SEQUENCE: 117
atggcgccca tcacggccta ctcccaacag acgcggggcc tacttggttg catcatcact      60
agccttacag gccgggacaa gaaccaggtc gagggagagg ttcaggtggt ttccaccgca     120
acacaatcct tcctggcgac ctgcgtcaac ggcgtgtgtt ggaccgttta ccatggtgct     180
ggctcaaaga cctagccgg cccaaagggg ccaatcaccc agatgtacac taatgtggac     240
caggacctcg tcggctggca ggcgcccccc ggggcgcgtt ccttgacacc atgcacctgt     300
```

```
ggcagctcag acctttactt ggtcacgaga catgctgacg tcattccggt gcgccggcgg    360
ggcgacagta gggggagcct gctctccccc aggcctgtct cctacttgaa gggctcttcg    420
ggtggtccac tgctctgccc ttcggggcac gctgtgggca tcttccgggc tgccgtatgc    480
acccgggggg ttgcgaaggc ggtggacttt gtgcccgtag agtccatgga aactactatg    540
cggtctccgg tcttcacgga caactcatcc cccccggccg taccgcagtc atttcaagtg    600
gcccacctac acgctcccac tggcagcggc aagagtacta aagtgccggc tgcatatgca    660
gcccaagggt acaaggtgct cgtcctcaat ccgtccgttg ccgctacctt agggtttggg    720
gcgtatatgt ctaaggcaca cggtattgac cccaacatca gaactggggt aaggaccatt    780
accacaggcg cccccgtcac atactctacc tatggcaagt tcttgccga tggtggttgc     840
tctgggggcg cttatgacat cataatatgt gatgagtgcc attcaactga ctcgactaca    900
atcttgggca tcggcacagt cctggaccaa gcggagacgc tggagcgcg gcttgtcgtg     960
ctcgccaccg ctacgcctcc gggatcggtc accgtgccac acccaaacat cgaggaggtg   1020
gccttgtcta atactggaga gatccccttc tatggcaaag ccatccccat tgaagccatc   1080
agggggggaa ggcatctcat tttctgtcat tccaagaaga agtgcgacga gctcgccgca   1140
aagctgtcag gcctcggaat caacgctgtg gcgtattacc gggggctcga tgtgtccgtc   1200
ataccaacta tcggagacgt cgttgtcgtg gcaacagacg ctctgatgac gggctatacg   1260
ggcgactttg actcagtgat cgactgtaac acatgtgtca cccagacagt cgacttcagc   1320
ttggatccca ccttcaccat tgagacgacg accgtgcctc aagacgcagt gtcgcgctcg   1380
cagcggcggg gtaggactgg cagggggtagg agaggcatct acaggtttgt gactccggga   1440
gaacggccct cgggcatgtt cgattcctcg gtcctgtgtg agtgctatga cgcgggctgt   1500
gcttggtacg agctcacccc cgccgagacc tcggttaggt tgcgggccta cctgaacaca   1560
ccagggttgc ccgtttgcca ggaccacctg gagttctggg agagtgtctt cacaggcctc   1620
acccacatag atgcacactt cttgtcccag accaagcagg caggagacaa cttcccctac   1680
ctggtagcat accaagccac ggtgtgcgcc agggctcagg ccccacctcc atcatgggat   1740
caaatgtgga agtgtctcat acggctgaaa cctacgctgc acgggccaac accttgctg    1800
tacaggctgg gagccgtcca aaatgaggtc accctcaccc accccataac caaatacatc   1860
atggcatgca tgtcggctga cctggaggtc gtcactagca cctgggtgct ggtgggcgga   1920
gtccttgcag ctctggccgc gtattgcctg acaacaggca gtgtggtcat tgtgggtagg   1980
attatcttgt ccgggaggcc ggctattgtt cccgacaggg agtttctcta ccaggagttc   2040
gatgaaatgg aagagtgcgc ctcgcacctc ccttacatcg agcagggaat gcagctcgcc   2100
gagcaattca gcagaaagc gctcgggtta ctgcaaacag ccaccaaaca agcggaggct   2160
gctgctcccg tggtggagtc caagtggcga gcccttgaga cattctgggc gaagcacatg   2220
tggaatttca tcagcgggat acagtactta gcaggcttat ccactctgcc tgggaacccc   2280
gcaatagcat cattgatggc attcacagcc tctatcacca gcccgctcac cacccaaagt   2340
accctcctgt ttaacatctt gggggggtgg gtggctgccc aactcgcccc cccagcgcc    2400
gcttcggctt tcgtgggcgc cggcatcgcc ggtgcgggctg ttggcagcat aggccttggg   2460
aaggtgcttg tggacattct ggcgggttat ggagcaggag tggccggcgc gctcgtggcc   2520
ttcaaggtca tgagcggcga gatgcccctc accgaggacc tggtcaatct acttcctgcc   2580
atcctctctc ctggcgccct ggtcgtcggg gtcgtgtgtg cagcaatact gcgtcgacac   2640
gtgggtccgg gagagggggc tgtgcagtgg atgaaccggc tgatagcgtt cgcctcgcgg   2700
```

```
ggtaatcatg tttcccccac gcactatgtg cctgagagcg acgccgcagc gcgtgttact   2760
cagatcctct ccagccttac catcactcag ctgctgaaaa ggctccacca gtggattaat   2820
gaagactgct ccacaccgtg ttccggctcg tggctaaggg atgtttggga ctggatatgc   2880
acggtgttga ctgacttcaa gacctggctc cagtccaagc tcctgccgca gctaccggga   2940 gtccctttt tctcgtgcca acgcgggtac aagggagtct ggcggggaga cggcatcatg   3000
caaaccacct gccatgtgg agcacagatc accggacatg tcaaaaacgg ttccatgagg   3060
atcgtcgggc ctaagacctg cagcaacacg tggcatggaa cattccccat caacgcatac   3120
accacgggcc cctgcacacc ctctccagcg ccaaactatt ctaggcgct gtggcgggtg   3180 gccgctgagg agtacgtgga ggtcacgcgg gtggggatt tccactacgt gacgggcatg   3240
accactgaca acgtaaagtg cccatgccag gttccggctc ctgaattctt cacggaggtg   3300
gacggagtgc ggttgcacag gtacgctccg gcgtgcaggc ctctcctacg ggaggaggtt   3360
acattccagg tcgggctcaa ccaatacctg gttgggtcac agctaccatg cgagcccgaa   3420
ccggatgtag cagtgctcac ttccatgctc accgacccct cccacatcac agcagaaacg   3480
gctaagcgta ggttggccag ggggtctccc ccctccttgg ccagctcttc agctagccag   3540
ttgtctgcgc cttccttgaa ggcgacatgc actacccacc atgtctctcc ggacgctgac   3600
ctcatcgagg ccaacctcct gtggcggcag gagatgggcg gaacatcac ccgcgtggag   3660 tcggagaaca aggtggtagt cctggactct ttcgacccgc ttcgagcgga ggaggatgag   3720
agggaagtat ccgttccggc ggagatcctg cggaaatcca agaagttccc cgcagcgatg   3780
cccatctggg cgcgcccgga ttacaaccct ccactgttag agtcctggaa ggacccggac   3840
tacgtccctc cggtggtgca cgggtgcccg ttgccaccta tcaaggcccc tccaatacca   3900
cctccacgga gaaagaggac ggttgtccta acagagtcct ccgtgtcttc tgccttagcg   3960
gagctcgcta ctaagacctt cggcagctcc gaatcatcgg ccgtcgacag cggcacggcg   4020 accgccttc ctgaccaggc ctccgacgac ggtgacaaag gatccgacgt tgagtcgtac   4080
tcctccatgc ccccccttga gggggaaccg ggggaccccg atctcagtga cgggtcttgg   4140
tctaccgtga gcgaggaagc tagtgaggat gtcgtctgct gctcaatgtc ctacacatgg   4200
acaggcgcct tgatcacgcc atgcgctgcg gaggaaagca agctgcccat caacgcgttg   4260
agcaactctt tgctgcgcca ccataacatg gtttatgcca caacatctcg cagcgcaggc   4320
ctgcggcaga agaaggtcac ctttgacaga ctgcaagtcc tggacgacca ctaccgggac   4380
gtgctcaagg agatgaaggc gaaggcgtcc acagttaagg ctaaactcct atccgtagag   4440
gaagcctgca gctgacgcc cccacattcg gccaaatcca gtttggcta tggggcaaag   4500 gacgtccgga acctatccag caaggccgtt aaccacatcc actccgtgtg gaaggacttg   4560
ctggaagaca ctgtgacacc aattgacacc accatcatgg caaaaaatga ggttttctgt   4620
gtccaaccag agaaggagg ccgtaagcca gcccgcctta tcgtattccc agatctggga   4680
gtccgtgtat gcgagaagat ggccctctat gatgtggtct ccaccttcc tcaggtcgtg   4740 atgggctcct catacggatt ccagtactct cctgggcagc gagtcgagtt cctggtgaat   4800
acctggaaat caaagaaaaa ccccatgggc ttttcatatg acactcgctg tttcgactca   4860
acggtcaccg agaacgacat ccgtgttgag gagtcaattt accaatgttg tgacttggcc   4920
cccgaagcca gacaggccat aaaatcgctc acagagcggc tttatatcgg gggtcctctg   4980
actaattcaa aagggcagaa ctgcggttat cgccggtgcc gcgcgagcgg cgtgctgacg   5040
```

```
actagctgcg gtaacaccct cacatgttac ttgaaggcct ctgcagcctg tcgagctgcg    5100
aagctccagg actgcacgat gctcgtgaac gccgccggcc ttgtcgttat ctgtgaaagc    5160
gcgggaaccc aagaggacgc ggcgagccta cgagtcttca cggaggctat gactaggtac    5220
tctgcccccc ccggggaccc gccccaacca gaatacgact tggagctgat aacatcatgt    5280
tcctccaatg tgtcggtcgc ccacgatgca tcaggcaaaa gggtgtacta cctcacccgt    5340
gatcccacca ccccccctcgc acgggctgcg tgggaaacag ctagacacac tccagttaac    5400
tcctggctag gcaacattat catgtatgcg cccactttgt gggcaaggat gattctgatg    5460
actcacttct tctccatcct tctagcacag gagcaacttg aaaaagcccct ggactgccag    5520 atctacgggg cctgttactc cattgagcca cttgacctac ctcagatcat tgaacgactc    5580
catggcctta gcgcattttc actccatagt tactctccag gtgagatcaa tagggtggct    5640
tcatgcctca ggaaacttgg ggtaccaccc ttgcgagtct ggagacatcg ggccaggagc    5700
gtccgcgcta ggctactgtc ccaggggggg agggccgcca cttgtggcaa gtacctcttc    5760
aactgggcag tgaagaccaa actcaaactc actccaatcc cggctgcgtc ccagctggac    5820
ttgtccggct ggttcgttgc tggttacagc gggggagaca tatatcacag cctgtctcgt    5880
gcccgacccc gctggttcat gctgtgccta ctcctacttt aa                       5922
```

<210> SEQ ID NO 118
<211> LENGTH: 8
<212> TYPE: PRT
<213> ORGANISM: Gallus gallus
<220> FEATURE:
<221> NAME/KEY: Misc_feature
<223> OTHER INFORMATION: OVA257-264 (SIINFEKL) peptide sequence

<400> SEQUENCE: 118

Ser Ile Ile Asn Phe Glu Lys Leu
1               5

<210> SEQ ID NO 119
<211> LENGTH: 9
<212> TYPE: PRT
<213> ORGANISM: Artificial Sequence
<220> FEATURE:
<223> OTHER INFORMATION: Amino acid sequence of the 'res' linker

<400> SEQUENCE: 119

Ser Asp Arg Tyr Leu Asn Arg Arg Ala
1               5

<210> SEQ ID NO 120
<211> LENGTH: 27
<212> TYPE: DNA
<213> ORGANISM: Artificial Sequence
<220> FEATURE:
<223> OTHER INFORMATION: Nucleotide sequence encoding the 'res' linker

<400> SEQUENCE: 120
agcgatcgct atttaaatag gcgcgcc                                          27

<210> SEQ ID NO 121
<211> LENGTH: 9
<212> TYPE: PRT
<213> ORGANISM: Artificial Sequence
<220> FEATURE:
<223> OTHER INFORMATION: Amino acid sequence of the HA tag

<400> SEQUENCE: 121

```
Tyr Pro Tyr Asp Val Pro Asp Tyr Ala
1               5
```

```
<210> SEQ ID NO 122
<211> LENGTH: 27
<212> TYPE: DNA
<213> ORGANISM: Artificial Sequence
<220> FEATURE:
<223> OTHER INFORMATION: Nucleotide sequence encoding the HA tag

<400> SEQUENCE: 122
tacccatacg atgttccaga ttacgct                                           27

<210> SEQ ID NO 123
<211> LENGTH: 952
<212> TYPE: PRT
<213> ORGANISM: Adenovirus

<400> SEQUENCE: 123

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Pro Cys Glu Trp Asp Glu Ala Thr Ala Leu Glu Ile
    130                 135                 140

Asn Leu Glu Glu Glu Asp Asp Asp Asn Glu Asp Glu Val Asp Glu Gln
145                 150                 155                 160

Ala Glu Gln Gln Lys Thr His Val Phe Gly Gln Ala Pro Tyr Ser Gly
                165                 170                 175

Ile Asn Ile Thr Lys Glu Gly Ile Gln Ile Gly Val Glu Gly Gln Thr
            180                 185                 190

Pro Lys Tyr Ala Asp Lys Thr Phe Gln Pro Glu Pro Gln Ile Gly Glu
        195                 200                 205

Ser Gln Trp Tyr Glu Thr Glu Ile Asn His Ala Ala Gly Arg Val Leu
    210                 215                 220

Lys Lys Thr Thr Pro Met Lys Pro Cys Tyr Gly Ser Tyr Ala Lys Pro
225                 230                 235                 240

Thr Asn Glu Asn Gly Gly Gln Gly Ile Leu Val Lys Gln Gln Asn Gly
                245                 250                 255

Lys Leu Glu Ser Gln Val Glu Met Gln Phe Phe Ser Thr Thr Glu Ala
            260                 265                 270

Thr Ala Gly Asn Gly Asp Asn Leu Thr Pro Lys Val Val Leu Tyr Ser
        275                 280                 285

Glu Asp Val Asp Ile Glu Thr Pro Asp Thr His Ile Ser Tyr Met Pro
    290                 295                 300
```

-continued

Thr Ile Lys Glu Gly Asn Ser Arg Glu Leu Met Gly Gln Gln Ser Met
305                 310                 315                 320

Pro Asn Arg Pro Asn Tyr Ile Ala Phe Arg Asp Asn Phe Ile Gly Leu
                325                 330                 335

Met Tyr Tyr Asn Ser Thr Gly Asn Met Gly Val Leu Ala Gly Gln Ala
            340                 345                 350

Ser Gln Leu Asn Ala Val Val Asp Leu Gln Asp Arg Asn Thr Glu Leu
            355                 360                 365

Ser Tyr Gln Leu Leu Leu Asp Ser Ile Gly Asp Arg Thr Arg Tyr Phe
        370                 375                 380

Ser Met Trp Asn Gln Ala Val Asp Ser Tyr Asp Pro Asp Val Arg Ile
385                 390                 395                 400

Ile Glu Asn His Gly Thr Glu Asp Glu Leu Pro Asn Tyr Cys Phe Pro
                405                 410                 415

Leu Gly Gly Val Ile Asn Thr Glu Thr Leu Thr Lys Val Lys Pro Lys
            420                 425                 430

Thr Gly Gln Glu Asn Gly Trp Glu Lys Asp Ala Thr Glu Phe Ser Asp
        435                 440                 445

Lys Asn Glu Ile Arg Val Gly Asn Asn Phe Ala Met Glu Ile Asn Leu
450                 455                 460

Asn Ala Asn Leu Trp Arg Asn Phe Leu Tyr Ser Asn Ile Ala Leu Tyr
465                 470                 475                 480

Leu Pro Asp Lys Leu Lys Tyr Ser Pro Ser Asn Val Lys Ile Ser Asp
                485                 490                 495

Asn Pro Asn Thr Tyr Asp Tyr Met Asn Lys Arg Val Val Ala Pro Gly
            500                 505                 510

Leu Val Asp Cys Tyr Ile Asn Leu Gly Ala Arg Trp Ser Leu Asp Tyr
        515                 520                 525

Met Asp Asn Val Asn Pro Phe Asn His His Arg Asn Ala Gly Leu Arg
530                 535                 540

Tyr Arg Ser Met Leu Leu Gly Asn Gly Arg Tyr Val Pro Phe His Ile
545                 550                 555                 560

Gln Val Pro Gln Lys Phe Phe Ala Ile Lys Asn Leu Leu Leu Leu Pro
                565                 570                 575

Gly Ser Tyr Thr Tyr Glu Trp Asn Phe Arg Lys Asp Val Asn Met Val
            580                 585                 590

Leu Gln Ser Ser Leu Gly Asn Asp Leu Arg Val Asp Gly Ala Ser Ile
        595                 600                 605

Lys Phe Asp Ser Ile Cys Leu Tyr Ala Thr Phe Phe Pro Met Ala His
610                 615                 620

Asn Thr Ala Ser Thr Leu Glu Ala Met Leu Arg Asn Asp Thr Asn Asp
625                 630                 635                 640

Gln Ser Phe Asn Asp Tyr Leu Ser Ala Ala Asn Met Leu Tyr Pro Ile
                645                 650                 655

Pro Ala Asn Ala Thr Asn Val Pro Ile Ser Ile Pro Ser Arg Asn Trp
            660                 665                 670

Ala Ala Phe Arg Gly Trp Ala Phe Thr Arg Leu Lys Thr Lys Glu Thr
        675                 680                 685

Pro Ser Leu Gly Ser Gly Tyr Asp Pro Tyr Tyr Thr Tyr Ser Gly Ser
690                 695                 700

Ile Pro Tyr Leu Asp Gly Thr Phe Tyr Leu Asn His Thr Phe Lys Lys
705                 710                 715                 720

```
Val Ala Ile Thr Phe Asp Ser Ser Val Ser Trp Pro Gly Asn Asp Arg
                725                 730                 735

Leu Leu Thr Pro Asn Glu Phe Glu Ile Lys Arg Ser Val Asp Gly Glu
            740                 745                 750

Gly Tyr Asn Val Ala Gln Cys Asn Met Thr Lys Asp Trp Phe Leu Val
        755                 760                 765

Gln Met Leu Ala Asn Tyr Asn Ile Gly Tyr Gln Gly Phe Tyr Ile Pro
    770                 775                 780

Glu Ser Tyr Lys Asp Arg Met Tyr Ser Phe Phe Arg Asn Phe Gln Pro
785                 790                 795                 800

Met Ser Arg Gln Val Val Asp Asp Thr Lys Tyr Lys Asp Tyr Gln Gln
                805                 810                 815

Val Gly Ile Leu His Gln His Asn Asn Ser Gly Phe Val Gly Tyr Leu
            820                 825                 830

Ala Pro Thr Met Arg Glu Gly Gln Ala Tyr Pro Ala Asn Phe Pro Tyr
        835                 840                 845

Pro Leu Ile Gly Lys Thr Ala Val Asp Ser Ile Thr Gln Lys Lys Phe
    850                 855                 860

Leu Cys Asp Arg Thr Leu Trp Arg Ile Pro Phe Ser Ser Asn Phe Met
865                 870                 875                 880

Ser Met Gly Ala Leu Thr Asp Leu Gly Gln Asn Leu Leu Tyr Ala Asn
                885                 890                 895

Ser Ala His Ala Leu Asp Met Thr Phe Glu Val Asp Pro Met Asp Glu
            900                 905                 910

Pro Thr Leu Leu Tyr Val Leu Phe Glu Val Phe Asp Val Val Arg Val
        915                 920                 925

His Arg Pro His Arg Gly Val Ile Glu Thr Val Tyr Leu Arg Thr Pro
    930                 935                 940

Phe Ser Ala Gly Asn Ala Thr Thr
945                 950

<210> SEQ ID NO 124
<211> LENGTH: 571
<212> TYPE: PRT
<213> ORGANISM: Adenovirus

<400> SEQUENCE: 124

Met Arg Arg Ala Ala Met Tyr Glu Glu Gly Pro Pro Ser Tyr Glu
1               5                   10                  15

Ser Val Val Ser Ala Ala Pro Val Ala Ala Leu Gly Ser Pro Phe
                20                  25                  30

Asp Ala Pro Leu Asp Pro Pro Phe Val Pro Pro Arg Tyr Leu Arg Pro
            35                  40                  45

Thr Gly Gly Arg Asn Ser Ile Arg Tyr Ser Glu Leu Ala Pro Leu Phe
        50                  55                  60

Asp Thr Thr Arg Val Tyr Leu Val Asp Asn Lys Ser Thr Asp Val Ala
65                  70                  75                  80

Ser Leu Asn Tyr Gln Asn Asp His Ser Asn Phe Leu Thr Thr Val Ile
                85                  90                  95

Gln Asn Asn Asp Tyr Ser Pro Gly Glu Ala Ser Thr Gln Thr Ile Asn
            100                 105                 110

Leu Asp Asp Arg Ser His Trp Gly Gly Asp Leu Lys Thr Ile Leu His
        115                 120                 125

Thr Asn Met Pro Asn Val Asn Glu Phe Met Phe Thr Asn Lys Phe Lys
    130                 135                 140
```

```
Ala Arg Val Met Val Ser Arg Leu Pro Thr Lys Asp Asn Gln Val Glu
145                 150                 155                 160

Leu Lys Tyr Glu Trp Val Glu Phe Thr Leu Pro Glu Gly Asn Tyr Ser
            165                 170                 175

Glu Thr Met Thr Ile Asp Leu Met Asn Asn Ala Ile Val Glu His Tyr
            180                 185                 190

Leu Lys Val Gly Arg Gln Asn Gly Val Leu Glu Ser Asp Ile Gly Val
            195                 200                 205

Lys Phe Asp Thr Arg Asn Phe Arg Leu Gly Phe Asp Pro Val Thr Gly
            210                 215                 220

Leu Val Met Pro Gly Val Tyr Thr Asn Glu Ala Phe His Pro Asp Ile
225                 230                 235                 240

Ile Leu Leu Pro Gly Cys Gly Val Asp Phe Thr His Ser Arg Leu Ser
                245                 250                 255

Asn Leu Leu Gly Ile Arg Lys Arg Gln Pro Phe Gln Glu Gly Phe Arg
            260                 265                 270

Ile Thr Tyr Asp Asp Leu Glu Gly Gly Asn Ile Pro Ala Leu Leu Asp
            275                 280                 285

Val Asp Ala Tyr Gln Ala Ser Leu Lys Asp Asp Thr Glu Gln Gly Gly
    290                 295                 300

Gly Gly Ala Gly Gly Ser Asn Ser Ser Gly Ser Gly Ala Glu Glu Asn
305                 310                 315                 320

Ser Asn Ala Ala Ala Ala Met Gln Pro Val Glu Asp Met Asn Asp
                325                 330                 335

His Ala Ile Arg Gly Asp Thr Phe Ala Thr Arg Ala Glu Glu Lys Arg
            340                 345                 350

Ala Glu Ala Glu Ala Ala Glu Ala Ala Pro Ala Ala Gln Pro
    355                 360                 365

Glu Val Glu Lys Pro Gln Lys Lys Pro Val Ile Lys Pro Leu Thr Glu
    370                 375                 380

Asp Ser Lys Lys Arg Ser Tyr Asn Leu Ile Ser Asn Asp Ser Thr Phe
385                 390                 395                 400

Thr Gln Tyr Arg Ser Trp Tyr Leu Ala Tyr Asn Tyr Gly Asp Pro Gln
                405                 410                 415

Thr Gly Ile Arg Ser Trp Thr Leu Leu Cys Thr Pro Asp Val Thr Cys
                420                 425                 430

Gly Ser Glu Gln Val Tyr Trp Ser Leu Pro Asp Met Met Gln Asp Pro
            435                 440                 445

Val Thr Phe Arg Ser Thr Arg Gln Ile Ser Asn Phe Pro Val Val Gly
    450                 455                 460

Ala Glu Leu Leu Pro Val His Ser Lys Ser Phe Tyr Asn Asp Gln Ala
465                 470                 475                 480

Val Tyr Ser Gln Leu Ile Arg Gln Phe Thr Ser Leu Thr His Val Phe
            485                 490                 495

Asn Arg Phe Pro Glu Asn Gln Ile Leu Ala Arg Pro Pro Ala Pro Thr
                500                 505                 510

Ile Thr Thr Val Ser Glu Asn Val Pro Ala Leu Thr Asp His Gly Thr
            515                 520                 525

Leu Pro Leu Arg Asn Ser Ile Gly Gly Val Gln Arg Val Thr Ile Thr
    530                 535                 540

Asp Ala Arg Arg Arg Thr Cys Pro Tyr Val Tyr Lys Ala Leu Gly Ile
545                 550                 555                 560
```

Val Ser Pro Arg Val Leu Ser Ser Arg Thr Phe
            565                 570

<210> SEQ ID NO 125
<211> LENGTH: 581
<212> TYPE: PRT
<213> ORGANISM: Adenovirus

<400> SEQUENCE: 125

Met Lys Arg Ala Arg Pro Ser Glu Asp Thr Phe Asn Pro Val Tyr Pro
1               5                   10                  15

Tyr Asp Thr Glu Thr Gly Pro Pro Thr Val Pro Phe Leu Thr Pro Pro
            20                  25                  30

Phe Val Ser Pro Asn Gly Phe Gln Glu Ser Pro Pro Gly Val Leu Ser
        35                  40                  45

Leu Arg Leu Ser Glu Pro Leu Val Thr Ser Asn Gly Met Leu Ala Leu
    50                  55                  60

Lys Met Gly Asn Gly Leu Ser Leu Asp Glu Ala Gly Asn Leu Thr Ser
65                  70                  75                  80

Gln Asn Val Thr Thr Val Ser Pro Pro Leu Lys Lys Thr Lys Ser Asn
                85                  90                  95

Ile Asn Leu Glu Ile Ser Ala Pro Leu Thr Val Thr Ser Glu Ala Leu
            100                 105                 110

Thr Val Ala Ala Ala Pro Leu Met Val Ala Gly Asn Thr Leu Thr
        115                 120                 125

Met Gln Ser Gln Ala Pro Leu Thr Val His Asp Ser Lys Leu Ser Ile
    130                 135                 140

Ala Thr Gln Gly Pro Leu Thr Val Ser Glu Gly Lys Leu Ala Leu Gln
145                 150                 155                 160

Thr Ser Gly Pro Leu Thr Thr Thr Asp Ser Ser Thr Leu Thr Ile Thr
                165                 170                 175

Ala Ser Pro Pro Leu Thr Thr Ala Thr Gly Ser Leu Gly Ile Asp Leu
            180                 185                 190

Lys Glu Pro Ile Tyr Thr Gln Asn Gly Lys Leu Gly Leu Lys Tyr Gly
        195                 200                 205

Ala Pro Leu His Val Thr Asp Asp Leu Asn Thr Leu Thr Val Ala Thr
    210                 215                 220

Gly Pro Gly Val Thr Ile Asn Asn Thr Ser Leu Gln Thr Lys Val Thr
225                 230                 235                 240

Gly Ala Leu Gly Phe Asp Ser Gln Gly Asn Met Gln Leu Asn Val Ala
                245                 250                 255

Gly Gly Leu Arg Ile Asp Ser Gln Asn Arg Arg Leu Ile Leu Asp Val
            260                 265                 270

Ser Tyr Pro Phe Asp Ala Gln Asn Gln Leu Asn Leu Arg Leu Gly Gln
        275                 280                 285

Gly Pro Leu Phe Ile Asn Ser Ala His Asn Leu Asp Ile Asn Tyr Asn
    290                 295                 300

Lys Gly Leu Tyr Leu Phe Thr Ala Ser Asn Asn Ser Lys Lys Leu Glu
305                 310                 315                 320

Val Asn Leu Ser Thr Ala Lys Gly Leu Met Phe Asp Ala Thr Ala Ile
                325                 330                 335

Ala Ile Asn Ala Gly Asp Gly Leu Glu Phe Gly Ser Pro Asn Ala Pro
            340                 345                 350

Asn Thr Asn Pro Leu Lys Thr Lys Ile Gly His Gly Leu Glu Phe Asp
        355                 360                 365

```
Ser Asn Lys Ala Met Val Pro Lys Leu Gly Thr Gly Leu Ser Phe Asp
    370                 375                 380

Ser Thr Gly Ala Ile Thr Val Gly Asn Lys Asn Asp Lys Leu Thr
385                 390                 395                 400

Leu Trp Thr Thr Pro Ala Pro Ser Pro Asn Cys Arg Leu Asn Ala Glu
                405                 410                 415

Lys Asp Ala Lys Leu Thr Leu Val Leu Thr Lys Cys Gly Ser Gln Ile
                420                 425                 430

Leu Ala Thr Val Ser Val Leu Ala Val Lys Gly Ser Leu Ala Pro Ile
                435                 440                 445

Ser Gly Thr Val Gln Ser Ala His Leu Ile Ile Arg Phe Asp Glu Asn
                450                 455                 460

Gly Val Leu Leu Asn Asn Ser Phe Leu Asp Pro Glu Tyr Trp Asn Phe
465                 470                 475                 480

Arg Asn Gly Asp Leu Thr Glu Gly Thr Ala Tyr Thr Asn Ala Val Gly
                485                 490                 495

Phe Met Pro Asn Leu Ser Ala Tyr Pro Lys Ser His Gly Lys Thr Ala
                500                 505                 510

Lys Ser Asn Ile Val Ser Gln Val Tyr Leu Asn Gly Asp Lys Thr Lys
                515                 520                 525

Pro Val Thr Leu Thr Ile Thr Leu Asn Gly Thr Gln Glu Thr Gly Asp
                530                 535                 540

Thr Thr Pro Ser Ala Tyr Ser Met Ser Phe Ser Trp Asp Trp Ser Gly
545                 550                 555                 560

His Asn Tyr Ile Asn Glu Ile Phe Ala Thr Ser Ser Tyr Thr Phe Ser
                565                 570                 575

Tyr Ile Ala Gln Glu
                580

<210> SEQ ID NO 126
<211> LENGTH: 960
<212> TYPE: PRT
<213> ORGANISM: Adenovirus

<400> SEQUENCE: 126

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
                20                  25                  30

Arg Ala Thr Glu Ser Tyr Phe Ser Leu Ser Asn Lys Phe Arg Asn Pro
            35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ser Leu Ala Pro Lys Gly
        115                 120                 125

Ala Pro Asn Ser Cys Glu Trp Glu Gln Glu Thr Gln Ala Val Glu
    130                 135                 140

Glu Ala Ala Glu Glu Glu Glu Asp Ala Asp Gly Gln Ala Glu Glu
```

```
            145                 150                 155                 160
        Glu Gln Ala Ala Thr Lys Lys Thr His Val Tyr Ala Gln Ala Pro Leu
                        165                 170                 175

Ser Gly Glu Lys Ile Ser Lys Asp Gly Leu Gln Ile Gly Thr Asp Ala
                        180                 185                 190

Thr Ala Thr Glu Gln Lys Pro Ile Tyr Ala Asp Pro Thr Phe Gln Pro
                        195                 200                 205

Glu Pro Gln Ile Gly Glu Ser Gln Trp Asn Glu Ala Asp Ala Thr Val
                    210                 215                 220

Ala Gly Gly Arg Val Leu Lys Lys Ser Thr Pro Met Lys Pro Cys Tyr
        225                 230                 235                 240

Gly Ser Tyr Ala Arg Pro Thr Asn Ala Asn Gly Gly Gln Gly Val Leu
                        245                 250                 255

Thr Ala Asn Ala Gln Gly Gln Leu Glu Ser Gln Val Glu Met Gln Phe
                        260                 265                 270

Phe Ser Thr Ser Glu Asn Ala Arg Asn Glu Ala Asn Asn Ile Gln Pro
                    275                 280                 285

Lys Leu Val Leu Tyr Ser Glu Asp Val His Met Glu Thr Pro Asp Thr
        290                 295                 300

His Leu Ser Tyr Lys Pro Ala Lys Ser Asp Asn Ser Lys Ile Met
        305                 310                 315                 320

Leu Gly Gln Gln Ser Met Pro Asn Arg Pro Asn Tyr Ile Gly Phe Arg
                        325                 330                 335

Asp Asn Phe Ile Gly Leu Met Tyr Tyr Asn Ser Thr Gly Asn Met Gly
                        340                 345                 350

Val Leu Ala Gly Gln Ala Ser Gln Leu Asn Ala Val Val Asp Leu Gln
                    355                 360                 365

Asp Arg Asn Thr Glu Leu Ser Tyr Gln Leu Leu Asp Ser Met Gly
                    370                 375                 380

Asp Arg Thr Arg Tyr Phe Ser Met Trp Asn Gln Ala Val Asp Ser Tyr
        385                 390                 395                 400

Asp Pro Asp Val Arg Ile Ile Glu Asn His Gly Thr Glu Asp Glu Leu
                        405                 410                 415

Pro Asn Tyr Cys Phe Pro Leu Gly Gly Ile Gly Val Thr Asp Thr Tyr
                        420                 425                 430

Gln Ala Val Lys Thr Asn Asn Gly Asn Asn Gly Gly Gln Val Thr Trp
                    435                 440                 445

Thr Lys Asp Glu Thr Phe Ala Asp Arg Asn Glu Ile Gly Val Gly Asn
            450                 455                 460

Asn Phe Ala Met Glu Ile Asn Leu Ser Ala Asn Leu Trp Arg Asn Phe
        465                 470                 475                 480

Leu Tyr Ser Asn Val Ala Leu Tyr Leu Pro Asp Lys Leu Lys Tyr Asn
                        485                 490                 495

Pro Ser Asn Val Asp Ile Ser Asp Asn Pro Asn Thr Tyr Asp Tyr Met
                    500                 505                 510

Asn Lys Arg Val Val Ala Pro Gly Leu Val Asp Cys Tyr Ile Asn Leu
                    515                 520                 525

Gly Ala Arg Trp Ser Leu Asp Tyr Met Asp Asn Val Asn Pro Phe Asn
        530                 535                 540

His His Arg Asn Ala Gly Leu Arg Tyr Arg Ser Met Leu Leu Gly Asn
        545                 550                 555                 560

Gly Arg Tyr Val Pro Phe His Ile Gln Val Pro Gln Lys Phe Phe Ala
                        565                 570                 575
```

```
Ile Lys Asn Leu Leu Leu Pro Gly Ser Tyr Thr Tyr Glu Trp Asn
            580                 585                 590

Phe Arg Lys Asp Val Asn Met Val Leu Gln Ser Ser Leu Gly Asn Asp
        595                 600                 605

Leu Arg Val Asp Gly Ala Ser Ile Lys Phe Glu Ser Ile Cys Leu Tyr
    610                 615                 620

Ala Thr Phe Phe Pro Met Ala His Asn Thr Ala Ser Thr Leu Glu Ala
625                 630                 635                 640

Met Leu Arg Asn Asp Thr Asn Asp Gln Ser Phe Asn Asp Tyr Leu Ser
                645                 650                 655

Ala Ala Asn Met Leu Tyr Pro Ile Pro Ala Asn Ala Thr Asn Val Pro
                660                 665                 670

Ile Ser Ile Pro Ser Arg Asn Trp Ala Ala Phe Arg Gly Trp Ala Phe
                675                 680                 685

Thr Arg Leu Lys Thr Lys Glu Thr Pro Ser Leu Gly Ser Gly Phe Asp
        690                 695                 700

Pro Tyr Tyr Thr Tyr Ser Gly Ser Ile Pro Tyr Leu Asp Gly Thr Phe
705                 710                 715                 720

Tyr Leu Asn His Thr Phe Lys Lys Val Ser Val Thr Phe Asp Ser Ser
                725                 730                 735

Val Ser Trp Pro Gly Asn Asp Arg Leu Leu Thr Pro Asn Glu Phe Glu
                740                 745                 750

Ile Lys Arg Ser Val Asp Gly Glu Gly Tyr Asn Val Ala Gln Cys Asn
                755                 760                 765

Met Thr Lys Asp Trp Phe Leu Val Gln Met Leu Ala Asn Tyr Asn Ile
                770                 775                 780

Gly Tyr Gln Gly Phe Tyr Ile Pro Glu Ser Tyr Lys Asp Arg Met Tyr
785                 790                 795                 800

Ser Phe Phe Arg Asn Phe Gln Pro Met Ser Arg Gln Val Val Asp Gln
                805                 810                 815

Thr Lys Tyr Lys Asp Tyr Gln Glu Val Gly Ile Ile His Gln His Asn
                820                 825                 830

Asn Ser Gly Phe Val Gly Tyr Leu Ala Pro Thr Met Arg Glu Gly Gln
                835                 840                 845

Ala Tyr Pro Ala Asn Phe Pro Tyr Pro Leu Ile Gly Lys Thr Ala Val
                850                 855                 860

Asp Ser Ile Thr Gln Lys Lys Phe Leu Cys Asp Arg Thr Leu Trp Arg
865                 870                 875                 880

Ile Pro Phe Ser Ser Asn Phe Met Ser Met Gly Ala Leu Ser Asp Leu
                885                 890                 895

Gly Gln Asn Leu Leu Tyr Ala Asn Ser Ala His Ala Leu Asp Met Thr
                900                 905                 910

Phe Glu Val Asp Pro Met Asp Glu Pro Thr Leu Leu Tyr Val Leu Phe
                915                 920                 925

Glu Val Phe Asp Val Val Arg Val His Gln Pro His Arg Gly Val Ile
            930                 935                 940

Glu Thr Val Tyr Leu Arg Thr Pro Phe Ser Ala Gly Asn Ala Thr Thr
945                 950                 955                 960

<210> SEQ ID NO 127
<211> LENGTH: 543
<212> TYPE: PRT
<213> ORGANISM: Adenovirus
```

<400> SEQUENCE: 127

```
Met Lys Arg Thr Lys Thr Ser Asp Glu Ser Phe Asn Pro Val Tyr Pro
1               5                   10                  15
Tyr Asp Thr Glu Ser Gly Pro Pro Ser Val Pro Phe Leu Thr Pro Pro
            20                  25                  30
Phe Val Ser Pro Asp Gly Phe Gln Glu Ser Pro Pro Gly Val Leu Ser
        35                  40                  45
Leu Asn Leu Ala Glu Pro Leu Val Thr Ser His Gly Met Leu Ala Leu
    50                  55                  60
Lys Met Gly Ser Gly Leu Ser Leu Asp Asp Ala Gly Asn Leu Thr Ser
65                  70                  75                  80
Gln Asp Ile Thr Thr Ala Ser Pro Pro Leu Lys Thr Lys Thr Asn
            85                  90                  95
Leu Ser Leu Glu Thr Ser Ser Pro Leu Thr Val Ser Thr Ser Gly Ala
            100                 105                 110
Leu Thr Val Ala Ala Ala Ala Pro Leu Ala Val Ala Gly Thr Ser Leu
        115                 120                 125
Thr Met Gln Ser Glu Ala Pro Leu Thr Val Gln Asp Ala Lys Leu Thr
    130                 135                 140
Leu Ala Thr Lys Gly Pro Leu Thr Val Ser Glu Gly Lys Leu Ala Leu
145                 150                 155                 160
Gln Thr Ser Ala Pro Leu Thr Ala Ala Asp Ser Ser Thr Leu Thr Val
            165                 170                 175
Ser Ala Thr Pro Pro Ile Asn Val Ser Ser Gly Ser Leu Gly Leu Asp
            180                 185                 190
Met Glu Asp Pro Met Tyr Thr His Asp Gly Lys Leu Gly Ile Arg Ile
        195                 200                 205
Gly Gly Pro Leu Arg Val Val Asp Ser Leu His Thr Leu Thr Val Val
    210                 215                 220
Thr Gly Asn Gly Leu Thr Val Asp Asn Asn Ala Leu Gln Thr Arg Val
225                 230                 235                 240
Thr Gly Ala Leu Gly Tyr Asp Thr Ser Gly Asn Leu Gln Leu Arg Ala
            245                 250                 255
Ala Gly Gly Met Arg Ile Asp Ala Asn Gly Gln Leu Ile Leu Asn Val
            260                 265                 270
Ala Tyr Pro Phe Asp Ala Gln Asn Asn Leu Ser Leu Arg Leu Gly Gln
        275                 280                 285
Gly Pro Leu Tyr Ile Asn Thr Asp His Asn Leu Asp Leu Asn Cys Asn
    290                 295                 300
Arg Gly Leu Thr Thr Thr Thr Asn Asn Thr Lys Lys Leu Glu Thr
305                 310                 315                 320
Lys Ile Ser Ser Gly Leu Asp Tyr Asp Thr Asn Gly Ala Val Ile Ile
            325                 330                 335
Lys Leu Gly Thr Gly Leu Ser Phe Asp Asn Thr Gly Ala Leu Thr Val
            340                 345                 350
Gly Asn Thr Gly Asp Asp Lys Leu Thr Leu Trp Thr Pro Asp Pro
        355                 360                 365
Ser Pro Asn Cys Arg Ile His Ser Asp Lys Asp Cys Lys Phe Thr Leu
    370                 375                 380
Val Leu Thr Lys Cys Gly Ser Gln Ile Leu Ala Ser Val Ala Ala Leu
385                 390                 395                 400
Ala Val Ser Gly Asn Leu Ala Ser Ile Thr Gly Thr Val Ala Ser Val
            405                 410                 415
```

```
Thr Ile Phe Leu Arg Phe Asp Gln Asn Gly Val Leu Met Glu Asn Ser
            420                 425                 430

Ser Leu Asp Arg Gln Tyr Trp Asn Phe Arg Asn Gly Asn Ser Thr Asn
        435                 440                 445

Ala Ala Pro Tyr Thr Asn Ala Val Gly Phe Met Pro Asn Leu Ala Ala
450                 455                 460

Tyr Pro Lys Thr Gln Ser Gln Thr Ala Lys Asn Asn Ile Val Ser Gln
465                 470                 475                 480

Val Tyr Leu Asn Gly Asp Lys Ser Lys Pro Met Thr Leu Thr Ile Thr
                485                 490                 495

Leu Asn Gly Thr Asn Glu Ser Ser Glu Thr Ser Gln Val Ser His Tyr
            500                 505                 510

Ser Met Ser Phe Thr Trp Ala Trp Glu Ser Gly Gln Tyr Ala Thr Glu
        515                 520                 525

Thr Phe Ala Thr Asn Ser Phe Thr Phe Ser Tyr Ile Ala Glu Gln
    530                 535                 540

<210> SEQ ID NO 128
<211> LENGTH: 958
<212> TYPE: PRT
<213> ORGANISM: Adenovirus

<400> SEQUENCE: 128

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Ser Tyr Phe Ser Leu Ser Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ser Leu Ala Pro Lys Gly
        115                 120                 125

Ala Pro Asn Ser Cys Glu Trp Glu Gln Leu Glu Glu Ala Gln Ala Ala
130                 135                 140

Leu Glu Asp Glu Glu Leu Glu Asp Glu Asp Glu Glu Pro Gln Asp Glu
145                 150                 155                 160

Ala Pro Val Lys Lys Thr His Val Tyr Ala Gln Ala Pro Leu Ser Gly
                165                 170                 175

Glu Glu Ile Thr Lys Asp Gly Leu Gln Ile Gly Ser Asp Asn Thr Glu
            180                 185                 190

Ala Gln Ser Lys Pro Ile Tyr Ala Asp Pro Thr Phe Gln Pro Glu Pro
        195                 200                 205

Gln Ile Gly Glu Ser Gln Trp Asn Glu Ala Asp Ala Thr Val Ala Gly
    210                 215                 220

Gly Arg Val Leu Lys Lys Thr Thr Pro Met Lys Pro Cys Tyr Gly Ser
225                 230                 235                 240

Tyr Ala Arg Pro Thr Asn Ala Asn Gly Gly Gln Gly Val Leu Val Ala
```

-continued

```
                245                 250                 255
Asp Asp Lys Gly Val Leu Gln Ser Lys Val Glu Leu Gln Phe Phe Ser
            260                 265                 270

Asn Thr Thr Thr Leu Asn Gln Arg Glu Gly Asn Asp Thr Lys Pro Lys
            275                 280                 285

Val Val Leu Tyr Ser Glu Asp Val His Met Glu Thr Pro Asp Thr His
            290                 295                 300

Ile Ser Tyr Lys Pro Thr Lys Ser Asp Asn Ser Lys Val Met Leu
305                 310                 315                 320

Gly Gln Gln Ser Met Pro Asn Arg Pro Asn Tyr Ile Gly Phe Arg Asp
                325                 330                 335

Asn Phe Ile Gly Leu Met Tyr Tyr Asn Ser Thr Gly Asn Met Gly Val
            340                 345                 350

Leu Ala Gly Gln Ala Ser Gln Leu Asn Ala Val Val Asp Leu Gln Asp
            355                 360                 365

Arg Asn Thr Glu Leu Ser Tyr Gln Leu Leu Asp Ser Met Gly Asp
            370                 375                 380

Arg Thr Arg Tyr Phe Ser Met Trp Asn Gln Ala Val Asp Ser Tyr Asp
385                 390                 395                 400

Pro Asp Val Arg Ile Ile Glu Asn His Gly Thr Glu Asp Glu Leu Pro
                405                 410                 415

Asn Tyr Cys Phe Pro Leu Gly Gly Ile Gly Val Thr Asp Thr Tyr Gln
            420                 425                 430

Val Ile Lys Thr Asn Gly Asn Gly Gln Ala Asp Pro Thr Trp Glu Lys
            435                 440                 445

Asp Thr Glu Phe Ala Asp Arg Asn Glu Ile Gly Val Gly Asn Asn Phe
            450                 455                 460

Ala Met Glu Ile Asn Leu Asn Ala Asn Leu Trp Arg Asn Phe Leu Tyr
465                 470                 475                 480

Ser Asn Val Ala Leu Tyr Leu Pro Asp Lys Leu Lys Tyr Asn Pro Ser
                485                 490                 495

Asn Val Asp Ile Ser Asp Asn Pro Asn Thr Tyr Asp Tyr Met Asn Lys
            500                 505                 510

Arg Val Val Ala Pro Gly Leu Val Asp Cys Tyr Ile Asn Leu Gly Ala
            515                 520                 525

Arg Trp Ser Leu Asp Tyr Met Asp Asn Val Asn Pro Phe Asn His His
            530                 535                 540

Arg Asn Ala Gly Leu Arg Tyr Arg Ser Met Leu Leu Gly Asn Gly Arg
545                 550                 555                 560

Tyr Val Pro Phe His Ile Gln Val Pro Gln Lys Phe Ala Ile Lys
                565                 570                 575

Asn Leu Leu Leu Pro Gly Ser Tyr Thr Tyr Glu Trp Asn Phe Arg
            580                 585                 590

Lys Asp Val Asn Met Val Leu Gln Ser Ser Leu Gly Asn Asp Leu Arg
            595                 600                 605

Val Asp Gly Ala Ser Ile Lys Phe Glu Ser Ile Cys Leu Tyr Ala Thr
            610                 615                 620

Phe Phe Pro Met Ala His Asn Thr Ala Ser Thr Leu Glu Ala Met Leu
625                 630                 635                 640

Arg Asn Asp Thr Asn Asp Gln Ser Phe Asn Asp Tyr Leu Ser Ala Ala
                645                 650                 655

Asn Met Leu Tyr Pro Ile Pro Ala Asn Ala Thr Asn Val Pro Ile Ser
            660                 665                 670
```

Ile Pro Ser Arg Asn Trp Ala Ala Phe Arg Gly Trp Ala Phe Thr Arg
            675                 680                 685

Leu Lys Thr Lys Glu Thr Pro Ser Leu Gly Ser Gly Phe Asp Pro Tyr
690                 695                 700

Tyr Thr Tyr Ser Gly Ser Ile Pro Tyr Leu Asp Gly Thr Phe Tyr Leu
705                 710                 715                 720

Asn His Thr Phe Lys Lys Val Ser Val Thr Phe Asp Ser Ser Val Ser
                725                 730                 735

Trp Pro Gly Asn Asp Arg Leu Leu Thr Pro Asn Glu Phe Glu Ile Lys
            740                 745                 750

Arg Ser Val Asp Gly Glu Gly Tyr Asn Val Ala Gln Cys Asn Met Thr
        755                 760                 765

Lys Asp Trp Phe Leu Val Gln Met Leu Ala Asn Tyr Asn Ile Gly Tyr
    770                 775                 780

Gln Gly Phe Tyr Ile Pro Glu Ser Tyr Lys Asp Arg Met Tyr Ser Phe
785                 790                 795                 800

Phe Arg Asn Phe Gln Pro Met Ser Arg Gln Val Val Asp Gln Thr Lys
                805                 810                 815

Tyr Lys Asp Tyr Gln Glu Val Gly Ile Ile His Gln His Asn Asn Ser
            820                 825                 830

Gly Phe Val Gly Tyr Leu Ala Pro Thr Met Arg Glu Gly Gln Ala Tyr
        835                 840                 845

Pro Ala Asn Phe Pro Tyr Pro Leu Ile Gly Lys Thr Ala Val Asp Ser
    850                 855                 860

Ile Thr Gln Lys Lys Phe Leu Cys Asp Arg Thr Leu Trp Arg Ile Pro
865                 870                 875                 880

Phe Ser Ser Asn Phe Met Ser Met Gly Ala Leu Thr Asp Leu Gly Gln
                885                 890                 895

Asn Leu Leu Tyr Ala Asn Ser Ala His Ala Leu Asp Met Thr Phe Glu
            900                 905                 910

Val Asp Pro Met Asp Glu Pro Thr Leu Leu Tyr Val Leu Phe Glu Val
        915                 920                 925

Phe Asp Val Val Arg Val His Gln Pro His Arg Gly Val Ile Glu Thr
    930                 935                 940

Val Tyr Leu Arg Thr Pro Phe Ser Ala Gly Asn Ala Thr Thr
945                 950                 955

<210> SEQ ID NO 129
<211> LENGTH: 543
<212> TYPE: PRT
<213> ORGANISM: Adenovirus

<400> SEQUENCE: 129

Met Lys Arg Thr Lys Thr Ser Asp Lys Ser Phe Asn Pro Val Tyr Pro
1               5                   10                  15

Tyr Asp Thr Glu Asn Gly Pro Pro Ser Val Pro Phe Leu Thr Pro Pro
            20                  25                  30

Phe Val Ser Pro Asp Gly Phe Gln Glu Ser Pro Pro Gly Val Leu Ser
        35                  40                  45

Leu Asn Leu Ala Glu Pro Leu Val Thr Ser His Gly Met Leu Ala Leu
    50                  55                  60

Lys Met Gly Ser Gly Leu Ser Leu Asp Asp Ala Gly Asn Leu Thr Ser
65                  70                  75                  80

Gln Asp Val Thr Thr Thr Thr Pro Pro Leu Lys Lys Thr Lys Thr Asn

```
                    85                  90                  95
Leu Ser Leu Glu Thr Ser Ala Pro Leu Thr Val Ser Thr Ser Gly Ala
                100                 105                 110

Leu Thr Leu Ala Ala Ala Ala Pro Leu Ala Val Ala Gly Thr Ser Leu
            115                 120                 125

Thr Met Gln Ser Glu Ala Pro Leu Thr Val Gln Asp Ala Lys Leu Thr
        130                 135                 140

Leu Ala Thr Lys Gly Pro Leu Thr Val Ser Glu Gly Lys Leu Ala Leu
145                 150                 155                 160

Gln Thr Ser Ala Pro Leu Thr Ala Ala Asp Ser Ser Thr Leu Thr Val
                165                 170                 175

Ser Ala Thr Pro Pro Ile Ser Val Ser Ser Gly Ser Leu Gly Leu Asp
                180                 185                 190

Met Glu Asp Pro Met Tyr Thr His Asp Gly Lys Leu Gly Ile Arg Ile
            195                 200                 205

Gly Gly Pro Leu Arg Val Val Asp Ser Leu His Thr Leu Thr Val Val
        210                 215                 220

Thr Gly Asn Gly Ile Ala Val Asp Asn Asn Ala Leu Gln Thr Arg Val
225                 230                 235                 240

Thr Gly Ala Leu Gly Tyr Asp Thr Ser Gly Asn Leu Gln Leu Arg Ala
                245                 250                 255

Ala Gly Gly Met Arg Ile Asp Ala Asn Gly Gln Leu Ile Leu Asp Val
                260                 265                 270

Ala Tyr Pro Phe Asp Ala Gln Asn Asn Leu Ser Leu Arg Leu Gly Gln
            275                 280                 285

Gly Pro Leu Tyr Val Asn Thr Asp His Asn Leu Asp Leu Asn Cys Asn
        290                 295                 300

Arg Gly Leu Thr Thr Thr Thr Asn Asn Thr Lys Lys Leu Glu Thr
305                 310                 315                 320

Lys Ile Gly Ser Gly Leu Asp Tyr Asp Thr Asn Gly Ala Val Ile Ile
                325                 330                 335

Lys Leu Gly Thr Gly Val Ser Phe Asp Ser Thr Gly Ala Leu Ser Val
                340                 345                 350

Gly Asn Thr Gly Asp Asp Lys Leu Thr Leu Trp Thr Thr Pro Asp Pro
            355                 360                 365

Ser Pro Asn Cys Arg Ile His Ser Asp Lys Asp Cys Lys Phe Thr Leu
        370                 375                 380

Val Leu Thr Lys Cys Gly Ser Gln Ile Leu Ala Ser Val Ala Ala Leu
385                 390                 395                 400

Ala Val Ser Gly Asn Leu Ala Ser Ile Thr Gly Thr Val Ser Ser Val
                405                 410                 415

Thr Ile Phe Leu Arg Phe Asp Gln Asn Gly Val Leu Met Glu Asn Ser
            420                 425                 430

Ser Leu Asp Lys Gln Tyr Trp Asn Phe Arg Asn Gly Asn Ser Thr Asn
        435                 440                 445

Ala Thr Pro Tyr Thr Asn Ala Val Gly Phe Met Pro Asn Leu Ala Ala
    450                 455                 460

Tyr Pro Lys Thr Gln Ser Gln Thr Ala Lys Asn Ile Val Ser Gln
465                 470                 475                 480

Val Tyr Leu Asn Gly Asp Lys Ser Lys Pro Met Thr Leu Thr Ile Thr
                485                 490                 495

Leu Asn Gly Thr Asn Glu Ser Ser Glu Thr Ser Gln Val Ser His Tyr
            500                 505                 510
```

-continued

```
Ser Met Ser Phe Thr Trp Ala Trp Glu Ser Gly Gln Tyr Ala Thr Glu
        515                 520                 525

Thr Phe Ala Thr Asn Ser Phe Thr Phe Ser Tyr Ile Ala Glu Gln
        530                 535                 540

<210> SEQ ID NO 130
<211> LENGTH: 941
<212> TYPE: PRT
<213> ORGANISM: Adenovirus

<400> SEQUENCE: 130

Met Ala Thr Pro Ser Met Leu Pro Gln Trp Ala Tyr Met His Ile Ala
1               5                   10                  15

Gly Gln Asp Ala Ser Glu Tyr Leu Ser Pro Gly Leu Val Gln Phe Ala
            20                  25                  30

Arg Ala Thr Asp Thr Tyr Phe Ser Leu Gly Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Val Pro Val Asp Arg Glu Asp Asn Thr Tyr Ser Tyr
65                  70                  75                  80

Lys Val Arg Tyr Thr Leu Ala Val Gly Asp Asn Arg Val Leu Asp Met
                85                  90                  95

Ala Ser Thr Tyr Phe Asp Ile Arg Gly Val Leu Asp Arg Gly Pro Ser
            100                 105                 110

Phe Lys Pro Tyr Ser Gly Thr Ala Tyr Asn Ser Leu Ala Pro Lys Gly
        115                 120                 125

Ala Pro Asn Thr Ser Gln Trp Lys Asp Ser Asp Ser Lys Met His Thr
    130                 135                 140

Phe Gly Val Ala Ala Met Pro Gly Val Val Gly Lys Lys Ile Glu Ala
145                 150                 155                 160

Asp Gly Leu Pro Ile Gly Ile Asp Ser Ser Ser Gly Thr Asp Thr Ile
                165                 170                 175

Ile Tyr Ala Asp Lys Thr Phe Gln Pro Glu Pro Gln Val Gly Ser Asp
            180                 185                 190

Ser Trp Val Asp Thr Asn Gly Ala Glu Glu Lys Tyr Gly Gly Arg Ala
        195                 200                 205

Leu Lys Asp Thr Thr Asn Met Lys Pro Cys Tyr Gly Ser Phe Ala Arg
    210                 215                 220

Pro Thr Asn Lys Glu Gly Gly Gln Ala Asn Ile Lys Asp Ser Glu Thr
225                 230                 235                 240

Ala Ser Thr Thr Pro Asn Tyr Asp Ile Asp Leu Ala Phe Phe Asp Ser
                245                 250                 255

Lys Asn Ile Ala Ala Asn Tyr Asp Pro Asp Ile Val Met Tyr Thr Glu
            260                 265                 270

Asn Val Glu Leu Gln Thr Pro Asp Thr His Ile Val Phe Lys Pro Gly
        275                 280                 285

Thr Ser Asp Glu Ser Ser Glu Ala Asn Leu Gly Gln Gln Ala Met Pro
    290                 295                 300

Asn Arg Pro Asn Tyr Ile Gly Phe Arg Asp Asn Phe Ile Gly Leu Met
305                 310                 315                 320

Tyr Tyr Asn Ser Thr Gly Asn Met Gly Val Leu Ala Gly Gln Ala Ser
                325                 330                 335

Gln Leu Asn Ala Val Val Asp Leu Gln Asp Arg Asn Thr Glu Leu Ser
```

-continued

```
                340             345             350
Tyr Gln Leu Leu Leu Asp Ser Leu Gly Asp Arg Thr Arg Tyr Phe Ser
            355             360             365

Met Trp Asn Gln Ala Val Asp Ser Tyr Asp Pro Asp Val Arg Ile Ile
370             375             380

Glu Asn His Gly Val Glu Asp Glu Leu Pro Asn Tyr Cys Phe Pro Leu
385             390             395             400

Asn Gly Val Gly Phe Thr Asp Thr Tyr Gln Gly Val Lys Val Lys Thr
            405             410             415

Asp Thr Ala Ala Thr Gly Thr Asn Gly Thr Gln Trp Asp Lys Asp Asp
            420             425             430

Thr Thr Val Ser Thr Ala Asn Glu Ile His Ser Gly Asn Pro Phe Ala
            435             440             445

Met Glu Ile Asn Ile Gln Ala Asn Leu Trp Arg Asn Phe Leu Tyr Ala
            450             455             460

Asn Val Ala Leu Tyr Leu Pro Asp Ser Tyr Lys Tyr Thr Pro Ala Asn
465             470             475             480

Ile Thr Leu Pro Thr Asn Thr Asn Thr Tyr Asp Tyr Met Asn Gly Arg
            485             490             495

Val Val Ala Pro Ser Leu Val Asp Ala Tyr Ile Asn Ile Gly Ala Arg
            500             505             510

Trp Ser Leu Asp Pro Met Asp Asn Val Asn Pro Phe Asn His His Arg
            515             520             525

Asn Ala Gly Leu Arg Tyr Arg Ser Met Leu Leu Gly Asn Gly Arg Tyr
            530             535             540

Val Pro Phe His Ile Gln Val Pro Gln Lys Phe Phe Ala Ile Lys Ser
545             550             555             560

Leu Leu Leu Leu Pro Gly Ser Tyr Thr Tyr Glu Trp Asn Phe Arg Lys
            565             570             575

Asp Val Asn Met Ile Leu Gln Ser Ser Leu Gly Asn Asp Leu Arg Thr
            580             585             590

Asp Gly Ala Ser Ile Ala Phe Thr Ser Ile Asn Leu Tyr Ala Thr Phe
            595             600             605

Phe Pro Met Ala His Asn Thr Ala Ser Thr Leu Glu Ala Met Leu Arg
            610             615             620

Asn Asp Thr Asn Asp Gln Ser Phe Asn Asp Tyr Leu Ser Ala Ala Asn
625             630             635             640

Met Leu Tyr Pro Ile Pro Ala Asn Ala Thr Asn Val Pro Ile Ser Ile
            645             650             655

Pro Ser Arg Asn Trp Ala Ala Phe Arg Gly Trp Ser Phe Thr Arg Leu
            660             665             670

Lys Thr Arg Glu Thr Pro Ser Leu Gly Ser Gly Phe Asp Pro Tyr Phe
            675             680             685

Val Tyr Ser Gly Ser Ile Pro Tyr Leu Asp Gly Thr Phe Tyr Leu Asn
            690             695             700

His Thr Phe Lys Lys Val Ser Ile Thr Phe Asp Ser Ser Val Ser Trp
705             710             715             720

Pro Gly Asn Asp Arg Leu Leu Thr Pro Asn Glu Phe Glu Ile Lys Arg
            725             730             735

Thr Val Asp Gly Glu Gly Tyr Asn Val Ala Gln Cys Asn Met Thr Lys
            740             745             750

Asp Trp Phe Leu Val Gln Met Leu Ala His Tyr Asn Ile Gly Tyr Gln
            755             760             765
```

Gly Phe Tyr Val Pro Glu Gly Tyr Lys Asp Arg Met Tyr Ser Phe Phe
            770                 775                 780
Arg Asn Phe Gln Pro Met Ser Arg Gln Val Val Asp Glu Val Asn Tyr
785                 790                 795                 800
Lys Asp Tyr Gln Ala Val Thr Leu Ala Tyr Gln His Asn Asn Ser Gly
                805                 810                 815
Phe Val Gly Tyr Leu Ala Pro Thr Met Arg Gln Gly Gln Pro Tyr Pro
                820                 825                 830
Ala Asn Tyr Pro Tyr Pro Leu Ile Gly Lys Ser Ala Val Ala Ser Val
                835                 840                 845
Thr Gln Lys Lys Phe Leu Cys Asp Arg Val Met Trp Arg Ile Pro Phe
                850                 855                 860
Ser Ser Asn Phe Met Ser Met Gly Ala Leu Thr Asp Leu Gly Gln Asn
865                 870                 875                 880
Met Leu Tyr Ala Asn Ser Ala His Ala Leu Asp Met Asn Phe Glu Val
                885                 890                 895
Asp Pro Met Asp Glu Ser Thr Leu Leu Tyr Val Val Phe Glu Val Phe
                900                 905                 910
Asp Val Val Arg Val His Gln Pro His Arg Gly Val Ile Glu Ala Val
                915                 920                 925
Tyr Leu Arg Thr Pro Phe Ser Ala Gly Asn Ala Thr Thr
                930                 935                 940

<210> SEQ ID NO 131
<211> LENGTH: 425
<212> TYPE: PRT
<213> ORGANISM: Adenovirus

<400> SEQUENCE: 131

Met Ser Lys Lys Arg Val Arg Val Asp Asp Asp Phe Asp Pro Val Tyr
1               5                   10                  15
Pro Tyr Asp Ala Asp Asn Ala Pro Thr Val Pro Phe Ile Asn Pro Pro
                20                  25                  30
Phe Val Ser Ser Asp Gly Phe Gln Glu Lys Pro Leu Gly Val Leu Ser
                35                  40                  45
Leu Arg Leu Ala Asp Pro Val Thr Thr Lys Asn Gly Glu Ile Thr Leu
                50                  55                  60
Lys Leu Gly Glu Gly Val Asp Leu Asp Ser Ser Gly Lys Leu Ile Ser
65                  70                  75                  80
Asn Thr Ala Thr Lys Ala Ala Pro Leu Ser Phe Ser Asn Asn Thr
                85                  90                  95
Ile Ser Leu Asn Met Asp His Pro Phe Tyr Thr Lys Asp Gly Lys Leu
                100                 105                 110
Ser Leu Gln Val Ser Pro Pro Leu Asn Ile Leu Arg Thr Ser Ile Leu
                115                 120                 125
Asn Thr Leu Ala Leu Gly Phe Gly Ser Gly Leu Gly Leu Arg Gly Ser
                130                 135                 140
Ala Leu Ala Val Gln Leu Val Ser Pro Leu Thr Phe Asp Thr Asp Gly
145                 150                 155                 160
Asn Ile Lys Leu Thr Leu Asp Arg Gly Leu His Val Thr Thr Gly Asp
                165                 170                 175
Ala Ile Glu Ser Asn Ile Ser Trp Ala Lys Gly Leu Lys Phe Glu Asp
                180                 185                 190
Gly Ala Ile Ala Thr Asn Ile Gly Asn Gly Leu Glu Phe Gly Ser Ser

```
            195                 200                 205
Ser Thr Glu Thr Gly Val Asp Asp Ala Tyr Pro Ile Gln Val Lys Leu
210                 215                 220

Gly Ser Gly Leu Ser Phe Asp Ser Thr Gly Ala Ile Met Ala Gly Asn
225                 230                 235                 240

Lys Glu Asp Asp Lys Leu Thr Leu Trp Thr Thr Pro Asp Pro Ser Pro
            245                 250                 255

Asn Cys Gln Ile Leu Ala Glu Asn Asp Ala Lys Leu Thr Leu Cys Leu
            260                 265                 270

Thr Lys Cys Gly Ser Gln Ile Leu Ala Thr Val Ser Val Leu Val Val
            275                 280                 285

Gly Ser Gly Asn Leu Asn Pro Ile Thr Gly Thr Val Ser Ser Ala Gln
290                 295                 300

Val Phe Leu Arg Phe Asp Ala Asn Gly Val Leu Leu Thr Glu His Ser
305                 310                 315                 320

Thr Leu Lys Lys Tyr Trp Gly Tyr Arg Gln Gly Asp Ser Ile Asp Gly
            325                 330                 335

Thr Pro Tyr Thr Asn Ala Val Gly Phe Met Pro Asn Leu Lys Ala Tyr
            340                 345                 350

Pro Lys Ser Gln Ser Ser Thr Thr Lys Asn Asn Ile Val Gly Gln Val
            355                 360                 365

Tyr Met Asn Gly Asp Val Ser Lys Pro Met Leu Leu Thr Ile Thr Leu
370                 375                 380

Asn Gly Thr Asp Asp Ser Asn Ser Thr Tyr Ser Met Ser Phe Ser Tyr
385                 390                 395                 400

Thr Trp Thr Asn Gly Ser Tyr Val Gly Ala Thr Phe Gly Ala Asn Ser
            405                 410                 415

Tyr Thr Phe Ser Tyr Ile Ala Gln Glu
            420                 425

<210> SEQ ID NO 132
<211> LENGTH: 964
<212> TYPE: PRT
<213> ORGANISM: Adenovirus

<400> SEQUENCE: 132

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
                20                  25                  30

Arg Ala Thr Asp Ser Tyr Phe Ser Leu Ser Asn Lys Phe Arg Asn Pro
            35                  40                  45

Thr Val Ala Pro Thr His Asp Val Thr Thr Asp Arg Ser Gln Arg Leu
        50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ser Leu Ala Pro Lys Gly
        115                 120                 125

Ala Pro Asn Ser Cys Glu Trp Glu Gln Glu Thr Gln Thr Ala Glu
    130                 135                 140
```

-continued

```
Glu Ala Gln Asp Glu Glu Asp Glu Ala Glu Ala Glu Glu Met
145                 150                 155                 160

Pro Gln Glu Glu Gln Ala Pro Val Lys Lys Thr His Val Tyr Ala Gln
                165                 170                 175

Ala Pro Leu Ser Gly Glu Lys Ile Thr Lys Asp Gly Leu Gln Ile Gly
            180                 185                 190

Thr Asp Ala Thr Ala Thr Glu Gln Lys Pro Ile Tyr Ala Asp Pro Thr
        195                 200                 205

Phe Gln Pro Glu Pro Gln Ile Gly Glu Ser Gln Trp Asn Glu Ala Asp
    210                 215                 220

Ala Ser Val Ala Gly Gly Arg Val Leu Lys Lys Thr Thr Pro Met Lys
225                 230                 235                 240

Pro Cys Tyr Gly Ser Tyr Ala Arg Pro Thr Asn Ala Asn Gly Gly Gln
                245                 250                 255

Gly Val Leu Val Glu Lys Asp Gly Gly Lys Met Glu Ser Gln Val Asp
            260                 265                 270

Met Gln Phe Phe Ser Thr Ser Glu Asn Ala Arg Asn Glu Ala Asn Asn
        275                 280                 285

Ile Gln Pro Lys Leu Val Leu Tyr Ser Glu Asp Val His Met Glu Thr
    290                 295                 300

Pro Asp Thr His Ile Ser Tyr Lys Pro Ala Lys Ser Asp Asp Asn Ser
305                 310                 315                 320

Lys Val Met Leu Gly Gln Ser Met Pro Asn Arg Pro Asn Tyr Ile
                325                 330                 335

Gly Phe Arg Asp Asn Phe Ile Gly Leu Met Tyr Tyr Asn Ser Thr Gly
            340                 345                 350

Asn Met Gly Val Leu Ala Gly Gln Ala Ser Gln Leu Asn Ala Val Val
        355                 360                 365

Asp Leu Gln Asp Arg Asn Thr Glu Leu Ser Tyr Gln Leu Leu Leu Asp
    370                 375                 380

Ser Met Gly Asp Arg Thr Arg Tyr Phe Ser Met Trp Asn Gln Ala Val
385                 390                 395                 400

Asp Ser Tyr Asp Pro Asp Val Arg Ile Ile Glu Asn His Gly Thr Glu
                405                 410                 415

Asp Glu Leu Pro Asn Tyr Cys Phe Pro Leu Gly Gly Ile Gly Val Thr
            420                 425                 430

Asp Thr Tyr Gln Ala Ile Lys Thr Asn Gly Asn Gly Asn Gly Gly Gly
        435                 440                 445

Asn Thr Thr Trp Thr Lys Asp Glu Thr Phe Ala Asp Arg Asn Glu Ile
    450                 455                 460

Gly Val Gly Asn Asn Phe Ala Met Glu Ile Asn Leu Ser Ala Asn Leu
465                 470                 475                 480

Trp Arg Asn Phe Leu Tyr Ser Asn Val Ala Leu Tyr Leu Pro Asp Lys
                485                 490                 495

Leu Lys Tyr Asn Pro Ser Asn Val Glu Ile Ser Asp Asn Pro Asn Thr
            500                 505                 510

Tyr Asp Tyr Met Asn Lys Arg Val Val Ala Pro Gly Leu Val Asp Cys
        515                 520                 525

Tyr Ile Asn Leu Gly Ala Arg Trp Ser Leu Asp Tyr Met Asp Asn Val
    530                 535                 540

Asn Pro Phe Asn His His Arg Asn Ala Gly Leu Arg Tyr Arg Ser Met
545                 550                 555                 560

Leu Leu Gly Asn Gly Arg Tyr Val Pro Phe His Ile Gln Val Pro Gln
```

565                 570                 575
Lys Phe Phe Ala Ile Lys Asn Leu Leu Leu Pro Gly Ser Tyr Thr
                580                 585                 590

Tyr Glu Trp Asn Phe Arg Lys Asp Val Asn Met Val Leu Gln Ser Ser
                595                 600                 605

Leu Gly Asn Asp Leu Arg Val Asp Gly Ala Ser Ile Lys Phe Glu Ser
    610                 615                 620

Ile Cys Leu Tyr Ala Thr Phe Phe Pro Met Ala His Asn Thr Ala Ser
625                 630                 635                 640

Thr Leu Glu Ala Met Leu Arg Asn Asp Thr Asn Asp Gln Ser Phe Asn
                645                 650                 655

Asp Tyr Leu Ser Ala Ala Asn Met Leu Tyr Pro Ile Pro Ala Asn Ala
                660                 665                 670

Thr Asn Val Pro Ile Ser Ile Pro Ser Arg Asn Trp Ala Ala Phe Arg
                675                 680                 685

Gly Trp Ala Phe Thr Arg Leu Lys Thr Lys Glu Thr Pro Ser Leu Gly
                690                 695                 700

Ser Gly Phe Asp Pro Tyr Tyr Thr Tyr Ser Gly Ser Ile Pro Tyr Leu
705                 710                 715                 720

Asp Gly Thr Phe Tyr Leu Asn His Thr Phe Lys Lys Val Ser Val Thr
                    725                 730                 735

Phe Asp Ser Ser Val Ser Trp Pro Gly Asn Asp Arg Leu Leu Thr Pro
                740                 745                 750

Asn Glu Phe Glu Ile Lys Arg Ser Val Asp Gly Glu Gly Tyr Asn Val
                755                 760                 765

Ala Gln Cys Asn Met Thr Lys Asp Trp Phe Leu Ile Gln Met Leu Ala
                770                 775                 780

Asn Tyr Asn Ile Gly Tyr Gln Gly Phe Tyr Ile Pro Glu Ser Tyr Lys
785                 790                 795                 800

Asp Arg Met Tyr Ser Phe Phe Arg Asn Phe Gln Pro Met Ser Arg Gln
                    805                 810                 815

Val Val Asp Glu Thr Lys Tyr Lys Asp Tyr Gln Gln Val Gly Ile Ile
                820                 825                 830

His Gln His Asn Asn Ser Gly Phe Val Gly Tyr Leu Ala Pro Thr Met
                835                 840                 845

Arg Glu Gly Gln Ala Tyr Pro Ala Asn Phe Pro Tyr Pro Leu Ile Gly
                850                 855                 860

Lys Thr Ala Val Asp Ser Val Thr Gln Lys Lys Phe Leu Cys Asp Arg
865                 870                 875                 880

Thr Leu Trp Arg Ile Pro Phe Ser Ser Asn Phe Met Ser Met Gly Ala
                    885                 890                 895

Leu Thr Asp Leu Gly Gln Asn Leu Leu Tyr Ala Asn Ser Ala His Ala
                900                 905                 910

Leu Asp Met Thr Phe Glu Val Asp Pro Met Asp Glu Pro Thr Leu Leu
                915                 920                 925

Tyr Val Leu Phe Glu Val Phe Asp Val Val Arg Val His Gln Pro His
                930                 935                 940

Arg Gly Val Ile Glu Thr Val Tyr Leu Arg Thr Pro Phe Ser Ala Gly
945                 950                 955                 960

Asn Ala Thr Thr

<210> SEQ ID NO 133
<211> LENGTH: 593

<212> TYPE: PRT
<213> ORGANISM: Adenovirus

<400> SEQUENCE: 133

```
Met Arg Arg Ala Ala Met Tyr Gln Glu Gly Pro Pro Ser Tyr Glu
1               5                   10                  15

Ser Val Val Gly Ala Ala Ala Ala Pro Ser Ser Pro Phe Ala Ser
            20                  25                  30

Gln Leu Leu Glu Pro Pro Tyr Val Pro Pro Arg Tyr Leu Arg Pro Thr
        35                  40                  45

Gly Gly Arg Asn Ser Ile Arg Tyr Ser Glu Leu Ala Pro Leu Phe Asp
    50                  55                  60

Thr Thr Arg Val Tyr Leu Val Asp Asn Lys Ser Ala Asp Val Ala Ser
65                  70                  75                  80

Leu Asn Tyr Gln Asn Asp His Ser Asn Phe Leu Thr Thr Val Ile Gln
                85                  90                  95

Asn Asn Asp Tyr Ser Pro Ser Glu Ala Ser Thr Gln Thr Ile Asn Leu
            100                 105                 110

Asp Asp Arg Ser His Trp Gly Gly Asp Leu Lys Thr Ile Leu His Thr
        115                 120                 125

Asn Met Pro Asn Val Asn Glu Phe Met Phe Thr Asn Lys Phe Lys Ala
130                 135                 140

Arg Val Met Val Ser Arg Ser His Thr Lys Glu Asp Arg Val Glu Leu
145                 150                 155                 160

Lys Tyr Glu Trp Val Glu Phe Glu Leu Pro Glu Gly Asn Tyr Ser Glu
                165                 170                 175

Thr Met Thr Ile Asp Leu Met Asn Asn Ala Ile Val Glu His Tyr Leu
            180                 185                 190

Lys Val Gly Arg Gln Asn Gly Val Leu Glu Ser Asp Ile Gly Val Lys
        195                 200                 205

Phe Asp Thr Arg Asn Phe Arg Leu Gly Leu Asp Pro Val Thr Gly Leu
210                 215                 220

Val Met Pro Gly Val Tyr Thr Asn Glu Ala Phe His Pro Asp Ile Ile
225                 230                 235                 240

Leu Leu Pro Gly Cys Gly Val Asp Phe Thr Tyr Ser Arg Leu Ser Asn
                245                 250                 255

Leu Leu Gly Ile Arg Lys Arg Gln Pro Phe Gln Glu Gly Phe Arg Ile
            260                 265                 270

Thr Tyr Glu Asp Leu Glu Gly Gly Asn Ile Pro Ala Leu Leu Asp Val
        275                 280                 285

Glu Ala Tyr Gln Asp Ser Leu Lys Glu Asn Glu Ala Gly Gln Glu Asp
290                 295                 300

Thr Ala Pro Ala Ala Ser Ala Ala Ala Glu Gln Gly Glu Asp Ala Ala
305                 310                 315                 320

Asp Thr Ala Ala Ala Asp Gly Ala Glu Ala Asp Pro Ala Met Val Val
                325                 330                 335

Glu Ala Pro Glu Gln Glu Glu Asp Met Asn Asp Ser Ala Val Arg Gly
            340                 345                 350

Asp Thr Phe Val Thr Arg Gly Glu Glu Lys Gln Ala Glu Ala Glu Ala
        355                 360                 365

Ala Ala Glu Glu Lys Gln Leu Ala Ala Ala Ala Ala Ala Ala Ala Leu
370                 375                 380

Ala Ala Ala Glu Ala Glu Ser Glu Gly Thr Lys Pro Ala Lys Glu Pro
385                 390                 395                 400
```

Val Ile Lys Pro Leu Thr Glu Asp Ser Lys Lys Arg Ser Tyr Asn Leu
            405                 410                 415

Leu Lys Asp Ser Thr Asn Thr Ala Tyr Arg Ser Trp Tyr Leu Ala Tyr
        420                 425                 430

Asn Tyr Gly Asp Pro Ser Thr Gly Val Arg Ser Trp Thr Leu Leu Cys
            435                 440                 445

Thr Pro Asp Val Thr Cys Gly Ser Glu Gln Val Tyr Trp Ser Leu Pro
450                 455                 460

Asp Met Met Gln Asp Pro Val Thr Phe Arg Ser Thr Arg Gln Val Ser
465                 470                 475                 480

Asn Phe Pro Val Val Gly Ala Glu Leu Leu Pro Val His Ser Lys Ser
            485                 490                 495

Phe Tyr Asn Asp Gln Ala Val Tyr Ser Gln Leu Ile Arg Gln Phe Thr
        500                 505                 510

Ser Leu Thr His Val Phe Asn Arg Phe Pro Glu Asn Gln Ile Leu Ala
            515                 520                 525

Arg Pro Pro Ala Pro Thr Ile Thr Thr Val Ser Glu Asn Val Pro Ala
530                 535                 540

Leu Thr Asp His Gly Thr Leu Pro Leu Arg Asn Ser Ile Gly Gly Val
545                 550                 555                 560

Gln Arg Val Thr Val Thr Asp Ala Arg Arg Thr Cys Pro Tyr Val
            565                 570                 575

Tyr Lys Ala Leu Gly Ile Val Ser Pro Arg Val Leu Ser Ser Arg Thr
            580                 585                 590

Phe

<210> SEQ ID NO 134
<211> LENGTH: 578
<212> TYPE: PRT
<213> ORGANISM: Adenovirus

<400> SEQUENCE: 134

Met Lys Arg Thr Lys Thr Ser Asp Glu Ser Phe Asn Pro Val Tyr Pro
1               5                   10                  15

Tyr Asp Thr Glu Ser Gly Pro Pro Ser Val Pro Phe Leu Thr Pro Pro
            20                  25                  30

Phe Val Ser Pro Asp Gly Phe Gln Glu Ser Pro Pro Gly Val Leu Ser
        35                  40                  45

Leu Asn Leu Ala Glu Pro Leu Val Thr Ser His Gly Met Leu Ala Leu
    50                  55                  60

Lys Met Gly Ser Gly Leu Ser Leu Asp Asp Ala Gly Asn Leu Thr Ser
65                  70                  75                  80

Gln Asp Ile Thr Thr Ala Ser Pro Pro Leu Lys Lys Thr Lys Thr Asn
                85                  90                  95

Leu Ser Leu Glu Thr Ser Ser Pro Leu Thr Val Ser Thr Ser Gly Ala
            100                 105                 110

Leu Thr Val Ala Ala Ala Pro Leu Ala Val Ala Gly Thr Ser Leu
        115                 120                 125

Thr Met Gln Ser Glu Ala Pro Leu Thr Val Gln Asp Ala Lys Leu Thr
    130                 135                 140

Leu Ala Thr Lys Gly Pro Leu Thr Val Ser Glu Gly Lys Leu Ala Leu
145                 150                 155                 160

Gln Thr Ser Ala Pro Leu Thr Ala Ala Asp Ser Ser Thr Leu Thr Val
                165                 170                 175

-continued

```
Ser Ala Thr Pro Pro Leu Ser Thr Ser Asn Gly Ser Leu Gly Ile Asp
            180                 185                 190

Met Gln Ala Pro Ile Tyr Thr Thr Asn Gly Lys Leu Gly Leu Asn Phe
            195                 200                 205

Gly Ala Pro Leu His Val Val Asp Ser Leu Asn Ala Leu Thr Val Val
            210                 215                 220

Thr Gly Gln Gly Leu Thr Ile Asn Gly Thr Ala Leu Gln Thr Arg Val
225                 230                 235                 240

Ser Gly Ala Leu Asn Tyr Asp Thr Ser Gly Asn Leu Glu Leu Arg Ala
                245                 250                 255

Ala Gly Gly Met Arg Val Asp Ala Asn Gly Gln Leu Ile Leu Asp Val
                260                 265                 270

Ala Tyr Pro Phe Asp Ala Gln Asn Asn Leu Ser Leu Arg Leu Gly Gln
                275                 280                 285

Gly Pro Leu Phe Val Asn Ser Ala His Asn Leu Asp Val Asn Tyr Asn
            290                 295                 300

Arg Gly Leu Tyr Leu Phe Thr Ser Gly Asn Thr Lys Lys Leu Glu Val
305                 310                 315                 320

Asn Ile Lys Thr Ala Lys Gly Leu Ile Tyr Asp Asp Thr Ala Ile Ala
                325                 330                 335

Ile Asn Ala Gly Asp Gly Leu Gln Phe Asp Ser Gly Ser Asp Thr Asn
                340                 345                 350

Pro Leu Lys Thr Lys Leu Gly Leu Gly Leu Asp Tyr Asp Ser Ser Arg
            355                 360                 365

Ala Ile Ile Ala Lys Leu Gly Thr Gly Leu Ser Phe Asp Asn Thr Gly
            370                 375                 380

Ala Ile Thr Val Gly Asn Lys Asn Asp Lys Leu Thr Leu Trp Thr
385                 390                 395                 400

Thr Pro Asp Pro Ser Pro Asn Cys Arg Ile Tyr Ser Glu Lys Asp Ala
                405                 410                 415

Lys Phe Thr Leu Val Leu Thr Lys Cys Gly Ser Gln Val Leu Ala Ser
            420                 425                 430

Val Ser Val Leu Ser Val Lys Gly Ser Leu Ala Pro Ile Ser Gly Thr
            435                 440                 445

Val Thr Ser Ala Gln Ile Val Leu Arg Phe Asp Glu Asn Gly Val Leu
450                 455                 460

Leu Ser Asn Ser Ser Leu Asp Pro Gln Tyr Trp Asn Tyr Arg Lys Gly
465                 470                 475                 480

Asp Leu Thr Glu Gly Thr Ala Tyr Thr Asn Ala Val Gly Phe Met Pro
                485                 490                 495

Asn Leu Thr Ala Tyr Pro Lys Thr Gln Ser Gln Thr Ala Lys Ser Asn
                500                 505                 510

Ile Val Ser Gln Val Tyr Leu Asn Gly Asp Lys Ser Lys Pro Met Thr
                515                 520                 525

Leu Thr Ile Thr Leu Asn Gly Thr Asn Glu Thr Gly Asp Ala Thr Val
            530                 535                 540

Ser Thr Tyr Ser Met Ser Phe Ser Trp Asn Trp Asn Gly Ser Asn Tyr
545                 550                 555                 560

Ile Asn Glu Thr Phe Gln Thr Asn Ser Phe Thr Phe Ser Tyr Ile Ala
                565                 570                 575

Gln Glu
```

<210> SEQ ID NO 135
<211> LENGTH: 215
<212> TYPE: PRT
<213> ORGANISM: Mus musculus

<400> SEQUENCE: 135

```
Met Asp Asp Gln Arg Asp Leu Ile Ser Asn His Glu Gln Leu Pro Ile
1               5                   10                  15

Leu Gly Asn Arg Pro Arg Glu Pro Glu Arg Cys Ser Arg Gly Ala Leu
            20                  25                  30

Tyr Thr Gly Val Ser Val Leu Val Ala Ala Ala Ala Gly Gln Ala
        35                  40                  45

Thr Thr Ala Tyr Phe Leu Tyr Gln Gln Gln Gly Arg Leu Asp Lys Leu
    50                  55                  60

Thr Ile Thr Ser Gln Asn Leu Gln Leu Glu Ser Leu Arg Met Lys Leu
65                  70                  75                  80

Pro Lys Ser Ala Lys Pro Val Ser Gln Met Arg Met Ala Thr Pro Leu
                85                  90                  95

Leu Met Arg Pro Met Ser Met Asp Asn Met Leu Leu Gly Pro Val Lys
            100                 105                 110

Asn Val Thr Lys Tyr Gly Asn Met Thr Gln Asp His Val Met His Leu
        115                 120                 125

Leu Thr Arg Ser Gly Pro Leu Glu Tyr Pro Gln Leu Lys Gly Thr Phe
    130                 135                 140

Pro Glu Asn Leu Lys His Leu Lys Asn Ser Met Asp Gly Val Asn Trp
145                 150                 155                 160

Lys Ile Phe Glu Ser Trp Met Lys Gln Trp Leu Leu Phe Glu Met Ser
                165                 170                 175

Lys Asn Ser Leu Glu Glu Lys Lys Pro Thr Glu Ala Pro Pro Lys Glu
            180                 185                 190

Pro Leu Asp Met Glu Asp Leu Ser Ser Gly Leu Gly Val Thr Arg Gln
        195                 200                 205

Glu Leu Gly Gln Val Thr Leu
    210                 215
```

<210> SEQ ID NO 136
<211> LENGTH: 215
<212> TYPE: PRT
<213> ORGANISM: Mus musculus

<400> SEQUENCE: 136

```
Met Asp Asp Gln Arg Asp Leu Ile Ser Asn His Glu Gln Leu Pro Ile
1               5                   10                  15

Leu Gly Asn Arg Pro Arg Glu Pro Glu Arg Cys Ser Arg Gly Ala Leu
            20                  25                  30

Tyr Thr Gly Val Ser Val Leu Val Ala Leu Leu Ala Gly Gln Ala
        35                  40                  45

Thr Thr Ala Tyr Phe Leu Tyr Gln Gln Gln Gly Arg Leu Asp Arg Leu
    50                  55                  60

Thr Ile Thr Ser Gln Asn Leu Gln Leu Glu Ser Leu Arg Met Lys Leu
65                  70                  75                  80

Pro Lys Ser Ala Lys Pro Val Ser Gln Met Arg Met Ala Thr Pro Leu
                85                  90                  95

Leu Met Arg Pro Met Ser Met Asp Asn Met Leu Leu Gly Pro Val Lys
            100                 105                 110

Asn Val Thr Lys Tyr Gly Asn Met Thr Gln Asp His Val Met His Leu
```

```
                115                 120                 125
Leu Thr Arg Ser Gly Pro Leu Glu Tyr Pro Gln Leu Lys Gly Thr Phe
            130                 135                 140

Pro Glu Asn Leu Lys His Leu Lys Asn Ser Met Asp Gly Val Asn Trp
145                 150                 155                 160

Lys Ile Phe Glu Ser Trp Met Lys Gln Trp Leu Leu Phe Glu Met Ser
                165                 170                 175

Lys Asn Ser Leu Glu Glu Lys Pro Thr Glu Ala Pro Pro Lys Glu
            180                 185                 190

Pro Leu Asp Met Glu Asp Leu Ser Ser Gly Leu Gly Val Thr Arg Gln
            195                 200                 205

Glu Leu Gly Gln Val Thr Leu
            210                 215

<210> SEQ ID NO 137
<211> LENGTH: 75
<212> TYPE: PRT
<213> ORGANISM: Mus musculus

<400> SEQUENCE: 137

Met Asp Asp Gln Arg Asp Leu Ile Ser Asn His Glu Gln Leu Pro Ile
1               5                   10                  15

Leu Gly Asn Arg Pro Arg Glu Pro Glu Arg Cys Ser Arg Gly Ala Leu
            20                  25                  30

Tyr Thr Gly Val Ser Val Leu Val Ala Leu Leu Ala Gly Gln Ala
        35                  40                  45

Thr Thr Ala Tyr Phe Leu Tyr Gln Gln Gln Gly Arg Leu Asp Arg Leu
50                  55                  60

Thr Ile Thr Ser Gln Asn Leu Gln Leu Glu Ser
65                  70                  75

<210> SEQ ID NO 138
<211> LENGTH: 231
<212> TYPE: PRT
<213> ORGANISM: Mus musculus

<400> SEQUENCE: 138

Met His Arg Arg Arg Ser Arg Ser Cys Arg Glu Asp Gln Lys Pro Val
1               5                   10                  15

Met Asp Asp Gln Arg Asp Leu Ile Ser Asn His Glu Gln Leu Pro Ile
            20                  25                  30

Leu Gly Asn Arg Pro Arg Glu Pro Glu Arg Cys Ser Arg Gly Ala Leu
        35                  40                  45

Tyr Thr Gly Val Ser Val Leu Val Ala Leu Leu Ala Gly Gln Ala
50                  55                  60

Thr Thr Ala Tyr Phe Leu Tyr Gln Gln Gln Gly Arg Leu Asp Lys Leu
65                  70                  75                  80

Thr Ile Thr Ser Gln Asn Leu Gln Leu Glu Ser Leu Arg Met Lys Leu
                85                  90                  95

Pro Lys Ser Ala Lys Pro Val Ser Gln Met Arg Met Ala Thr Pro Leu
            100                 105                 110

Leu Met Arg Pro Met Ser Met Asp Asn Met Leu Leu Gly Pro Val Lys
            115                 120                 125

Asn Val Thr Lys Tyr Gly Asn Met Thr Gln Asp His Val Met His Leu
            130                 135                 140

Leu Thr Arg Ser Gly Pro Leu Glu Tyr Pro Gln Leu Lys Gly Thr Phe
```

```
                145                 150                 155                 160
Pro Glu Asn Leu Lys His Leu Lys Asn Ser Met Asp Gly Val Asn Trp
                165                 170                 175

Lys Ile Phe Glu Ser Trp Met Lys Gln Trp Leu Leu Phe Glu Met Ser
            180                 185                 190

Lys Asn Ser Leu Glu Glu Lys Lys Pro Thr Glu Ala Pro Pro Lys Glu
                195                 200                 205

Pro Leu Asp Met Glu Asp Leu Ser Ser Gly Leu Gly Val Thr Arg Gln
            210                 215                 220

Glu Leu Gly Gln Val Thr Leu
225                 230

<210> SEQ ID NO 139
<211> LENGTH: 199
<212> TYPE: PRT
<213> ORGANISM: Mus musculus

<400> SEQUENCE: 139

Met Gly Asn Arg Pro Arg Glu Pro Glu Arg Cys Ser Arg Gly Ala Leu
1               5                   10                  15

Tyr Thr Gly Val Ser Val Leu Val Ala Leu Leu Ala Gly Gln Ala
            20                  25                  30

Thr Thr Ala Tyr Phe Leu Tyr Gln Gln Gln Gly Arg Leu Asp Lys Leu
        35                  40                  45

Thr Ile Thr Ser Gln Asn Leu Gln Leu Glu Ser Leu Arg Met Lys Leu
    50                  55                  60

Pro Lys Ser Ala Lys Pro Val Ser Gln Met Arg Met Ala Thr Pro Leu
65                  70                  75                  80

Leu Met Arg Pro Met Ser Met Asp Asn Met Leu Leu Gly Pro Val Lys
                85                  90                  95

Asn Val Thr Lys Tyr Gly Asn Met Thr Gln Asp His Val Met His Leu
            100                 105                 110

Leu Thr Arg Ser Gly Pro Leu Glu Tyr Pro Gln Leu Lys Gly Thr Phe
        115                 120                 125

Pro Glu Asn Leu Lys His Leu Lys Asn Ser Met Asp Gly Val Asn Trp
    130                 135                 140

Lys Ile Phe Glu Ser Trp Met Lys Gln Trp Leu Leu Phe Glu Met Ser
145                 150                 155                 160

Lys Asn Ser Leu Glu Glu Lys Lys Pro Thr Glu Ala Pro Pro Lys Glu
                165                 170                 175

Pro Leu Asp Met Glu Asp Leu Ser Ser Gly Leu Gly Val Thr Arg Gln
            180                 185                 190

Glu Leu Gly Gln Val Thr Leu
        195

<210> SEQ ID NO 140
<211> LENGTH: 166
<212> TYPE: PRT
<213> ORGANISM: Mus musculus

<400> SEQUENCE: 140

Met Ala Tyr Phe Leu Tyr Gln Gln Gln Gly Arg Leu Asp Lys Leu Thr
1               5                   10                  15

Ile Thr Ser Gln Asn Leu Gln Leu Glu Ser Leu Arg Met Lys Leu Pro
            20                  25                  30

Lys Ser Ala Lys Pro Val Ser Gln Met Arg Met Ala Thr Pro Leu Leu
```

```
                35                  40                  45
Met Arg Pro Met Ser Met Asp Asn Met Leu Leu Gly Pro Val Lys Asn
            50                  55                  60

Val Thr Lys Tyr Gly Asn Met Thr Gln Asp His Val Met His Leu Leu
65                  70                  75                  80

Thr Arg Ser Gly Pro Leu Glu Tyr Pro Gln Leu Lys Gly Thr Phe Pro
                85                  90                  95

Glu Asn Leu Lys His Leu Lys Asn Ser Met Asp Gly Val Asn Trp Lys
                100                 105                 110

Ile Phe Glu Ser Trp Met Lys Gln Trp Leu Leu Phe Glu Met Ser Lys
                115                 120                 125

Asn Ser Leu Glu Glu Lys Lys Pro Thr Glu Ala Pro Pro Lys Glu Pro
                130                 135                 140

Leu Asp Met Glu Asp Leu Ser Ser Gly Leu Gly Val Thr Arg Gln Glu
145                 150                 155                 160

Leu Gly Gln Val Thr Leu
                165
```